US008703776B2

(12) United States Patent
Novack et al.

(10) Patent No.: US 8,703,776 B2
(45) Date of Patent: Apr. 22, 2014

(54) AGONISTS OF GPR131 AND USES THEREOF

(75) Inventors: Aaron Robert Novack, San Jose, CA (US); Dong-Fang Shi, Fremont, CA (US); Jingyuan Ma, Sunnyvale, CA (US); Imad Nashashibi, San Jose, CA (US); Phuongly Pham, San Francisco, CA (US); Jiangao Song, Sunnyvale, CA (US); David W. G. Wone, Newark, CA (US); Xueyan Wang, Foster City, CA (US); Jeffrey D. Johnson, Moraga, CA (US); Brian Edward Lavan, San Francisco, CA (US); Charles A. McWherter, San Mateo, CA (US); Xin Chen, San Ramon, CA (US)

(73) Assignee: Cymabay Therapeutics, Inc., Newark, CA (US)

( * ) Notice: Subject to any disclaimer, the term of this patent is extended or adjusted under 35 U.S.C. 154(b) by 0 days.

(21) Appl. No.: 13/495,878

(22) Filed: Jun. 13, 2012

(65) Prior Publication Data

US 2013/0059856 A1 Mar. 7, 2013

Related U.S. Application Data

(60) Provisional application No. 61/497,457, filed on Jun. 15, 2011, provisional application No. 61/497,927, filed on Jun. 16, 2011.

(51) Int. Cl.
*A61K 31/4965* (2006.01)
*A01N 43/60* (2006.01)

(52) U.S. Cl.
USPC ...... 514/255.05; 514/249; 514/256; 514/397; 514/398

(58) Field of Classification Search
USPC ............... 514/249, 255.05, 256, 397, 398
See application file for complete search history.

(56) References Cited

U.S. PATENT DOCUMENTS

| | | | | |
|---|---|---|---|---|
| 5,210,092 | A | 5/1993 | Oku et al. | |
| 5,225,414 | A | 7/1993 | Henning et al. | |
| 7,326,708 | B2 * | 2/2008 | Cypes et al. | 514/249 |
| 8,552,022 | B2 * | 10/2013 | Wood et al. | 514/275 |
| 2010/0323011 | A1 * | 12/2010 | Pourkavoos | 514/249 |
| 2010/0330177 | A1 * | 12/2010 | Pourkavoos | 424/465 |
| 2011/0152295 | A1 * | 6/2011 | Leclerc et al. | 514/256 |
| 2011/0166152 | A1 * | 7/2011 | Leclerc et al. | 514/249 |
| 2011/0294767 | A1 * | 12/2011 | Gedulin et al. | 514/171 |
| 2013/0034536 | A1 * | 2/2013 | Gedulin | 424/94.64 |
| 2013/0059845 | A1 * | 3/2013 | Song et al. | 514/233.2 |

FOREIGN PATENT DOCUMENTS

WO    WO-2010/117090 A1    10/2010

OTHER PUBLICATIONS

Alkhader et al. (1994); "Synthesis of some newer indazolyl-oxadiazoles, thiadiazoles and 1,2,4-trazoles," Qatar Univ. Sci. J. 14(C):114-122.
Database CA [Online], Chemical Abstracts Service, Columbus, Ohio, US; Lahser et al.: "Antiviral HCV inhibitors and combination therapy," XP002684729, retrieved from STN Database accession No. 2010:1277297 abstract & WO 2010/117939 A1 .
Database Registry [Online], Chemical Abstracts Service, Columbus, Ohio, US; Sep 14, 2011, XP002684731, retrieved from STN Database accession No. 1332091-62-9 abstract.
Gmeiner et al. (2003), "Synthesis and dopamine receptor binding of some pyrazolo [3',4':6,7]azepino[5,4,3-cd]indoles," Heterocycles 60(6):1339-1350.
Kaim et al. (2011); "Four-component synthesis of indazole through ugi-azide coupling," Synlett 23:295-297.
International Search Report for Application No. PCT/US2012/052364 dated Oct. 19, 2012.
Barrett-Connor, "Epidemiology, obesity, and non-insulin-dependent diabetes mellitus," Epidemol. Rev. (1989) 11:172-181.
Berge, et al., "Pharmaceutical Salts," J. Pharma. Sciences (1977) 66(1):1-19.
Drucker, "Biological Actions and Therapeutic Potential of the Glucagon-like Peptides," Gastroenterology (2002) 122:531-544.
Expert Committee on the Diagnosis and Classification of Diabetes Mellitus, The, "Report of the expert committee on the diagnosis and classification of diabetes mellitus," Diabetes Care (1999) 2(Suppl 1):S5-S19.
Flier, "Insulin receptors and insulin resistance," Ann. Rev. Med. (1983) 34:145-160.
Katsuma et al., "Bile acids promote glucagon-like peptide-1 secretion through TGR5 in a murine enteroendocrine cell line STC-1," Biochem. Biophys. Res. Commun. (2005) 329(1):386-390.
Kawamata, et al., "A G protein-coupled receptor responsive to bile acids," J. Biological Chemistry (2003) 278(11):9435-9440.
Keitel, et al., "Expression and function of the bile acid receptor TGR5 in Kupffer cells," Biochemical and Biophysical Research Communications (2008) 372:78-84.
Knowler et al., "Obesity in the Pima Indians: its magnitude and relationship with diabetes," Am. J. Clin. Nutr. (1991) 53:1543S-1551S.
Maruyama, et al., "Identification of membrane-type receptor for bile acids (M-BAR)," Biochemical and Biophysical Research Communications (2002) 298:714-719.
Maruyama, et al., "Targeted disruption of G protein-coupled bile acid receptor 1 (Gpbar1/M-Bar) in mice," J. Endocrinology (2006) 191:197-205.
Rautio, et al., "Prodrugs: design and clinical applications," Nature Reviews (2008) 7:255-270.
Reaven, "Insulin resistance and human disease: a short history," J. Basic & Clin. Phys. & Pharm., (1998) 9(2-4):387-406.
Remington: The Science and Practice of Pharmacy, R. Hendrickson, ed., 21st edition, Lippincott, Williams & Wilkins, Philadelphia, PA, (2005), at p. 732, Table 38-5.
Thomas, et al., "TGR5-mediated bile acid sensing controls glucose homeostasis," Cell Metabolism (2009) 10:167-177.
Watanabe, et al., "Bile acids induce energy expenditure by promoting intracellular thyroid hormone activation," Nature (2006) 439:484-489.

* cited by examiner

Primary Examiner — My-Chau T Tran
(74) Attorney, Agent, or Firm — Foley & Lardner LLP

(57) ABSTRACT

Chemical compounds which act as agonists of, or otherwise modulate the activity of, GPR131 are disclosed. Related compositions, formulations and methods of use are also described.

20 Claims, 2 Drawing Sheets

AGONISTS OF GPR131 AND USES THEREOF

CROSS-REFERENCE TO RELATED APPLICATIONS

This application claims the benefit under 35 U.S.C. 119(e) of U.S. Provisional Application No. 61/497,457, filed Jun. 15, 2011 and U.S. Provisional Application No. 61/497,927, filed Jun. 16, 2011, which are incorporated by reference in their entirety into this application.

BACKGROUND

This application relates to chemical compounds which act as agonists of, or otherwise modulate the activity of, GPR131, and to compositions and formulations containing such compounds, and methods of using and making such compounds. The compounds described herein may be used to treat one or more diseases such as diabetes, metabolic syndrome, and liver disease, conditions or symptoms of a disease such as inflammation, and other diseases or conditions for which modulation of GPR131 can provide a therapeutic benefit.

G protein-coupled receptors (GPCRs) comprise a large family of transmembrane receptors that sense molecules outside a cell and modulate signal transduction pathways and, consequently, various cellular responses. GPR131 (also known as BG37, TGR5, M-BAR, GPCR19, MGC40597, GPBAR1, and RUP43) is a GPCR that is activated by bile acids (BAs) such as lithocholic acid (LCA) and taurolithocholic acid (TLC), and oleanolic acid. Muruyama et al., *Biochem Biophys Res. Commun.*, 298:714-9 (2002) [PMID: 12419312] (2002); Kawamata et al., *J. Biol. Chem.*, 278: 9435-40 (2003) [PMID: 12524422]. GPR131 is expressed in the gastro-intestinal tract and adipose as well as other tissues, and is also present in GLP-1 secreting entero-endocrine cell lines such as STC-1 (Katsuma et al., *Biochem. Biophys. Res. Commun.*, 329(1):386-90 (2005) [PMID: 15721318]) and NCI-H716. Since this receptor is coupled to signaling through the GαS protein, activation of GPR131 results in increases in cAMP. Bile acid ligands of GPR131 can increase cAMP and consequent release of the incretin hormone glucagon-like-peptide 1 (GLP-1) from enteroendocrine cell lines. Katsuma et al., supra.

GPR131 agonists also increase serum levels of glucagon-like peptide-1 ("GLP-1") in vivo, and this likely contributes to their ability to improve glucose homeostasis in rodent models. Thomas et al., *Cell Metab.*, 10:167-77 (2009) [PMID: 19723493]. Acute improvements in glucose homeostasis due to raising of blood GLP-1 levels by GPR131 agonists may result from increased glucose sensitive insulin secretion (GSIS) from pancreatic beta cells, reduced glucagon secretion from pancreatic alpha cells, and from a delay of gastric emptying, all of which are known effects of GLP-1 in rodents and humans. Drucker, *Gastroenterology*, 122:531-44 (2002). Multiple current and proposed therapeutic agents for diabetes, obesity and metabolic syndrome have their effect via increased stimulation of the receptor for GLP-1 in pancreatic beta cells or other tissues.

Other consequences of GPR131 activation may also contribute to improvements in glucose homeostasis and other metabolic parameters. GPR131 agonists have been described as having the capacity to increase energy expenditure in rodents, and thus may provide an additional means for improving glucose homeostasis via improvements in insulin sensitivity. Watanabe et al., *Nature*, 439:484-9 (2006) [PMID: 16400329]. In one study, knock-out mice that lacked GPR131 had a higher body weight and increased fat mass relative to wild type mice when placed on a high fat diet suggesting that reduced signaling through GPR131 could contribute to obesity and insulin resistance Muruyama et al., *J. Endocrinol.*, 191:197-205 (2006).

Additionally, GPR131 is expressed in human CD14+ monocytes and spleen, and may play a role in mediating anti-inflammatory effects of BAs and GPR131 agonists. Agonists of this receptor can increase cAMP levels and reduce phagocytic activity in alveolar macrophages. The latter effect may be due to decreased release of pro-inflammatory cytokines in the presence of GPR131 agonists. Kawamata et al, supra. A similar effect has been observed in the resident macrophages of liver (Kupffer cells) [Keitel et al., *Biochem. Biophys. Res. Commun.*, 372:78-84 (2008). Since adipose tissue inflammations can contribute to an insulin resistant state, it is contemplated that part of the effect of GPR131 agonists to improve glucose homeostasis arises from their capacity to reduce inflammation in adipose tissue.

While certain GPR131 agonists are in early development, none are yet commercially available. Additional agonists of GPR131 for the treatment or prevention of diabetes, metabolic syndrome, liver disease, inflammation, and other diseases and conditions are therefore needed.

SUMMARY

One embodiment provides for a compound of Formula (I)

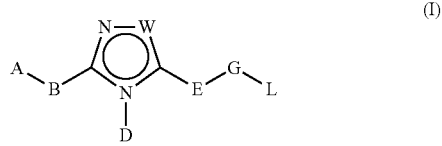

or a derivative thereof, wherein

A is H, —OH, halo, alkyl, alkoxy, aryl, arylalkyl, aryloxy, cycloalkyl, heteroalkyl, heteroaryl, or heterocycloalkyl, each of which may be optionally substituted;

B is alkyl, alkenyl, or alkynyl, each of which may be optionally substituted, or —$(CR^{a1}R^{a2})_iO(CR^{a3}R^{a4})_j$—, —$(CR^{a1}R^{a2})_iC(O)(CR^{a3}R^{a4})_j$—, —$(CR^{a1}R^{a2})_iS(CR^{a3}R^{a4})_j$—, —$(CR^{a1}R^{a2})_iS(O)(CR^{a3}R^{a4})_j$—, —$(CR^{a1}R^{a2})_iS(O)_2(CR^{a3}R^{a4})_j$—, —$(CR^{a1}R^{a2})_iN(R^{a5})(CR^{a3}R^{a4})_j$—, C(O)C$(R^{a1}R^{a2})_iS$—, or absent;

D is H, alkyl, aryl, arylalkyl, cycloalkyl, heteroalkyl, heteroaryl, or heterocycloalkyl, each of which may be optionally substituted;

E is —$(CR^{b1}R^{b2})_kO$—, —$(CR^{b1}R^{b2})_kC(O)$—, —$(CR^{b1}R^{b2})_kOC(O)$—, —$(CR^{b1}R^{b2})_kS$—, —$(CR^{b1}R^{b2})_kS(O)$—, —$(CR^{b1}R^{b2})_kS(O)_2$—, —$(CR^{b1}R^{b2})_kN(R^{b3})$—, —$(CR^{b1}R^{b2})_kC(O)N(R^{b3})$—, —$(CR^{b1}R^{b2})_kS(O)_2N(R^{b3})$—, or absent;

G is —$(CR^{c1}R^{c2})_m$—, —C(O)—, or optionally substituted alkenyl;

L is H, —OH, halo, alkyl, aryl, arylalkyl, cycloalkyl, heteroalkyl, heteroaryl, or heterocycloalkyl, each of which may be optionally substituted;

W is $CR^1$ or N;

each i, j, and k is independently 0, 1, or 2;

m is 1, 2, or 3;

each $R^{a1}$, $R^{a2}$, $R^{a3}$, $R^{a4}$, $R^{a5}$, $R^{b1}$, $R^{b2}$, $R^{c1}$, and $R^{c2}$ is independently H, F, or optionally substituted alkyl;

$R^{b3}$ is H or optionally substituted alkyl;

or $R^{a1}$ and $R^{b3}$ together with the atoms to which they are attached may form an optionally substituted heterocycloalkyl; and each $R^1$ is independently H, halo, cyano, amino, or optionally substituted alkyl;

with the proviso that if G is —(CR$^{c1}$R$^{c2}$) wherein $R^{a1}$ and $R^{c2}$ are both —CH$_3$ and m is 1, then E is not absent.

Another embodiment provides for a compound of Formula (II)

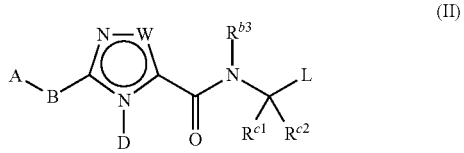

(II)

or a derivate thereof, wherein

A is H, —OH, halo, alkyl, alkoxy, aryl, arylalkyl, aryloxy, cycloalkyl, heteroalkyl, heteroaryl, or heterocycloalkyl, each of which may be optionally substituted;

B is alkyl, alkenyl, or alkynyl, each of which may be optionally substituted, or —(CR$^{a1}$R$^{a2}$)$_i$O(CR$^{a3}$R$^{a4}$)$_j$—, —(CR$^{a1}$R$^{a2}$)$_i$C(O)(CR$^{a3}$R$^{a4}$)$_j$—, —(CR$^{a1}$R$^{a2}$)$_i$S(CR$^{a3}$R$^{a4}$)$_j$—, —(CR$^{a1}$R$^{a2}$)$_i$S(O)(CR$^{a3}$R$^{a4}$)$_j$—, —(CR$^{a1}$R$^{a2}$)$_i$S(O)$_2$(CR$^{a3}$R$^{a4}$)$_j$—, —(CR$^{a1}$R$^{a2}$)$_i$N(R$^{a5}$)(CR$^{a3}$R$^{a4}$)$_j$—, C(O)C(R$^{a1}$R$^{a2}$)$_i$S—, or absent;

D is H, alkyl, aryl, arylalkyl, cycloalkyl, heteroalkyl, heteroaryl, or heterocycloalkyl, each of which may be optionally substituted;

L is H, halo, alkyl, aryl, arylalkyl, cycloalkyl, heteroalkyl, heteroaryl, or heterocycloalkyl, each of which may be optionally substituted;

W is CR$^1$ or N;

each i and j is independently 0, 1, or 2;

each $R^{a1}$, $R^{a2}$, $R^{a3}$, $R^{a4}$, $R^{a5}$, $R^{b3}$, $R^{c1}$, and $R^{c2}$ is independently H or optionally substituted alkyl, or $R^{c1}$ and $R^{b3}$ together with the atoms to which they are attached may form an optionally substituted heterocycloalkyl; and each $R^1$ is independently H, halo, or optionally substituted alkyl.

Another embodiment provides for a compound of Formula (III)

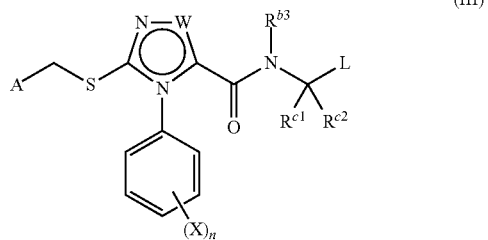

(III)

or a derivate thereof, wherein

A is H, halo, alkyl, alkoxy, aryl, arylalkyl, aryloxy, cycloalkyl, heteroalkyl, heteroaryl, or heterocycloalkyl, each of which may be optionally substituted;

L is H, halo, alkyl, aryl, arylalkyl, cycloalkyl, heteroalkyl, heteroaryl, or heterocycloalkyl, each of which may be optionally substituted;

W is CR$^1$ or N;

each X is independently halo, cyano, sulfonamide, optionally substituted alkyl, or —OR$^a$, —NR$^a$R$^b$, —C(O)R$^a$, —C(O)OR$^a$, —C(O)NR$^a$R$^b$, —NR$^a$C(O)R$^b$, —SR$^a$, —S(O)R$^a$, —S(O)$_2$R$^a$, and —NR$^a$S(O)$_2$R$^b$, wherein $R^a$ and $R^b$ are independently H or optionally substituted alkyl;

n is 0 to 5;

each $R^{a1}$, $R^{a2}$, $R^{a3}$, $R^{a4}$, $R^{a5}$, $R^{b3}$, $R^{c1}$, and $R^{c2}$ is independently H or optionally substituted alkyl, or $R^{c1}$ and $R^{b3}$ together with the atoms to which they are attached may form an optionally substituted heterocycloalkyl; and each $R^1$ is independently H, halo, or optionally substituted alkyl.

Another embodiment provides for a compound selected from the group consisting of N-Benzyl-2-((2-chloro-6-fluorobenzyl)thio)-1-(4-fluorophenyl)-N-methyl-1H-imidazole-5-carboxamide;

1-(1,3-Dimethyl-1H-pyrazol-4-yl)-N-((1-(4-fluorophenyl)-2-((2,3,6-trifluorobenzyl)sulfinyl)-1H-imidazol-5-yl)methyl)-N-methylmethanamine;

1-(4-Fluorophenyl)-N-methyl-N-((3-methylpyridin-4-yl)methyl)-2-((2,3,6-trifluorobenzyl)thio)-1H-imidazole-5-carboxamide;

4-((1-(4-Fluorophenyl)-N-methyl-2-((2,3,6-trifluorobenzyl)sulfonyl)-1H-imidazole-5-carboxamido)methyl)-3-methylpyridine 1-oxide;

Ethyl 1-(4-fluorophenyl)-2-((2,3,6-trifluorobenzyl)thio)-1H-imidazole-5-carboxylate;

N-((1,3-Dimethyl-1H-pyrazol-4-yl)methyl)-1-(4-fluorophenyl)-N-methyl-2-((2,3,6-trifluorobenzyl)thio)-1H-imidazole-5-carboxamide;

1-(1,3-Dimethyl-1H-pyrazol-4-yl)-N-((1-(4-fluorophenyl)-2-((2,3,6-trifluorobenzyl)thio)-1H-imidazol-5-yl)methyl)-N-methylmethanamine;

N-(3,4-Dimethoxybenzyl)-1-(4-fluorophenyl)-N-methyl-2-((2,3,6-trifluorobenzyl)thio)-1H-imidazole-5-carboxamide;

N-((1,3-Dimethyl-1H-pyrazol-4-yl)methyl)-1-(4-fluorophenyl)-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-1H-imidazole-5-carboxamide;

(E)-N-((1,3-Dimethyl-1H-pyrazol-4-yl)methyl)-1-(4-fluorophenyl)-N-methyl-2-((2,3,6-trifluorostyryl)-1H-imidazole-5-carboxamide;

N-((1,3-Dimethyl-1H-pyrazol-4-yl)methyl)-1-(4-fluorophenyl)-N-methyl-2-((2,3,6-trifluorobenzyl)sulfinyl)-1H-imidazole-5-carboxamide;

N-((1,3-Dimethyl-1H-pyrazol-4-yl)methyl)-1-(4-fluorophenyl)-N-methyl-2-((2,3,6-trifluorobenzyl)sulfonyl)-1H-imidazole-5-carboxamide;

N-((1,3-Dimethyl-1H-pyrazol-4-yl)methyl)-1-(4-fluorophenyl)-N-methyl-2-(((2,3,6-trifluorophenyl)amino)methyl)-1H-imidazole-5-carboxamide;

N-((1,3-Dimethyl-1H-pyrazol-4-yl)methyl)-1-(4-fluorophenyl)-N-methyl-2-(2,3,6-trifluorophenyl)-1H-imidazole-5-carboxamide;

N-((1-Ethyl-3-methyl-1H-pyrazol-4-yl)methyl)-1-(4-fluorophenyl)-N-methyl-2-((2,3,6-trifluorobenzyl)thio)-1H-imidazole-5-carboxamide;

1-(4-Fluorophenyl)-N-methyl-2-((2,3,6-trifluorobenzyl)thio)-N-((1,3,5-trimethyl-1H-pyrazol-4-yl)methyl)-1H-imidazole-5-carboxamide;

1-(4-Fluorophenyl)-N-methyl-N-((1-methylpiperidin-4-yl)methyl)-2-((2,3,6-trifluorobenzyl)thio)-1H-imidazole-5-carboxamide;

1-(4-Fluorophenyl)-N-methyl-N-(pyridin-4-ylmethyl)-2-((2,3,6-trifluorobenzyl)thio)-1H-imidazole-5-carboxamide;

N-((1,3-Dimethyl-1H-pyrazol-4-yl)methyl)-N-ethyl-1-(4-fluorophenyl)-2-((2,3,6-trifluorobenzyl)thio)-1H-imidazole-5-carboxamide;

1-(4-Fluorophenyl)-N-methyl-N-((1-methyl-1H-pyrazol-4-yl)methyl)-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-2-((methyl(2,3,6-trifluorophenyl)amino)methyl)-1H-imidazole-5-carboxamide;

N-((2,4-Dimethylthiazol-5-yl)methyl)-1-(4-fluorophenyl)-N-methyl-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-2-(2,3,6-trifluorophenethyl)-1H-imidazole-5-carboxamide;

1-(4-Fluorophenyl)-N-methyl-N-((1-methylpyrrolidin-3-yl)methyl)-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-2-((2-oxo-2-phenylethyl)thio)-1H-imidazole-5-carboxamide;

N-(1-(1,3-Dimethyl-1H-pyrazol-4-yl)ethyl)-1-(4-fluorophenyl)-N-methyl-2-((2,3,6-trifluorobenzyl)thio)-1H-imidazole-5-carboxamide;

N-((1-(4-Fluorophenyl)-2-((2,3,6-trifluorobenzyl)thio)-1H-imidazol-5-yl)methyl)-N-1,3-trimethyl-1H-pyrazole-4-carboxamide;

1-(4-Fluorophenyl)-N-methyl-N-(pyridin-4-ylmethyl)-2-(2,3,6-trifluorophenethyl)-1H-imidazole-5-carboxamide;

N-((1,3-Dimethyl-1H-pyrazol-4-yl)methyl)-1-(4-fluorophenyl)-N-methyl-2-((2-methyl-1-oxo-1-phenylpropan-2-yl)thio)-1H-imidazole-5-carboxamide;

4-(((1-(4-Fluorophenyl)-2-((2,3,6-trifluorobenzyl)thio)-1H-imidazol-5-yl)methoxy)methyl)pyridine;

1-(1,3-Dimethyl-1H-pyrazol-4-yl)-N-((1-(4-fluorophenyl)-2-((2,3,6-trifluorobenzyl)thio)-1H-imidazol-5-yl)methyl)methanamine;

2-((2-Chloro-6-fluorobenzyl)thio)-N-((1,3-dimethyl-1H-pyrazol-4-yl)methyl)-1-(4-fluorophenyl)-N-methyl-1H-imidazole-5-carboxamide;

2-((2-Chloro-6-fluorobenzyl)thio)-1-(4-fluorophenyl)-N-methyl-N-(pyridin-4-ylmethyl)-1H-imidazole-5-carboxamide;

1-(4-Fluorophenyl)-N-methyl-2-(2-methyl-1-(2,3,6-trifluorophenyl)propan-2-yl)-N-(pyridin-4-ylmethyl)-1H-imidazole-5-carboxamide;

2-((2-Chloro-6-fluorobenzyl)thio)-1-(4-fluorophenyl)-N,N-dimethyl-1H-imidazole-5-carboxamide;

2-((2-Chloro-6-fluorobenzyl)oxy)-1-(4-fluorophenyl)-N-methyl-N-(pyridin-4-ylmethyl)-1H-imidazole-5-carboxamide;

2-((2-Chloro-6-fluorophenyl)ethynyl)-1-(4-fluorophenyl)-N-methyl-N-(pyridin-4-ylmethyl)-1H-imidazole-5-carboxamide;

2-(2-Fluorophenethyl)-1-(4-fluorophenyl)-N-methyl-N-(pyridin-4-ylmethyl)-1H-imidazole-5-carboxamide;

(2-((2-Chloro-6-fluorobenzyl)thio)-1-(4-fluorophenyl)-1H-imidazol-5-yl)(2-(pyridin-4-yl)pyrrolidin-1-yl)methanone;

1-(4-Fluorophenyl)-N-methyl-N-(pyridin-4-ylmethyl)-2-(2-(trifluoromethyl)phenethyl)-1H-imidazole-5-carboxamide;

(2-((2-Chloro-6-fluorobenzyl)thio)-1-(4-fluorophenyl)-1H-imidazol-5-yl)(2-(pyridin-4-yl)piperidin-1-yl)methanone;

tert-butyl 4-(((5-(((1,3-Dimethyl-1H-pyrazol-4-yl)methyl)(methyl)carbamoyl)-1-(4-fluorophenyl)-1H-imidazol-2-yl)thio)methyl)-3,5-difluorobenzoate;

4-(((5-(((1,3-Dimethyl-1H-pyrazol-4-yl)methyl)(methyl)carbamoyl)-1-(4-fluorophenyl)-1H-imidazol-2-yl)thio)methyl)-3,5-difluorobenzoic acid;

N-((1,3-Dimethyl-1H-pyrazol-4-yl)methyl)-1-(4-fluorophenyl)-N-methyl-2-((3,3,3-trifluoro-2-oxopropyl)thio)-1H-imidazole-5-carboxamide;

2-((Cyclopropylmethyl)thio)-N-((1,3-dimethyl-1H-pyrazol-4-yl)methyl)-1-(4-fluorophenyl)-N-methyl-1H-imidazole-5-carboxamide;

N-((1,3-Dimethyl-1H-pyrazol-4-yl)methyl)-1-(4-fluorophenyl)-N-methyl-2-(neopentylthio)-1H-imidazole-5-carboxamide;

N-((1,3-Dimethyl-1H-pyrazol-4-yl)methyl)-1-(4-fluorophenyl)-2-(isobutylthio)-N-methyl-1H-imidazole-5-carboxamide;

N-((1,3-Dimethyl-1H-pyrazol-4-yl)methyl)-2-((3,3-dimethyl-2-oxobutyl)thio)-1-(4-fluorophenyl)-N-methyl-1H-imidazole-5-carboxamide;

2-((2-Chlorobenzyl)thio)-N-((1,3-dimethyl-1H-pyrazol-4-yl)methyl)-1-(4-fluorophenyl)-N-methyl-1H-imidazole-5-carboxamide;

2-((2-Chlorobenzyl)thio)-1-(4-fluorophenyl)-N-methyl-N-((2-methylpyridin-4-yl)methyl)-1H-imidazole-5-carboxamide;

2-((3-Chloropyridin-2-yl)methyl)thio)-N-((1,3-dimethyl-1H-pyrazol-4-yl)methyl)-1-(4-fluorophenyl)-N-methyl-1H-imidazole-5-carboxamide;

N-((1,3-Dimethyl-1H-pyrazol-4-yl)methyl)-1-(4-fluorophenyl)-N-methyl-2-(((5-methyl-1,2,4-oxadiazol-3-yl)methyl)thio)-1H-imidazole-5-carboxamide;

2-((2-Chloro-6-fluorobenzyl)thio)-1-(4-chlorophenyl)-N-((1,3-dimethyl-1H-pyrazol-4-yl)methyl)-N-methyl-1H-imidazole-5-carboxamide;

2-((2-Chloro-6-fluorobenzyl)thio)-N-((1,3-dimethyl-1H-pyrazol-4-yl)methyl)-N-methyl-1-phenyl-1H-imidazole-5-carboxamide;

2-((2-Chloro-6-fluorobenzyl)thio)-N-methyl-1-phenyl-N-(pyridin-4-ylmethyl)-1H-imidazole-5-carboxamide;

2-((2-Chloro-6-fluorobenzyl)thio)-1-(4-chlorophenyl)-N-methyl-N-(pyridin-4-ylmethyl)-1H-imidazole-5-carboxamide;

2-((2-Chloro-6-fluorobenzyl)thio)-N-methyl-N-(pyridin-4-ylmethyl)-1-(4-(trifluoromethyl)phenyl)-1H-imidazole-5-carboxamide;

2-((2-Chloro-6-fluorobenzyl)thio)-1-(4-ethylphenyl)-N-methyl-N-(pyridin-4-ylmethyl)-1H-imidazole-5-carboxamide;

2-((2-Chloro-6-fluorobenzyl)thio)-1-(4-methoxyphenyl)-N-methyl-N-(pyridin-4-ylmethyl)-1H-imidazole-5-carboxamide;

2-((2,6-Dimethylbenzyl)thio)-1-(4-fluorophenyl)-N-methyl-N-(pyridin-4-ylmethyl)-1H-imidazole-5-carboxamide;

2-((2,6-Dichlorobenzyl)thio)-1-(4-fluorophenyl)-N-methyl-N-(pyridin-4-ylmethyl)-1H-imidazole-5-carboxamide;

1-(4-Fluorophenyl)-N-methyl-2-((2-methylbenzyl)thio)-N-(pyridin-4-ylmethyl)-1H-imidazole-5-carboxamide;

2-((2-Chloro-6-fluorobenzyl)thio)-N-methyl-N-(pyridin-4-ylmethyl)-1-(p-tolyl)-1H-imidazole-5-carboxamide;

2-((2-Chloro-6-fluorobenzyl)thio)-1-(3-fluorophenyl)-N-methyl-N-(pyridin-4-ylmethyl)-1H-imidazole-5-carboxamide;

2-((2-Chloro-6-fluorobenzyl)thio)-1-cyclohexyl-N-methyl-N-(pyridin-4-ylmethyl)-1H-imidazole-5-carboxamide;

2-((2-Chloro-6-fluorobenzyl)thio)-N-methyl-1-neopentyl-N-(pyridin-4-ylmethyl)-1H-imidazole-5-carboxamide;
2-(((2,6-Dichlorophenyl)thio)methyl)-N-((1,3-dimethyl-1H-pyrazol-4-yl)methyl)-1-(4-fluorophenyl)-N-methyl-1H-imidazole-5-carboxamide;
N-((1,3-Dimethyl-1H-pyrazol-4-yl)methyl)-1-(4-fluorophenyl)-N-methyl-2-((2,3,6-trifluorophenoxy)methyl)-1H-imidazole-5-carboxamide;
N-((1,3-Dimethyl-1H-pyrazol-4-yl)methyl)-1-(4-fluorophenyl)-N-methyl-2-(((2,3,5,6-tetrafluorophenyl)thio)methyl)-1H-imidazole-5-carboxamide;
N-((1,3-Dimethyl-1H-pyrazol-4-yl)methyl)-1-(4-fluorophenyl)-N-methyl-2-((2-(2,3,6-trifluorophenyl)propan-2-yl)thio)-1H-imidazole-5-carboxamide;
1-(4-Fluorophenyl)-N-methyl-N-(pyridin-4-ylmethyl)-2-((2,3,6-trifluorobenzyl)sulfinyl)-1H-imidazole-5-carboxamide;
N-((1,3-Dimethyl-1H-pyrazol-4-yl)methyl)-1-(4-fluorophenyl)-N-methyl-2-(((2,3,6-trifluorobenzyl)thio)methyl)-1H-imidazole-5-carboxamide;
N-((1,3-Dimethyl-1H-pyrazol-4-yl)methyl)-1-(4-fluorophenyl)-N-methyl-2-(((2,3,6-trifluorobenzyl)sulfonyl)methyl)-1H-imidazole-5-carboxamide;
(E)-3-(1,3-Dimethyl-1H-pyrazol-4-yl)-1-(1-(4-fluorophenyl)-2-((2,3,6-trifluorobenzyl)thio)-1H-imidazol-5-yl)prop-2-en-1-one;
N-((1,3-Dimethyl-1H-pyrazol-4-yl)methyl)-1-(4-fluorophenyl)-N-methyl-2-((2,3,6-trifluorobenzyl)amino)-1H-imidazole-5-carboxamide;
N-((1,3-Dimethyl-1H-pyrazol-4-yl)methyl)-1-(4-fluorophenyl)-N-methyl-2-((2,3,6-trifluorobenzyl)oxy)methyl)-1H-imidazole-5-carboxamide;
1-(4-Fluorophenyl)-N-methyl-N-((2-methylpyridin-4-yl)methyl)-2-((2,3,6-trifluorobenzyl)thio)-1H-imidazole-5-carboxamide;
N-((2-Chloropyridin-4-yl)methyl)-1-(4-fluorophenyl)-N-methyl-2-((2,3,6-trifluorobenzyl)thio)-1H-imidazole-5-carboxamide;
N-((1,3-Dimethyl-1H-pyrazol-4-yl)methyl)-1-(4-fluorophenyl)-N-methyl-2-((pyridine-4-ylmethyl)thio)-1H-imidazole-5-carboxamide;
N-((1,3-Dimethyl-1H-pyrazol-4-yl)methyl)-1-(4-fluorophenyl)-N-methyl-2-(methyl(2,3,6-trifluorobenzyl)amino)-1H-imidazole-5-carboxamide;
N-((4-Ethyl-2-methylthiazol-5-yl)methyl)-1-(4-fluorophenyl)-2-((2,3,6-trifluorobenzyl)sulfinyl)-1H-imidazole-5-carboxamide;
1-(4-Fluorophenyl)-N-methyl-N-((1-methyl-5-phenoxy-3-(trifluoromethyl)-1H-pyrazol-4-yl)methyl)-2-((2,3,6-trifluorobenzyl)sulfinyl)-1H-imidazole-5-carboxamide;
2-((3-Chloro-4-fluorophenethyl)thio)-1-(4-fluorophenyl)-N-((2-methylpyridin-4-yl)methyl)-1H-imidazole-5-carboxamide;
N-(4-(Dimethylamino)benzyl))-1-(4-fluorophenyl)-N-methyl-2-((2,3,6-trifluorobenzyl)thio)-1H-imidazole-5-carboxamide;
1-(4-Fluorophenyl)-N-4-dimethyl-N-((2-methylpyridin-4-yl)methyl)-2-((2,3,6-trifluorobenzyl)thio)-1H-imidazole-5-carboxamide;
2-((3-Chloro-4-fluorophenethyl)sulfonyl)-1-(4-fluorophenyl)-N-methyl-N-((2-methylpyridin-4-yl)methyl)-1H-imidazole-5-carboxamide;
1-(4-Fluorophenyl)-N-methyl-2-((2,3,6-trifluorobenzyl)thio)-N-((2-trifluoromethyl)pyridin-4-yl)methyl)-1H-imidazole-5-carboxamide;
2-((2-Chloro-6-fluorophenethyl)sulfonyl)-1-(4-fluorophenyl)-N-methyl-N-((2-methylpyridin-4-yl)methyl)-1H-imidazole-5-carboxamide;
1-(4-Fluorophenyl)-2-iodo-N-methyl-N-((2-methylpyridin-4-yl)methyl)-1H-imidazole-5-carboxamide;
2-Bromo-N-((1,3-dimethyl-1H-pyrazol-4-yl)methyl)-1-(4-fluorophenyl)-N-methyl-1H-imidazole-5-carboxamine;
(2-((6-Chloro-2-fluoro-3-methoxybenzyl)thio)-1-(4-fluorophenyl)-1H-imidazol-5-yl)(2-(pyridin-4-yl)pyrrolidin-1-yl)methanone;
(2-(2-Fluorophenethyl)-1-(4-fluorophenyl)-1H-imidazol-5-yl)(2-(pyridin-4-yl)pyrrolidin-1-yl)methanone;
2-(Benzylthio)-N-((1,3-dimethyl-1H-pyrazol-4-yl)methyl)-1-(4-fluorophenyl)-N-methyl-1H-imidazole-5-carboxamide;
5-((6-Chloro-2-fluoro-3-methoxybenzyl)thio)-4-(4-fluorophenyl)-N-methyl-N-(pyridin-4-ylmethyl)-4H-1,2,4-triazole-3-carboxamide;
5-((6-Chloro-2-fluoro-3-methylbenzyl)thio)-4-(4-fluorophenyl)-N-methyl-N-(pyridin-4-ylmethyl)-4H-1,2,4-triazole-3-carboxamide;
2-((6-Chloro-2-fluoro-3-methoxybenzyl)thio)-N-((1,3-dimethyl-1H-pyrazol-4-yl)methyl)-1-(4-fluorophenyl)-N-methyl-1H-imidazole-5-carboxamide;
2-((6-Chloro-2-fluoro-3-methylbenzyl)thio)-N-((1,3-dimethyl-1H-pyrazol-4-yl)methyl)-1-(4-fluorophenyl)-N-methyl-1H-imidazole-5-carboxamide;
3-((2-Chloro-6-fluorobenzyl)oxy)-5-((2-chloro-6-fluorobenzyl)thio)-4-(2-(trifluoromethyl)phenyl)-4H-1,2,4-triazole;
4-(3-Chlorophenyl)-3-((2,4-dichlorobenzyl)thio)-5-((2,3-difluorobenzyl)oxy)-4H-1,2,4-triazole;
1-(4-Fluorophenyl)-N-methyl-N-((2-methylthiazol-5-yl)methyl)-2-((2,3,6-trifluorobenzyl)-sulfinyl)-1H-imidazole-5-carboxamide;
1-(4-Fluorophenyl)-N-methyl-N-((4-methylthiophen-2-yl)methyl)-2-((2,3,6-trifluorobenzyl)-sulfinyl)-1H-imidazole-5-carboxamide;
1-(4-Fluorophenyl)-N-methyl-N-((2-methylthiazol-5-yl)methyl)-2-((2,3,6-trifluorobenzyl)thio)-1H-imidazole-5-carboxamide;
1-(4-Fluorophenyl)-N-methyl-N-(pyridin-3-ylmethyl)-2-((2,3,6-trifluorobenzyl)thio)-1H-imidazole-5-carboxamide;
1-(4-Fluorophenyl)-N-methyl-N-(pyrazin-2-ylmethyl)-2-((2,3,6-trifluorobenzyl)thio)-1H-imidazole-5-carboxamide;
1-(4-Fluorophenyl)-N-methyl-N-(pyrazin-2-ylmethyl)-2-((2,3,6-trifluorobenzyl)sulfinyl)-1H-imidazole-5-carboxamide;
4-(((1-(4-Fluorophenyl)-2-((2,3,6-trifluorobenzyl)thio)-1H-imidazol-5-yl)methoxy)methyl)-pyridine;
2-((2-Fluoro-6-(trifluoromethyl)benzyl)thio)-1-(4-fluorophenyl)-N-methyl-N-(pyridin-4-ylmethyl)-1H-imidazole-5-carboxamide;
2-((4-Fluoro-2-(trifluoromethyl)benzyl)thio)-1-(4-fluorophenyl)-N-methyl-N-(pyridin-4-ylmethyl)-1H-imidazole-5-carboxamide;
2-((4-Chloro-2-(trifluoromethyl)benzyl)thio)-1-(4-fluorophenyl)-N-methyl-N-(pyridin-4-ylmethyl)-1H-imidazole-5-carboxamide;
2-((2-Fluoro-3-(trifluoromethyl)benzyl)thio)-1-(4-fluorophenyl)-N-methyl-N-(pyridin-4-ylmethyl)-1H-imidazole-5-carboxamide;
2-((2,5-Difluorobenzyl)thio)-1-(4-fluorophenyl)-N-methyl-N-(pyridin-4-ylmethyl)-1H-imidazole-5-carboxamide;

2-((6-Chloro-2-fluoro-3-methoxybenzyl)thio)-1-(4-fluorophenyl)-N-methyl-N-(pyridin-4-ylmethyl)-1H-imidazole-5-carboxamide;
2-((2-Fluorobenzyl)thio)-1-(4-fluorophenyl)-N-methyl-N-(pyridin-4-ylmethyl)-1H-imidazole-5-carboxamide;
1-(4-Fluorophenyl)-N-methyl-N-(pyridin-4-ylmethyl)-2-((2-(trifluoromethyl)benzyl)thio)-1H-imidazole-5-carboxamide;
2-((2-Chloro-5-fluorobenzyl)thio)-1-(4-fluorophenyl)-N-methyl-N-(pyridin-4-ylmethyl)-1H-imidazole-5-carboxamide;
2-((5-Chloro-2-fluorobenzyl)thio)-1-(4-fluorophenyl)-N-methyl-N-(pyridin-4-ylmethyl)-1H-imidazole-5-carboxamide;
2-((2-Chloro-3,6-difluorobenzyl)thio)-1-(4-fluorophenyl)-N-methyl-N-(pyridin-4-ylmethyl)-1H-imidazole-5-carboxamide;
2-((2-Chloro-4,5-difluorobenzyl)thio)-1-(4-fluorophenyl)-N-methyl-N-(pyridin-4-ylmethyl)-1H-imidazole-5-carboxamide;
1-(4-Fluorophenyl)-N-methyl-N-(pyridin-4-ylmethyl)-2-((2,3,5-trifluorobenzyl)thio)-1H-imidazole-5-carboxamide;
2-((2-Chloro-6-fluoro-3-methylbenzyl)thio)-1-(4-fluorophenyl)-N-methyl-N-(pyridin-4-ylmethyl)-1H-imidazole-5-carboxamide;
1-(4-Fluorophenyl)-N-methyl-N-(pyridin-4-ylmethyl)-2-((3-(trifluoromethyl)benzyl)thio)-1H-imidazole-5-carboxamide;
2-((6-Chloro-2-fluoro-3-methylbenzyl)thio)-1-(4-fluorophenyl)-N-methyl-N-(pyridin-4-ylmethyl)-1H-imidazole-5-carboxamide;
2-((5-Chloro-2-(trifluoromethyl)benzyl)thio)-1-(4-fluorophenyl)-N-methyl-N-(pyridin-4-ylmethyl)-1H-imidazole-5-carboxamide;
2-((2-Cyanobenzyl)thio)-1-(4-fluorophenyl)-N-methyl-N-(pyridin-4-ylmethyl)-1H-imidazole-5-carboxamide;
1-(4-Fluorophenyl)-N-methyl-2-((5-methyl-2-(trifluoromethyl)benzyl)thio)-N-(pyridin-4-ylmethyl)-1H-imidazole-5-carboxamide;
2-((6-Chloro-2-fluoro-3-methoxybenzyl)thio)-N-ethyl-1-(4-fluorophenyl)-N-(pyridin-4-ylmethyl)-1H-imidazole-5-carboxamide;
2-((6-Chloro-2-fluoro-3-methylbenzyl)thio)-N-ethyl-1-(4-fluorophenyl)-N-(pyridin-4-ylmethyl)-1H-imidazole-5-carboxamide;
4-((1-(1-(4-Fluorophenyl)-4-methyl-2-((2,3,6-trifluorobenzyl)thio)-1H-imidazol-5-yl)ethoxy)methyl)pyridine;
2-((Benzo[d]oxazol-2-ylmethyl)thio)-N-((1,3-dimethyl-1H-pyrazol-4-yl)methyl)-1-(4-fluorophenyl)-N-methyl-1H-imidazole-5-carboxamide;
N-((1,3-Dimethyl-1H-pyrazol-4-yl)methyl)-2-(((3-ethyl-1,2,4-oxadiazol-5-yl)methyl)thio)-1-(4-fluorophenyl)-N-methyl-1H-imidazole-5-carboxamide;
N-((1,3-Dimethyl-1H-pyrazol-4-yl)methyl)-1-(4-fluorophenyl)-2-(((3-isopropylisoxazol-5-yl)methyl)thio)-N-methyl-1H-imidazole-5-carboxamide;
N-((1,3-Dimethyl-1H-pyrazol-4-yl)methyl)-1-(4-fluorophenyl)-N-methyl-2-((pyrazolo[1,5-a]pyridin-2-ylmethyl)thio)-1H-imidazole-5-carboxamide;
N-((1,3-Dimethyl-1H-pyrazol-4-yl)methyl)-1-(4-fluorophenyl)-N-methyl-2-(((1-methyl-1H-pyrazol-3-yl)methyl)thio)-1H-imidazole-5-carboxamide;
N-((1,3-Dimethyl-1H-pyrazol-4-yl)methyl)-1-(4-fluorophenyl)-N-methyl-2-(((1-methyl-1H-1,2,4-triazol-3-yl)methyl)thio)-1H-imidazole-5-carboxamide;
N-((1,3-Dimethyl-1H-pyrazol-4-yl)methyl)-1-(4-fluorophenyl)-N-methyl-2-((pyrimidin-2-ylmethyl)thio)-1H-imidazole-5-carboxamide;
N-((1,3-Dimethyl-1H-pyrazol-4-yl)methyl)-1-(4-fluorophenyl)-N-methyl-2-(((4-methylthiazol-2-yl)methyl)thio)-1H-imidazole-5-carboxamide; and
Ethyl 2-((5-(((1,3-dimethyl-1H-pyrazol-4-yl)methyl)(methyl)carbamoyl)-1-(4-fluorophenyl)-1H-imidazol-2-yl)thio)acetate.

Another embodiment provides for a pharmaceutical composition comprising a compound as described herein and a pharmaceutically acceptable carrier.

Another embodiment provides for a method of treating a subject suffering from or at risk of a disease or condition for which GPR131 modulation provides a therapeutic benefit, comprising administering to the subject an effective amount of a compound as described herein.

Another embodiment provides for a method of treating a subject suffering from or at risk of a disease or condition for which GPR131 modulation provides a therapeutic benefit, comprising the concomitant administration of a compound as described herein and a DPP IV inhibitor.

DETAILED DESCRIPTION

Figure 1:
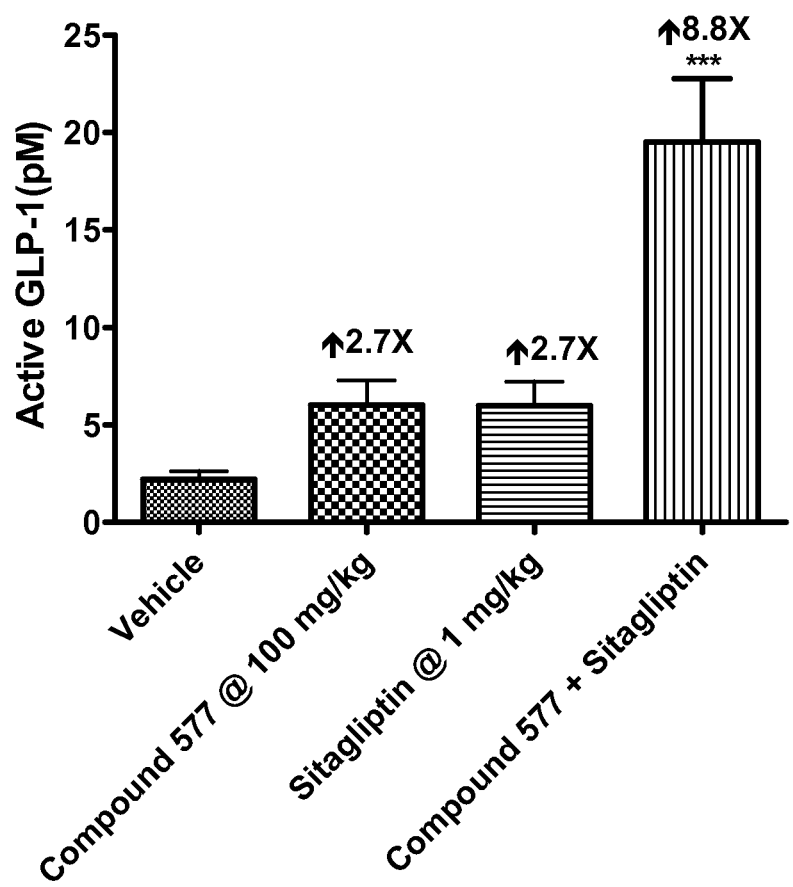
FIG. 1 shows a chart of active GLP-1 assessment of test compound and sitagliptin in normal C57BL/6 mice.

Described herein are compounds of Formula (I), which include compounds of Formulae (II) and (III), and compositions and formulations containing such compounds, and methods of using and making such compounds. These compounds are useful in treating diseases or conditions modulated at least in part by GPR131.

One aspect of the current disclosure relates to compounds of Formula (I)

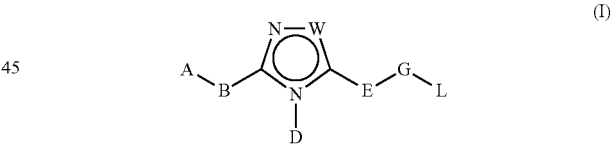

or a derivative thereof, wherein
A is H, —OH, halo, alkyl, alkoxy, aryl, arylalkyl, aryloxy, cycloalkyl, heteroalkyl, heteroaryl, or heterocycloalkyl, each of which may be optionally substituted;
B is alkyl, alkenyl, or alkynyl, each of which may be optionally substituted, or —(CR$^{a1}$R$^{a2}$)$_i$O(CR$^{a3}$R$^{a4}$)$_j$—, —(CR$^{a1}$R$^{a2}$)$_i$C(O)(CR$^{a3}$R$^{a4}$)$_j$—, —(CR$^{a1}$R$^{a2}$)$_i$S(CR$^{a3}$R$^{a4}$)$_j$—, —(CR$^{a1}$R$^{a2}$)$_i$S(O)(CR$^{a3}$R$^{a4}$)$_j$—, —(CR$^{a1}$R$^{a2}$)$_i$S(O)$_2$(CR$^{a3}$R$^{a4}$)$_j$—, —(CR$^{a1}$R$^{a2}$)$_i$N(R$^{a5}$)(CR$^{a3}$R$^{a4}$)$_j$—, C(O)C(R$^{a1}$R$^{a2}$)$_i$S—, or absent;
D is H, alkyl, aryl, arylalkyl, cycloalkyl, heteroalkyl, heteroaryl, or heterocycloalkyl, each of which may be optionally substituted;
E is —(CR$^{b1}$R$^{b2}$)$_k$O—, —(CR$^{b1}$R$^{b2}$)$_k$C(O)—, —(CR$^{b1}$R$^{b2}$)$_k$OC(O)—, —(CR$^{b1}$R$^{b2}$)$_k$S—, —(CR$^{b1}$R$^{b2}$)$_k$S(O)—, —(CR$^{b1}$R$^{b2}$)$_k$S(O)$_2$—, —(CR$^{b1}$R$^{b2}$)$_k$N(R$^{b3}$)—, —(CR$^{b1}$R$^{b2}$)$_k$C(O)N(R$^{b3}$)—, —(CR$^{b1}$R$^{b2}$)$_k$S(O)$_2$N(R$^{b3}$)—, or absent;

G is —(CR$^{c1}$R$^{c2}$)$_m$—, —C(O)—, or optionally substituted alkenyl;

L is H, —OH, halo, alkyl, aryl, arylalkyl, cycloalkyl, heteroalkyl, heteroaryl, or heterocycloalkyl, each of which may be optionally substituted;

W is CR$^1$ or N;

each i, j, and k is independently 0, 1, or 2;

m is 1, 2, or 3;

each R$^{a1}$, R$^{a2}$, R$^{a3}$, R$^{a4}$, R$^{a5}$, R$^{b1}$, R$^{b2}$, R$^{b3}$, R$^{c1}$, and R$^{c2}$ is independently H or optionally substituted alkyl, or R$^{c1}$ and R$^{b3}$ together with the atoms to which they are attached may form an optionally substituted heterocycloalkyl; and each R$^1$ is independently H, halo, cyano, amino, or optionally substituted alkyl;

with the proviso that if G is —(CR$^{c1}$R$^{c2}$) wherein R$^{c1}$ and R$^{c2}$ are both —CH$_3$ and m is 1, then E is not absent.

In some compounds of Formula (I), A is an optionally substituted aryl or heteroaryl. In other compounds of Formula (I), A is an optionally substituted alkyl. For example, and without limitation, in certain compounds of Formula (I), A can be phenyl; a haloaryl such as a chlorophenyl (e.g. 2-chlorophenyl, 3-chlorophenyl, or 4-chlorophenyl), a fluorophenyl (e.g. 2-fluorophenyl, 3-fluorophenyl, or 4-fluorophenyl), a trifluorophenyl (e.g. 2,3,6-trifluorophenyl), and a fluorochlorophenyl (e.g. 2-chloro-6-fluorophenyl); 6-chloro-2-fluoro-3-methyoxyphenyl; 2-trifluoromethylphenyl; or 2-methylphenyl. In some compounds of Formula (I), A is a pyridyl, pyrazinyl, pirimidinyl, pyrrolyl, imidazolyl, pyrazolyl, thiazolyl, or isothiazolyl, each of which may be optionally substituted.

In some compounds of Formula (I), B is alkyl. In some compounds of Formula (I), B is —(CR$^{a1}$R$^{a2}$)$_i$O(CR$^{a3}$R$^{a4}$)$_j$—, —(CR$^{a1}$R$^{a2}$)$_i$C(O)(CR$^{a3}$R$^{a4}$)$_j$—, —(CR$^{a1}$R$^{a2}$)$_i$S(CR$^{a3}$R$^{a4}$)$_j$—, —(CR$^{a1}$R$^{a2}$)$_i$S(O)(CR$^{a3}$R$^{a4}$)$_j$—, —(CR$^{a1}$R$^{a2}$)$_i$S(O)$_2$(CR$^{a3}$R$^{a4}$)$_j$—, —(CR$^{a1}$R$^{a2}$)$_i$N(R$^{a5}$)(CR$^{a3}$R$^{a4}$)$_j$—, or —C(O)C(R$^{a1}$R$^{a2}$)$_i$S—, wherein each R$^{a1}$, R$^{a2}$, R$^{a3}$, R$^{a4}$ and R$^{a5}$ are independently H or alkyl and i and j are 0, 1, or 2. In some compounds of Formula (I), B is —CH$_2$CH$_2$—, —CH$_2$O—, —CH$_2$S—, —CH$_2$S(O)—, or —CH$_2$S(O)$_2$.

In some compounds of Formula (I), D is aryl or alkyl, each of which may be optionally substituted. In some compounds of Formula (I), D is an optionally substituted phenyl. In some compounds of Formula (I), D is a haloaryl. In some compounds of Formula (I), D is 4-fluorophenyl. In some compounds of Formula (I), D is 4-chlorophenyl.

In some compounds of Formula (I), E is —(CR$^{b1}$R$^{b2}$)$_k$C(O)N(R$^{b3}$)— wherein R$^{b3}$ is H or —CH$_3$, and k is 0. In some compounds of Formula (I), E is —(CR$^{b1}$R$^{b2}$)$_k$O—, —(CR$^{b1}$R$^{b2}$)$_k$C(O)—, —(CR$^{b1}$R$^{b2}$)$_k$S—; —(CR$^{b1}$R$^{b2}$)$_k$S(O)—; —(CR$^{b1}$R$^{b2}$)$_k$S(O)$_2$—, or —(CR$^{b1}$R$^{b2}$)$_k$N(R$^{b3}$)—, wherein each R$^{b1}$ and R$^{b2}$ is independently H, R$^{b3}$ is H or C$_{1-3}$alkyl, and k is 1.

In some compounds of Formula (I), G is —CH$_2$—.

In some compounds of Formula (I), L is aryl or heteroaryl, each of which may be optionally substituted. In some compounds of Formula (I), L is optionally substituted pyridinyl, 1,3-dimethyl-1H-pyrazol-4-yl, 2,4-dimethylthiazol-5-yl, or 3,4-dimethoxyphenyl.

In some compounds of Formula (I), W is N. In some compounds of Formula (I), W is CR$^1$ wherein R$^1$ is H or C$_{1-3}$alkyl.

In some compounds of Formula (I), i is 1 and j is 0.

In some compounds of Formula (I), k is 0 or 1.

In some compounds of Formula (I), m is 1.

Another aspect of the current disclosure relates to compounds of Formula (II)

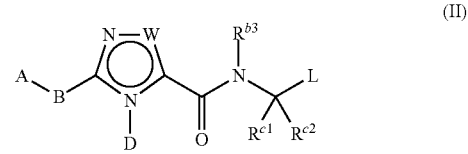

(II)

or a derivate thereof, wherein

A is H, —OH, halo, alkyl, alkoxy, aryl, arylalkyl, aryloxy, cycloalkyl, heteroalkyl, heteroaryl, or heterocycloalkyl, each of which may be optionally substituted;

B is alkyl, alkenyl, or alkynyl, each of which may be optionally substituted, or —(CR$^{a1}$R$^{a2}$)$_i$O(CR$^{a3}$R$^{a4}$)$_j$—, —(CR$^{a1}$R$^{a2}$)$_i$C(O)(CR$^{a3}$R$^{a4}$)$_j$—, —(CR$^{a1}$R$^{a2}$)$_i$S(CR$^{a3}$R$^{a4}$)$_j$—, —(CR$^{a1}$R$^{a2}$)$_i$S(O)(CR$^{a3}$R$^{a4}$)$_j$—, —(CR$^{a1}$R$^{a2}$)$_i$S(O)$_2$(CR$^{a3}$R$^{a4}$)$_j$—, —(CR$^{a1}$R$^{a2}$)$_i$N(R$^{a5}$)(CR$^{a3}$R$^{a4}$)$_j$—, —C(O)C(R$^{a1}$R$^{a2}$)$_i$S—, or absent;

D is H, alkyl, aryl, arylalkyl, cycloalkyl, heteroalkyl, heteroaryl, or heterocycloalkyl, each of which may be optionally substituted;

L is H, halo, alkyl, aryl, arylalkyl, cycloalkyl, heteroalkyl, heteroaryl, or heterocycloalkyl, each of which may be optionally substituted;

W is CR$^1$ or N;

each i and j is independently 0, 1, or 2;

each R$^{a1}$, R$^{a2}$, R$^{a3}$, R$^{a4}$, R$^{a5}$, R$^{b1}$, R$^{b2}$, R$^{c1}$, and R$^{c2}$ is independently H, F, or optionally substituted alkyl;

R$^{b3}$ is H or optionally substituted alkyl;

or R$^{c1}$ and R$^{b3}$ together with the atoms to which they are attached may form an optionally substituted heterocycloalkyl; and each R$^1$ is independently H, halo, cyano, amino, or optionally substituted alkyl.

In some compounds of Formula (II), A is an optionally substituted aryl or heteroaryl. In other compounds of Formula (II), A is an optionally substituted alkyl. For example, and without limitation, in certain compounds of Formula (II), A can be phenyl; a haloaryl such as a chlorophenyl (e.g. 2-chlorophenyl, 3-chlorophenyl, or 4-chlorophenyl), a fluorophenyl (e.g. 2-fluorophenyl, 3-fluorophenyl, or 4-fluorophenyl), a trifluorophenyl (e.g. 2,3,6-trifluorophenyl), a fluorochlorophenyl (e.g. 2-chloro-6-fluorophenyl); 6-chloro-2-fluoro-3-methyoxyphenyl, 2-trifluoromethylphenyl, or 2-methylphenyl. In some compounds of Formula (II), A is a pyridyl, pyrazinyl, pirimidinyl, pyrrolyl, imidazolyl, pyrazolyl, thiazolyl, or isothiazolyl, each of which may be optionally substituted.

In some compounds of Formula (II), B is alkyl. In some compounds of Formula (II), B is —(CR$^{a1}$R$^{a2}$)$_i$O(CR$^{a3}$R$^{a4}$)$_j$—, —(CR$^{a1}$R$^{a2}$)$_i$C(O)(CR$^{a3}$R$^{a4}$)$_j$—, —(CR$^{a1}$R$^{a2}$)$_i$S(CR$^{a3}$R$^{a4}$)$_j$—, —(CR$^{a1}$R$^{a2}$)$_i$S(O)(CR$^{a3}$R$^{a4}$)$_j$—, —(CR$^{a1}$R$^{a2}$)$_i$S(O)$_2$(CR$^{a3}$R$^{a4}$)$_j$—, —(CR$^{a1}$R$^{a2}$)$_i$N(R$^{a5}$)(CR$^{a3}$R$^{a4}$)$_j$—, or —C(O)C(R$^{a1}$R$^{a2}$)$_i$S—, wherein each R$^{a1}$, R$^{a2}$, R$^{a3}$, R$^{a4}$ and R$^{a5}$ are independently H or alkyl and and j are 0, 1, or 2. In some compounds of Formula (II), B is —CH$_2$CH$_2$—, —CH$_2$O—, —CH$_2$S—, —CH$_2$S(O)—, or —CH$_2$S(O)$_2$.

In some compounds of Formula (II), D is aryl or alkyl, each of which may be optionally substituted. In some compounds of Formula (I), D is an optionally substituted phenyl. In some compounds of Formula (I), D is a haloaryl. In some compounds of Formula (II), D is 4-fluorophenyl. In some compounds of Formula (II), D is 4-chlorophenyl.

In some compounds of Formula (II), L is aryl or heteroaryl, each of which may be optionally substituted. In some compounds of Formula (II), L is optionally substituted pyridinyl, 1,3-dimethyl-1H-pyrazol-4-yl, 2,4-dimethylthiazol-5-yl, or 3,4-dimethoxyphenyl.

In some compounds of Formula (II), W is N. In some compounds of Formula (I), W is $CR^1$ wherein $R^1$ is H or alkyl, e.g. —$CH_3$.

In some compounds of Formula (II), i is 1 and j is 0.

In some compounds of Formula (II), $R^{b3}$ is H or alkyl.

In some compounds of Formula (II), $R^{c1}$ and $R^{c2}$ are both H.

Another aspect of the current disclosure relates to compounds of Formula (III)

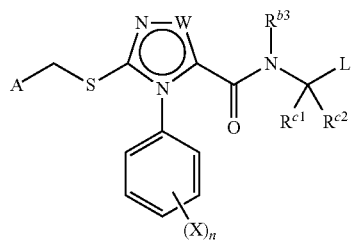

or a derivate thereof, wherein

A is H, halo, alkyl, alkoxy, aryl, arylalkyl, aryloxy, cycloalkyl, heteroalkyl, heteroaryl, or heterocycloalkyl, each of which may be optionally substituted;

L is H, halo, alkyl, aryl, arylalkyl, cycloalkyl, heteroalkyl, heteroaryl, or heterocycloalkyl, each of which may be optionally substituted;

W is $CR^1$ or N;

each X is independently halo, cyano, sulfonamide, optionally substituted alkyl, or —$OR^a$, —$NR^aR^b$, —$C(O)R^a$, —$C(O)OR^a$, —$C(O)NR^aR^b$, —$NR^aC(O)R^b$, —$SR^a$, —$S(O)R^a$, —$S(O)_2R^a$, and —$NR^aS(O)_2R^b$, wherein $R^a$ and $R^b$ are independently H or optionally substituted alkyl;

n is 0 to 5;

each $R^{a1}$, $R^{a2}$, $R^{a3}$, $R^{a4}$, $R^{a5}$, $R^{b3}$, $R^{c1}$, and $R^{c2}$ is independently H or optionally substituted alkyl, or $R^{c1}$ and $R^{b3}$ together with the atoms to which they are attached may form an optionally substituted heterocycloalkyl; and each $R^1$ is independently H, halo, cyano, amino, or optionally substituted alkyl.

In some compounds of Formula (III), A is an optionally substituted aryl or heteroaryl. In other compounds of Formula (III), A is an optionally substituted alkyl. For example, and without limitation, in certain compounds of Formula (III), A can be phenyl; a haloaryl such as a chlorophenyl (e.g. 2-chlorophenyl, 3-chlorophenyl, or 4-chlorophenyl), a fluorophenyl (e.g. 2-fluorophenyl, 3-fluorophenyl, or 4-fluorophenyl), a trifluorophenyl (e.g. 2,3,6-trifluorophenyl), and a fluorochlorophenyl (e.g. 2-chloro-6-fluorophenyl); 6-chloro-2-fluoro-3-methyoxyphenyl; 2-trifluoromethylphenyl; or 2-methylphenyl. In some compounds of Formula (III), A is a pyridyl, pyrazinyl, pirimidinyl, pyrrolyl, imidazolyl, pyrazolyl, thiazolyl, or isothiazolyl, each of which may be optionally substituted.

In some compounds of Formula (II), L is aryl or heteroaryl, each of which may be optionally substituted. In some compounds of Formula (II), L is optionally substituted pyridinyl, 1,3-dimethyl-1H-pyrazol-4-yl, 2,4-dimethylthiazol-5-yl, or 3,4-dimethoxyphenyl.

In some compounds of Formula (III), W is N. In some compounds of Formula (I), W is $CR^1$ wherein $R^1$ is H or alkyl, e.g. —$CH_3$.

In some compounds of Formula (III), X is halo. In some compounds of Formula (III), X is optionally substituted alkyl. In some compounds of Formula (III), X is —$OR^a$ where $R^a$ is H or alkyl.

In some compounds of Formula (III), n is 1.

In some compounds of Formula (III), $R^{b3}$ is H or alkyl.

In some compounds of Formula (III), $R^{c1}$ and $R^{c2}$ are both H.

Other aspects of the current disclosure are described below.

ABBREVIATIONS AND DEFINITIONS

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structural formula indicates a point of attachment of a group. Unless chemically or structurally required, no directionality is indicated or implied by the order in which a chemical group is written. For instance, the group "—$SO_2CH_2$—" is equivalent to "—$CH_2SO_2$—" and both may be connected in either direction. The prefix "$C_{u-v}$" indicates that the following group has from u to v carbon atom. For example, "$C_{1-6}$alkyl" indicates that the alkyl group has from 1 to 6 carbon atoms.

Also, certain commonly used alternative chemical names may or may not be used. For example, a divalent group such as a divalent "alkyl" group, or a divalent "aryl" group, etc., may also be referred to as an "alkylene" group or an "alkylenyl" group, or an "arylene" group, respectively.

"Alkyl" refers to any aliphatic hydrocarbon group, i.e. any linear, branched or cyclic nonaromatic hydrocarbon group or an isomer or combination thereof. As used herein, the term "alkyl" includes terms used in the art to describe saturated and unsaturated aliphatic hydrocarbon groups with one or more points of attachment, including alkenyl (an aliphatic group containing at least one carbon-carbon double bond), alkylene (a divalent aliphatic group), alkynyl (an aliphatic group containing at least one carbon-carbon triple bond), cycloalkyl (a cyclic aliphatic group), alkylcycloalkyl (a linear or branched aliphatic group attached to a cyclic aliphatic group), and the like. Alkyl groups include, but are not limited to, methyl; ethyl; propyls such as propan-1-yl, propan-2-yl (iso-propyl), cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; pentyls; hexyls; octyls; dodecyls; octadecyls; cyclopentyl, cyclohexyl, methylcyclohexyl, and the like. An alkyl group comprises from 1 to about 10 carbon atoms, e.g., from 1 to 6 carbon atoms.

"Alkenyl" is a subset of "alkyl" and refers to an aliphatic group containing at least one carbon-carbon double bond and having from 2 to about 10 carbon atoms, e.g., from 2 to 6 carbon atoms or 2 to 4 carbon atoms and having at least one site of vinyl unsaturation (>C═C<). Alkenyl groups include ethenyl, propenyl, 1,3-butadienyl, and the like.

"Alkynyl" is a subset of "alkyl" and refers to an aliphatic group containing at least one carbon-carbon triple bond. The term "alkynyl" is also meant to include those groups having one triple bond and one double bond.

"Alkoxy" refers to the group —O-alkyl, wherein the alkyl group may be optionally substituted. Alkoxy includes, by way of example, methoxy, ethoxy, n-propoxy, isopropoxy, n-butoxy, t-butoxy, sec-butoxy, and n-pentoxy.

"Acyl" refers to a group —C(═O)R, where R is hydrogen, alkyl, cycloalkyl, cycloheteroalkyl, aryl, arylalkyl, heteroalkyl, heteroaryl or heteroarylalkyl as defined herein, each of which may be optionally substituted, as defined herein. Representative examples include, but are not limited to formyl, acetyl, cylcohexylcarbonyl, cyclohexylmethylcarbonyl, benzoyl, benzyloxycarbonyl and the like.

"Amino" refers to the group —NR$^x$R$^y$ wherein R$^x$ and R$^y$ are independently selected from the group consisting of hydrogen, alkyl, aryl, heteroaryl (each of which may be optionally substituted), and where R$^y$ and R$^z$ are optionally joined together with the nitrogen bound thereto to form an optionally substituted heterocycloalkyl.

"Amidino" refers to the group —C(═NR$^x$)NR$^y$R$^z$ where R$^x$, R$^y$, and R$^z$ are independently selected from the group consisting of hydrogen, alkyl, aryl, heteroaryl (each of which may be optionally substituted), and where R$^y$ and R$^z$ are optionally joined together with the nitrogen bound thereto to form an optionally substituted heterocycloalkyl.

"Aryl" refers to a group with one or more aromatic rings. It may be a single aromatic ring or multiple aromatic rings which are fused together, linked covalently, or linked via one or more such as a methylene or ethylene moiety. Aryl groups include, but are not limited to, those groups derived from acenaphthylene, anthracene, azulene, benzene, biphenyl, chrysene, cyclopentadienyl anion, diphenylmethyl, fluoranthene, fluorene, indane, indene, naphthalene, perylene, phenalene, phenanthrene, pyrene, triphenylene, and the like. An aryl group comprises from 5 to about 20 carbon atoms, e.g., from 6 to 20 carbon atoms, e.g. from 6 to 10 carbon atoms.

"Arylalkyl" (also "aralkyl") refers to an aryl group attached to an alkyl group. Arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl may be used. An arylalkyl group comprises from 6 to about 30 carbon atoms, e.g. the alkyl group can comprise from 1 to about 10 carbon atoms and the aryl group can comprise from 5 to about 20 carbon atoms.

"Aryloxy" refers to the group —O-aryl, including by way of example, phenoxy and naphthoxy.

"Azido" refers to the group —N$_3$.

"Carbonyl" refers to the divalent group —C(O)— which is equivalent to —C(═O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" or "carbonitrile" refers to the group —CN.

"Cycloalkyl" is a subset of "alkyl" and refers to a saturated or partially saturated cyclic group of from 3 to about 10 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl.

"Derivative" refers to salts, prodrugs, racemates, and tautomers. Derivatives include pharmaceutically acceptable derivatives, including pharmaceutically acceptable salts and prodrugs.

"Guanidino" refers to the group —NHC(═NH)NH$_2$.

"Halo" or "halogen" refers to fluoro, chloro, bromo and iodo.

"Haloalkyl" refers to substitution of alkyl groups with 1 to 5 or, in some embodiments, 1 to 3 halo groups, e.g., —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Haloaryl" refers to aryl groups with one or more halo or halogen substituents. For example, haloaryl groups include phenyl groups in which from 1 to 5 hydrogens are replaced with a halogen. Haloaryl groups include, for example, fluorophenyl, difluorophenyl, trifluorophenyl, chlorophenyl, clorofluorophenyl, and the like.

"Heteroalkyl" refers to an alkyl group in which one or more of the carbon atoms (and any associated hydrogen atoms) are each independently replaced with the same or different a heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. The term "heteroalkyl" includes heterocycloalkyl (a cyclic heteroalkyl group), alkyl-heterocycloalkyl (a linear or branched aliphatic group attached to a cyclic heteroalkyl group), and the like. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, and the like, where R is defined above. A heteroalkyl group comprises from 1 to about 10 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatomic groups, as defined above. Heteroaryl groups include, but are not limited to, groups derived from acridine, carbazole, carboline, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 atoms, e.g., from 5 to 20 atoms, e.g. from 5 to 10 atoms.

"Heterocycloalkyl" is a subset of "heteroalkyl" and refers to a saturated or unsaturated cycloalkyl group in which one or more carbon atoms (and any associated hydrogen atoms) are independently replaced with the same or different heteroatom. Heteroatoms include, but are not limited to, N, P, O, S, etc. A heterocycloalkyl group may also contain a charged heteroatom or group, e.g., a quaternized ammonium group such as —N$^+$(R)$_2$— wherein R is alkyl, e.g., methyl, ethyl, etc. Heterocycloalkyl groups include, but are not limited to, groups derived from epoxides, imidazolidine, morpholine, piperazine, piperidine, pyrazolidine, piperidine, pyrrolidine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidium, and the like. The heterocycloalkyl group comprises from 3 to about 10 carbon and hetero atoms in the ring.

"Hydrazino" refers to the group —NHNH$_2$.

"Hydroxy" or "hydroxyl" refers to the group —OH.

"Imino" refers to the group —C(=NR)— wherein R can be hydrogen or alkyl, aryl, heteroalkyl, or heteroaryl, each of which may be optionally substituted.

"Nitro" refers to the group —NO$_2$.

The terms "optional" or "optionally" mean that the subsequently described event or circumstance may but need not occur, and that the description includes instances where the event or circumstance occurs and instances in which it does not.

"Oxide" refers to products resulting from the oxidation of one or more heteroatoms. Examples include N-oxides, sulfoxides, and sulfones.

"Oxo" refers to the atom (=O).

"Racemates" refers to a mixture of enantiomers.

"Spirocycloalkyl" refers to a 3- to 10-member cyclic substituent formed by replacement of two hydrogen atoms at a common carbon atom with an alkylene group having 2 to 9 carbon atoms, as exemplified by the following structure wherein the methylene group shown below attached to bonds marked with wavy lines is substituted with a spirocycloalkyl group:

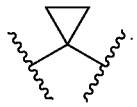

"Stereoisomer" or "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of *Advanced Organic Chemistry*, 4th ed., J. March, John Wiley and Sons, New York, 1992).

"Substituted" (as in, e.g., "substituted alkyl") refers to a group wherein one or more hydrogens have been independently replaced with one or more substituents including, but not limited to, alkyl, alkenyl, alkynyl, alkoxy, acyl, amino, amidino, aryl, azido, carbamoyl, carboxyl, carboxyl ester, cyano, cycloalkyl, guanidino, halo, heteroalkyl, heteroaryl, heterocycloalkyl, hydroxy, hydrazino, hydroxyl, imino, oxo, nitro, sulfonamide, sulfonic acid, thiocyanate, thiol, thione, or a combination thereof. Polymers arrived at by defining substituents with further substituents to themselves ad infinitum (e.g., substituted aryl having a substituted aryl group as a substituent which is itself substituted with a substituted aryl group, which is further substituted by a substituted aryl group, etc.) are not intended for inclusion herein. Unless otherwise noted, the maximum number of such substitutions in compounds described herein is three. For example, serial substitutions of substituted aryl groups with two other substituted aryl groups are limited to -substituted aryl-(substituted aryl)-substituted aryl. Similarly, it is understood that the above definitions are not intended to include impermissible substitution patterns (e.g., methyl substituted with 5 fluoro groups or heteroaryl groups having two adjacent oxygen ring atoms). Such impermissible substitution patterns are well known to the skilled artisan.

"Sulfonamide" refers to the group —S(O)$_2$NR$^x$R$^y$ where R$^x$ and R$^y$ are independently selected from the group consisting of hydrogen, alkyl, aryl, heteroaryl, each of which may be optionally substituted.

"Sulfonyl" refers to the divalent group —S(O)$_2$—.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

"Thiocyanate" refers to the group —SCN.

"Thiol" refers to the group —SH.

"Thione" refers to the atom (=S).

"Pharmaceutically acceptable" refers to that which is useful in preparing a pharmaceutical composition that is generally safe, non-toxic, and neither biologically nor otherwise undesirable, and includes that which is acceptable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napthhalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., *J. Pharma Sci.*, 66(1), 1-19 (1977), and *Remington: The Science and Practice of Pharmacy*, R. Hendrickson, ed., 21st edition, Lippincott, Williams & Wilkins, Philadelphia, Pa., (2005), at p. 732, Table 38-5, both of which are hereby incorporated by reference herein.

"Prodrug" refers to any derivative of a compound of the embodiments that is capable of directly or indirectly providing a compound of the embodiments or an active metabolite or residue thereof when administered to a subject. Prodrugs of a compound are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound is bonded to any group that may be cleaved in vivo to regenerate the free hydroxyl, amino, or sulfhydryl group, respectively. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester, amide, and carbamate (e.g., N,N-dimethylaminocarbonyl) forms of hydroxy functional groups of compounds. Examples of ester prodrugs include formate, acetate, propionate, butyrate, acrylate, and ethylsuccinate derivatives. Further examples of prodrugs can be found in J. Rautio et al. *Prodrugs: design and clinical applications*, Nat. Rev. Drug Discov., 7, 255-270 (2008); Edward B. Roche, ed., *Bioreversible Carriers in Drug Design*, American Pharmaceutical Association and Pergamon Press, (1987); and T. Higuchi and V. Stella, *Pro-drugs as Novel Delivery Systems*, Vol. 14 of the A.C.S. Symposium Series (1975), each of which are hereby incorporated by reference herein.

The following abbreviations may also be used: AcOH: acetic acid; nBuLi: n-butyllithium; $Cs_2CO_3$: cesium carbonate; $CH_2Cl_2$ or DCM: dichloromethane; $CH_3MgI$: methyl magnesium iodide; $CuCl_2$: copper chloride; DAST: (diethylamino)sulfur trifluoride; DEAD: diethyl azodicarboxylate; DIBAL: diisobutylaluminum hydride; DIPEA: diisopropylethylamine; DMF: dimethylformamide; DMSO: dimethyl sulfoxide; $Et_3N$: triethylamine; EtOAc: ethyl acetate; EtOH: ethanol; g: gram(s); h: hour; $H_2$: hydrogen; HBr: hydrogen bromide; HCl: hydrogen chloride; $H_2O$: water; $H_2O_2$: hydrogen peroxide; HPLC: high performance liquid chromatography; KCN: potassium cyanide; LHMDS: lithium hexamethyldisilazide; $LiAlH_4$: lithium aluminum hydride; LiOH: lithium hydroxide; M: molar; MeCN: acetonitrile; MeI: methyl iodide; MeOH: methanol; $MgSO_4$: magnesium sulfate; $MgCO_3$: magnesium carbonate; mg: milligram; MsCl: mesyl chloride; mmol: millimoles mL: milliliter; sodium hydrogen sulfite; mCPBA: meta-chloroperoxybenzoic acid; N: normality; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinimide; $NH_4Cl$: ammonium chloride; $NH_4OAc$: ammonium acetate; NMR: nuclear magnetic resonance; Pd/C: palladium on carbon; $PPh_3$: triphenyl phosphine; iPrOH: isopropyl alcohol; $SOCl_2$: thionyl chloride; THF: tetrahydrofuran; TLC: thin layer chromatography; µL: microliter.

With reference to the various methods described herein, the following terms are also used.

"Activate" and "activation" refer to increasing the cellular function of a receptor, for example GPR131.

"Agonist" refers to a compound or moiety that binds to a receptor and triggers a response in a cell or enhances GTP binding to membranes. An agonist may mimic (wholly or partially) the cell response to an endogenous ligand, e.g. a hormone, and produce a physiological response similar to that produced by the endogenous ligand.

"Antihyperlipidemic" refers to the lowering of excessive lipid concentrations in blood to desired levels.

"Atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

"Beta cell" refers to cells found in the islet of Langerhans that secrete insulin, amylin, and other hormones.

"cAMP," "cyclic AMP" and "cyclic adenosine monophosphate" refer to an intracellular signaling molecule involved in many biological processes, including glucose and lipid metabolism.

"Diabetes" and "diabetes mellitus" refer to a disease or condition that is generally characterized by metabolic defects in production and utilization of glucose that result in the failure to maintain appropriate blood sugar levels in the body. The result of these defects is elevated blood glucose, referred to as "hyperglycemia." Two major forms of diabetes are type 1 diabetes and type 2 diabetes. Type 1 diabetes is generally the result of an absolute deficiency of insulin, the hormone that regulates glucose utilization. Type 2 diabetes often occurs in the face of normal or even elevated levels of insulin and can result from the inability of tissues to respond appropriately to insulin. Most type 2 diabetics are insulin resistant and have a relative deficiency of insulin, in that insulin secretion can not compensate for the resistance of peripheral tissues to respond to insulin. In addition, many type 2 diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in females (e.g. women) with no previous history of type 1 or type 2 diabetes. The guidelines for diagnosis of type 2 diabetes, impaired glucose tolerance, and gestational diabetes have been outlined by the American Diabetes Association (see, e.g., The Expert Committee on the Diagnosis and Classification of Diabetes Mellitus, *Diabetes Care*, (1999) Vol. 2 (Suppl 1):S5-19). As used herein, "diabetes" and "diabetes mellitus" also include "prediabetes," "borderline diabetes," "impaired glucose tolerance," and "impared fasting glucose," which refer to states in which some but not all of the diagnostic criteria for diabetes are met, e.g. where blood glucose levels are higher than normal but not yet high enough to result in a diagnosis of diabetes.

"Dyslipidemia" refers to abnormal levels of lipoproteins in blood plasma including both depressed and/or elevated levels of lipoproteins (e.g., elevated levels of LDL and/or VLDL, and depressed levels of HDL), including hyperlipidemia. Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

"Effective amount" or "therapeutically effective amount" means the amount of a compound described herein that may be effective to elicit the desired biological or medical response. These terms include the amount of a compound that, when administered to a subject for treating a disease, is sufficient to effect such treatment for the disease. The effective amount will vary depending on the compound, the disease and its severity and the age, weight, etc., of the subject to be treated.

"Endocrine cell" refers to cells that secrete hormones into the blood stream. Endocrine cells are found various glands and organ systems of the body including the pancreas, intestines, and other organs.

"GIP" or "gastric inhibitory peptide" or "glucose dependent insulinotropic polypeptide" refers to a peptide hormone produced primarily by K cells. GIP stimulates insulin secretion. GIP also has significant effects on lipid metabolism.

"GLP-1" or "glucagon-like peptide-1" is a peptide hormone primarily produced by L cells. GLP-1 increases insulin secretion, decreases glucagon secretion, increases beta cell mass and insulin gene expression, inhibits acid secretion and gastric emptying in the stomach, and decreases food intake by increasing satiety.

"GLP-2" or "glucagon-like peptide-2" is a peptide hormone primarily produced by L cells. GLP-2 stimulates mucosal growth, increases intestinal nutrient absorption, inhibits gastric emptying, inhibits gastric acid secretion, stimulates intestinal blood flow and relaxes intestinal smooth muscle.

"Hyperlipidemia" includes, but is not limited to (1) Familial Hyperchylomicronemia, a rare genetic disorder that causes a deficiency in an enzyme, LP lipase, that breaks down fat molecules. The LP lipase deficiency can cause the accumulation of large quantities of fat or lipoproteins in the blood; (2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma; (3) Familial Combined Hyperlipidemia, also known as multiple lipoprotein-type hyperlipidemia is an inherited disorder where subjects and their affected first-degree relatives can at various times manifest high cholesterol and high triglycerides. Levels of HDL cholesterol are often moderately decreased; (4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels; (5) Familial Dysbetaliproteinemia, also referred to as type 3 hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated TG levels (and usually not cholesterol levels) and can often be associated with low plasma HDL levels. Risk factors for hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various β-blockers; (3) dietary risk factors include dietary fat intake per total calories greater than 40%; saturated fat intake per total calories greater than 10%; cholesterol intake greater than 300 mg per day; habitual and excessive alcohol use; and obesity.

"Incretin" refers to a group of hormones that increases insulin secretion in response to food intake. Incretins include GLP-1 and GIP.

"Insulin resistance" refers generally to a disorder of glucose metabolism associated with diabetes. More specifically, insulin resistance can be defined as the diminished ability of insulin to exert its biological action across a broad range of concentrations producing less than the expected biologic effect (see, e.g., Reaven G M, *J. Basic & Clin. Phys. & Pharm.* (1998) 9:387-406 and Flie J, *Ann. Rev. Med.* (1983) 34:145-60). Insulin resistant subjects have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant subjects can progress to a point where a diabetic state is reached.

"Insulin" refers to a polypeptide hormone that regulates glucose metabolism. Insulin binds to insulin receptors in insulin sensitive cells and mediates glucose uptake. Insulin is used to treat type 1 diabetes and may be used to treat type 2 diabetes.

"Islet" or "islet of Langerhans" refers to endocrine cells of the pancreas that are grouped together in islets and secrete insulin and other hormones.

"K cell" refers to gut endocrine cells that produce GIP.

"L cell" refers to gut endocrine cells that produce GLP-1.

"Liver disease" refers to various diseases and disorders of the liver including nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, .alpha.1-antitrypsin deficiency, total parenteral nutrition (TPN), cholelithiasis, TPN-associated cholestasis and sepsis.

"Metabolic syndrome" refers to various metabolic abnormalities including obesity, insulin resistance, glucose intolerance, diabetes (both type 1 and type 2), hypertension and dyslipidemia.

"Modulate" and "modulating" refer to the treating, prevention, suppression, activation, enhancement, or induction of a function or condition. For example, compounds can modulate type 2 diabetes by increasing insulin in a human, thereby suppressing hyperglycemia. Compounds can also modulate GPR131 by acting as GPR131 agonists.

"Obese" and "obesity" refer to an excess of body fat. As an exemplary guideline, the World Health Organization describes obesity as a body mass index ("BMI") greater than 27.8 kg/m$^2$ for men and 27.3 kg/m$^2$ for women (BMI is weight (kg)/height (m$^2$)). Obesity is linked to a variety of medical conditions including diabetes and hyperlipidemia. Obesity is also a known risk factor for the development of type 2 diabetes (see, e.g., Barrett-Conner E, *Epidemol. Rev.* (1989) 11:172-181; and Knowler, et al., *Am. J. Clin. Nutr.* (1991) 53:1543-1551).

"Pancreas" refers to a gland organ in the digestive and endocrine system of vertebrates, including mammals. The pancreas secretes both digestive enzymes and hormones such as insulin, GLP-1 and GIP as well as other hormones.

"Partial agonist" refers to a compound or moiety that, when exposed to a receptor, triggers a response in a cell to a lesser degree or extent than does an agonist, or enhances GTP binding to membranes to a lesser degree or extent than does an agonist.

"PYY" or "peptide YY" is a peptide hormone primarily produced by L cells. PYY increases satiety, reduces food intake, inhibits gastric emptying and acid secretion and promotes weight loss.

"Polyuria" refers to the passage of a large volume of urine during a given period.

"Polydipsia" refers to chronic or excessive thirst.

"polyphagia" refers to excessive eating.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

"Symptoms" of diabetes, include, but are not limited to, polyuria, polydipsia, polyphagia, extreme hunger, unusual weight loss, extreme fatigue and irritability, increased susceptibility to certain infections (especially fungal and staphylococcal infections), blurred vision, nausea, cuts or bruises that are slow to heal, tingling or numbness in the hand or feet, recurring skin, gum, or bladder infections, and ketoacidosis (enhanced production of ketone bodies in the blood).

"Treating" and "treatment" of a disease include (1) preventing or reducing the risk of developing the disease, i.e., causing the clinical symptoms of the disease not to develop in a subject that may be exposed to or predisposed to the disease but does not yet experience or display symptoms of the disease; (2) inhibiting the disease, i.e., arresting or reducing the development of the disease or its clinical symptoms; and (3) relieving the disease, i.e., causing regression of the disease or its clinical symptoms.

"Triglyceride(s)" ("TGs"), as used herein, incorporates its common usage. Triglycerides consist of three fatty acid molecules esterified to a glycerol molecule. Triglycerides serve to store fatty acids that are used by muscle cells for energy production or are taken up and stored in adipose tissue.

Methods

Methods of treating a disease or condition selected from the group consisting of diabetes (e.g. type 1 or type 2 diabetes), metabolic syndrome, liver disease, and inflammation are provided. The methods comprise administering to a subject in need of such treatment an effective amount of a compound described herein. In some embodiments, the subject is a human.

As described above, compounds of Formula (I) herein may modulate GPR131. In some embodiments, the compounds described herein may act as agonists or may activate GPR131. Accordingly, also provided herein are methods of treating a subject suffering from or at risk of a disease or condition for which GPR131 modulation can provide a therapeutic benefit, such methods comprising administering to the subject an effective amount of a compound described herein. In some embodiments, the disease or condition is modulated by GPR131. In some embodiments, the subject is a human.

Diseases and conditions which are modulated by GPR131 include diabetes (type 1 or type 2 diabetes), metabolic syndrome, liver disease, and inflammation. Other diseases and conditions modulated by GPR131 include autoimmune diseases such as rheumatoid arthritis and multiple sclerosis; inflammatory diseases such as allergy, osteoarthritis, chronic obstructive pulmonary disease, appendicitis, bronchial asthma, pancreatitis, allergic rash, and psoriasis; gastrointestinal disease such as inflammatory bowel disease, Crohn's disease, ulcerative colitis, short bowel syndrome (e.g. post-radiation colitis), microscopic colitis, irritable bowel syndrome and short bowel syndrome (e.g. malabsorption or to improve nutrient absorption in patients who have had intestinal segments surgically removed), and bacterial overgrowth; kidney diseases such as diabetic nephropathy, chronic renal failure, glomerular nephritis, hypertensive nephrosclerosis, chronic glomerulonephritis, chronic transplant glomerulopathy, chronic interstitial nephritis, and polysystic kidney disease; certain cancers such as colorectal cancer, liver cancer, heptacellular carcinoma, cholangio carcinoma, renal cancer, gastric cancer, pancreatic cancer, prostate cancer, and insulanoma; cardiac diseases such as congestive heart failure, myocardial infarction, atherosclerosis, angina pectoris, arteriosclerosis and cerebrovascular disease (hemorrhage, stroke, cerebrovascular infarction); and osteoporosis and other conditions characterized by low bone mass.

Still another aspect provides methods for decreasing inflammation by decreasing the pro-inflammatory activity of immune cells of the myeloid lineage in tissue in a subject, e.g. a human. The methods comprise administering an effective amount of a compound described herein to the subject. In response to administration of compound to subject, inflammatory markers and biological consequences of inflammation are reduced. In subcutaneous adipose tissue, a reduction in pro-inflammatory activity of immune cells can lead to decreased insulin resistance.

Another aspect provides for methods of treating liver disease in a subject, e.g. a human. In certain embodiments, the liver disease is nonalcoholic steatohepatitis. The methods comprise administering an effective amount of a compound described herein to the subject. In response to administration of compound to subject, inflammatory mediators, liver fats and liver fibrosis are reduced.

Other aspects of the present disclosure relate to methods of increasing insulin secretion, decreasing glucagon secretion, increasing beta cell mass, increasing insulin gene expression, inhibiting acid secretion, inhibiting, slowing or delaying gastric emptying, increasing satiety, stimulating mucosal growth, increasing intestinal nutrient absorption, inhibiting or lowering gastric acid secretion, stimulating intestinal blood flow, relaxing intestinal smooth muscle, and promoting weight loss. Such methods comprise administering to a subject an effective amount of a compound described herein.

Also provided herein are methods of improving glucose tolerance in a subject, e.g. a human. The methods comprise administering an effective amount of a compound described herein to the subject.

Another aspect provides methods of lowering blood glucose in a subject, e.g. a human. The methods comprise administering an effective amount of a compound described herein to the subject. In response to administration of a compound to the subject, blood glucose levels are lowered. The methods further comprise steps to measure blood glucose levels before and after administration of a compound described herein.

Blood glucose levels are easily measured by numerous commercially available glucose monitoring devices that measure blood glucose from samples of blood or urine. Blood glucose can also be measured by commercially available glucometers that do not require blood or urine samples.

Yet another aspect provides methods for increasing energy expenditure in peripheral tissues such as adipose and skeletal muscle in a subject, e.g. a human. The methods comprise administering an effective amount of a compound described herein to the subject. In response to administration of compound to subject, net energy expenditure by the subject is elevated.

Other aspects of the current disclosure provide for methods of decreasing glucagon secretion in a subject, e.g. a human. The methods comprise administering and effect amount of a compound described herein to the subject. For example, in certain methods, after administration to the subject, glucagon secretion from the pancreatic alpha cell is reduced.

Other aspects of the present disclosure provide for methods of stimulating incretin production in a subject, e.g. a human. The methods comprise administering an effective amount of a compound described herein to the subject.

Methods of raising intracellular levels of cAMP in a cell expressing GPR131 are also provided. The methods comprise exposing a cell that expresses GPR131 to a compound described herein. In certain embodiments, the cell that expresses GPR131 is a gastro-intestinal endocrine cell (e.g. a GLP-1 secreting L-cell), a gastro-intestinal chemosensory cell, an adipose tissue cell, a skeletal muscle cell, or an immune system cell of the myeloid lineage including a circulating CD 14+ monocyte, macrophage and Kupffer cell.

Other aspects of the present disclosure provide for methods of stimulating or increasing glucagon-like peptide-1 secretion from cells, e.g. human cells, or in a subject, e.g. a human. The methods comprise exposing an effective amount of a compound described herein to the cell or subject.

Other aspects of the present disclosure provide for methods of stimulating or increasing glucagon-like peptide-2 secretion from cells, e.g. human cells, or in a subject, e.g. a human. The methods comprise exposing an effective amount of a compound described herein to the cell or subject.

Other aspects of the present disclosure provide for methods of stimulating or increasing protein YY secretion from cells, e.g. human cells, or in a subject, e.g. a human. The methods comprise exposing an effective amount of a compound described herein to the cell or subject.

The present disclosure further contemplates combination therapy and methods of concomitant administration of a first agent and a second agent wherein the first agent is a compound of Formula (I) and the second agent is selected from the group consisting of biguanides (such as metformin); thiazolidinediones (such as ciglitazone, pioglitazone, troglitazone, and rosiglitazone); dipeptidyl-peptidase-4 ("DPP IV") inhibitors (such as vildagliptin and sitagliptin); glucagon-like peptide-1 ("GLP-1") receptor agonists (such as exanatide and liraglutide) (or GLP-1 mimetics); PPAR gamma agonists or partial agonists; dual PPAR alpha, PPAR gamma agonists or partial agonists; dual PPAR delta, PPAR gamma agonists or partial agonists; pan PPAR agonists or partial agonists; dehydroepiandrosterone (also referred to as DHEA or its conjugated sulphate ester, DHEA-SO$_4$); antiglucocorticoids; TNFα inhibitors; α-glucosidase inhibitors (such as acarbose, miglitol, and voglibose); sulfonylureas (such as chlorpropamide, tolbutamide, acetohexamide, tolazamide, glyburide, gliclazide, glynase, glimepiride, and glipizide); pramlintide (a synthetic analog of the human hormone amylin); other insulin secretogogues (such as repaglinide, gliquidone, and nateglinide); insulin; insulin mimetics; insulin sensitizers; glucagon receptor antagonists; gastric inhibitory peptide ("GIP"); and GIP mimetics.

Combination therapy and concomitant administration refer to the administration of the two agents (i.e., a first agent and a second agent, as described above) in any manner in which the pharmacological effects of both are manifested in the patient at the same time. Thus, such administration does not require that a single pharmaceutical composition, the same type of formulation, the same dosage form, or even the same route of administration be used for administration of both the first and second agents, or that the two agents be administered at the same time. However, such administration will be accomplished most conveniently by the same dosage form and the same route of administration, at substantially the same time. Such administration most advantageously proceeds by delivering both active ingredients simultaneously in a novel pharmaceutical composition in accordance with the present disclosure.

In certain embodiments, the second agent is a DPP IV inhibitor listed as one of compound A-F as follows: A. Sitagliptin; B. Vildagliptin; C. Saxagliptin; D. Denagliptin; E. Alogliptin; F. Linagliptin.

In further embodiments, it is contemplated that one or more compounds of Formula (I) when administered with one or more DPP IV inhibitors identified above as A-F, act synergistically in treating diabetes. Compounds of Formula (I) include compounds identified as compounds 500-637 in Examples 1-138. Specific combinations include a synergistically effective amount of each compound in the following combinations: 500A, 500B, 500C, 500D, 500E, 500F, 501A, 501B, 501C, 501D, 501E, 501F, 502A, 502B, 502C, 502D, 502E, 502F, 503A, 503B, 503C, 503D, 503E, 503F, 504A, 504B, 504C, 504D, 504E, 504F, 505A, 505B, 505C, 505D, 505E, 505F, 506A, 506B, 506C, 506D, 506E, 506F, 507A, 507B, 507C, 507D, 507E, 507F, 508A, 508B, 508C, 508D, 508E, 508F, 509A, 509B, 509C, 509D, 509E, 509F, 510A, 510B, 510C, 510D, 510E, 510F, 511A, 511B, 511C, 511D, 511E, 511F, 512A, 512B, 512C, 512D, 512E, 512F, 513A, 513B, 513C, 513D, 513E, 513F, 514A, 514B, 514C, 514D, 514E, 514F, 515A, 515B, 515C, 515D, 515E, 515F, 516A, 516B, 516C, 516D, 516E, 516F, 517A, 517B, 517C, 517D, 517E, 517F, 518A, 518B, 518C, 518D, 518E, 518F, 519A, 519B, 519C, 519D, 519E, 519F, 520A, 520B, 520C, 520D, 520E, 520F, 521A, 521B, 521C, 521D, 521E, 521F, 522A, 522B, 522C, 522D, 522E, 522F, 523A, 523B, 523C, 523D, 523E, 523F, 524A, 524B, 524C, 524D, 524E, 524F, 525A, 525B, 525C, 525D, 525E, 525F, 526A, 526B, 526C, 526D, 526E, 526F, 527A, 527B, 527C, 527D, 527E, 527F, 528A, 528B, 528C, 528D, 528E, 528F, 529A, 529B, 529C, 529D, 529E, 529F, 530A, 530B, 530C, 530D, 530E, 530F, 531A, 531B, 531C, 531D, 531E, 531F, 532A, 532B, 532C, 532D, 532E, 532F, 533A, 533B, 533C, 533D, 533E, 533F, 534A, 534B, 534C, 534D, 534E, 534F, 535A, 535B, 535C, 535D, 535E, 535F, 536A, 536B, 536C, 536D, 536E, 536F, 537A, 537B, 537C, 537D, 537E, 537F, 538A, 538B, 538C, 538D, 538E, 538F, 539A, 539B, 539C, 539D, 539E, 539F, 540A, 540B, 540C, 540D, 540E, 540F, 541A, 541B, 541C, 541D, 541E, 541F, 542A, 542B, 542C, 542D, 542E, 542F, 543A, 543B, 543C, 543D, 543E, 543F, 544A, 544B, 544C, 544D, 544E, 544F, 545A, 545B, 545C, 545D, 545E, 545F, 546A, 546B, 546C, 546D, 546E, 546F, 547A, 547B, 547C, 547D, 547E, 547F, 548A, 548B, 548C, 548D, 548E, 548F, 549A, 549B, 549C, 549D, 549E, 549F, 550A, 550B, 550C, 550D, 550E, 550F, 551A, 551B, 551C, 551D, 551E, 551F, 552A, 552B, 552C, 552D, 552E, 552F, 553A, 553B, 553C, 553D, 553E, 553F, 554A, 554B, 554C, 554D, 554E, 554F, 555A, 555B, 555C, 555D, 555E, 555F, 556A, 556B, 556C, 556D, 556E, 556F, 557A, 557B, 557C, 557D, 557E, 557F, 558A, 558B, 558C, 558D, 558E, 558F, 559A, 559B, 559C, 559D, 559E, 559F, 560A, 560B, 560C, 560D, 560E, 560F, 561A, 561B, 561C, 561D, 561E, 561F, 562A, 562B, 562C, 562D, 562E, 562F, 563A, 563B, 563C, 563D, 563E, 563F, 564A, 564B, 564C, 564D, 564E, 564F, 565A, 565B, 565C, 565D, 565E, 565F, 566A, 566B, 566C, 566D, 566E, 566F, 567A, 567B, 567C, 567D, 567E, 567F, 568A, 568B, 568C, 568D, 568E, 568F, 569A, 569B, 569C, 569D, 569E, 569F, 570A, 570B, 570C, 570D, 570E, 570F, 571A, 571B, 571C, 571D, 571E, 571F, 572A, 572B, 572C, 572D, 572E, 572F, 573A, 573B, 573C, 573D, 573E, 573F, 574A, 574B, 574C, 574D, 574E, 574F, 575A, 575B, 575C, 575D, 575E, 575F, 576A, 576B, 576C, 576D, 576E, 576F, 577A, 577B, 577C, 577D, 577E, 577F, 578A, 578B, 578C, 578D, 578E, 578F, 579A, 579B, 579C, 579D, 579E, 579F, 580A, 580B, 580C, 580D, 580E, 580F, 581A, 581B, 581C, 581D, 581E, 581F, 582A, 582B, 582C, 582D, 582E, 582F, 583A, 583B, 583C, 583D, 583E, 593F, 584A, 584B, 584C, 584D, 584E, 584F, 585A, 585B, 585C, 585D, 585E, 585F, 586A, 586B, 586C, 586D, 586E, 586F, 587A, 587B, 587C, 587D, 587E, 587F, 588A, 588B, 588C, 588D, 588E, 588F, 589A, 589B, 589C, 589D, 589E, 589F, 590A, 590B, 590C, 590D, 590E, 590F, 591A, 591B, 591C, 591D, 591E, 591F, 592A, 592B, 592C, 592D, 592E, 592F, 593A, 593B, 593C, 593D, 593E, 593F, 594A, 594B, 594C, 594D, 594E, 594F, 595A, 595B, 595C, 595D, 595E, 595F, 596A, 596B, 596C, 596D, 596E, 596F, 597A, 597B, 597C, 597D, 597E, 597F, 598A, 598B, 598C, 598D, 598E, 598F, 599A, 599B, 599C, 599D, 599E, 599F, 600A, 600B, 600C, 600D, 600E, 600F, 601A, 601B, 601C, 601D, 601E, 601F, 602A, 602B, 602C, 602D, 602E, 602F, 603A, 603B, 603C, 603D, 603E, 603F, 604A, 604B, 604C, 604D, 604E, 604F, 605A, 605B, 605C, 605D, 605E, 605F, 606A, 606B, 606C, 606D, 606E, 606F, 607A, 607B, 607C, 607D, 607E, 607F, 608A, 608B, 608C, 608D, 608E, 608F, 609A, 609B, 609C, 609D, 609E, 609F, 610A, 610B, 610C, 610D, 610E, 610F, 611A, 611B, 611C, 611D, 611E, 611F, 612A, 612B, 612C, 612D, 612E, 612F, 613A, 613B, 613C, 613D, 613E, 613F, 614A, 614B, 614C, 614D, 614E, 614F, 615A, 615B, 615C, 615D, 615E, 615F, 616A, 616B, 616C, 616D, 616E, 616F, 617A, 617B, 617C, 617D, 617E, 617F, 618A, 618B, 618C, 618D, 618E, 618F, 619A, 619B, 619C, 619D, 619E, 619F, 620A, 620B, 620C, 620D, 620E, 620F, 621A, 621B, 621C, 621D, 621E, 621F, 622A, 622B, 622C, 622D, 622E, 622F, 623A, 623B, 623C, 623D, 623E, 623F, 624A, 624B, 624C, 624D, 624E, 624F, 625A, 625B, 625C, 625D, 625E, 625F, 626A, 626B, 626C, 626D, 626E, 626F, 627A, 627B, 627C, 627D, 627E, 627F, 628A, 628B, 628C, 628D, 628E, 628F, 629A, 629B, 629C, 629D, 629E, 629F, 630A, 630B, 630C, 630D, 630E, 630F, 631A, 631B, 631C, 631D, 631E, 631F, 632A, 632B, 632C, 632D, 632E, 632F, 633A, 633B, 633C, 633D, 633E, 633F, 634A, 634B, 634C, 634D, 634E, 634F, 635A, 635B, 635C, 635D, 635E, 635F, 636A, 636B, 636C, 636D, 636E, 636F, 637A, 637B, 637C, 637D, 637E, or 637F.

In accordance with the description above, other diseases, conditions and disorders described herein (including but not limited to metabolic syndrome, liver disease, and inflammation) may also be treated with a first agent comprising a compound of Formula (I) and a second agent described above.

Compounds of Formula (I) can be incorporated into a variety of formulations and medicaments for therapeutic administration. More particularly, compounds of Formula (I) can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, and/or intratracheal administration. Moreover, the compound can be administered in a local rather than systemic manner, in a depot or sustained release formulation. In addition, the compounds can be administered in a liposome.

Compounds of Formula (I) can also be formulated with common excipients, diluents or carriers and compressed into tablets, or formulated as elixirs or solutions for convenient oral administration, or administered by the intramuscular or intravenous routes. The compounds can be administered transdermally, and can be formulated as sustained release dosage forms and the like.

EXAMPLES

General Synthetic Methods

All operations of chemical synthesis involving moisture and/or oxygen sensitive materials were conducted under an atmosphere of dry nitrogen in pre-dried glassware. Unless noted otherwise, materials were obtained from commercially available sources and used without further purification.

Flash chromatography was performed on an Isco Combiflash Companion using RediSep Rf silica gel cartridges by Teledyne Isco. Thin layer chromatography was performed using precoated plates purchased from E. Merck (silica gel 60 $PF_{254}$, 0.25 mm) and spots were visualized with long-wave ultraviolet light followed by an appropriate staining reagent.

Nuclear magnetic resonance ("NMR") spectra were recorded on a Varian Inova-400 resonance spectrometer. $^1$H NMR chemical shifts are given in parts per million ($\delta$) downfield from tetramethylsilane ("TMS") using TMS or the residual solvent signal ($CHCl_3$=$\delta$ 7.24, DMSO=$\delta$ 2.50) as internal standard. $^1$H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

LCMS analysis was performed using a PE SCIEX API 2000 spectrometer with a Phenomenex Luna 5 micron $C_{18}$ column.

Preparatory HPLC was performed on a Gilson HPLC 215 liquid handler with a Phenomenex column (Gemini 10µ, $C_{18}$, 110A) and a UV/VIS 156 detector.

Compounds of Formula (I) and derivatives thereof can be synthesized via a variety of different synthetic routes using commercially available starting materials and/or starting materials prepared by conventional synthetic methods. When production of starting materials is not particularly described, the compounds are known or may be prepared analogously to methods known in the art or as disclosed in the examples. One of skill in the art will appreciate that synthetic methodologies described herein are only representative of methods for preparation of the compounds described herein, and that other well known methods may be used.

Although many of the synthetic schemes discussed herein do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in *Protective Groups in Organic Synthesis*, Greene & Wuts, 2nd Ed., John Wiley & Sons, New York, 1991.

Prodrugs as described herein may be prepared by routine modification of the synthetic methods described herein. Conditions for carrying out such reactions and for deprotecting the product to yield a prodrugs as described herein are well-known.

Synthesis of certain compounds, and intermediates used to prepare such compounds, is detailed in the following sections. Compound numbers are listed for convenience.

Preparation of Intermediates

Intermediate 1

1-(4-Fluorophenyl)-2-mercapto-N-methoxy-N-methyl-1H-imidazole-5-carboxamide (5)

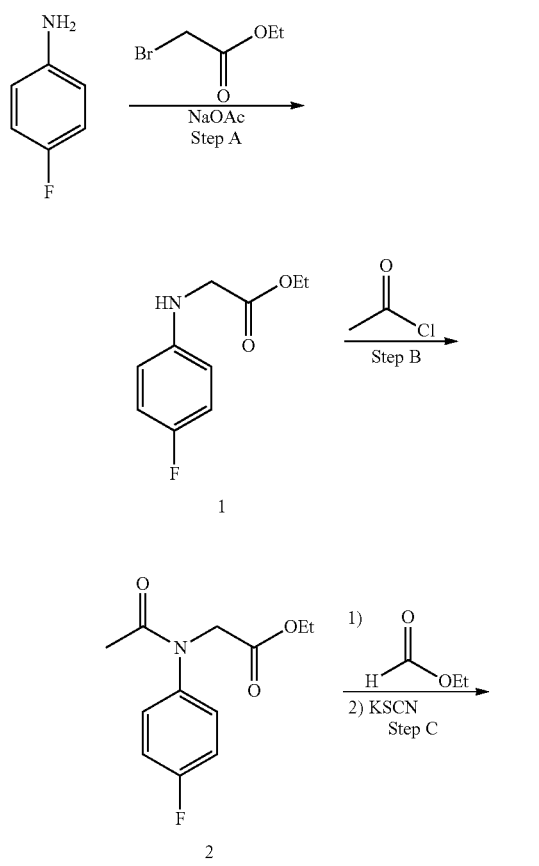

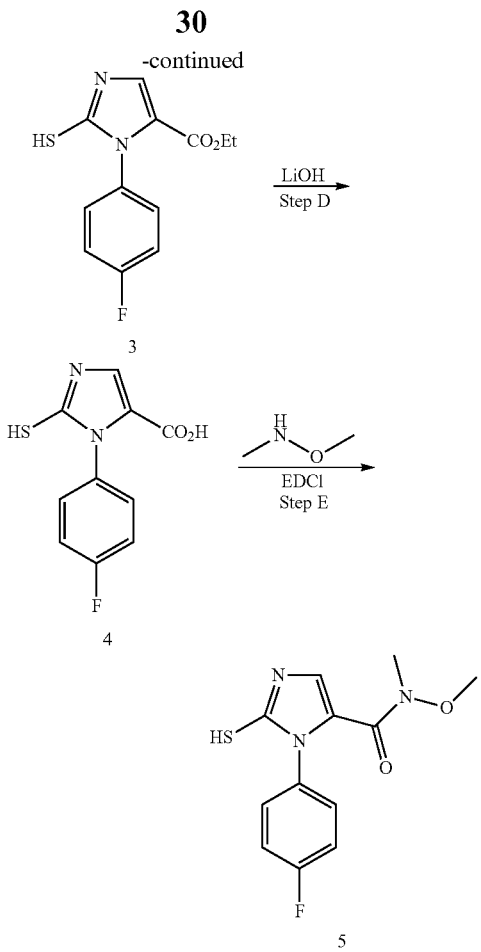

Step A:

Ethyl bromoacetate (8.09 g, 48.4 mmol) was slowly added to a solution of 4-fluoroaniline (5.38 g, 48.4 mmol) and sodium acetate (5.16 g, 62.9 mmol) in ethanol (62 mL) and the mixture was heated at 80° C. for 2 h. Water was added and the reaction was extracted with ethyl acetate. The combined organic layers were dried over sodium sulfate, filtered and concentrated in vacuo. The residue was purified by flash column chromatography on silica gel (0-20% EtOAc in hexanes) to afford ethyl 2-((4-fluorophenyl)amino)acetate (1).

Step B:

To a solution of 2-((4-fluorophenyl)amino)acetate (1) (6.68 g, 33.9 mmol) in THF (84 mL) was added acetyl chloride (2.88 mL, 40.6 mmol) and the reaction was stirred overnight at room temperature. Water was added and the reaction was extracted with ethyl acetate. The combined organic layers were dried over sodium sulfate, filtered and concentrated in vacuo to yield ethyl 2-(N-(4-fluorophenyl)acetamido)acetate (2) as an orange solid.

Step C:

Potassium ethoxide (2.89 g, 34.7 mmol) was added to a solution of ethyl 2-(N-(4-fluorophenyl)acetamido)acetate (2) (8.3 g, 34.7 mmol) and ethyl formate (9.21 mL, 114.5 mmol) in benzene (16 mL) at 0° C. The solution was placed in the refrigerator overnight. Water (50 mL) was added and the reaction was extracted with ethyl acetate. To the aqueous solution was added potassium thiocyanate (3.71 g, 38.2 mmol) and 5M HCl (6.5 mL). The reaction was heated at 60° C. for 2 h, cooled to room temperature and extracted with ethyl acetate. The organic layers were dried over sodium sulfate, filtered and concentrated in vacuo to give ethyl 1-(4-fluorophenyl)-2-mercapto-1H-imidazole-5-carboxylate (3) as a white solid.

Step D:

To a solution of ethyl 1-(4-fluorophenyl)-2-mercapto-1H-imidazole-5-carboxylate (3) (2.62 g, 9.84 mmol) in 1,4-dioxane (21 mL) and methanol (10 mL) was added lithium hydroxide (825 mg, 19.7 mmol) in water (21 mL). The reaction was stirred at 50° C. overnight and the organic solvents were removed in vacuo. The mixture was acidified with 1M HCl until a white solid crashed out of the solution. The solid was collected by vacuum filtration and washed with water to afford 1-(4-fluorophenyl)-2-mercapto-1H-imidazole-5-carboxylic acid (4).

Step E:

A solution of 1-(4-fluorophenyl)-2-mercapto-1H-imidazole-5-carboxylic acid (4) (2.2 g, 9.23 mmol), N,O-dimethylhydroxylamine (0.9 g, 9.23 mmol), and 1-ethyl-3-(3-dimethylaminopropyl) carbodiimide (EDCI) (1.77 g, 9.23 mmol) in pyridine was heated at 40° C. overnight. The reaction was cooled to room temperature, water was added and the solution was extracted with ethyl acetate. The combined organic layers were dried over sodium sulfate, filtered and concentrated in vacuo to yield 1-(4-fluorophenyl)-2-mercapto-N-methoxy-N-methyl-1H-imidazole-5-carboxamide (5) as a light yellow solid.

Intermediate 2

N-((1,3-Dimethyl-1H-pyrazol-4-yl)methyl)-1-(4-fluorophenyl)-2-mercapto-N-methyl-1H-imidazole-5-carboxamide (7)

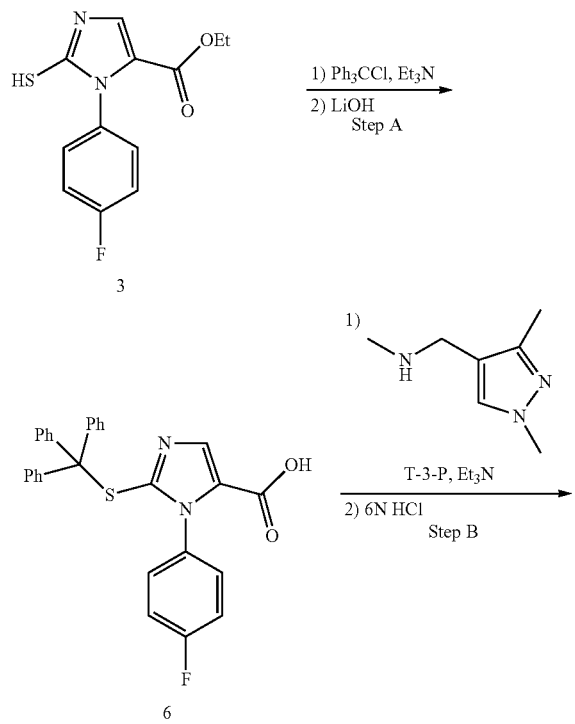

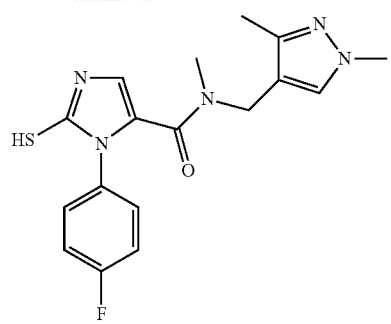

7

Step A:

To a solution of ethyl 1-(4-fluorophenyl)-2-mercapto-1H-imidazole-5-carboxylate (3) (4.09 g, 15.34 mmol) in THF (70 mL) was added triethyl amine (4.50 mL, 32.29) and triphenylmethyl chloride (4.67 g, 16.76 mmol) and the solution was stirred for 1 hour at room temperature. The reaction was concentrated in vacuo and the residue was purified by flash column chromatography on silica gel (10%-40% EtOAc in hexanes) to give ethyl 1-(4-fluorophenyl)-2-(tritylthio)-1H-imidazole-5-carboxylate. A solution of ethyl 1-(4-fluorophenyl)-2-(tritylthio)-1H-imidazole-5-carboxylate (6.34 g, 12.47 mmol), sodium hydroxide (0.74 g, 18.39 mmol), methanol (10 mL), THF (20 mL), and water (10 mL) was stirred at room temperature for 16 hour and was then concentrated in vacuo. The aqueous was extracted with ethyl acetate. The combined organic extracts were dried over sodium sulfate, filtered, and the filtrate was concentrated in vacuo to yield 1-(4-fluorophenyl)-2-(tritylthio)-1H-imidazole-5-carboxylic acid (6).

Step B:

A solution of 1-(4-fluorophenyl)-2-(tritylthio)-1H-imidazole-5-carboxylic acid (6) (3.24 g, 6.74 mmol), 1-(1,3-dimethyl-1H-pyrazol-4-yl)-N-methylmethanamine (0.95 g, 6.80 mmol), triethylamine (5.70 mL, 40.9 mmol) and propylphosphonic anhydride (T-3-P)(50% in ethyl acetate, 4.85 mL, 8.15 mmol) in dichloromethane (50 mL) was stirred overnight at room temperature. To the reaction 6N HCl (10 mL) was carefully added and was stirred at room temperature for 40 minutes. The solution was basified with saturated sodium bicarbonate and was extracted with ethyl acetate. The combined organic layers were dried over sodium sulfate, filtered and concentrated in vacuo. The residue was purified by flash column chromatography on silica gel (0-20% MeOH in dichloromethane) to afford N-((1,3-dimethyl-1H-pyrazol-4-yl)methyl)-1-(4-fluorophenyl)-2-mercapto-N-methyl-1H-imidazole-5-carboxamide

Intermediate 3

1-(4-Fluorophenyl)-N-methoxy-N-methyl-2-((2,3,6-trifluorobenzyl)thio)-1H-imidazole-5-carboxamide (9)

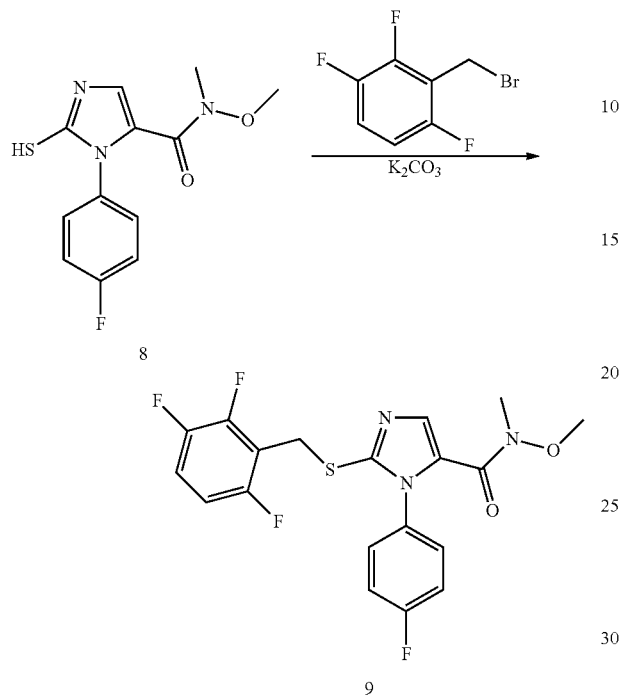

A mixture of 1-(4-fluorophenyl)-2-mercapto-N-methoxy-N-methyl-1H-imidazole-5-carboxamide (8) (153 mg, 0.54 mmol), 2,3,6-trifluorobenzyl bromide (71 µL, 0.54 mmol), and potassium carbonate (90 mg, 0.65 mmol) in acetone (5 mL) was heated at reflux for 3 h. The reaction was concentrated in vacuo and the residue was purified by flash column chromatography on silica gel (0-100% EtOAc in hexanes) to afford 1-(4-fluorophenyl)-N-methoxy-N-methyl-2-((2,3,6-trifluorobenzyl)thio)-1H-imidazole-5-carboxamide (9) as a white solid.

Intermediate 4

1-(4-Fluorophenyl)-2-((2,3,6-trifluorobenzyl)thio)-1H-imidazole-5-carboxylic acid (11)

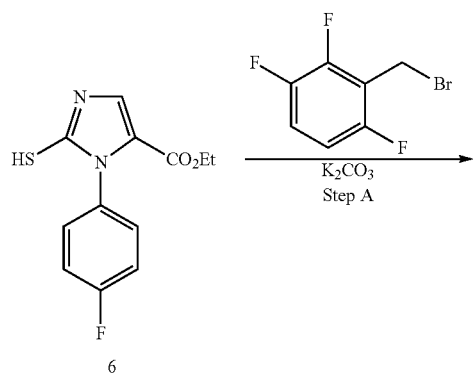

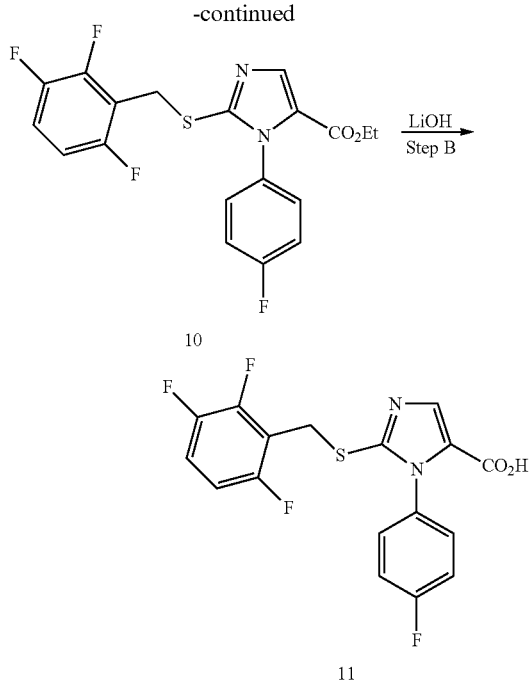

Step A:

Ethyl 1-(4-fluorophenyl)-2-((2,3,6-trifluorobenzyl)thio)-1H-imidazole-5-carboxylate (10) was prepared in a similar manner as that described for the synthesis of compound 9 using ethyl 1-(4-fluorophenyl)-2-mercapto-1H-imidazole-5-carboxylate (6) (202 mg, 0.76 mmol), 2,3,6-trifluorobenzyl bromide (0.1 mL, 0.76 mmol), and potassium carbonate (125.9 mg, 0.91 mmol) in acetone (3 mL).

Step B:

1-(4-Fluorophenyl)-2-((2,3,6-trifluorobenzyl)thio)-1H-imidazole-5-carboxylic acid (11) was prepared in a similar manner as that described for the synthesis of compound 7 using ethyl 1-(4-fluorophenyl)-2-((2,3,6-trifluorobenzyl)thio)-1H-imidazole-5-carboxylate (10) (284 mg, 0.69 mmol), lithium hydroxide monohydrate (66 mg, 2.76 mmol), THF (0.2 mL), methanol (0.4 mL), and water (0.8 mL).

Intermediate 5

5-((((1,3-Dimethyl-1H-pyrazol-4-yl)methyl)(methyl)amino)methyl)-1-(4-fluorophenyl)-1H-imidazole-2-thiol (13)

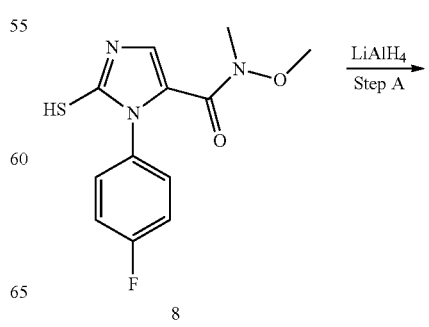

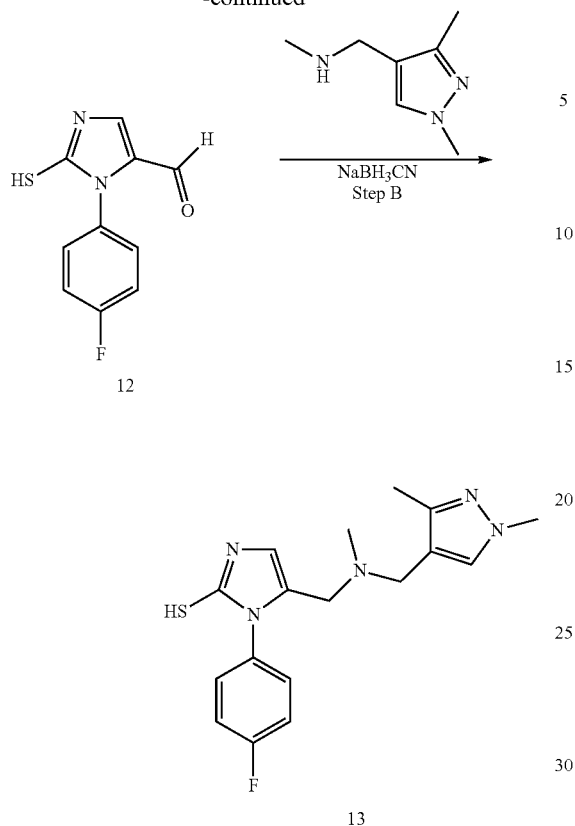

Step A:

To a solution of 1-(4-fluorophenyl)-2-mercapto-N-methoxy-N-methyl-1H-imidazole-5-carboxamide (8) (1 g, 3.55 mmol) in anhydrous THF (71 mL) at 0° C. was added lithium aluminum hydride (2M in THF, 5.3 mL, 10.65 mmol). The reaction was stirred at 0° C. for 1 h and for an additional 3 h at room temperature. The reaction was quenched at 0° C. with 15% sodium bicarbonate (40 mL) and water (40 mL) and extracted with ethyl acetate. The combined organic layers were dried over sodium sulfate, filtered and concentrated in vacuo. The residue was purified by flash column chromatography on silica gel (0-100% EtOAc in hexanes) to afford 1-(4-fluorophenyl)-2-mercapto-1H-imidazole-5-carbaldehyde (12).

Step B:

A solution of 1-(4-fluorophenyl)-2-mercapto-1H-imidazole-5-carbaldehyde (12) (170 mg, 0.76 mmol) in 1:1 DMF/acetic acid (3 mL) was stirred at room temperature for 1 h, followed by the addition of sodium cyanoborohydride (72 mg, 1.15 mmol). The reaction was stirred overnight at room temperature, quenched with water, and extracted with ethyl acetate. The combined organic layers were dried over sodium sulfate, filtered and concentrated in vacuo. The residue was purified by reverse phase HPLC to yield 5-((((1,3-dimethyl-1H-pyrazol-4-yl)methyl)(methyl)amino)methyl)-1-(4-fluorophenyl)-1H-imidazole-2-thiol (13).

Intermediate 6

1-(4-Fluorophenyl)-1H-imidazole-5-carboxylic acid (14b)

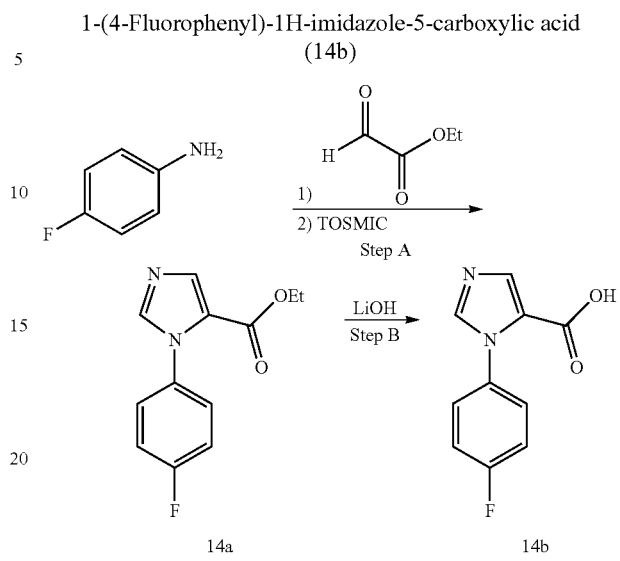

Step A:

A mixture of 4-fluoroaniline (2.8 g, 25.0 mmol), ethyl glyoxylate (50% solution, 5.14 g, 25.0 mmol), in toluene (30 mL) was refluxed overnight. The reaction was filtered and concentrated in vacuo. To the residue was added ethanol (30 mL), toluenesulfonylmethyl isocyanide (TOSMIC) (4.9 g, 25 mmol), and potassium carbonate (6.9 g, 50.0 mmol) and the mixture was stirred at room temperature for 1 h. Brine was added and mixture was extracted with ethyl acetate. The combined organic layers were dried over sodium sulfate, filtered and concentrated in vacuo. The residue was purified by flash column chromatography on silica gel (0-60% EtOAc in hexanes) to afford ethyl 1-(4-fluorophenyl)-1H-imidazole-5-carboxylate (14a).

Step B:

1-(4-Fluorophenyl)-1H-imidazole-5-carboxylic acid (14b) was prepared in a similar manner as that described for the synthesis of compound 7 using ethyl 1-(4-fluorophenyl)-1H-imidazole-5-carboxylate (14a) (143 mg, 0.61 mmol), lithium hydroxide (59 mg, 2.44 mmol), THF (0.2 mL), methanol (0.4 mL), and water (0.8 mL).

Intermediate 7

1-(4-Fluorophenyl)-2-(2,3,6-trifluorophenethyl)-1H-imidazole-5-carboxylic acid (19)

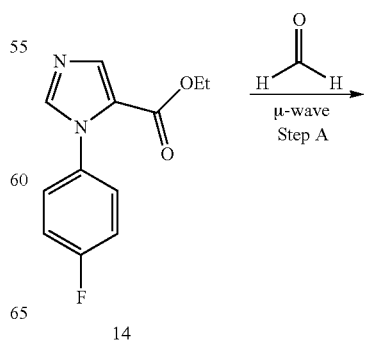

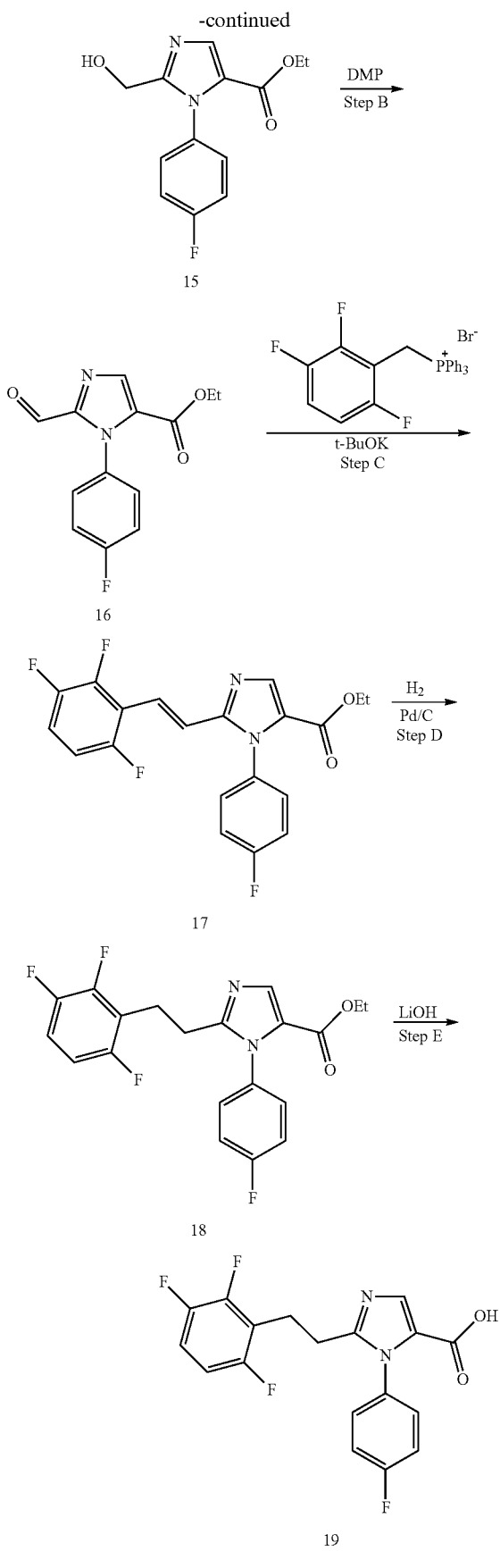

Step A:

A solution of 14 (500 mg, 2.13 mmol) in 37% formaldehyde (20 mL) was heated in a microwave reactor for 2 h at 140° C. Water was added and the reaction was extracted with ethyl acetate. The combined organic layers were dried over sodium sulfate, filtered and concentrated in vacuo. The residue was purified by flash column chromatography on silica gel (0-60% EtOAc in hexanes) to afford ethyl 1-(4-fluorophenyl)-2-(hydroxymethyl)-1H-imidazole-5-carboxylate (15) as an off-white solid.

Step B:

A solution of ethyl 1-(4-fluorophenyl)-2-(hydroxymethyl)-1H-imidazole-5-carboxylate (15) (210 mg, 0.80 mmol), and Dess-Martin Periodinane (DMP) (562 mg, 1.32 mmol) in dichloromethane (8 mL) was stirred at room temperature for 1 h. The reaction was added to a 1:1 mixture of $Na_2S_2O_3$ (10% aq.) and $NaHCO_3$ (sat.), then extracted with dichloromethane. The combined organic layers were washed with water, dried over sodium sulfate, filtered and concentrated in vacuo. The residue was purified by flash column chromatography on silica gel (0-30% EtOAc in hexanes) to give ethyl 1-(4-fluorophenyl)-2-formyl-1H-imidazole-5-carboxylate (16).

Step C:

To a solution of triphenyl(2,3,6-trifluorobenzyl)phosphonium bromide (428 mg, 0.88 mmol) in THF at 0° C. was added potassium tert-butoxide (99 mg, 0.88 mmol). After the reaction was stirred for 1 h, it was warmed to room temperature and a solution of ethyl 1-(4-fluorophenyl)-2-formyl-1H-imidazole-5-carboxylate (16) (210 mg, 0.80) in THF (1 mL) was added. The mixture was refluxed for 6 h, cooled to room temperature, filtered, and concentrated in vacuo. The residue was purified by flash column chromatography on silica gel (0-40% EtOAc in hexanes, $R_f$=0.2 in 80/20 hexanes/ethyl acetate) to yield (E)-ethyl 1-(4-fluorophenyl)-2-(2,3,6-trifluorostyryl)-1H-imidazole-5-carboxylate (17) as the only stereoisomer.

Step D:

To a solution of (E)-ethyl 1-(4-fluorophenyl)-2-(2,3,6-trifluorostyryl)-1H-imidazole-5-carboxylate (17) (60 mg, 0.16 mmol) in ethanol (10 mL) was added Pd/C (10% Degussa type, 10 mg). A balloon of hydrogen gas was attached and the reaction was evacuated and back-filled with hydrogen three times. The reaction was stirred under a hydrogen balloon overnight at room temperature, filtered through a pad of celite and concentrated in vacuo to give ethyl 1-(4-fluorophenyl)-2-(2,3,6-trifluorophenethyl)-1H-imidazole-5-carboxylate (18).

Step E:

1-(4-fluorophenyl)-2-(2,3,6-trifluorophenethyl)-1H-imidazole-5-carboxylic acid (19) was prepared in a similar manner as that described for the synthesis of compound 7 using ethyl 1-(4-fluorophenyl)-2-(2,3,6-trifluorophenethyl)-1H-imidazole-5-carboxylate (18) (50 mg, 0.13 mmol), lithium hydroxide (12 mg, 0.51 mmol), THF (0.2 mL), methanol (0.4 mL), and water (0.8 mL).

Intermediate 8

1-(4-Fluorophenyl)-2-((2,3,6-trifluorobenzyl)sulfinyl)-1H-imidazole-5-carboxylic acid (20)

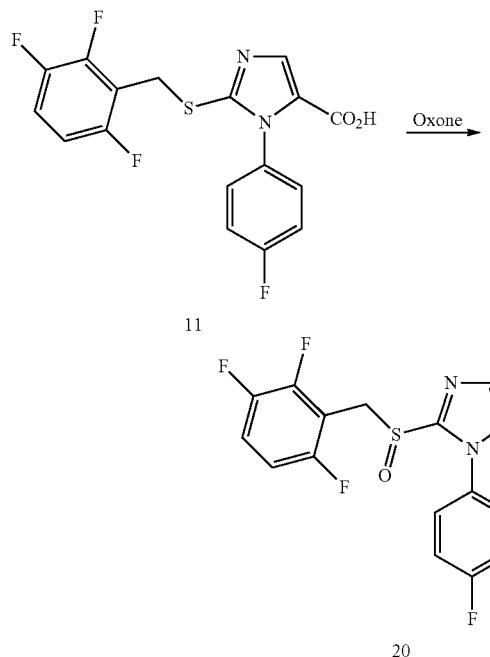

A solution of 1-(4-fluorophenyl)-2-((2,3,6-trifluorobenzyl)thio)-1H-imidazole-5-carboxylic acid (11) (261 mg, 0.68 mmol) in acetone (7 mL) was added 0.2 M NaHCO$_3$ (7 mL) and Oxone (1.05 g, 1.71 mmol) and stirred at room temperature for 2 h. Water was added and the mixture was extracted with ethyl acetate. The combined organic layers were washed with water, dried over sodium sulfate, filtered and concentrated in vacuo to obtain 1-(4-fluorophenyl)-2-((2,3,6-trifluorobenzyl)sulfinyl)-1H-imidazole-5-carboxylic acid (20) as a white solid.

Intermediate 9

1-(4-Fluorophenyl)-2-((2,3,6-trifluorobenzyl)sulfonyl)-1H-imidazole-5-carboxylic acid (22)

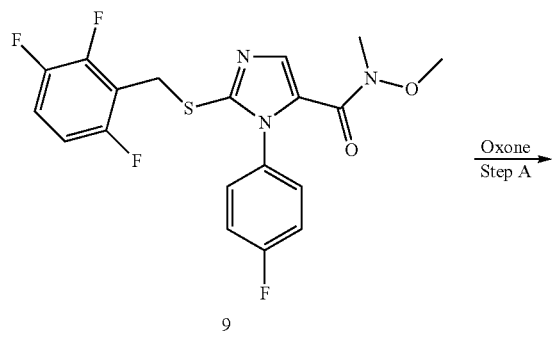

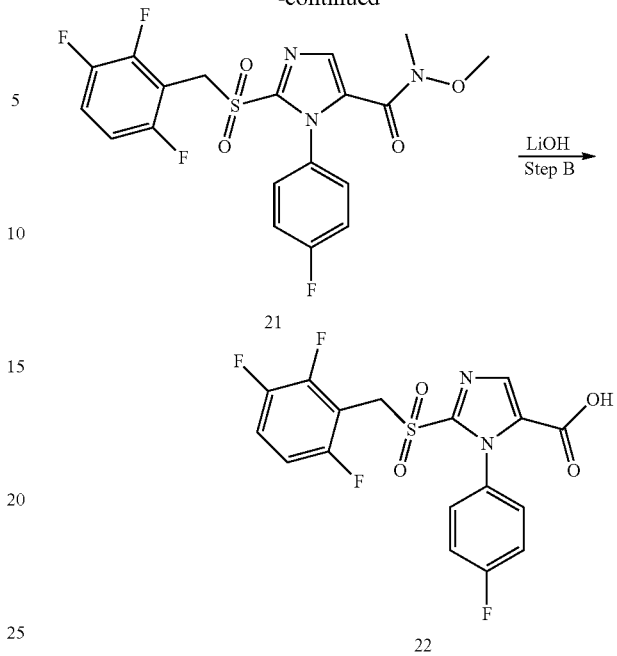

Step A:
A solution of 1-(4-fluorophenyl)-N-methoxy-N-methyl-2-((2,3,6-trifluorobenzyl)thio)-1H-imidazole-5-carboxamide (9) (100 mg, 0.24 mmol) in acetone (2.5 mL) was added 0.2 M NaHCO$_3$ (2.5 mL) and Oxone (722 g, 1.18 mmol) and stirred at 50° C. overnight. Water was added and the mixture was extracted with ethyl acetate. The combined organic layers were washed with water, dried over sodium sulfate, filtered and concentrated in vacuo. The residue was purified by flash column chromatography on silica gel (0-100% EtOAc in hexanes) to give 1-(4-fluorophenyl)-N-methoxy-N-methyl-2-((2,3,6-trifluorobenzyl)sulfonyl)-1H-imidazole-5-carboxamide (21).

Step B:
1-(4-Fluorophenyl)-2-((2,3,6-trifluorobenzyl)sulfonyl)-1H-imidazole-5-carboxylic acid (22) was prepared in a similar manner as that described for the synthesis of compound 7 using 1-(4-fluorophenyl)-N-methoxy-N-methyl-2-((2,3,6-trifluorobenzyl)sulfonyl)-1H-imidazole-5-carboxamide (21) (50 mg, 0.11 mmol), lithium hydroxide (10 mg, 0.44 mmol), THF (0.1 mL), methanol (0.2 mL), and water (0.4 mL).

Intermediate 10

1-(4-Fluorophenyl)-2-((methyl(2,3,6-trifluorophenyl)amino)methyl)-1H-imidazole-5-carboxylic acid (24)

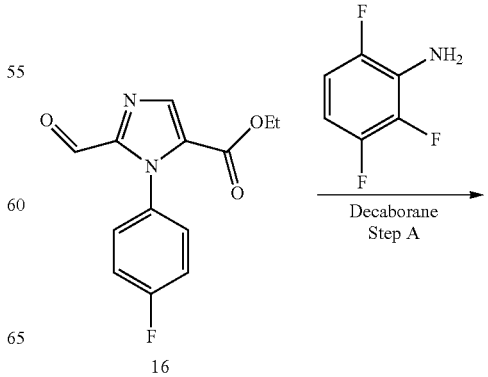

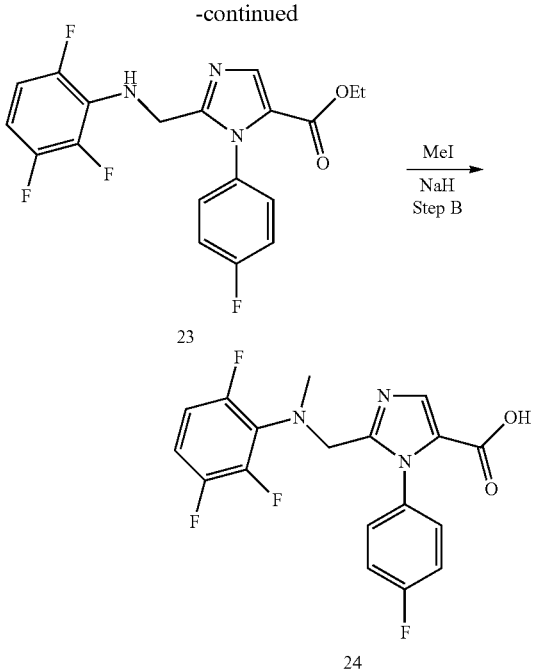

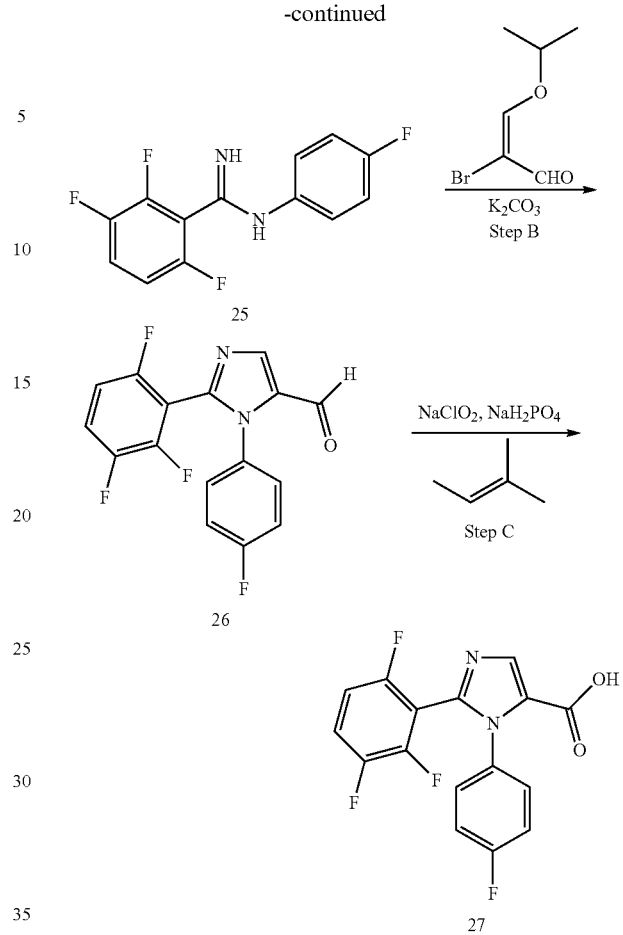

Step A:

A solution of ethyl 1-(4-fluorophenyl)-2-formyl-1H-imidazole-5-carboxylate (16) (150 mg, 0.57 mmol), 2,3,6-trifluoroaniline (60.4 µL, 0.57 mmol), decaborane (14 mg, 0.11 mmol), acetic acid (2 drops), and methanol (6 mL) was stirred at room temperature overnight. The reaction was concentrated and the residue was purified by flash column chromatography on silica gel (0-30% EtOAc in hexanes) to yield ethyl 1-(4-fluorophenyl)-2-(((2,3,6-trifluorophenyl)amino)methyl)-1H-imidazole-5-carboxylate (23).

Step B:

To a solution of ethyl 1-(4-fluorophenyl)-2-(((2,3,6-trifluorophenyl)amino)methyl)-1H-imidazole-5-carboxylate (23) (56 mg, 0.14 mmol) in DMF (2 mL) was added sodium hydride (60% in mineral oil, 7 mg, 0.28 mmol) and stirred for 30 minutes. To the solution was added methyl iodide (18 µL, 0.28 mmol) and again stirred overnight at room temperature. Ethyl acetate was added and the reaction was acidified with 2N HCl. The ethyl acetate was separated and the aqueous layer was extracted again with ethyl acetate. The combined organic layers were dried over sodium sulfate, filtered and concentrated in vacuo to give 1-(4-fluorophenyl)-2-((methyl (2,3,6-trifluorophenyl)amino)methyl)-1H-imidazole-5-carboxylic acid (24).

Intermediate 11

1-(4-Fluorophenyl)-2-(2,3,6-trifluorophenyl)-1H-imidazole-5-carboxylic acid (27)

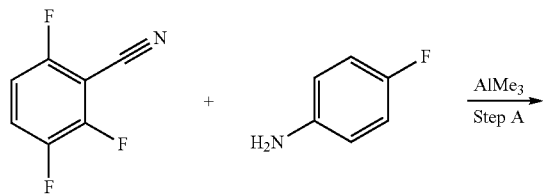

Step A:

To a solution of 4-fluoroaniline (0.47 mL, 4.89 mmol) in toluene (25 mL) at 0° C. was added trimethyl aluminum (2M solution in toluene, 3.42 mL, 6.37 mmol). The reaction was stirred for 30 minutes at 0° C. and was then warmed to room temperature and stirred an additional 3 h. A solution of 2,3,6-benzonitrile (1.0 g, 6.37 mmol) in toluene (5 mL) was added and the reaction was stirred at 70° C. overnight, concentrated in vacuo and the residue was purified by flash column chromatography on silica gel (0-50% EtOAc in hexanes) to yield 2,3,6-trifluoro-N-(4-fluorophenyl)benzimidamide (25).

Step B:

A mixture of 2,3,6-trifluoro-N-(4-fluorophenyl)benzimidamide (25) (0.98 mg, 3.65 mmol), (E)-2-bromo-3-isopropoxyacrylaldehyde (1.1 g, 5.48 mmol), and potassium carbonate (0.76 g, 5.48 mmol) in chloroform (7 mL) and water (1 mL) was stirred at room temperature overnight. Dichloromethane and water were added and the layers were separated. The aqueous layer was extracted with dichloromethane and the combined organic layers were dried over sodium sulfate, filtered and concentrated in vacuo. The residue was purified by flash column chromatography on silica gel (0-40% EtOAc in hexanes) to afford 1-(4-fluorophenyl)-2-(2,3,6-trifluorophenyl)-1H-imidazole-5-carbaldehyde (26).

Step C:

A solution of sodium chlorite (80%, 2.53 g, 22.5 mmol), sodium phosphate mono-basic (210.6 mg, 1.76 mmol) in water was added to a solution of 1-(4-fluorophenyl)-2-(2,3,6-trifluorophenyl)-1H-imidazole-5-carb aldehyde (26) (720 mg, 2.25 mmol) and 2-methyl-2-butene (2M in THF, 7.53 mL, 15.1 mmol) in tert-butanol and the reaction was stirred for 15 minutes. Water and ethyl acetate were added and the layers were separated. The organic layer was washed with saturated sodium bicarbonate. The aqueous layer was acidified to pH 6 with 2N HCl and extracted with ethyl acetate. The combined organic layers were dried over sodium sulfate, filtered and concentrated in vacuo to give 1-(4-fluorophenyl)-2-(2,3,6-trifluorophenyl)-1H-imidazole-5-carboxylic acid (27).

Intermediate 12

N-((1-(4-Fluorophenyl)-2-((2,3,6-trifluorobenzyl)thio)-1H-imidazol-5-yl)methyl)-1,3-dimethyl-1H-pyrazole-4-carboxamide (31)

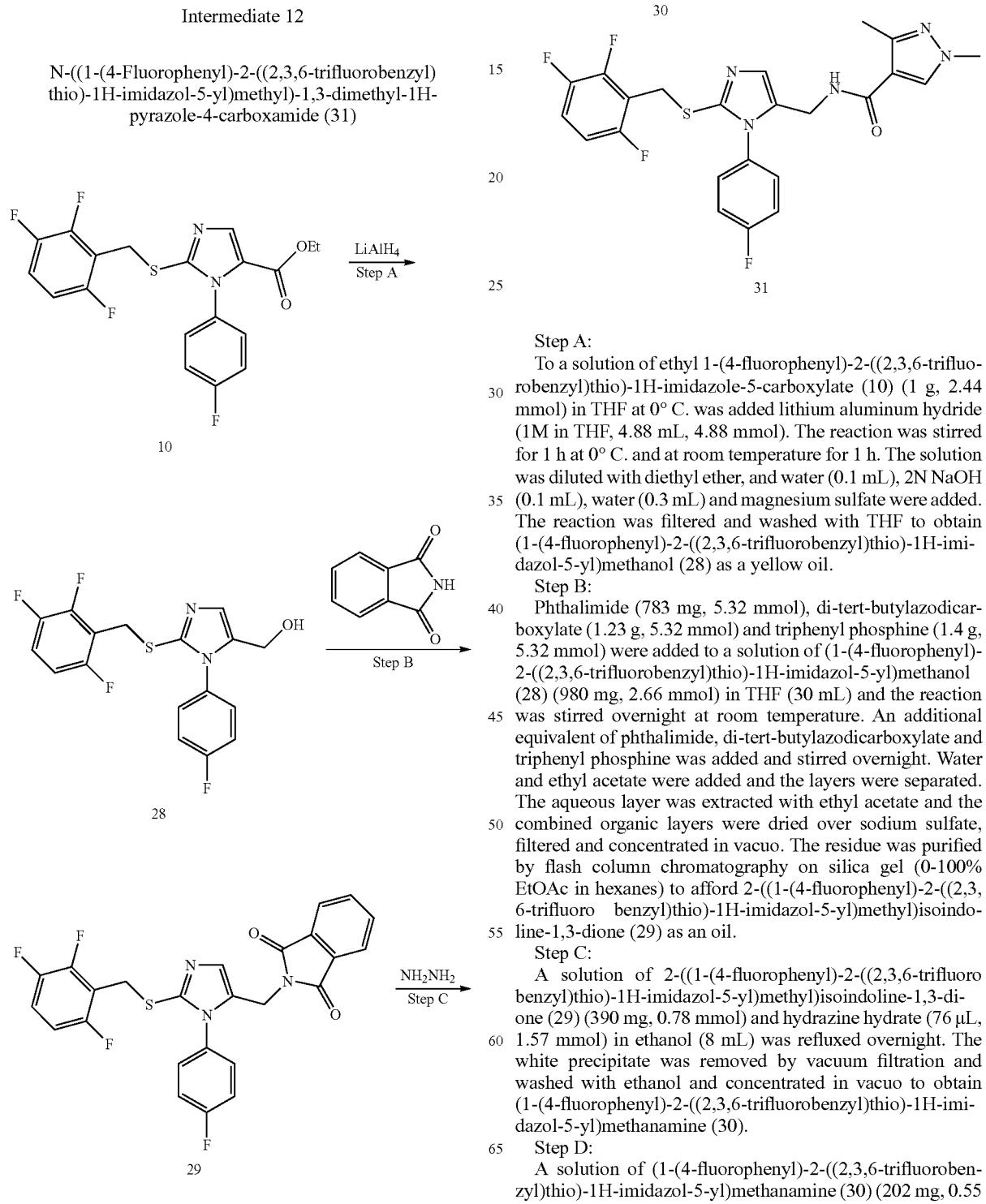

Step A:
To a solution of ethyl 1-(4-fluorophenyl)-2-((2,3,6-trifluorobenzyl)thio)-1H-imidazole-5-carboxylate (10) (1 g, 2.44 mmol) in THF at 0° C. was added lithium aluminum hydride (1M in THF, 4.88 mL, 4.88 mmol). The reaction was stirred for 1 h at 0° C. and at room temperature for 1 h. The solution was diluted with diethyl ether, and water (0.1 mL), 2N NaOH (0.1 mL), water (0.3 mL) and magnesium sulfate were added. The reaction was filtered and washed with THF to obtain (1-(4-fluorophenyl)-2-((2,3,6-trifluorobenzyl)thio)-1H-imidazol-5-yl)methanol (28) as a yellow oil.

Step B:
Phthalimide (783 mg, 5.32 mmol), di-tert-butylazodicarboxylate (1.23 g, 5.32 mmol) and triphenyl phosphine (1.4 g, 5.32 mmol) were added to a solution of (1-(4-fluorophenyl)-2-((2,3,6-trifluorobenzyl)thio)-1H-imidazol-5-yl)methanol (28) (980 mg, 2.66 mmol) in THF (30 mL) and the reaction was stirred overnight at room temperature. An additional equivalent of phthalimide, di-tert-butylazodicarboxylate and triphenyl phosphine was added and stirred overnight. Water and ethyl acetate were added and the layers were separated. The aqueous layer was extracted with ethyl acetate and the combined organic layers were dried over sodium sulfate, filtered and concentrated in vacuo. The residue was purified by flash column chromatography on silica gel (0-100% EtOAc in hexanes) to afford 2-((1-(4-fluorophenyl)-2-((2,3,6-trifluoro benzyl)thio)-1H-imidazol-5-yl)methyl)isoindoline-1,3-dione (29) as an oil.

Step C:
A solution of 2-((1-(4-fluorophenyl)-2-((2,3,6-trifluoro benzyl)thio)-1H-imidazol-5-yl)methyl)isoindoline-1,3-dione (29) (390 mg, 0.78 mmol) and hydrazine hydrate (76 µL, 1.57 mmol) in ethanol (8 mL) was refluxed overnight. The white precipitate was removed by vacuum filtration and washed with ethanol and concentrated in vacuo to obtain (1-(4-fluorophenyl)-2-((2,3,6-trifluorobenzyl)thio)-1H-imidazol-5-yl)methanamine (30).

Step D:
A solution of (1-(4-fluorophenyl)-2-((2,3,6-trifluorobenzyl)thio)-1H-imidazol-5-yl)methanamine (30) (202 mg, 0.55 mmol), 1,3-dimethyl-1H-pyrazole-4-carboxyclic acid (77 mg, 0.55 mmol), triethylamine (0.46 mL, 3.29 mmol) and propylphosphonic anhydride (50% in ethyl acetate, 0.46 mL, 0.77 mmol) in dichloromethane (6 mL) was stirred overnight at room temperature. The reaction was concentrated in vacuo and the residue was purified by flash column chromatography on silica gel (50%-100% EtOAc in hexanes) to give N-((1-(4-fluorophenyl)-2-((2,3,6-trifluorobenzyl)thio)-1H-imidazol-5-yl)methyl)-1,3-dimethyl-1H-pyrazole-4-carboxamide (31).

Intermediate 13

1-(4-Fluorophenyl)-2-((2,3,6-trifluorobenzyl)sulfinyl)-1H-imidazole-5-carbaldehyde (33)

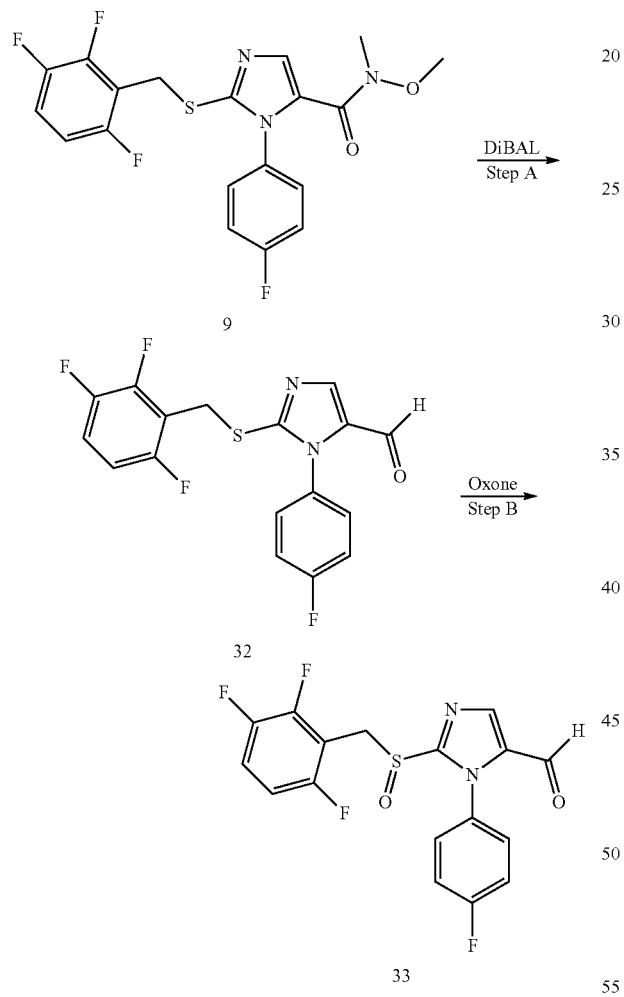

Step A:
1-(4-Fluorophenyl)-2-((2,3,6-trifluorobenzyl)thio)-1H-imidazole-5-carbaldehyde (32) was prepared in a similar manner as that described for the synthesis of compound 12 using 1-(4-fluorophenyl)-N-methoxy-N-methyl-2-((2,3,6-trifluorobenzyl)thio)-1H-imidazole-5-carboxamide (9) (1.15 g, 2.7 mmol), diisobutyl aluminum hydride (DiBAL) (1M in THF, 5.5 mL, 5.5 mmol), and THF (5 mL).

Step B:
1-(4-Fluorophenyl)-2-((2,3,6-trifluorobenzyl)sulfinyl)-1H-imidazole-5-carbaldehyde (33) was prepared in a similar manner as that described for the synthesis of compound 20 using 1-(4-fluorophenyl)-2-((2,3,6-trifluorobenzyl)thio)-1H-imidazole-5-carbaldehyde (32) (150 mg, 0.41 mmol), Oxone (629 mg, 1.02 mmol), acetone (4 mL) and 0.2M sodium bicarbonate (4 mL).

Intermediate 14

1-(4-Fluorophenyl)-2-(2-methyl-1-(2,3,6-trifluorophenyl)propan-2-yl)-1H-imidazole-5-carboxylic acid (37)

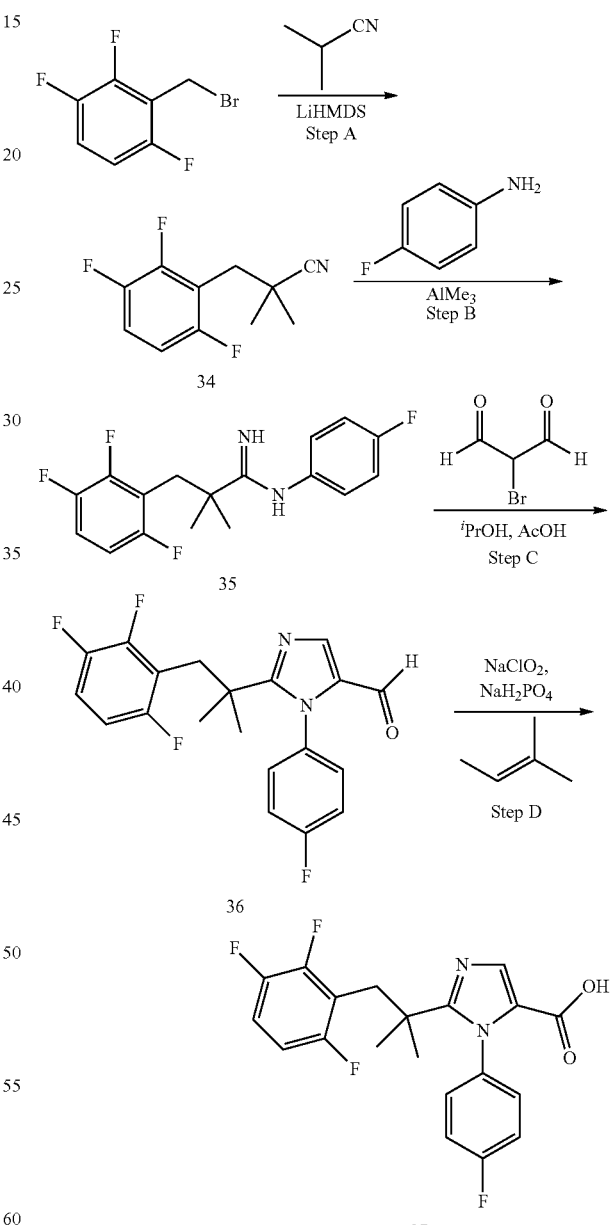

Step A:
A solution of lithium bis(trimethylsilyl)amide (LiHMDS) (1M in THF, 26.6 mL, 26.6 mmol) was added to a solution of isobutyronitrile (2.4 mL, 26.6 mmol) in THF at −78° C. and stirred for 25 minutes. 2,3,6-trifluorobenzyl bromide (2.3 mL, 17.8 mmol) was added and the reaction was warmed to room temperature and stirred for 1.5 h. Water was added to quench the reaction and it was extracted with ethyl acetate. The combined organic layers were dried over sodium sulfate, filtered and concentrated in vacuo to yield 2,2-dimethyl-3-(2, 3,6-trifluorophenyl)propanenitrile (34) as a white solid.

Step B:

N-(4-fluorophenyl)-2,2-dimethyl-3-(2,3,6-trifluorophenyl)propanimidamide (35) was prepared in a similar manner as that described for the synthesis of compound 25 using 2,2-dimethyl-3-(2,3,6-trifluorophenyl)propanenitrile (34) (500 mg, 2.35 mmol), 4-fluoroaniline (0.38 mL, 4.0 mmol), trimethyl aluminum (2M in heptanes, 1.99 mL, 3.99 mmol) and toluene (10 mL).

Step C:

A solution of N-(4-fluorophenyl)-2,2-dimethyl-3-(2,3,6-trifluorophenyl) propanimidamide (35) (72.8 mg, 0.22 mmol), acetic acid (14 µL, 0.24 mmol), triethylamine (33 µL, 0.24 mmol), and bromomalonaldehyde (33.9 mg, 0.22 mmol) in isopropyl alcohol (1 mL) was refluxed for 4 h. The reaction was concentrated in vacuo, dichloromethane was added and washed with water. The aqueous phase was extracted with dichloromethane and the combined organic layers were dried over sodium sulfate, filtered and concentrated in vacuo. The residue was purified by flash column chromatography on silica gel (0-30% EtOAc in hexanes) to afford 1-(4-fluorophenyl)-2-(2-methyl-1-(2,3,6-trifluorophenyl)propan-2-yl)-1H-imidazole-5-carbaldehyde (36).

Step D:

1-(4-fluorophenyl)-2-(2-methyl-1-(2,3,6-trifluorophenyl) propan-2-yl)-1H-imidazole-5-carboxylic acid (37) was prepared in a similar manner as that described for the synthesis of compound 27 using 1-(4-fluorophenyl)-2-(2-methyl-1-(2,3, 6-trifluorophenyl)propan-2-yl)-1H-imidazole-5-carbaldehyde (36) (59.2 mg, 0.16 mmol), 2-methyl-2-butene (2M in THF, 0.53 mL, 1.05 mmol), sodium chlorite (80%, 59.6 mg, 1.6 mmol), sodium phosphate mono-basic (14.7 mg, 0.12 mmol), tert-butanol (1.6 mL), and water (0.8 mL).

Intermediate 15

2-((2-Chloro-6-fluorobenzyl)oxy)-1-(4-fluorophenyl)-1H-imidazole-5-carboxylic acid (40)

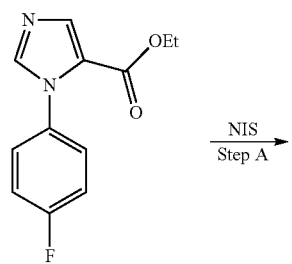

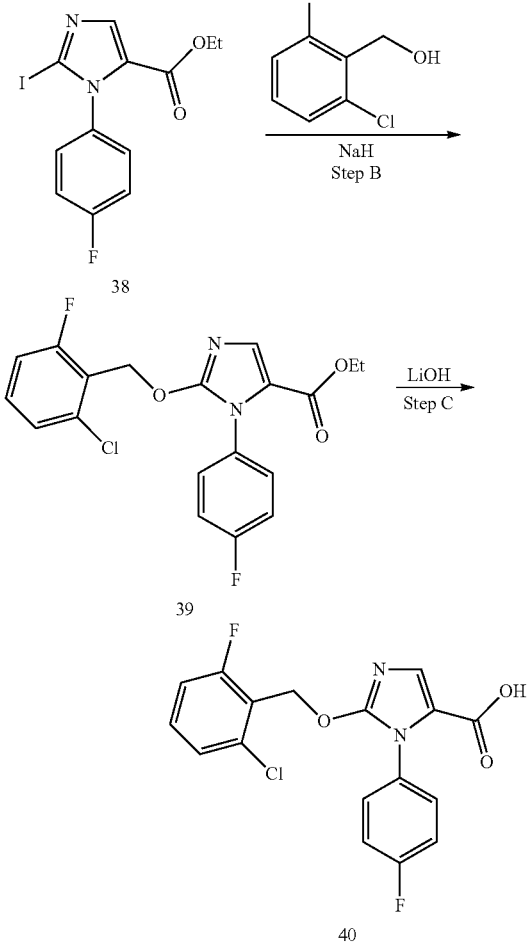

Step A:

A solution of ethyl 1-(4-fluorophenyl)-1H-imidazole-5-carboxylate (14) (5 g, 21.4 mmol), N-iodosuccinimide (12 g, 53.4 mmol), and THF (100 mL) was refluxed overnight. A solution of saturated sodium thiosulfate was added and the reaction was extracted with ethyl acetate. The combined organic layers were dried over sodium sulfate, filtered and concentrated in vacuo. The residue was purified by flash column chromatography on silica gel (0-100% EtOAc in hexanes) to give ethyl 1-(4-fluorophenyl)-2-iodo-1H-imidazole-5-carboxylate (38).

Step B:

To a solution of (2-chloro-6-fluorophenyl)methanol (160.5 mg, 0.99 mmol) in THF (8 mL) was added sodium hydride (40 mg, 0.99 mmol) and the reaction was stirred at room temperature. After 25 minutes ethyl 1-(4-fluorophenyl)-2-iodo-1H-imidazole-5-carboxylate (38) (300 mg, 0.83 mmol) was added and the reaction was refluxed overnight. Water was added slowly and the solution was extracted with ethyl acetate. The combined organic layers were dried over sodium sulfate, filtered and concentrated in vacuo to afford ethyl 2-((2-chloro-6-fluorobenzyl)oxy)-1-(4-fluorophenyl)-1H-imidazole-5-carboxylate (39).

Step C:

2-((2-Chloro-6-fluorobenzyl)oxy)-1-(4-fluorophenyl)-1H-imidazole-5-carboxylic acid (40) was prepared in a similar manner as that described for the synthesis of compound 7 using ethyl 2-((2-chloro-6-fluorobenzyl)oxy)-1-(4-fluorophenyl)-1H-imidazole-5-carboxylate (39) (105 mg, 0.27 mmol), lithium hydroxide (26 mg, 1.07 mmol), THF (0.1 mL), methanol (0.2 mL), and water (0.4 mL).

Intermediate 16

2-((2-Chloro-6-fluorophenyl)ethynyl)-1-(4-fluorophenyl)-1H-imidazole-5-carboxylic acid (43)

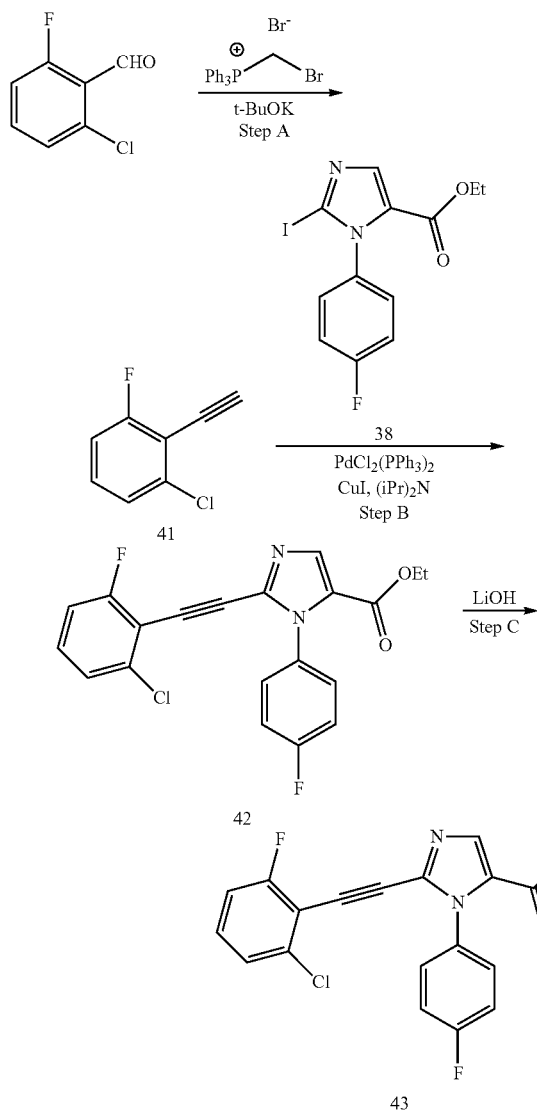

Step A:
To a cooled solution of (bromomethyl)triphenylphosphonium bromide (3.3 g, 7.6 mmol) in THF at 0° C. was added potassium tert-butoxide (2.12 g, 18.9 mmol). The reaction was stirred for 30 minutes and a solution of 2-chloro-6-fluorobenzaldehyde (1 g, 6.31 mmol) in THF was added. The reaction was allowed to warm to room temperature overnight and water was added. The solution was extracted with ethyl acetate and the combined organic layers were dried over sodium sulfate, filtered and concentrated in vacuo. The residue was purified by flash column chromatography on silica gel (0-10% EtOAc in hexanes) to give 1-chloro-2-ethynyl-3-fluorobenzene (41).

Step B:
Ethyl 1-(4-fluorophenyl)-2-iodo-1H-imidazole-5-carboxylate (38) (847 mg, 2.35 mmol), PdCl$_2$(PPh$_3$)$_2$ (82 mg, 0.12 mmol), copper (I) iodide (22 mg, 0.12 mmol), and THF (50 mL) were added to a pressure tube. Diisopropyl amine (6 mL) and 1-chloro-2-ethynyl-3-fluorobenzene (41) (400 mg, 2.59 mmol) were added to the pressure tube and the reaction was stirred at 50° C. overnight. The reaction was concentrated in vacuo and the residue was purified by flash column chromatography on silica gel (0-30% EtOAc in hexanes) to provide ethyl 2-((2-chloro-6-fluorophenyl)ethynyl)-1-(4-fluorophenyl)-1H-imidazole-5-carboxylate (42).

Step C:
2-((2-Chloro-6-fluorophenyl)ethynyl)-1-(4-fluorophenyl)-1H-imidazole-5-carboxylic acid (43) was prepared in a similar manner as that described for the synthesis of compound 7 using ethyl 2-((2-chloro-6-fluorophenyl)ethynyl)-1-(4-fluorophenyl)-1H-imidazole-5-carboxylate (42) (44 mg, 0.11 mmol), lithium hydroxide (11 mg, 0.46 mmol), THF (0.1 mL), methanol (0.2 mL), and water (0.4 mL).

Intermediate 17

2-(2-Fluorophenethyl)-1-(4-fluorophenyl)-1H-imidazole-5-carboxylic acid (45)

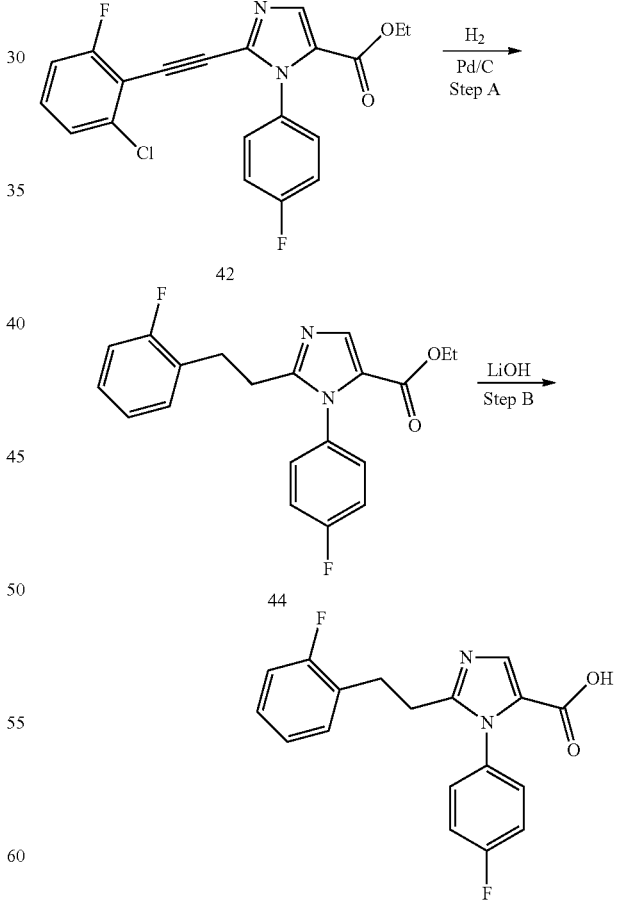

Step A:
Ethyl 2-(2-fluorophenethyl)-1-(4-fluorophenyl)-1H-imidazole-5-carboxylate (44) was prepared in a similar manner as that described for the synthesis of compound 18 using ethyl 2-((2-chloro-6-fluorophenyl)ethynyl)-1-(4-fluorophenyl)-1H-imidazole-5-carboxylate (42) (236 mg, 0.61 mmol), Pd/C (10% Degussa type, 23 mg), and ethyl acetate/ethanol (1:2) (61 mL).

Step B:

2-(2-Fluorophenethyl)-1-(4-fluorophenyl)-1H-imidazole-5-carboxylic acid (45) was prepared in a similar manner as that described for the synthesis of compound 7 using ethyl 2-(2-fluorophenethyl)-1-(4-fluorophenyl)-1H-imidazole-5-carboxylate (44) (222 mg, 0.62 mmol), lithium hydroxide (60 mg, 2.5 mmol), THF (1.0 mL), methanol (1.0 mL), and water (2 mL).

Intermediate 18

1-(4-Fluorophenyl)-2-(2-(trifluoromethyl)phenethyl)-1H-imidazole-5-carboxylic acid (48)

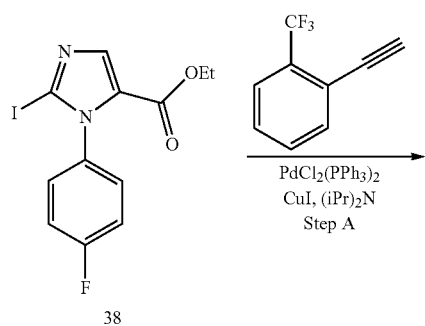

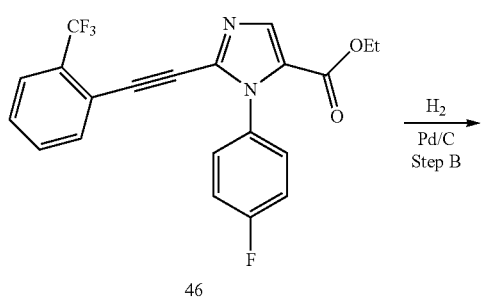

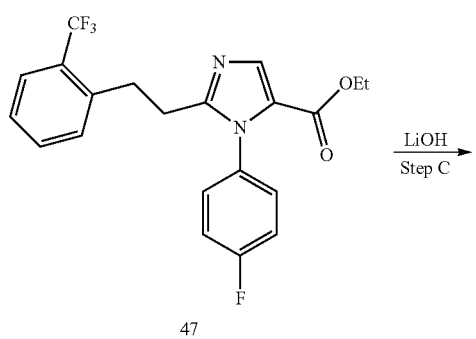

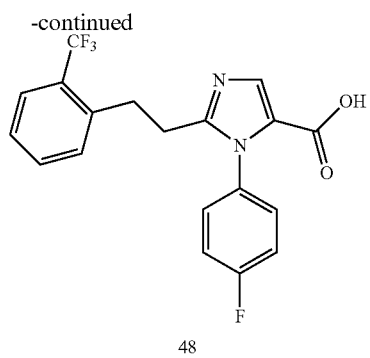

Step A:

Ethyl 1-(4-fluorophenyl)-2-((2-(trifluoromethyl)phenyl)ethynyl)-1H-imidazole-5-carboxylate (46) was prepared in a similar manner as that described for the synthesis of compound 42 using ethyl 1-(4-fluorophenyl)-2-iodo-1H-imidazole-5-carboxylate (38) (900 mg, 2.5 mmol), 1-ethynyl-2-(trifluoromethyl)benzene (0.42 mL, 3.0 mmol), PdCl$_2$(PPh$_3$)$_2$ (88 mg, 0.13 mmol), copper (I) iodide (23 mg, 0.13 mmol), diisopropyl amine (7 mL), and THF (50 mL).

Step B:

Ethyl 1-(4-fluorophenyl)-2-((2-(trifluoromethyl)phenethyl)-1H-imidazole-5-carboxylate (47) was prepared in a similar manner as that described for the synthesis of compound 18 using ethyl 1-(4-fluorophenyl)-2-((2-(trifluoromethyl)phenyl)ethynyl)-1H-imidazole-5-carboxylate (46) (651 mg, 1.62 mmol), Pd/C (10% Degussa type, 65 mg), and ethyl acetate/ethanol (1:2) (61 mL).

Step C:

1-(4-Fluorophenyl)-2-(2-(trifluoromethyl)phenethyl)-1H-imidazole-5-carboxylic acid (48) was prepared in a similar manner as that described for the synthesis of compound 7 using ethyl 1-(4-fluorophenyl)-2-(2-(trifluoromethyl)phenethyl)-1H-imidazole-5-carboxylate (47), lithium hydroxide, THF, methanol, and water.

Intermediate 19

Pyridine-4-ylmethyl methanesulfonate (49)

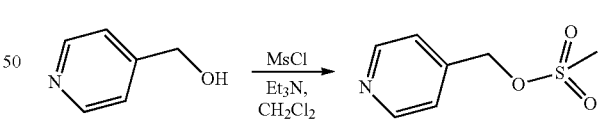

Pyridin-4-ylmethanol (4.0 g, 37 mmol) was dissolved in dichloromethane (50 mL), and triethylamine (11.21 g, 111 mmol) was added to the reaction mixture. The solution was cooled to 0° C. and methanesulfonyl chloride (MsCl) (6.3 g, 55.5 mmol) was added slowly. After the addition was complete, the reaction was stirred at 0° C. for 15 min and then stirred at room temperature for 2 hours. Water was slowly added and the solution was extracted with dichloromethane. The organic layer was washed with brine, and dried over sodium sulfate and concentrated in vacuo. The residue was dissolved in methanol, and activated charcoal was added. After the mixture was stirred for 1 hour the mixture was filtered through a plug of celite and concentrated in vacuo to afford pyridine-4-ylmethyl methanesulfonate (49).

Intermediate 20

1-(4-Fluorophenyl)-2-((pyridin-4-ylmethyl)thio)-1H-imidazole-5-carboxylic acid (51)

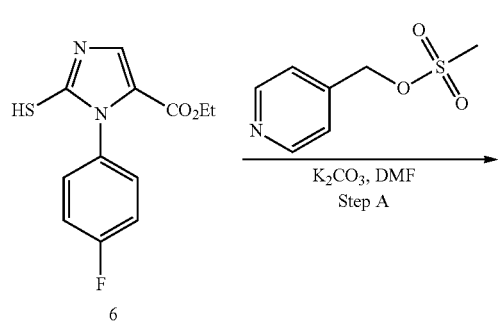

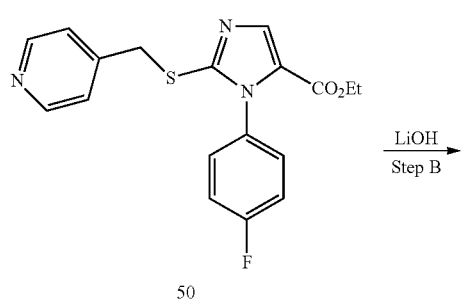

Step A:

Ethyl 1-(4-fluorophenyl)-2-(pyridine-4-ylmethyl)thio)-1H-imidazole-5-carboxylate (50) was prepared in a similar manner as that described for the synthesis of compound 9 using ethyl 1-(4-fluorophenyl)-2-mercapto-1H-imidazole-5-carboxylate (6) (300 mg, 1.127 mmol), pyridine-4-ylmethyl methanesulfonate (253 mg, 1.352 mmol), potassium carbonate (777 mg, 5.635 mmol) in DMF (20 mL).

Step B:

1-(4-Fluorophenyl)-2-((pyridin-4-ylmethyl)thio)-1H-imidazole-5-carboxylic acid (51) was prepared in a similar manner as that described for the synthesis of compound 11 using ethyl 1-(4-fluorophenyl)-2-(pyridine-4-ylmethyl)thio)-1H-imidazole-5-carboxylate (50) (390 mg, 1.09 mmol), 1N LiOH (5 mL) in THF (5 mL) and MeOH (5 mL).

Intermediate 21

2-Chloro-6-fluorophenethyl methanesulfonate (52)

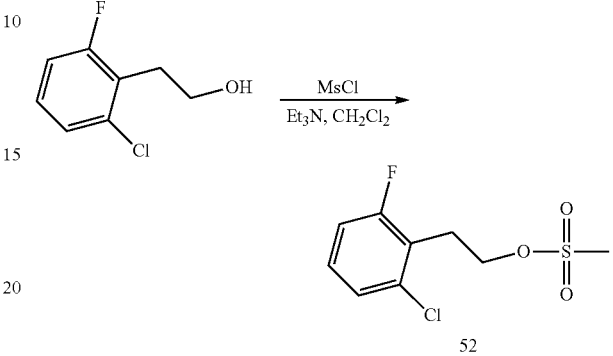

2-(2-chloro-6-fluorophenyl)ethanol (500 mg, 2.87 mmol), was dissolved in dichloromethane (20 mL), and triethylamine (870 mg, 8.61 mmol) was added to the reaction mixture. The solution was cooled to 0° C. and methanesulfonyl chloride (492 mg, 4.31 mmol) was added slowly. After the addition was complete, the reaction was stirred at 0° C. for 15 min and at room temperature for 4 hours. Water was slowly added and the solution was extracted with dichloromethane. The organic layer was washed with brine, and dried over sodium sulfate and concentrated in vacuo to give the residue 2-chloro-6-fluorophenethyl methanesulfonate (52) as a clear oil.

Intermediate 22

2-((2-Chloro-6-fluorophenethyl)sulfonyl)-1-(4-fluorophenyl)-1H-imidazole-5-carboxylic acid (55)

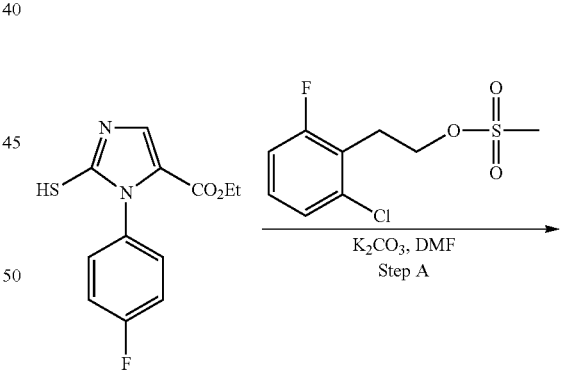

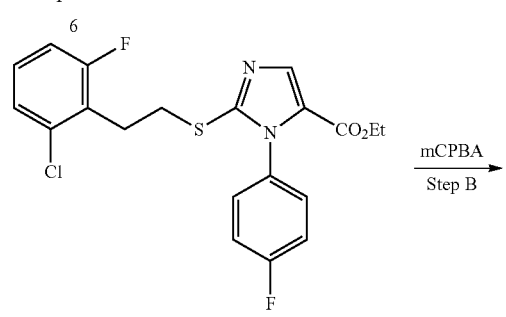

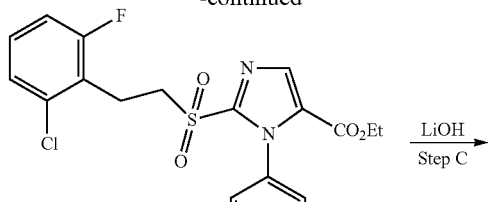
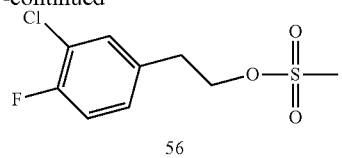

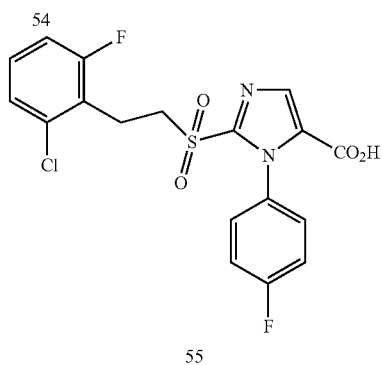

3-Chloro-4-fluorophenethyl methanesulfonate (59) was prepared in a similar manner as that described for the synthesis of compound 52 using 3-chloro-4-fluorophenethanol (1 g, 5.72 mmol), sulfonyl chloride (1 g, 8.58 mmol), and triethylamine (1.7 g, 17.16 mmol) in CH$_2$Cl$_2$ (40 mL).

Intermediate 24

1-(4-Fluorophenyl)-4-methyl-2-((2,3,6-trifluorobenzyl)thio)-1H-imidazole-5-carboxylic acid (59)

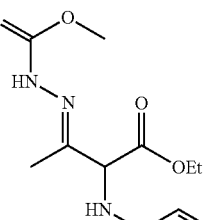

Step A:

Ethyl 2-((2-chloro-6-fluorophenethyl)thio)-1-(4-fluorophenyl)-1H-imidazole-5-carboxylate (53) was prepared in a similar manner as that described for the synthesis of compound 9 using ethyl 1-(4-fluorophenyl)-2-mercapto-1H-imidazole-5-carboxylate (6) (700 mg, 2.62 mmol), 2-chloro-6-fluorophenethyl methanesulfonate (813 mg, 3.144 mmol), potassium carbonate (1.1 g, 7.86 mmol) in DMF (20 mL).

Step B:

Ethyl 2-((2-chloro-6-fluorophenethyl)sulfonyl)-1-(4-fluorophenyl)-1H-imidazole-5-carboxylate (54) was prepared in a similar manner as that described for the synthesis of compound 20 using ethyl 2-((2-chloro-6-fluorophenethyl)thio)-1-(4-fluorophenyl)-1H-imidazole-5-carboxylate (53) (100 mg, 0.236 mmol), m-CPBA (122 mg, 0.708 mmol) in CH$_2$Cl$_2$ (10 mL).

Step C:

2-((2-Chloro-6-fluorophenethyl)sulfonyl)-1-(4-fluorophenyl)-1H-imidazole-5-carboxylic acid (55) was prepared in a similar manner as that described for the synthesis of compound 11 using ethyl 2-((2-chloro-6-fluorophenethyl)sulfonyl)-1-(4-fluorophenyl)-1H-imidazole-5-carboxylate (54) (250 mg, 0.5495 mmol), 1N LiOH (5 mL) in THF (5 mL) and MeOH (5 mL).

Intermediate 23

3-Chloro-4-fluorophenethyl methanesulfonate (56)

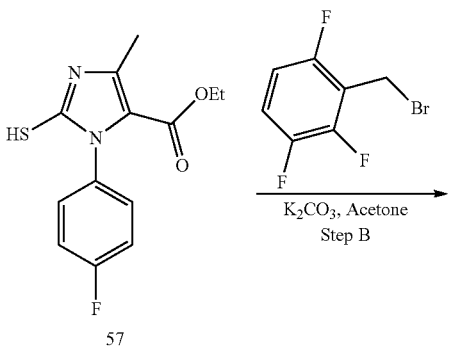

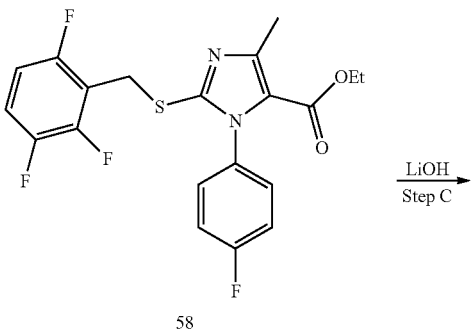

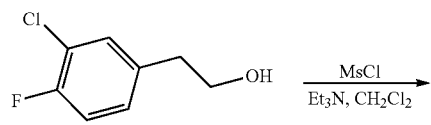

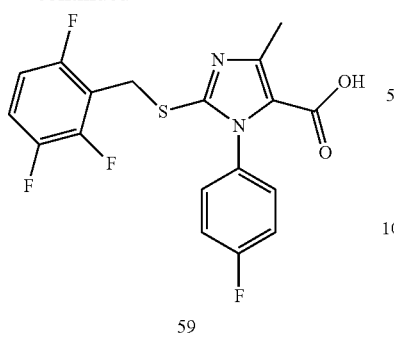

59

Step A:

To a suspension of methyl 2-(4-ethoxy-3-((4-fluorophenyl)amino)-4-oxobutan-2-ylidene)hydrazinecarboxylate (3.1 g, 10 mmol) (this material was synthesized according to the protocol described in *J. Org. Chem. Soc.* 1978, 43, 3392) in 4N HCl (100 mL) was added potassium thiocyanate (1.5 g, 15 mmol) and the mixture was heated to 70° C. for 2 hours. After cooling to room temperature, the solid was filtered and dried to afford ethyl 1-(4-fluorophenyl)-2-mercapto-4-methyl-1H-imidazole-5-carboxylate (57).

Step B:

Ethyl 1-(4-fluorophenyl)-4-methyl-2-((2,3,6-trifluorobenzyl)thio)-1H-imidazole-5-carboxylate (58) was prepared in a similar manner as that described for the synthesis of compound 10 using 1-(4-fluorophenyl)-2-mercapto-4-methyl-1H-imidazole-5-carboxylate (57) (500 mg, 1.78 mmol), 2,3,6-trifluorobenzyl bromide (560 mg, 2.49 mmol) and potassium carbonate (736 mg, 6 mmol) in acetone (18 mL).

Step C:

1-(4-Fluorophenyl)-4-methyl-2-((2,3,6-trifluorobenzyl)thio)-1H-imidazole-5-carboxylic acid (59) was prepared in a similar manner as that described for the synthesis of compound 11 using ethyl 1-(4-fluorophenyl)-4-methyl-2-((2,3,6-trifluorobenzyl)thio)-1H-imidazole-5-carboxylate (58) (300 mg, 0.71 mmol), 1N LiOH (5 mL) in THF (5 mL) and MeOH (5 mL).

Intermediate 25

1-(1-(4-Fluorophenyl)-4-methyl-2-((2,3,6-trifluorobenzyl)thio)-1H-imidazol-5-yl)ethanol (62)

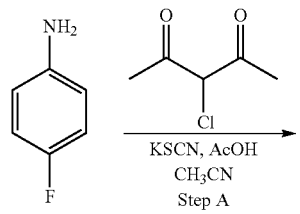

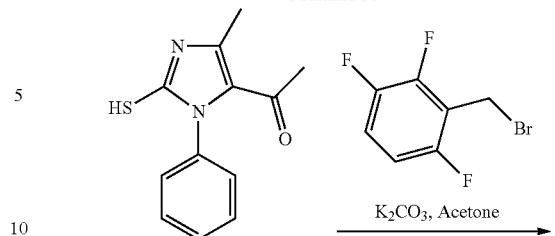

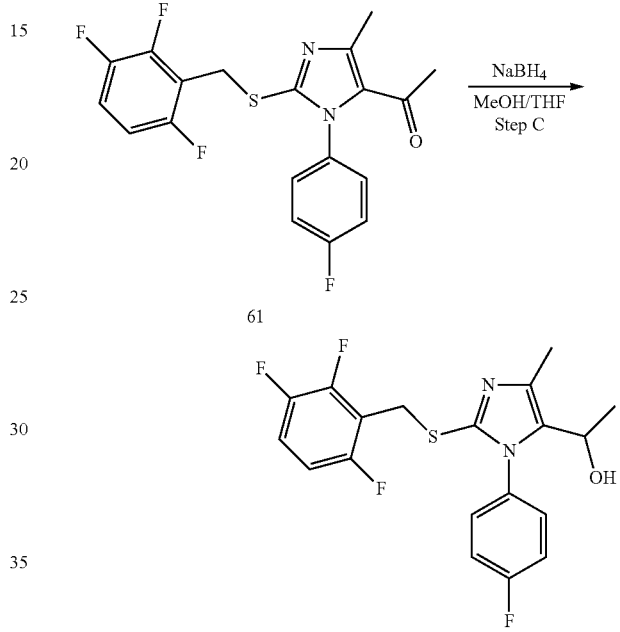

Step A:

1-(1-(4-Fluorophenyl)-2-mercapto-4-methyl-1H-imidazol-5-yl)ethanone (60) was prepared in a similar manner as that described for the synthesis of compound 57 using 4-fluoroaniline (2 g, 18 mmol), 3-chloropentane-2,4-dione (2.7 g, 19.8 mmol), potassium thiocyanate (3.5 g, 36 mmol) and acetic acid (10 mL) in acetonitrile (100 mL).

Step B:

Methyl 1-(4-fluorophenyl)-4-methyl-2-((2,3,6-trifluorobenzyl)thio)-1H-imidazol-5-yl)ethanone (61) was prepared in a similar manner as that described for the synthesis of compound 10 using 1-(1-(4-fluorophenyl)-2-mercapto-4-methyl-1H-imidazol-5-yl)ethanone (60) (500 mg, 2 mmol), 2,3,6-trifluorobenzyl bromide (540 mg, 2.4 mmol) and potassium carbonate (828 mg, 6 mmol) in acetone (20 mL).

Step C:

Methyl 1-(4-fluorophenyl)-4-methyl-2-((2,3,6-trifluorobenzyl)thio)-1H-imidazol-5-yl)ethanone (61) (190 mg, 0.482 mmol) was dissolved in MeOH/THF (5 mL/10 mL) and sodium borohydride (60 mg, 1.45 mmol) was added to the reaction mixture. The reaction was stirred overnight at room temperature, water was added and the solution was extracted with ethyl acetate. The combined organic layer was washed with brine, dried over sodium sulfate, filtered and concentrated in vacuo to afford 1-(1-(4-fluorophenyl)-4-methyl-2-((2,3,6-trifluorobenzyl)thio)-1H-imidazol-5-yl)ethanol (62) as a clear oil.

Intermediate 26

Methyl 1-(4-fluorophenyl)-2-((2,3,6-trifluorobenzyl)amino)-1H-imidazole-5-carboxylic acid (69)

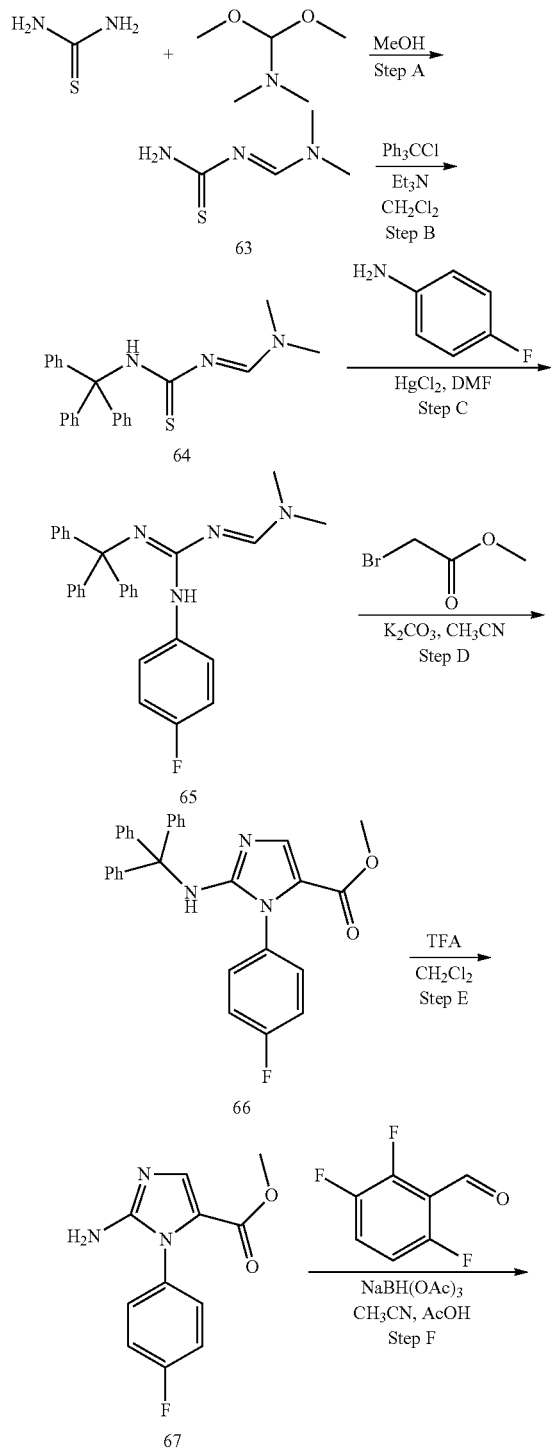

Step A:
N,N-dimethylformamide dimethylacetal (15.22 g, 128 mmol) and thiourea (9.8 g, 128 mmol) were stirred in MeOH (150 mL) at room temperature for 4 hours. The reaction mixture was concentrated and dried in vacuo to provide (E)-N'-carbamothioyl-N,N-dimethylformimidamide (63).

Step B:
(E)-N'-carbamothioyl-N,N-dimethylformimidamide (63) (5 g, 38 mmol), tritylchloride (11.6 g, 41.8 mmol) and trietheylamine (16 mL, 114 mmol) were refluxed in dichloromethane overnight. The reaction mixture was cooled to room temperature and filtered through a plug of celite. The resulting filtrate was washed with saturated sodium bicarbonate solution, followed with brine. The organic layer was dried with sodium sulfate, filtered and concentrated in vacuo. The residue was purified by flash chromatography on silica gel column (40%-100% EtOAc in hexanes) to afford (E)-N,N-dimethyl-N'-(tritylcarbamothioyl) formimidamide (64) as a white solid.

Step C:
(E)-N,N-dimethyl-N'-(tritylcarbamothioyl)formimidamide (64) (2.47 g, 6.6 mmol), 4-fluoroaniline (0.70 mL, 7.26 mmol), and mercuric chloride (3.6 g, 13.2 mmol) were stirred at room temperature in DMF (50 mL) overnight. The reaction mixture was filtered through a plug of celite and washed with ethyl acetate. The organic filtrate was washed with water, saturated sodium bicarbonate, and brine. The organic layer was dried over sodium sulfate, filtered, and concentrated in vacuo. The residue was purified by flash column chromatography on silica gel (10-100% EtOAc in hexanes) to provide (E)-N'-((E)-N(4-fluorophenyl)-N'-tritylcarbamimdidoyl)-N,N-dimethylformimidamide (65).

Step D:
(E)-N'-((E)-N(4-fluorophenyl)-N'-tritylcarbamimdidoyl)-N,N-dimethylformimidamide (65) (660 mg, 1.47 mmol), methyl bromoacetate (270 mg, 1.76 mmol), and K$_2$CO$_3$ (610 mg, 4.41 mmol) were stirred in acetonitrile (20 mL) at room temperature overnight. The reaction mixture was filtered through a plug of celite and concentrated in vacuo to give methyl 1-(4-fluorophenyl)-2-(tritylamino)-1H-imidazole-5-carboxylate (66).

Step E:

To a solution of methyl 1-(4-fluorophenyl)-2-(tritylamino)-1H-imidazole-5-carboxylate (66) (200 mg, 0.419 mmol) in dichloromethane (10 mL) was added trifluoroacetic acid (5 mL). The reaction was stirred at room temperature overnight, concentrated and the residue was dissolved in ethyl acetate. The organic layer was washed with saturated sodium bicarbonate, brine, dried over sodium sulfate, filtered, and concentrated and in vacuo to afford methyl 2-amino-1-(4-fluorophenyl)-1H-imidazole-5-carboxylate (67) as a yellow solid.

Step F:

Methyl 2-amino-1-(4-fluorophenyl)-1H-imidazole-5-carboxylate (67) (200 mg, 0.85 mmol), 2,3,6-trifluorobenzaldehyde (163 mg, 1.02 mmol), sodium triacetoxyborohydride (450 mg, 2.13 mmol) and catalytic amounts of acetic acid in acetonitrile (5 mL) was heated under microwave radiation for 2 hours. The reaction mixture was quenched with saturated sodium bicarbonate solution and extracted with ethyl acetate. The organic layer was washed with brine, dried over sodium sulfate, filtered, and concentrated in vacuo. The residue was purified by flash column chromatography on silica gel (0-100% EtOAc in hexanes) to afford methyl 1-(4-fluorophenyl)-2-((2,3,6-trifluorobenzyl)amino)-1H-imidazole-5-carboxylate (68).

Step G:

Methyl 1-(4-fluorophenyl)-2-((2,3,6-trifluorobenzyl)amino)-1H-imidazole-5-carboxylic acid (69) was prepared in a similar manner as that described for the synthesis of compound 11 using 1-(4-fluorophenyl)-2-((2,3,6-trifluorobenzyl)amino)-1H-imidazole-5-carboxylate (68) (60 mg, 0.158 mmol), 1N LiOH (5 mL) in THF (5 mL) and MeOH (5 mL).

Intermediate 27

1-(4-Fluorophenyl)-2-(methyl(2,3,6-trifluorobenzyl)amino)-1H-imidazole-5-carboxylic acid (71)

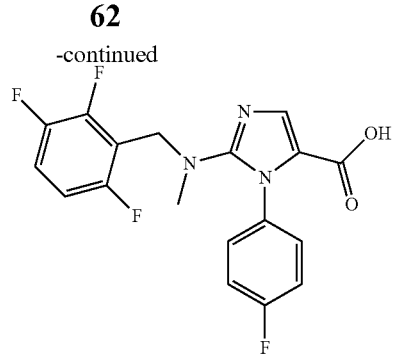

71

Step A:

Methyl 1-(4-fluorophenyl)-2-((2,3,6-trifluorobenzyl)amino)-1H-imidazole-5-carboxylate (68) (115 mg, 0.303 mmol), sodium bis(trimethylsilyl)amide in THF (1M, 0.6 mL, 0.606 mmol), and MeI (141 mg, 0.909 mmol) in THF (2 mL) were sealed in a tube and stirred at room temperature overnight. The reaction was quenched with water and extracted with ethyl acetate. The organic layer was washed with brine, dried over sodium sulfate, filtered, and concentrated in vacuo. The residue was purified by flash column chromatography on silica gel (0-100% EtOAc in hexanes) to afford methyl 1-(4-fluorophenyl)-2-(methyl(2,3,6-trifluorobenzylamino)-1H-imidazole-5-carboxylate (70).

Step B:

1-(4-Fluorophenyl)-2-(methyl(2,3,6-trifluorobenzyl)amino)-1H-imidazole-5-carboxylic acid (71) was prepared in a similar manner as that described for the synthesis of compound 11 using 1-(4-fluorophenyl)-2-(methyl(2,3,6-trifluorobenzylamino)-1H-imidazole-5-carboxylate (70) (24 mg, 0.061 mmol) and 1N LiOH (5 mL) in THF (5 mL) and MeOH (5 mL).

Intermediate 28

2-(((2,6-Dichlorophenyl)thio)methyl)-1-(4-fluorophenyl)-1H-imidazole-5-carboxylic acid (73)

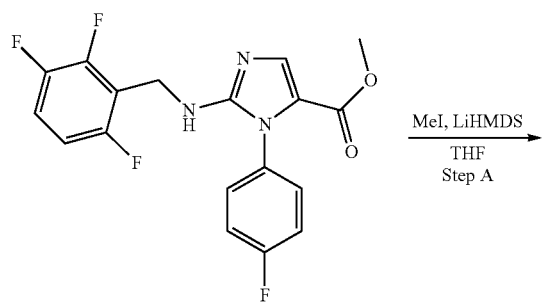

68

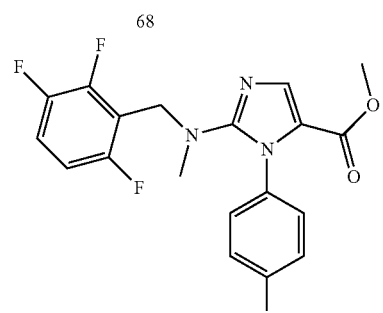

70

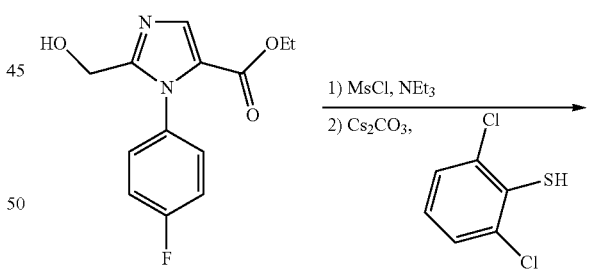

15

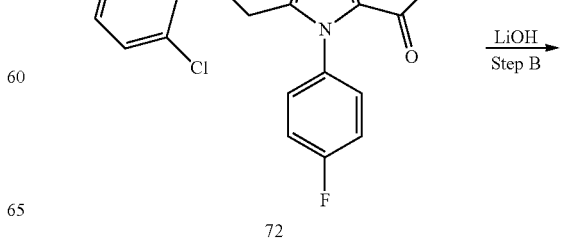

72

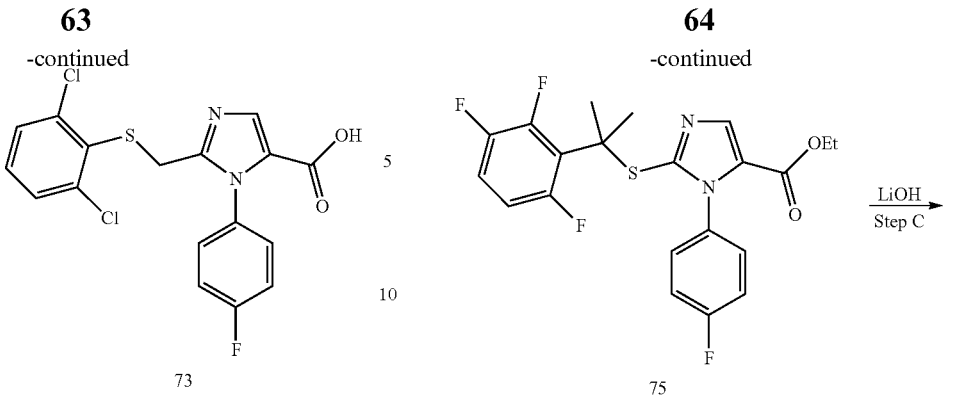

Step A:

To a solution of ethyl 1-(4-fluorophenyl)-2-(hydroxymethyl)-1H-imidazole-5-carboxylate (15) (1.25 g, 4.7 mmol) and triethylamine (0.95 g, 9.4 mmol) in $CH_2Cl_2$ (30 mL) was added methanesulfonyl chloride (0.65 g, 5.64 mmol) at 0° C. and the reaction was stirred at 0° C. After 3 hours, 2,6-dichlorobenzenethiol (0.84 g mg, 4.7 mmol) and cesium carbonate (2.28 g, 7 mmol) were added and the reaction was stirred at room temperature for 1 hour. The mixture was filtered by vacuum filtration, and concentrated in vacuo. The residue was purified by flash column chromatography on silica gel to afford ethyl 2-(((2,6-dichlorophenyl)thio)methyl)-1-(4-fluorophenyl)-1H-imidazole-5-carboxylate (72).

Step B:

2-(((2,6-Dichlorophenyl)thio)methyl)-1-(4-fluorophenyl)-1H-imidazole-5-carboxylic acid (73) was prepared in a similar manner as that described for the synthesis of compound 7 using ethyl 2-(((2,6-dichlorophenyl)thio)methyl)-1-(4-fluorophenyl)-1H-imidazole-5-carboxylate (72) (1.5 g, 3.5 mmol), lithium hydroxide (1.6 g, 40 mmol), THF (50 mL), methanol (50 mL), and water (20 mL).

Intermediate 29

1-(4-Fluorophenyl)-2-((2-(2,3,6-trifluorophenyl)propan-2-yl)thio)-1H-imidazole-5-carboxylic acid (76)

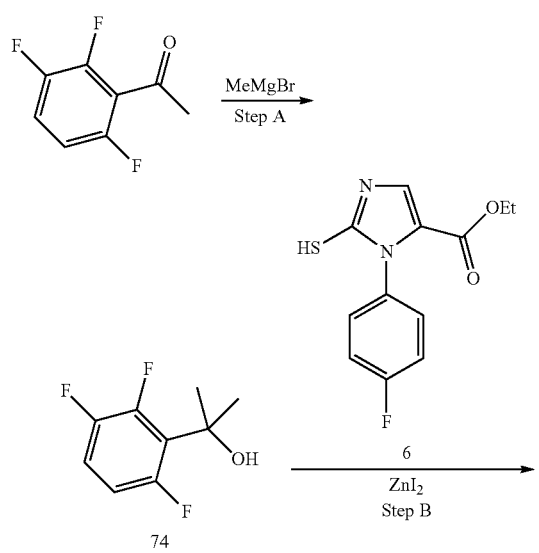

Step A:

To a solution of 1-(2,3,6-trifluorophenyl)ethanone (1.74 g, 10 mmol) in THF (10 mL) was added methyl magnesium bromide (7 mL, 21 mmol) at 0° C. The mixture was stirred at 0° C. for 1 hour. The reaction was quenched by addition of saturated aqueous ammonium chloride and was then extracted with EtOAc. The combined organic layers were washed with water, dried over sodium sulfate, filtered and concentrated in vacuo. The residue was purified by flash column chromatography on silica gel to afford 2-(2,3,6-trifluorophenyl)propan-2-ol. (74).

Step B:

To a solution of 2-(2,3,6-trifluorophenyl)propan-2-ol (74) (0.73 g, 3.8 mmol) and ethyl 1-(4-fluorophenyl)-2-mercapto-1H-imidazole-5-carboxylate (6) (1.12 g, 4.2 mmol) in $CH_2Cl_2$ (5 mL) was added zinc iodide (1.7 g, 5.3 mmol) at room temperature. The mixture was stirred at room temperature overnight. The reaction was diluted with EtOAc and washed with 0.5 N NaOH, water, brine, dried over sodium sulfate, filtered and concentrated in vacuo. The residue was purified by flash column chromatography on silica gel to afford ethyl 1-(4-fluorophenyl)-2-((2-(2,3,6-trifluorophenyl)propaN-2-yl)thio)-1H-imidazole-5-carboxylate. (75).

Step C:

1-(4-Fluorophenyl)-2-((2-(2,3,6-trifluorophenyl)propan-2-yl)thio)-1H-imidazole-5-carboxylic acid (76) was prepared in a similar manner as that described for the synthesis of compound 7 using ethyl 1-(4-fluorophenyl)-2-((2-(2,3,6-trifluorophenyl)propaN-2-yl)thio)-1H-imidazole-5-carboxylate (75) (0.14 g, 3.5 mmol), lithium hydroxide (15 mg, 0.64 mmol), THF (5 mL), methanol (3 mL), and water (2 mL).

Intermediate 30

4-(4-Fluorophenyl)-5-mercapto-N-methyl-N-(pyridin-4-ylmethyl)-4H-1,2,4-triazole-3-carboxamide (80)

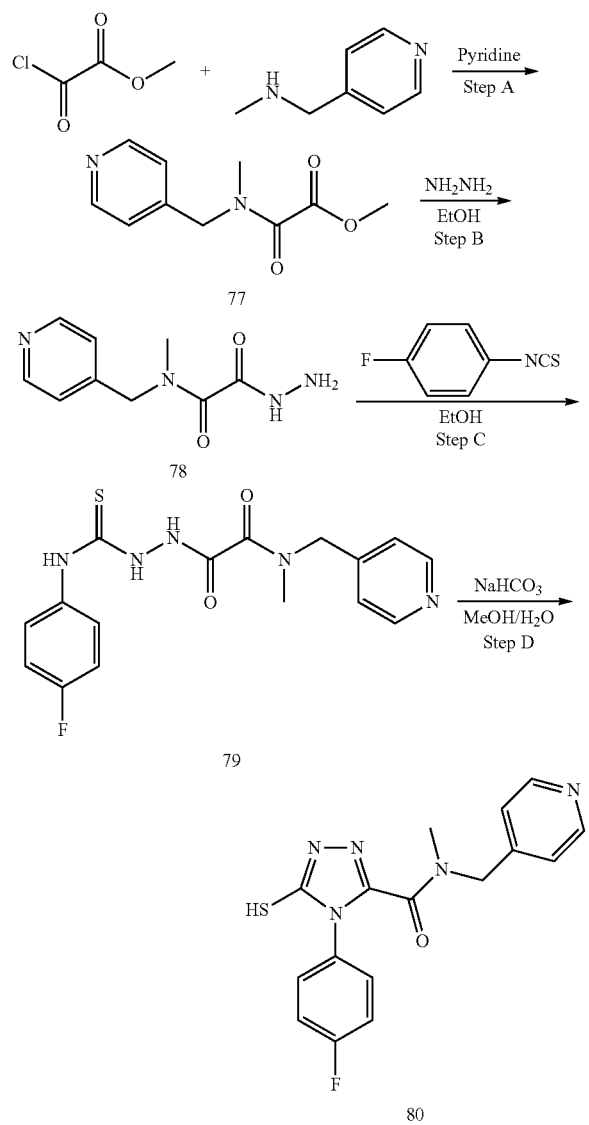

Step A:

A solution of methyl chlorooxoacetate (2.01 g, 16.37 mmol), N-methyl-N-(4-pyridinylmethyl)amine (2.0 g, 16.37 mmol) and pyridine (1.6 mL, 19.64 mmol) in anhydrous dichloromethane (10 mL) was stirred at 50° C. for 2 h. The mixture was evaporated in vacuo and the residue was purified by flash column chromatography on silica gel (40%-100% EtOAc in hexanes) to afford methyl 2-(methyl(pyridin-4-ylmethyl)amino)-2-oxoacetate (77) as a pale yellow oil (0.96 g).

Step B:

A mixture of 2-(methyl(pyridin-4-ylmethyl)amino)-2-oxoacetate (77) (0.96 g, 4.61 mmol) and hydrazine (0.21 mL, 5.82 mmol) in EtOH (15 mL) was stirred at 80° C. for 18 h. The solvent was removed in vacuo to provide 2-hydrazinyl-N-methyl-2-oxo-N-(pyridin-4-ylmethyl)acetamide (78) as a pale yellow solid. This product was directly used in the next step reaction without further purification.

Step C:

A mixture of 2-hydrazinyl-N-methyl-2-oxo-N-(pyridin-4-ylmethyl)acetamide (78) (0.96 g, 4.61 mmol) and 4-fluorophenyl isothiocyanate (0.71 g, 4.16 mmol) in EtOH was refluxed for 2 h. The reaction was cooled down to room temperature and concentrated in vacuo to afford 2-(2-((4-fluorophenyl)carbamothioyl)hydrazinyl)-N-methyl-2-oxo-N-(pyridin-4-ylmethyl)acetamide (79) as yellow crystals was obtained in a quantitative yield.

Step D:

A mixture of 2-(2-((4-fluorophenyl)carbamothioyl)hydrazinyl)-N-methyl-2-oxo-N-(pyridin-4-ylmethyl)acetamide (79) (0.75 g, 2.075 mmol) and sodium bicarbonate (0.35 g, 4.17 mmol) in methanol/water (1:1) (20 mL) was stirred at 80° C. for 26 h. After evaporation of solvent, the residue was extracted with dichloromethane/methanol (10:1) (3×60 mL). The combined organic phase was evaporated and the crude product was purified by flash column chromatography on silica gel (0%-20% MeOH in dichloromethane) to provide 4-(4-fluorophenyl)-5-mercapto-N-methyl-N-(pyridin-4-ylmethyl)-4H-1,2,4-triazole-3-carboxamide (80) as a white solid (0.11 g).

Intermediates 31-70

The following compounds were prepared in a similar manner as that described for the synthesis of compound 11.

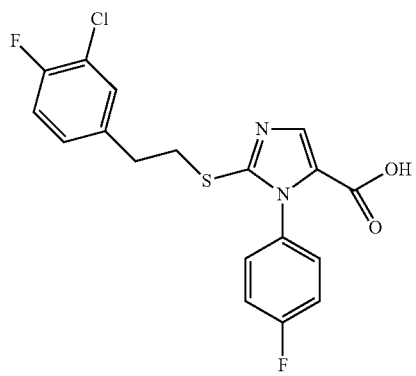

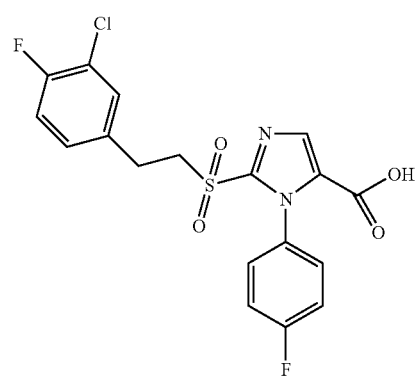

-continued
83
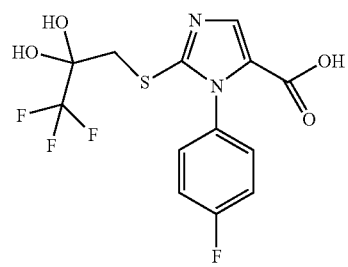
84
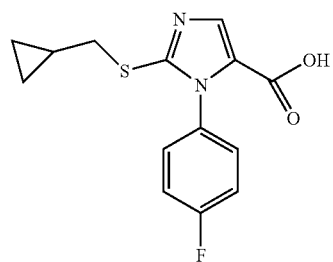
85
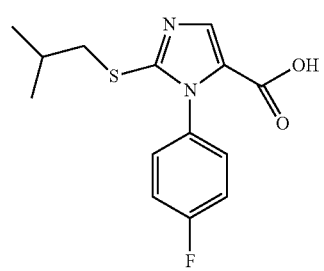
86
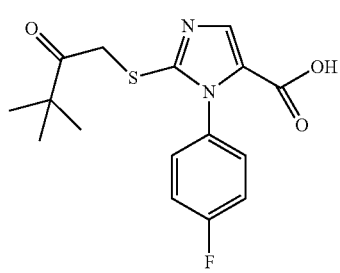
87
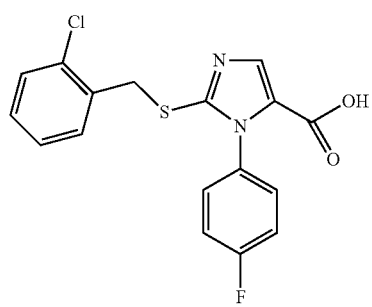
-continued
88
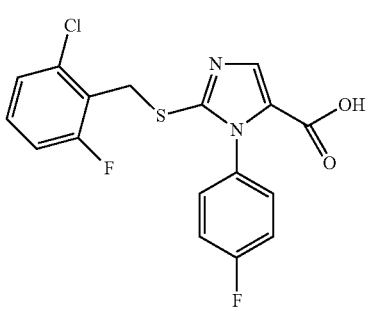
89
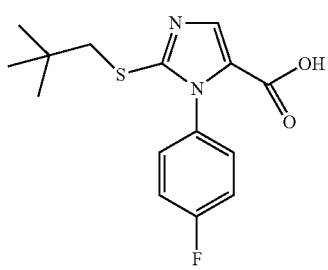
90
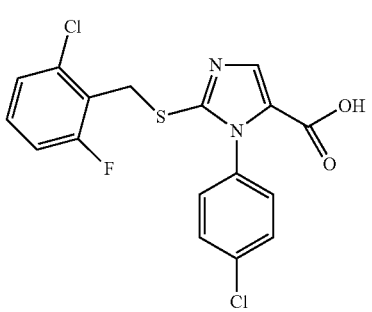
91
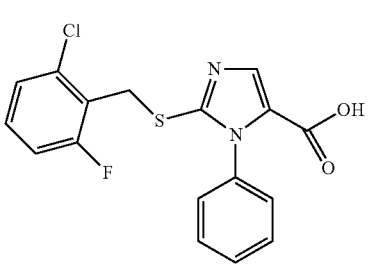
92
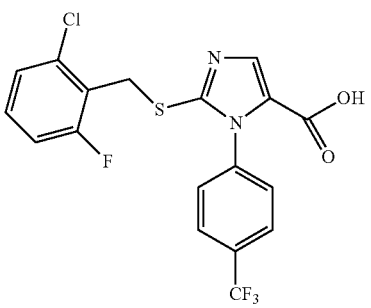

93
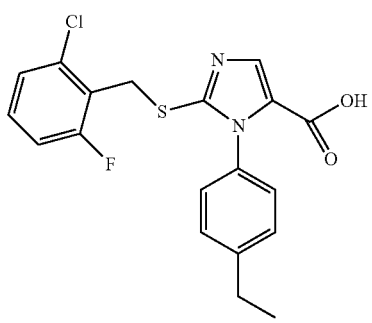
94
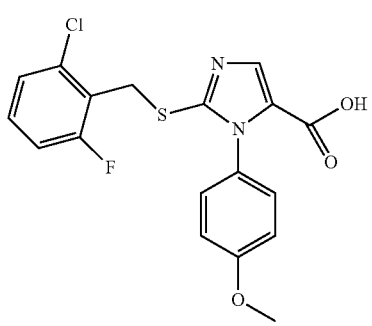
95
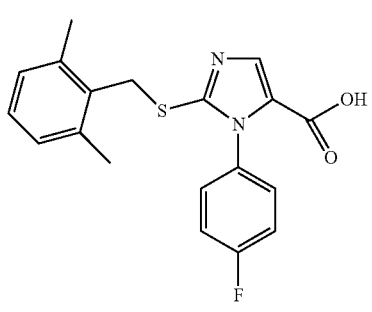
96
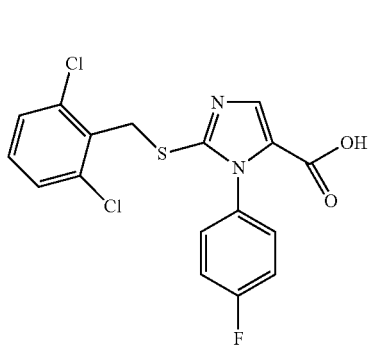
97
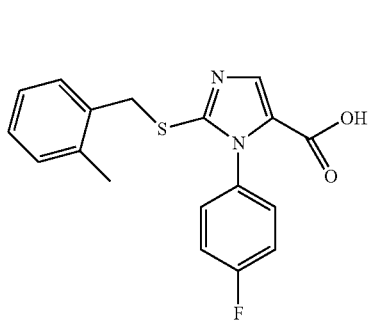
98
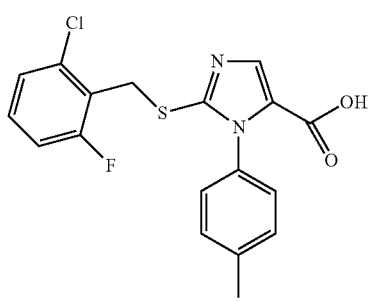
99
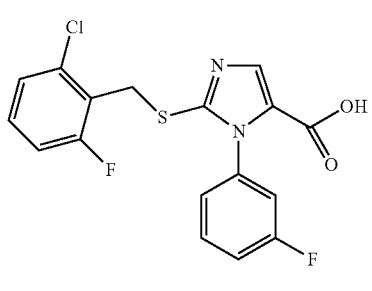
100
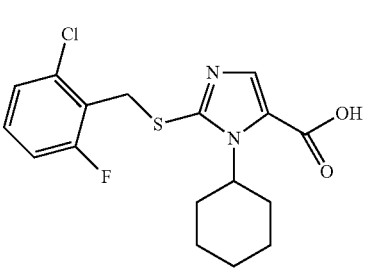
101
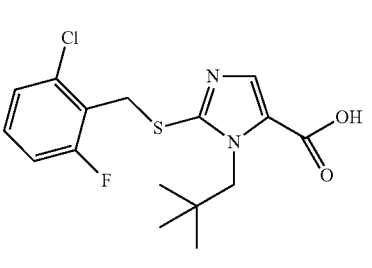
102
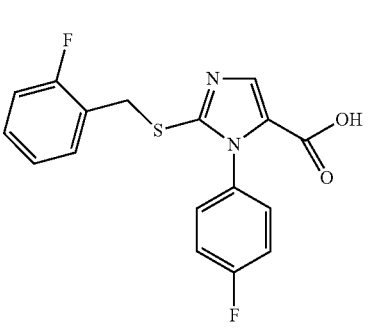

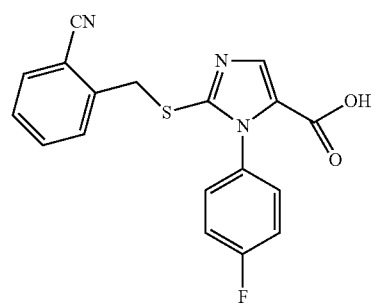
103
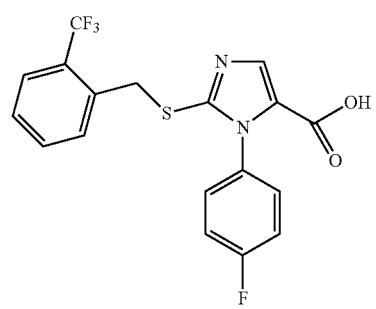
104
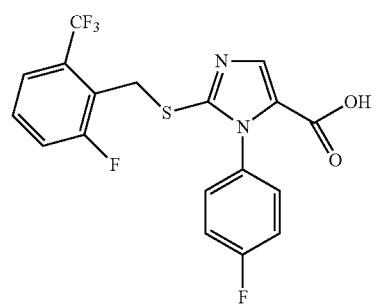
105
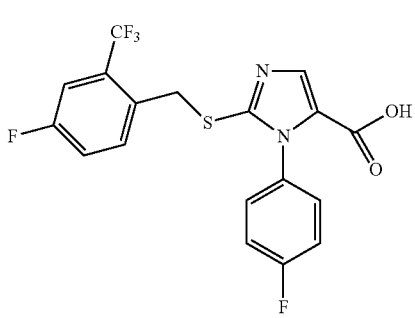
106
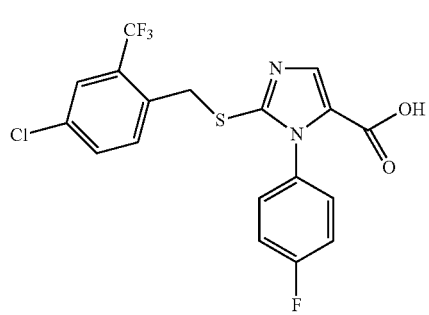
107
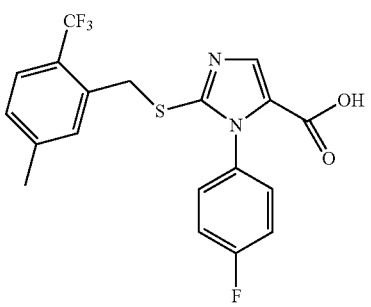
108
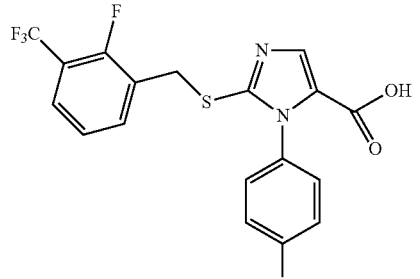
109
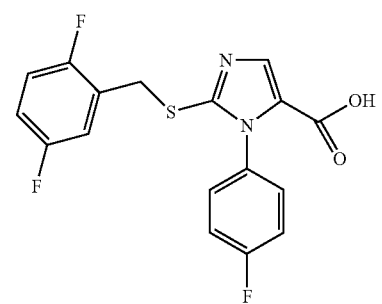
110

113 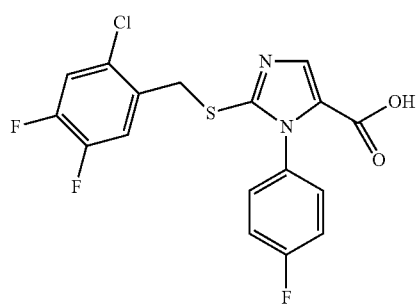
114 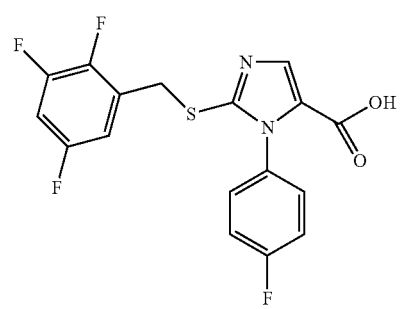
115 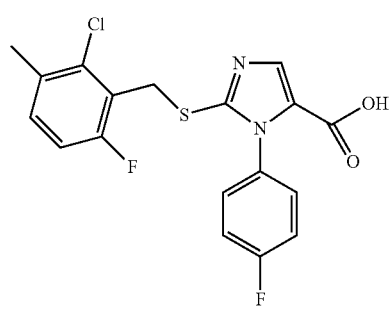
116 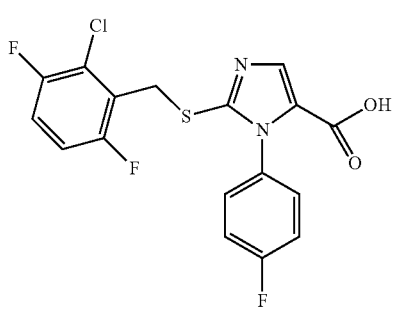
117 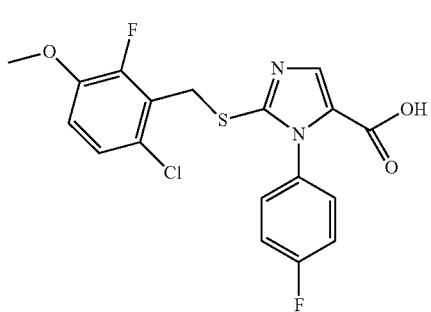
118 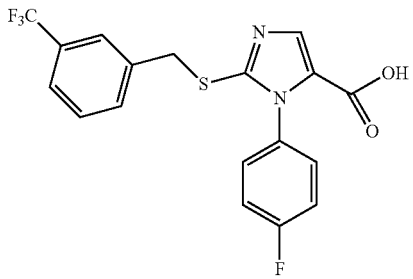
119 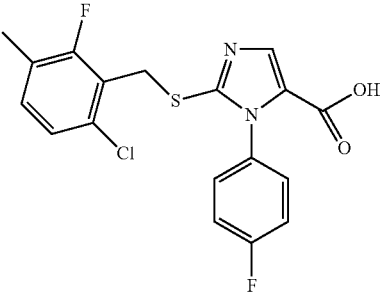
120 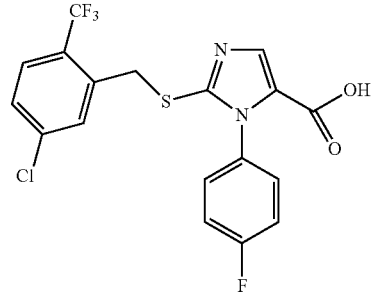
Preparation of Examples
Example 1
N-Benzyl-2-((2-chloro-6-fluorobenzyl)thio)-1-(4-fluorophenyl)-N-methyl-1H-imidazole-5-carboxamide (500)
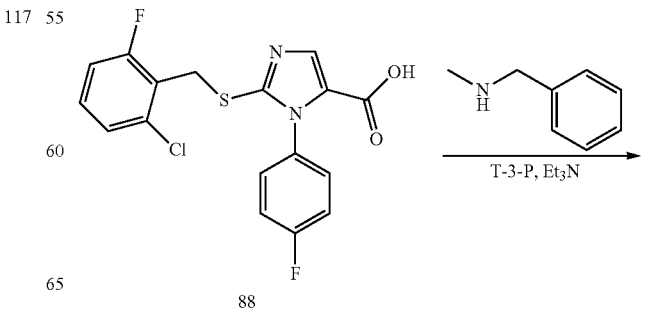

-continued

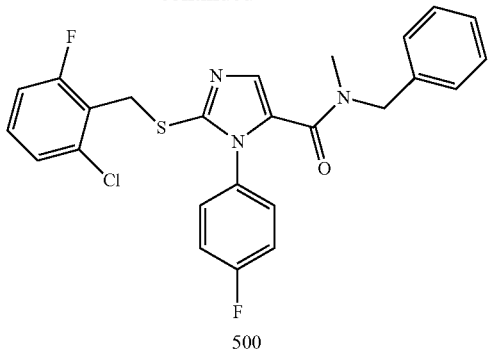

500

A solution of 2-((2-chloro-6-fluorobenzyl)thio)-1-(4-fluorophenyl)-1H-imidazole-5-carboxylic acid (88) (50 mg, 0.13 mmol), N-benzylmethylamine (16 mg, 0.13 mmol), triethylamine (0.12 mL, 0.79 mmol) and propylphosphonic anhydride (T-3-P)(50% in ethyl acetate, 0.12 mL, 0.20 mmol) in dichloromethane (1.5 mL) was stirred overnight at room temperature. The reaction was concentrated in vacuo and the residue was purified by flash column chromatography on silica gel (50%-100% EtOAc in hexanes) to give N-benzyl-2-((2-chloro-6-fluorobenzyl)thio)-1-(4-fluorophenyl)-N-methyl-1H-imidazole-5-carboxamide (500). $^1$H NMR (400 MHz, CDCl$_3$) δ: 7.37-7.25 (m, 4H), 7.20-6.99 (m, 8H), 6.93-6.90 (m, 1H), 4.64 (s, 2H), 4.45 (s, 2H), 2.96 (s, 3H). LC-MS ESI m/z; found 484.1 [M+H]$^+$.

Example 2

1-(1,3-Dimethyl-1H-pyrazol-4-yl)-N-((1-(4-fluorophenyl)-2-((2,3,6-trifluorobenzyl)sulfinyl)-1H-imidazol-5-yl)methyl)-N-methylmethanamine (501)

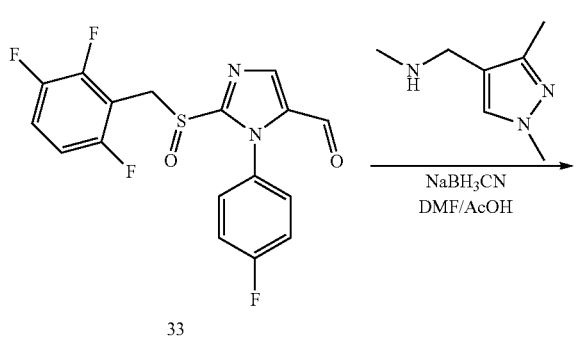

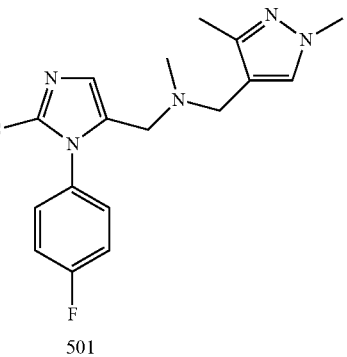

501

A solution of 1-(4-fluorophenyl)-2-((2,3,6-trifluorobenzyl)sulfinyl)-1H-imidazole-5-carbaldehyde (33) (39 mg, 0.10 mmol), 1-(1,3-dimethyl-1H-pyrazol-4-yl)-N-methylmethanamine (15 mg, 0.11 mmol), sodium cyanoborohydride (30 mg, 0.11 mmol) and DMF/acetic acid (10/1, 1 mL) was stirred at room temperature overnight. The reaction mixture was directly loaded on to reverse phase preparative HPLC column and purified to yield 1-(1,3-dimethyl-1H-pyrazol-4-yl)-N-((1-(4-fluorophenyl)-2-((2,3,6-trifluorobenzyl)sulfinyl)-1H-imidazol-5-yl)methyl)-N-methylmethanamine (501). $^1$H NMR (400 MHz, CDCl$_3$) δ: 7.63 (s, 1H), 7.52 (s, 1H), 7.45-7.36 (m, 1H), 7.24-7.09 (m, 4H), 6.90-6.85 (m, 1H), 4.87 (d, J=13.0, 1H), 4.58 (d, J=13.0, 1H), 4.27 (d, J=14.5, 1H), 4.11 (s, 1H), 3.99 (d, J=13.2, 1H), 3.90-3.79 (m, 4H), 2.57 (s, 3H), 2.18 (s, 3H). LC-MS ESI m/z; found 506.2 [M+H]$^+$.

Example 3

1-(4-Fluorophenyl)-N-methyl-N-((3-methylpyridin-4-yl)methyl)-2-((2,3,6-trifluorobenzyl)thio)-1H-imidazole-5-carboxamide (502)

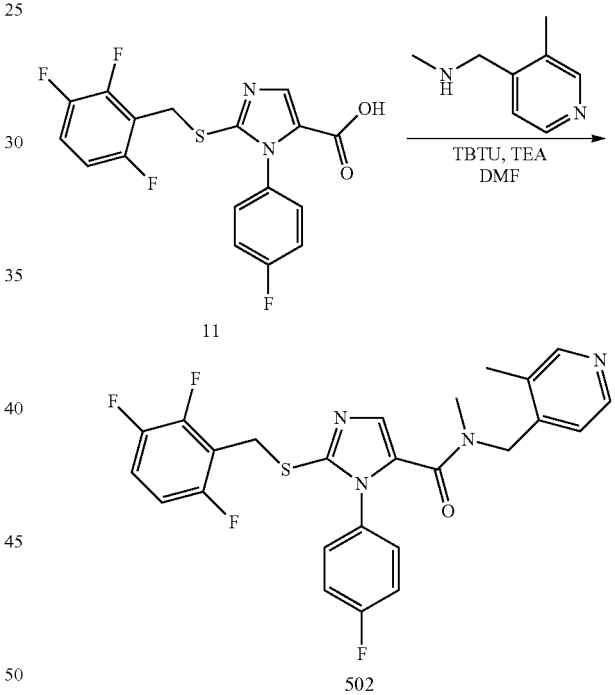

502

To a solution of 1-(4-fluorophenyl)-2-((2,3,6-trifluorobenzyl)thio)-1H-imidazole-5-carboxylic acid (11) (200 mg, 0.52 mmol) in DMF (5 mL) N-methyl-1-(3-methylpyridin-4-yl)methanamine (86 mg, 0.63 mmol), and triethylamine (159 mg, 1.57 mmol) was added. At room temperature, TBTU (252 mg, 0.785 mmol) was added in one portion and the mixture was stirred at room temperature overnight. The mixture was quenched with water, and extracted with ethyl acetate. The organic layer was washed with brine, and dried over sodium sulfate. The mixture was filtered and concentrated in vacuo. The residue was purified by flash chromatography on silica gel (10%-80% ethyl acetate in hexanes) to give 1-(4-fluorophenyl)-N-methyl-N-((3-methylpyridin-4-yl)methyl)-2-((2,3,6-trifluorobenzyl)thio)-1H-imidazole-5-carboxamide (502). $^1$H NMR (400 MHz, CDCl$_3$) δ: 8.41-8.36 (m, 2H), 7.20-7.17 (m, 2H) 7.12-6.99 (m, 3H), 6.78-6.74 (m, 3H), 4.62 (s, 2H), 4.35 (s, 2H), 3.04 (s, 3H), 2.20 (s, 3H). LC-MS ESI m/z; found 501.1 [M+H]⁺.

Example 4

4-((1-(4-Fluorophenyl)-N-methyl-2-((2,3,6-trifluorobenzyl)sulfonyl)-1H-imidazole-5-carboxamido)methyl)-3-methylpyridine 1-oxide (503)

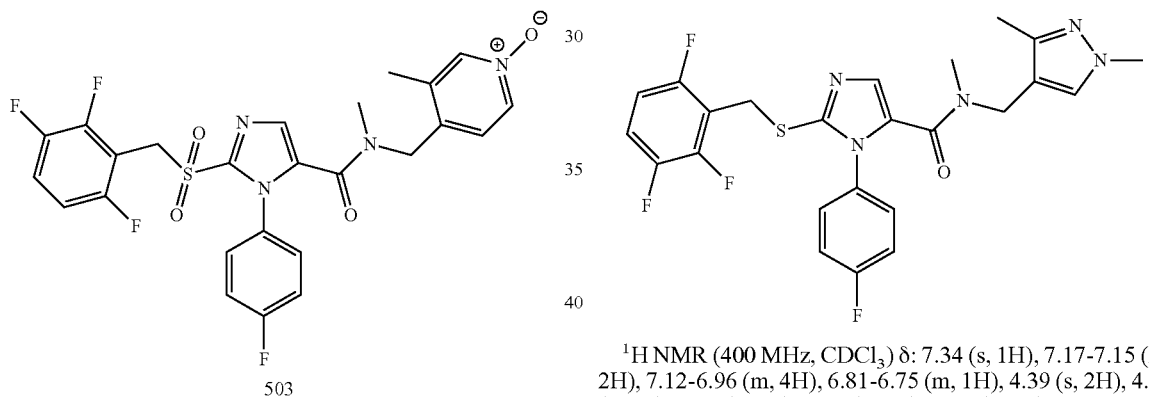

1-(4-Fluorophenyl)-N-methyl-N-((3-methylpyridin-4-yl)methyl)-2-((2,3,6-trifluorobenzyl)thio)-1H-imidazole-5-carboxamide (502) (82 mg, 0.164 mmol) was dissolved in CH₂Cl₂ (5 mL), and m-CPBA (141 mg, 0.82 mmol) was added in portions. The reaction was stirred at room temperature for 5 hours and the solvent was removed in vacuo. The residue was purified by flash column chromatography on silica gel (10-80% EtOAc in hexanes) to afford 4-((1-(4-fluorophenyl)-N-methyl-2-((2,3,6-trifluorobenzyl)sulfonyl)-1H-imidazole-5-carboxamido)methyl)-3-methylpyridine 1-oxide (503) as a white solid. ¹H NMR (400 MHz, CDCl₃) δ: 8.10-7.88 (m, 2H) 7.32-7.28 (m, 2H), 7.25-7.10 (m, 4H), 6.89-6.85 (m, 1H), 6.48 (s, 1H), 4.73 (s, 2H), 4.50 (s, 2H), 2.98 (s, 3H), 2.13 (s, 3H). LC-MS ESI m/z; found 549.1 [M+H]⁺.

Additional representative compounds of this application, prepared by following procedures described in the above examples using appropriate starting materials that will be apparent to those skilled in the art, are shown below.

Example 5

Ethyl 1-(4-fluorophenyl)-2-((2,3,6-trifluorobenzyl)thio)-1H-imidazole-5-carboxylate (504)

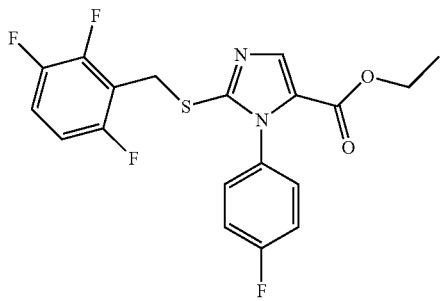 [SMILES: CCOC(=O)c1cnc(SCc2c(F)ccc(F)c2F)n1-c1ccc(F)cc1]

¹H NMR (400 MHz, CDCl₃) δ: 7.86 (s, 1H), 7.22-7.01 (m, 4H), 6.83-6.75 (m, 2H), 4.46 (s, 2H), 4.16 (q, J=7.1, 2H), 1.21 (t, J=7.1, 3H). LC-MS ESI m/z; found 410.6 [M+H]⁺.

Example 6

N-((1,3-Dimethyl-1H-pyrazol-4-yl)methyl)-1-(4-fluorophenyl)-N-methyl-2-((2,3,6-trifluorobenzyl)thio)-1H-imidazole-5-carboxamide (505)

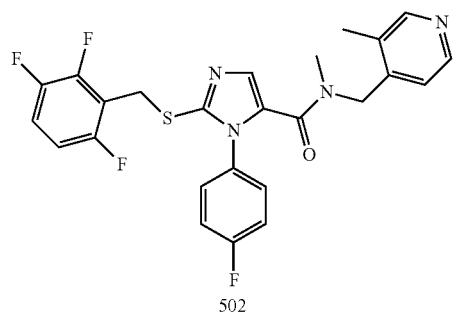

¹H NMR (400 MHz, CDCl₃) δ: 7.34 (s, 1H), 7.17-7.15 (m, 2H), 7.12-6.96 (m, 4H), 6.81-6.75 (m, 1H), 4.39 (s, 2H), 4.35 (s, 2H), 3.77 (s, 3H), 2.98 (s, 3H), 2.14 (s, 3H). LC-MS ESI m/z; found 503.6 [M+H]⁺.

Example 7

1-(1,3-Dimethyl-1H-pyrazol-4-yl)-N-((1-(4-fluorophenyl)-2-((2,3,6-trifluorobenzyl)thio)-1H-imidazol-5-yl)methyl)-N-methylmethanamine (506)

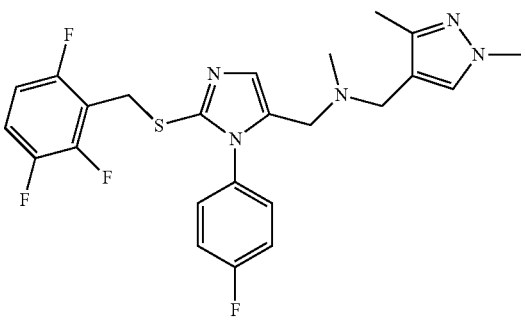 [SMILES: Cc1nn(C)cc1CN(C)Cc1cnc(SCc2c(F)ccc(F)c2F)n1-c1ccc(F)cc1]

$^1$H NMR (400 MHz, CDCl$_3$) δ: 7.11-7.00 (m, 6H), 6.83 (s, 1H), 6.77-6.72 (m, 1H), 4.14 (s, 2H), 3.75 (s, 3H), 3.19 (s, 2H), 3.16 (s, 2H), 2.08 (s, 3H), 2.04 (s, 3H). LC-MS ESI m/z; found 490.0 [M+H]$^+$.

Example 8

N-(3,4-Dimethoxybenzyl)-1-(4-fluorophenyl)-N-methyl-2-((2,3,6-trifluorobenzyl)thio)-1H-imidazole-5-carboxamide (507)

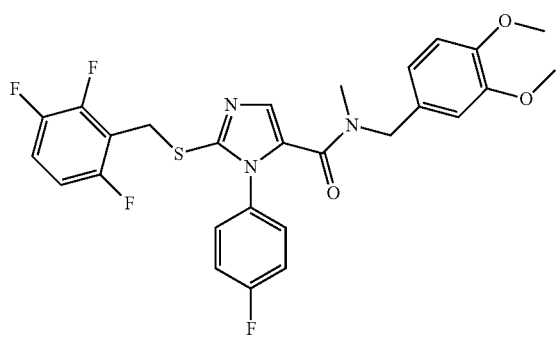 [SMILES: COc1ccc(CN(C)C(=O)c2cnc(SCc3c(F)ccc(F)c3F)n2-c2ccc(F)cc2)cc1OC]

$^1$H NMR (400 MHz, CDCl$_3$) δ: 7.41 (s, 1H), 7.21-6.97 (m, 5H), 6.81-6.75 (m, 2H), 6.67-6.65 (m, 2H), 4.51 (s, 2H), 4.35 (s, 2H), 3.88 (s, 3H), 3.80 (s, 3H), 3.00 (s, 3H). LC-MS ESI m/z; found 545.4 [M+H]$^+$.

Example 9

N-((1,3-Dimethyl-1H-pyrazol-4-yl)methyl)-1-(4-fluorophenyl)-2-((2,3,6-trifluorobenzyl)thio)-1H-imidazole-5-carboxamide (508)

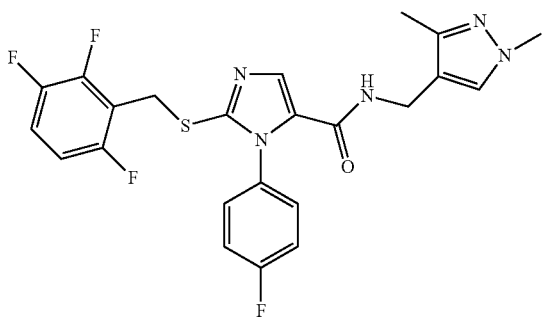 [SMILES: Cc1nn(C)cc1CNC(=O)c1cnc(SCc2c(F)ccc(F)c2F)n1-c1ccc(F)cc1]

$^1$H NMR (400 MHz, CDCl$_3$) δ: 7.54 (s, 1H), 7.22-6.99 (m, 6H), 6.79 (s, 1H), 5.73 (br, 1H), 4.39 (s, 2H), 4.24 (d, J=5.3, 2H), 3.80 (s, 3H), 2.18 (s, 3H). LC-MS ESI m/z; found 489.8 [M+H]$^+$.

Example 10

N-((1,3-Dimethyl-1H-pyrazol-4-yl)methyl)-1-(4-fluorophenyl)-N-methyl-1H-imidazole-5-carboxamide (509)

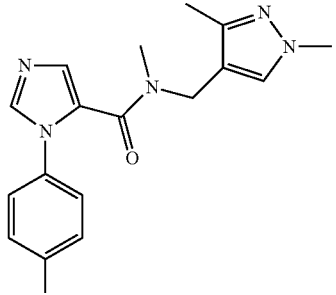

$^1$H NMR (400 MHz, CDCl$_3$) δ: 7.65 (d, J=0.8, 1H), 7.34 (s, 1H), 7.28-7.26 (m, 2H), 7.13 (m, 3H), 4.42 (s, 2H), 3.78 (s, 3H), 2.97 (s, 3H), 2.16 (s, 3H). LC-MS ESI m/z; found 327.6 [M+H]$^+$.

Example 11

(E)-N-((1,3-Dimethyl-1H-pyrazol-4-yl)methyl)-1-(4-fluorophenyl)-N-methyl-2-(2,3,6-trifluorostyryl)-1H-imidazole-5-carboxamide (510)

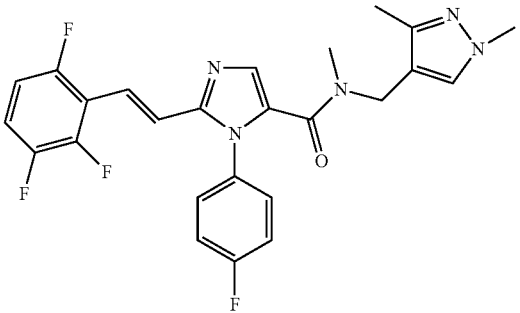 [SMILES: Cc1nn(C)cc1CN(C)C(=O)c1cnc(/C=C/c2c(F)ccc(F)c2F)n1-c1ccc(F)cc1]

$^1$H NMR (400 MHz, CDCl$_3$) δ: 7.69 (d, J=16.4, 1H), 7.40 (s, 1H), 7.32-7.26 (m, 2H), 7.21-7.16 (m, 2H), 7.09 (s, 1H), 7.05-6.97 (m, 1H), 6.90 (d, J=16.3, 1H), 6.83-6.78 (m, 1H), 4.42 (s, 2H), 3.79 (s, 3H), 3.02 (s, 3H), 2.15 (s, 3H). LC-MS ESI m/z; found 483.8 [M+H]$^+$.

Example 12

N-((1,3-Dimethyl-1H-pyrazol-4-yl)methyl)-1-(4-fluorophenyl)-N-methyl-2-((2,3,6-trifluorobenzyl)sulfinyl)-1H-imidazole-5-carboxamide (511)

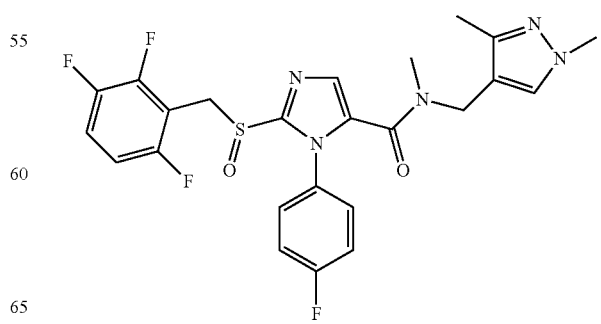

¹H NMR (400 MHz, CDCl₃) δ: 7.43 (s, 1H), 7.30-7.27 (m, 2H), 7.17-7.10 (m, 3H), 7.02 (s, 1H), 6.88-6.83 (m, 1H), 4.86 (d, J=12.9, 1H), 4.58 (d, J=12.8, 1H), 4.40 (d, J=14.6, 1H), 4.34 (d, J=14.6, 1H), 3.78 (s, 3H), 2.92 (s, 3H), 2.12 (s, 3H). LC-MS ESI m/z; found 520.0 [M+H]⁺.

Example 13

N-((1,3-Dimethyl-1H-pyrazol-4-yl)methyl)-1-(4-fluorophenyl)-N-methyl-2-((2,3,6-trifluorobenzyl)sulfonyl)-1H-imidazole-5-carboxamide (512)

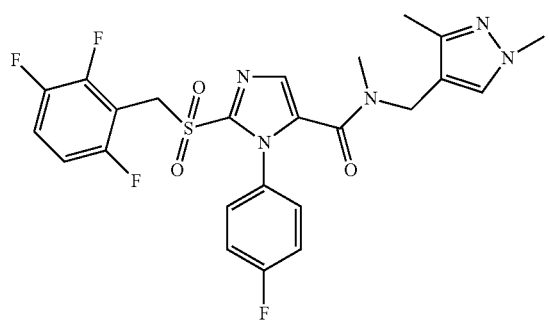 [SMILES: Cc1nn(C)cc1CN(C)C(=O)c1cnc(S(=O)(=O)Cc2c(F)ccc(F)c2F)n1-c1ccc(F)cc1]

¹H NMR (400 MHz, CDCl₃) δ: 7.34 (s, 1H), 7.28-7.25 (m, 2H), 7.20-7.18 (m, 1H), 7.11-7.07 (m, 2H), 6.94-6.88 (m, 2H), 4.75 (s, 2H), 4.34 (s, 2H), 3.76 (s, 3H), 2.90 (s, 3H), 2.11 (s, 3H). LC-MS ESI m/z; found 535.7 [M+H]⁺.

Example 14

N-((1,3-Dimethyl-1H-pyrazol-4-yl)methyl)-1-(4-fluorophenyl)-N-methyl-2-(((2,3,6-trifluorophenyl)amino)methyl)-1H-imidazole-5-carboxamide (513)

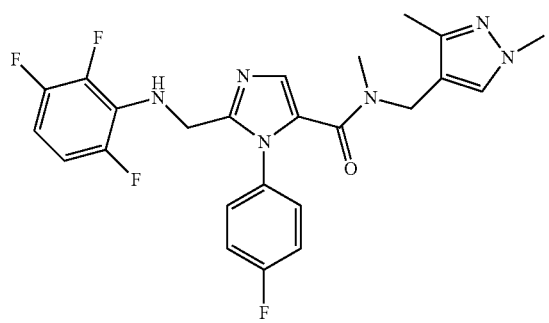 [SMILES: Cc1nn(C)cc1CN(C)C(=O)c1cnc(CNc2c(F)ccc(F)c2F)n1-c1ccc(F)cc1]

¹H NMR (400 MHz, CDCl₃) δ: 7.28-7.21 (m, 3H), 7.16-7.12 (m, 2H), 7.06 (s, 1H), 6.71-6.65 (m, 1H), 6.54-6.46 (m, 1H), 4.43 (s, 2H), 4.38 (d, J=5.76, 2H), 3.78 (s, 3H), 2.99 (s, 3H), 2.13 (s, 3H). LC-MS ESI m/z; found 486.9 [M+H]⁺.

Example 15

N-((1,3-Dimethyl-1H-pyrazol-4-yl)methyl)-1-(4-fluorophenyl)-N-methyl-2-(2,3,6-trifluorophenyl)-1H-imidazole-5-carboxamide (514)

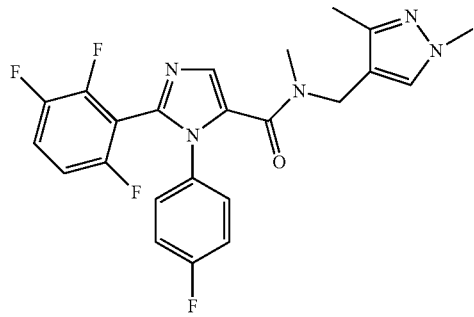 [SMILES: Cc1nn(C)cc1CN(C)C(=O)c1cnc(-c2c(F)ccc(F)c2F)n1-c1ccc(F)cc1]

¹H NMR (400 MHz, CDCl₃) δ: 7.49 (s, 1H), 7.22-7.14 (m, 3H), 7.08 (s, 1H), 7.02-6.98 (m, 2H), 6.83-6.77 (s, 1H), 4.41 (s, 2H), 3.78 (s, 3H), 3.05 (s, 3H), 2.16 (s, 3H). LC-MS ESI m/z; found 457.9 [M+H]⁺.

Example 16

N-((1-Ethyl-3-methyl-1H-pyrazol-4-yl)methyl)-1-(4-fluorophenyl)-N-methyl-2-((2,3,6-trifluorobenzyl)thio)-1H-imidazole-5-carboxamide (515)

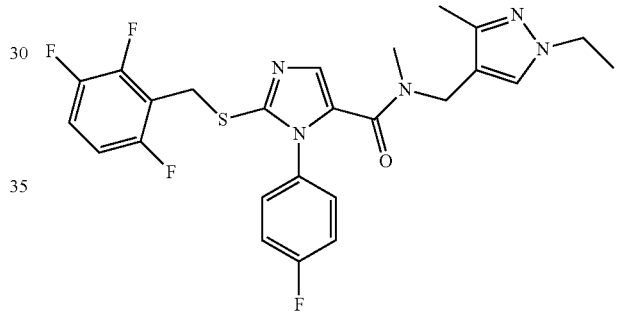

¹H NMR (400 MHz, CDCl₃) δ: 7.34 (s, 1H), 7.28 (s, 1H), 7.17-7.14 (m, 2H), 7.12-6.98 (m, 3H), 6.81-6.75 (m, 1H), 4.41 (s, 2H), 4.35 (s, 2H), 4.07 (q, J=7.2, 2H), 2.98 (s, 3H), 2.14 (s, 3H), 1.39 (t, J=7.2, 3H). LC-MS ESI m/z; found 518.0 [M+H]⁺.

Example 17

1-(4-Fluorophenyl)-N-methyl-2-((2,3,6-trifluorobenzyl)thio)-N-((1,3,5-trimethyl-1H-pyrazol-4-yl)methyl)-1H-imidazole-5-carboxamide (516)

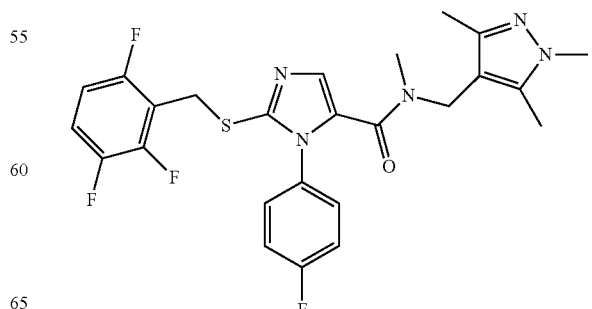

¹H NMR (400 MHz, CDCl₃) δ: 7.33 (s, 1H), 7.19-7.16 (m, 2H), 7.11-7.00 (m, 3H), 6.80-6.75 (m, 1H), 4.41 (s, 2H), 4.35 (s, 2H), 3.71 (s, 3H), 2.91 (s, 3H), 2.11 (s, 3H), 2.09 (s, 3H). LC-MS ESI m/z; found 518.0 [M+H]⁺.

Example 18

1-(4-Fluorophenyl)-N-methyl-N-((1-methylpiperidin-4-yl)methyl)-2-((2,3,6-trifluorobenzyl)thio)-1H-imidazole-5-carboxamide (517)

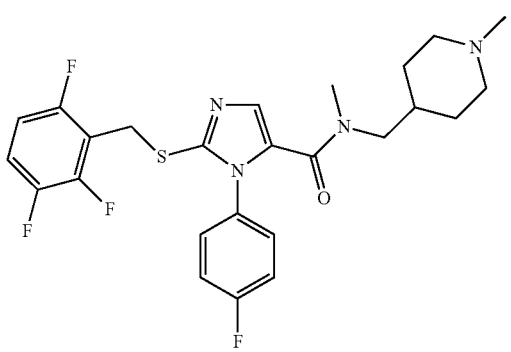 [SMILES: CN1CCC(CN(C)C(=O)c2cnc(SCc3c(F)ccc(F)c3F)n2-c2ccc(F)cc2)CC1]

¹H NMR (400 MHz, CDCl₃) δ: 7.33 (s, 1H), 7.19-7.17 (m, 2H), 7.11-7.00 (m, 3H), 6.81-6.76 (m, 1H), 4.33 (s, 2H), 3.34-3.21 (m, 2H), 3.07 (s, 3H), 2.87-2.76 (m, 2H), 2.28 (s, 3H), 1.97-1.80 (m, 2H), 1.67-1.54 (m, 1H), 1.54-1.42 (m, 2H), 1.33-1.15 (m, 2H). LC-MS ESI m/z; found 506.9 [M+H]⁺.

Example 19

1-(4-Fluorophenyl)-N-methyl-N-(pyridin-4-ylmethyl)-2-((2,3,6-trifluorobenzyl)thio)-1H-imidazole-5-carboxamide (518)

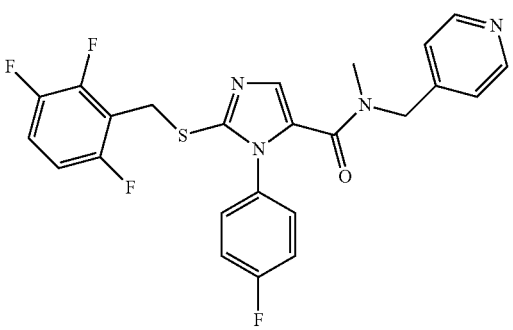 [SMILES: CN(Cc1ccncc1)C(=O)c1cnc(SCc2c(F)ccc(F)c2F)n1-c1ccc(F)cc1]

¹H NMR (400 MHz, CDCl₃) δ: 8.57 (s, 2H), 7.43-7.31 (m, 1H), 7.21-1.18 (m, 2H), 7.16-6.97 (m, 5H), 6.82-6.75 (m, 1H), 4.67 (s, 2H), 4.38 (s, 2H), 3.08 (s, 3H). LC-MS ESI m/z; found 486.8 [M+H]⁺.

Example 20

N-((1,3-Dimethyl-1H-pyrazol-4-yl)methyl)-N-ethyl-1-(4-fluorophenyl)-2-((2,3,6-trifluorobenzyl)thio)-1H-imidazole-5-carboxamide (519)

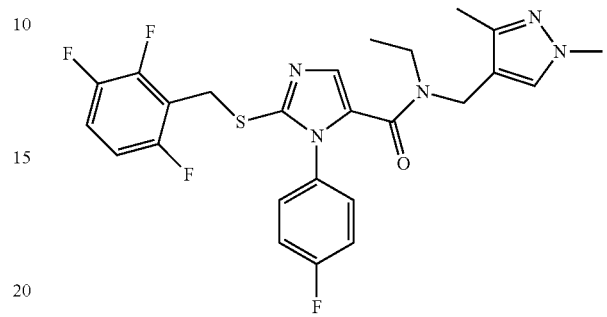

To a solution of N-((1,3-dimethyl-1H-pyrazol-4-yl)methyl)-1-(4-fluorophenyl)-2-((2,3,6-trifluorobenzyl)thio)-1H-imidazole-5-carboxamide (508) (70 mg, 0.143 mmol) in DMF (1.5 mL) was added sodium hydride (60% in mineral oil, 7 mg, 0.172 mmol) and the reaction was stirred for 15 minutes. Iodoethane (13 mL, 0.172 mmol) was added and stirred for 1 hour. Water was added slowly and the reaction was extracted with 1:1 EtOAc:Hexane, dried over sodium sulfate, filtered and concentrated in vacuo. The residue was purified by flash column chromatography on silica gel (90-100% EtOAc in hexanes) to afford N-((1,3-dimethyl-1H-pyrazol-4-yl)methyl)-N-ethyl-1-(4-fluorophenyl)-2-((2,3,6-trifluorobenzyl)thio)-1H-imidazole-5-carboxamide (519). ¹H NMR (400 MHz, CDCl₃) δ: 7.33 (s, 1H), 7.18-6.91 (m, 6H), 6.82-6.73 (m, 1H), 4.37 (s, 2H), 4.34 (s, 2H), 3.77 (s, 3H), 3.37 (q, J=7.0, 2H), 2.16-2.06 (m, 3H), 1.25-1.00 (m, 3H). LC-MS ESI m/z; found 518.0 [M+H]⁺.

Example 21

1-(4-Fluorophenyl)-N-methyl-N-((1-methyl-1H-pyrazol-4-yl)methyl)-2-((2,3,6-trifluorobenzyl)thio)-1H-imidazole-5-carboxamide (520)

¹H NMR (400 MHz, CDCl₃) δ: 7.36 (s, 1H), 7.32 (s, 1H), 7.20-6.98 (m, 6H), 6.81-6.75 (m, 1H), 4.45-4.29 (m, 4H), 3.85 (s, 3H), 3.01 (s, 3H). LC-MS ESI m/z; found 489.8 [M+H]⁺.

Example 22

N-((1,3-Dimethyl-1H-pyrazol-4-yl)methyl)-1-(4-fluorophenyl)-N-methyl-2-((methyl(2,3,6-trifluorophenyl)amino)methyl)-1H-imidazole-5-carboxamide (521)

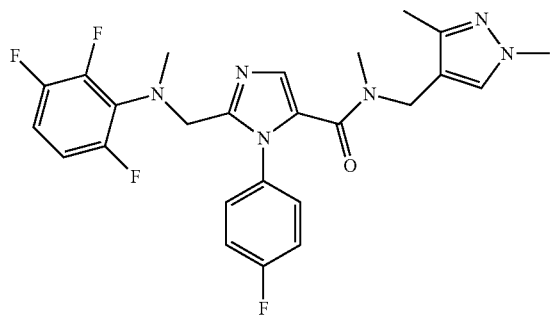 [SMILES: Cc1nn(C)cc1CN(C)C(=O)c1cnc(CN(C)c2c(F)ccc(F)c2F)n1-c1ccc(F)cc1]

¹H NMR (400 MHz, CDCl₃) δ: 7.59 (s, 1H), 7.34-7.31 (m, 2H), 7.16-7.06 (m, 3H), 6.90-6.82 (m, 1H), 6.75-6.68 (m, 1H), 4.40 (s, 2H), 4.35 (s, 2H), 3.86 (s, 3H), 3.01 (s, 3H), 2.80 (s, 3H), 2.17 (s, 3H). LC-MS ESI m/z; found 501.1 [M+H]⁺.

Example 23

N-((2,4-Dimethylthiazol-5-yl)methyl)-1-(4-fluorophenyl)-N-methyl-2-((2,3,6-trifluorobenzyl)thio)-1H-imidazole-5-carboxamide (522)

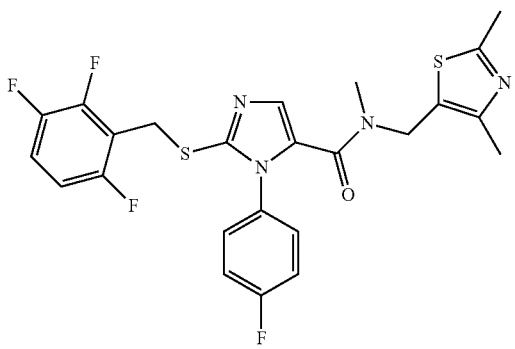 [SMILES: Cc1nc(C)c(CN(C)C(=O)c2cnc(SCc3c(F)ccc(F)c3F)n2-c2ccc(F)cc2)s1]

¹H NMR (400 MHz, CDCl₃) δ: 7.38 (s, 1H), 7.20-7.13 (m, 2H), 7.13-6.99 (m, 3H), 6.81-6.76 (m, 1H), 4.63 (s, 2H), 4.36 (s, 2H), 3.02 (s, 3H), 2.62 (s, 3H), 2.34 (s, 3H). LC-MS ESI m/z; found 520.7 [M+H]⁺.

Example 24

N-((1,3-Dimethyl-1H-pyrazol-4-yl)methyl)-1-(4-fluorophenyl)-N-methyl-2-(2,3,6-trifluorophenethyl)-1H-imidazole-5-carboxamide (523)

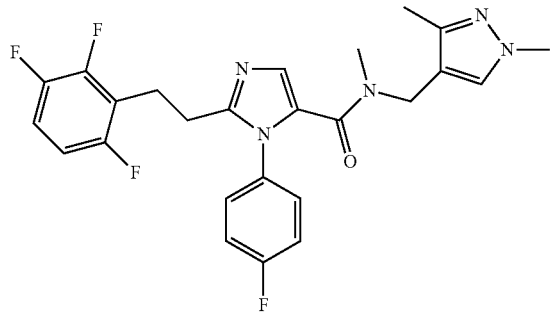 [SMILES: Cc1nn(C)cc1CN(C)C(=O)c1cnc(CCc2c(F)ccc(F)c2F)n1-c1ccc(F)cc1]

¹H NMR (400 MHz, CDCl₃) δ: 7.15-7.11 (m, 5H), 7.06 (s, 1H), 7.01-6.93 (m, 1H), 6.76-6.70 (m, 1H), 4.40 (s, 2H), 3.79 (s, 3H), 3.05 (t, J=7.5, 2H), 2.99 (s, 3H), 2.83 (t, J=7.5, 2H), 2.13 (s, 3H). LC-MS ESI m/z; found 485.9 [M+H]⁺.

Example 25

1-(4-Fluorophenyl)-N-methyl-N-((1-methylpyrrolidin-3-yl)methyl)-2-((2,3,6-trifluorobenzyl)thio)-1H-imidazole-5-carboxamide (524)

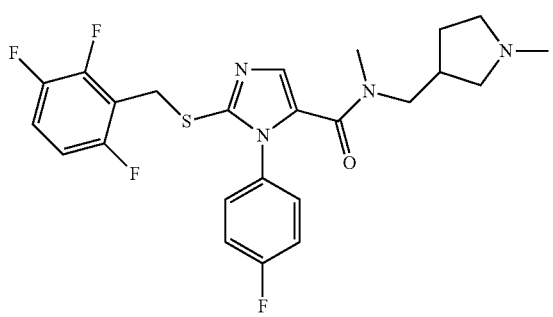 [SMILES: CN1CCC(CN(C)C(=O)c2cnc(SCc3c(F)ccc(F)c3F)n2-c2ccc(F)cc2)C1]

¹H NMR (400 MHz, CDCl₃) δ: 7.54-7.51 (m, 1H), 7.22-7.02 (m, 5H), 6.82-6.78 (m, 1H), 4.95 (s, 3H), 4.35-4.17 (m, 2H), 3.79-3.76 (m, 1H), 3.56-3.48 (m, 1H), 3.21 (s, 3H), 2.92-2.85 (m, 2H), 2.77-2.71 (m, 2H), 2.56-2.48 (m, 1H), 2.30-2.07 (m, 1H), 1.80-1.62 (m, 1H).

Example 26

N-((1,3-Dimethyl-1H-pyrazol-4-yl)methyl)-1-(4-fluorophenyl)-N-methyl-2-((2-oxo-2-phenylethyl)thio)-1H-imidazole-5-carboxamide (525)

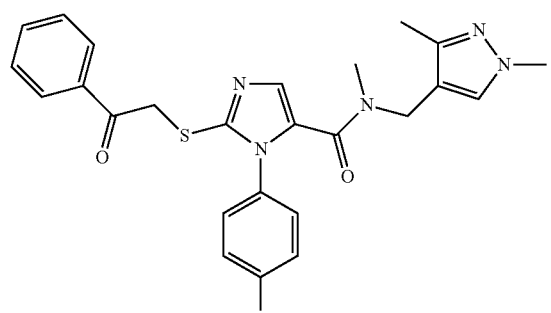

¹H NMR (400 MHz, CDCl₃) δ: 8.00 (d, J=7.2, 2H), 7.62-7.58 (m, 1H), 7.49-7.46 (m, 2H), 7.33-7.22 (m, 3H), 7.16-7.11 (m, 2H), 7.06 (s, 1H), 4.79 (s, 2H), 4.39 (s, 2H), 3.78 (s, 3H), 2.96 (s, 3H), 2.14 (s, 3H). LC-MS ESI m/z; found 478.20 [M+H]⁺.

Example 27

N-(1-(1,3-Dimethyl-1H-pyrazol-4-yl)ethyl)-1-(4-fluorophenyl)-N-methyl-2-((2,3,6-trifluorobenzyl)thio)-1H-imidazole-5-carboxamide (526)

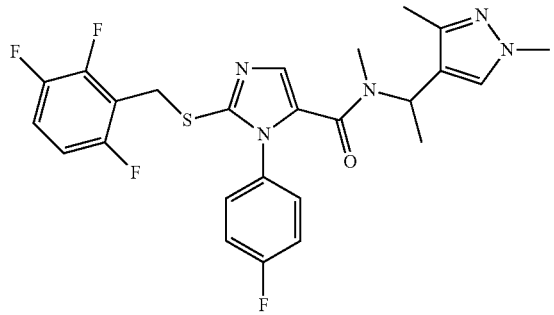 [SMILES: Cc1nn(C)cc1C(C)N(C)C(=O)c1cnc(SCc2c(F)ccc(F)c2F)n1-c1ccc(F)cc1]

$^1$H NMR (400 MHz, CDCl$_3$) δ: 7.36 (s, 1H), 7.20-7.16 (m, 3H), 7.13-6.98 (m, 3H), 6.81-6.76 (s, 1H), 5.83-5.50 (m, 1H), 4.37 (s, 2H), 3.81 (s, 3H), 2.75 (s, 3H), 1.98 (s, 3H), 1.41-1.32 (m, 3H). LC-MS ESI m/z; found 518.20 [M+H]$^+$.

Example 28

N-((1-(4-Fluorophenyl)-2-((2,3,6-trifluorobenzyl)thio)-1H-imidazol-5-yl)methyl)-N-1,3-trimethyl-1H-pyrazole-4-carboxamide (527)

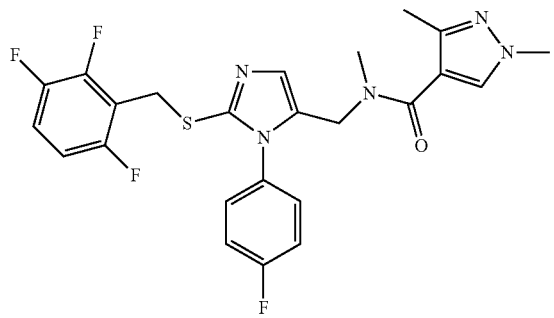 [SMILES: Cc1nn(C)cc1C(=O)N(C)Cc1cnc(SCc2c(F)ccc(F)c2F)n1-c1ccc(F)cc1]

$^1$H NMR (400 MHz, CDCl$_3$) δ: 7.19-7.00 (m, 7H), 6.80-6.74 (m, 1H), 4.50 (s, 2H), 4.17 (s, 2H), 3.80 (s, 3H), 2.89 (s, 3H), 2.22 (s, 3H). LC-MS ESI m/z; found 504.1 [M+H]$^+$.

Example 29

1-(4-Fluorophenyl)-N-methyl-N-(pyridin-4-ylmethyl)-2-(2,3,6-trifluorophenethyl)-1H-imidazole-5-carboxamide (528)

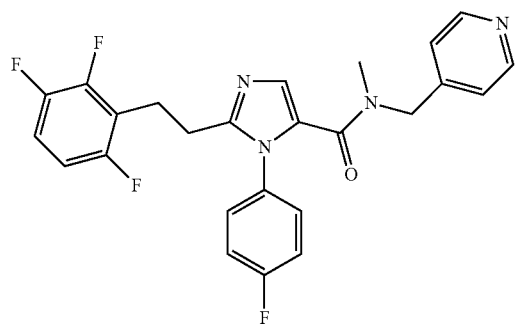 [SMILES: CN(Cc1ccncc1)C(=O)c1cnc(CCc2c(F)ccc(F)c2F)n1-c1ccc(F)cc1]

$^1$H NMR (400 MHz, CDCl$_3$) δ: 8.78 (d, J=5.7, 2H), 7.87-7.73 (m, 1H), 7.51 (d, J=5.7, 2H), 7.30-7.19 (m, 4H), 7.09-7.00 (m, 1H), 6.80-6.75 (m, 1H), 4.78 (s, 2H), 3.26 (s, 3H), 3.11 (t, J=6.9, 2H), 3.03 (t, J=6.9, 2H). LC-MS ESI m/z; found 469.2 [M+H]$^+$.

Example 30

N-((1,3-Dimethyl-1H-pyrazol-4-yl)methyl)-1-(4-fluorophenyl)-N-methyl-2-((2-methyl-1-oxo-1-phenylpropan-2-yl)thio)-1H-imidazole-5-carboxamide (529)

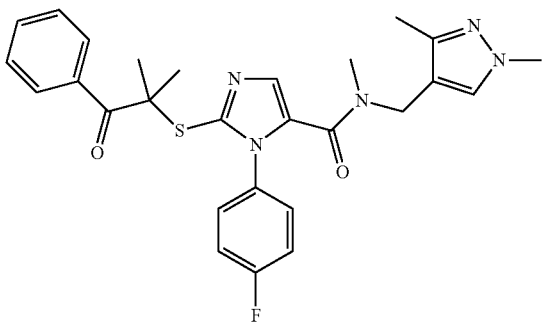 [SMILES: Cc1nn(C)cc1CN(C)C(=O)c1cnc(SC(C)(C)C(=O)c2ccccc2)n1-c1ccc(F)cc1]

$^1$H NMR (400 MHz, CDCl$_3$) δ: 7.73 (s, 1H), 7.55-7.32 (m, 4H), 7.34-7.25 (m, 1H), 7.13-7.07 (m, 3H), 6.81 (s, 2H), 4.31 (s, 2H), 3.85 (s, 6H), 3.02 (s, 3H), 2.18 (s, 6H). LC-MS ESI m/z; found 506.20 [M+H]$^+$.

Example 31

4-(((1-(4-Fluorophenyl)-2-((2,3,6-trifluorobenzyl)thio)-1H-imidazol-5-yl)methoxy)methyl)pyridine (530)

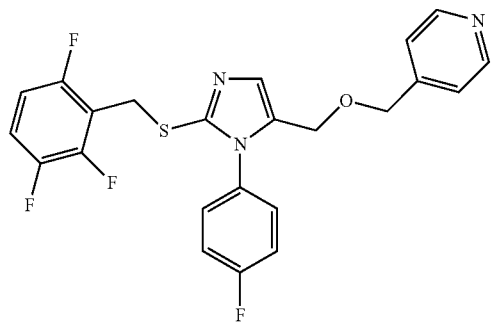 [SMILES: Fc1ccc(-n2c(COCc3ccncc3)cnc2SCc2c(F)ccc(F)c2F)cc1]

$^1$H NMR (400 MHz, CDCl$_3$) δ: 8.58 (dd, J=4.7, 1.5, 2H), 7.30-7.21 (m, 3H), 7.21-7.08 (m, 4H), 7.05-7.00 (m, 1H), 6.79-6.73 (m, 1H), 4.47 (s, 2H), 4.36 (s, 2H), 4.25 (s, 2H). LC-MS ESI m/z; found 460.1 [M+H]$^+$.

Example 32

1-(1,3-Dimethyl-1H-pyrazol-4-yl)-N-((1-(4-fluorophenyl)-2-((2,3,6-trifluorobenzyl)thio)-1H-imidazol-5-yl)methyl)methanamine (531)

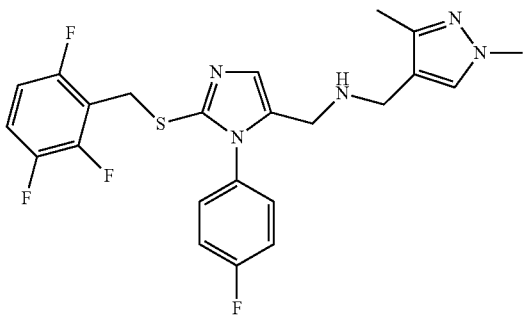 [SMILES: Cc1nn(C)cc1CNCc1cnc(SCc2c(F)ccc(F)c2F)n1-c1ccc(F)cc1]

¹H NMR (400 MHz, CDCl₃) δ: 7.94 (s, 1H), 7.45 (s, 1H), 7.24-7.21 (m, 4H), 7.15-7.02 (m, 1H), 6.82-6.78 (m, 1H), 4.21 (s, 2H), 4.01 (s, 2H), 3.99 (s, 2H), 3.78 (s, 3H), 2.15 (s, 3H). LC-MS ESI m/z; found 476.20 [M+H]⁺.

Example 33

2-((2-Chloro-6-fluorobenzyl)thio)-N-((1,3-dimethyl-1H-pyrazol-4-yl)methyl)-1-(4-fluorophenyl)-N-methyl-1H-imidazole-5-carboxamide (532)

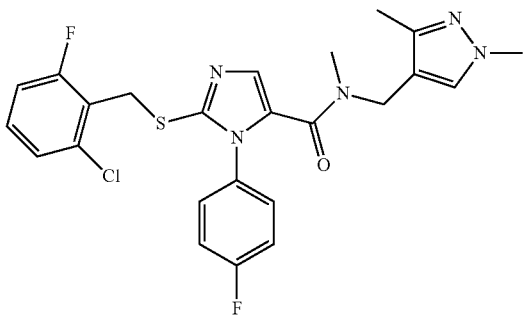 [SMILES: Cc1nn(C)cc1CN(C)C(=O)c1cnc(SCc2c(F)cccc2Cl)n1-c1ccc(F)cc1]

¹H NMR (400 MHz, CDCl₃) δ: 7.37 (s, 1H), 7.22-7.10 (m, 4H), 7.08-7.04 (m, 3H), 6.95-6.91 (s, 1H), 4.48 (s, 2H), 4.39 (s, 2H), 3.79 (s, 3H), 2.97 (s, 3H), 2.14 (s, 3H). LC-MS ESI m/z; found 502.1 [M+H]⁺.

Example 34

2-((2-Chloro-6-fluorobenzyl)thio)-1-(4-fluorophenyl)-N-methyl-N-(pyridin-4-ylmethyl)-1H-imidazole-5-carboxamide (533)

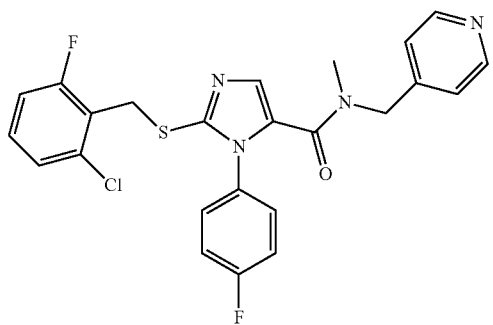 [SMILES: CN(Cc1ccncc1)C(=O)c1cnc(SCc2c(F)cccc2Cl)n1-c1ccc(F)cc1]

¹H NMR (400 MHz, CDCl₃) δ: 8.58 (d, J=4.7, 2H), 7.41 (s, 1H), 7.23-7.03 (m, 8H), 6.96-6.92 (m, 1H), 4.69 (s, 2H), 4.50 (s, 2H), 3.10 (s, 3H). LC-MS ESI m/z; found 485.1 [M+H]⁺.

Example 35

1-(4-Fluorophenyl)-N-methyl-2-(2-methyl-1-(2,3,6-trifluorophenyl)propan-2-yl)-N-(pyridin-4-ylmethyl)-1H-imidazole-5-carboxamide (534)

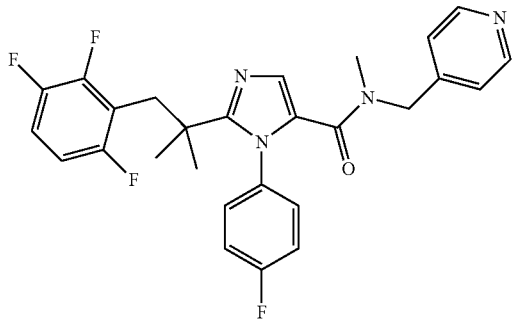 [SMILES: CN(Cc1ccncc1)C(=O)c1cnc(C(C)(C)Cc2c(F)ccc(F)c2F)n1-c1ccc(F)cc1]

¹H NMR (400 MHz, CDCl₃) δ: 8.59-8.42 (m, 2H), 7.44-7.35 (m, 2H), 7.23-6.61 (m, 7H), 4.79-4.54 (m, 2H), 3.21-2.77 (m, 5H), 1.20 (s, 6H). LC-MS ESI m/z; found 497.20 [M+H]⁺.

Example 36

2-((2-Chloro-6-fluorobenzyl)thio)-1-(4-fluorophenyl)-N,N-dimethyl-1H-imidazole-5-carboxamide (535)

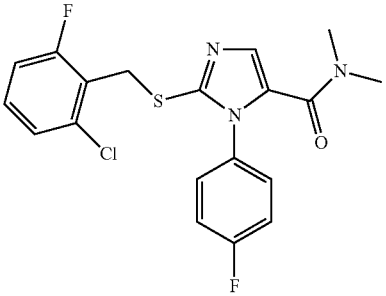 [SMILES: CN(C)C(=O)c1cnc(SCc2c(F)cccc2Cl)n1-c1ccc(F)cc1]

¹H NMR (400 MHz, CDCl₃) δ: 7.43 (s, 1H), 7.18-7.13 (m, 4H), 7.09-7.05 (m, 2H), 6.96-6.92 (m, 1H), 4.54 (s, 2H), 3.11-2.95 (m, 6H). LC-MS ESI m/z; found 408.1 [M+H]⁺.

Example 37

2-((2-Chloro-6-fluorobenzyl)oxy)-1-(4-fluorophenyl)-N-methyl-N-(pyridin-4-ylmethyl)-1H-imidazole-5-carboxamide (536)

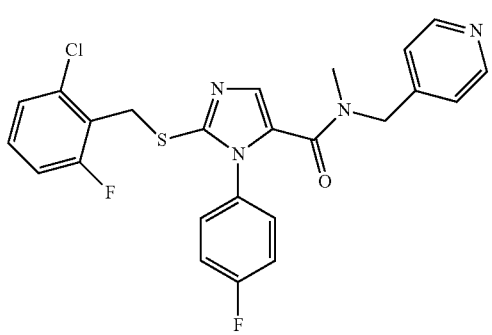 [SMILES: CN(Cc1ccncc1)C(=O)c1cnc(SCc2c(F)cccc2Cl)n1-c1ccc(F)cc1]

¹H NMR (400 MHz, CDCl₃) δ: 8.56 (d, J=5.5, 2H), 7.33-7.16 (m, 4H), 7.12-6.95 (m, 6H), 5.56 (s, 2H), 4.67 (s, 2H), 3.07 (s, 3H). LC-MS ESI m/z; found 469.1 [M+H]⁺.

Example 38

2-((2-Chloro-6-fluorophenyl)ethynyl)-1-(4-fluorophenyl)-N-methyl-N-(pyridin-4-ylmethyl)-1H-imidazole-5-carboxamide (537)

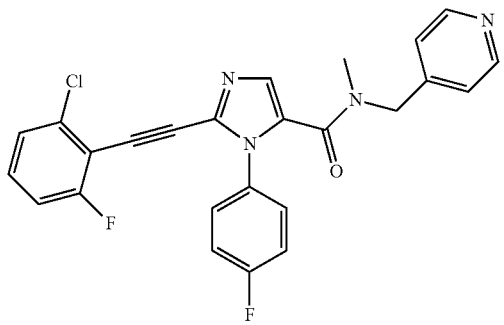 [SMILES: CN(Cc1ccncc1)C(=O)c1cnc(C#Cc2c(F)cccc2Cl)n1-c1ccc(F)cc1]

¹H NMR (400 MHz, CDCl₃) δ: 8.55 (s, 2H), 7.41 (s, 2H), 7.31-7.10 (m, 5H), 7.07-6.91 (m, 3H), 4.61 (s, 2H), 3.06 (s, 3H). LC-MS ESI m/z; found 463.1 [M+H]⁺.

Example 39

2-(2-Fluorophenethyl)-1-(4-fluorophenyl)-N-methyl-N-(pyridin-4-ylmethyl)-1H-imidazole-5-carboxamide (538)

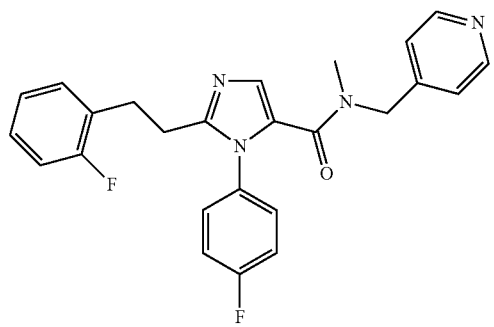 [SMILES: CN(Cc1ccncc1)C(=O)c1cnc(CCc2ccccc2F)n1-c1ccc(F)cc1]

¹H NMR (400 MHz, CDCl₃) δ: 8.59-8.48 (m, 2H), 7.22-7.06 (m, 3H), 7.06-6.86 (m, 8H), 4.62 (s, 2H), 3.14-2.90 (m, 4H), 2.81-2.79 (m, 3H). LC-MS ESI m/z; found 433.2 [M+H]⁺.

Example 40

(2-((2-Chloro-6-fluorobenzyl)thio)-1-(4-fluorophenyl)-1H-imidazol-5-yl)(2-(pyridin-4-yl)pyrrolidin-1-yl)methanone (539)

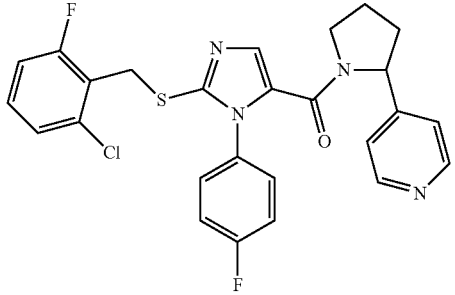 [SMILES: O=C(c1cnc(SCc2c(F)cccc2Cl)n1-c1ccc(F)cc1)N1CCCC1c1ccncc1]

¹H NMR (400 MHz, CDCl₃) δ: 8.67-8.42 (m, 2H), 7.63 (s, 1H), 7.23-6.89 (m, 9H), 5.35-5.10 (m, 1H), 4.60-4.35 (m, 2H), 4.05-3.63 (m, 2H), 2.48-2.30 (m, 1H), 2.09-1.89 (m, 2H), 1.88-1.74 (m, 1H). LC-MS ESI m/z; found 511.1 [M+H]⁺.

Example 41

1-(4-Fluorophenyl)-N-methyl-N-(pyridin-4-ylmethyl)-2-(2-(trifluoromethyl)phenethyl)-1H-imidazole-5-carboxamide (540)

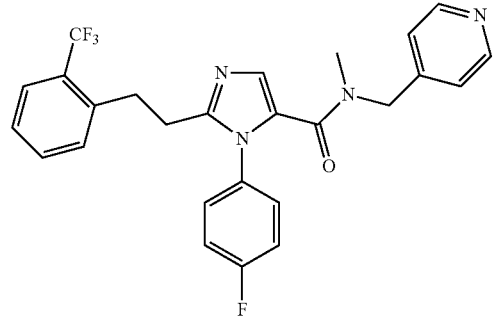 [SMILES: CN(Cc1ccncc1)C(=O)c1cnc(CCc2ccccc2C(F)(F)F)n1-c1ccc(F)cc1]

¹H NMR (400 MHz, CDCl₃) δ: 8.59-8.46 (m, 2H), 7.57 (d, J=7.8, 1H), 7.40-7.37 (m, 1H), 7.30-7.26 (m, 2H), 7.18-7.05 (m, 3H), 7.03-6.93 (m, 4H), 4.62 (s, 2H), 3.17 (t, J=7.9, 2H), 3.06 (s, 3H), 2.81 (t, J=7.9, 2H). LC-MS ESI m/z; found 483.2 [M+H]⁺.

Example 42

(2-((2-Chloro-6-fluorobenzyl)thio)-1-(4-fluorophenyl)-1H-imidazol-5-yl)(2-(pyridin-4-yl)piperidin-1-yl)methanone (541)

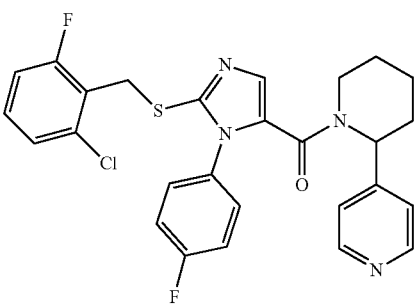 [SMILES: O=C(c1cnc(SCc2c(F)cccc2Cl)n1-c1ccc(F)cc1)N1CCCCC1c1ccncc1]

¹H NMR (400 MHz, CDCl₃) δ: 8.52 (d, J=5.2, 2H), 7.37-7.31 (s, 1H), 7.22-7.06 (m, 6H), 6.97-6.87 (m, 3H), 5.78-5.65 (m, 1H), 4.45 (s, 2H), 4.23-4.00 (m, 1H), 2.87-2.71 (m, 1H), 2.42-2.31 (m, 1H), 1.89-1.83 (m, 1H), 1.71-1.64 (m, 1H), 1.48-1.31 (m, 3H). LC-MS ESI m/z; found 525.1 [M+H]⁺.

Example 43 tert-butyl 4-(((5-(((1,3-Dimethyl-1H-pyrazol-4-yl)methyl)(methyl)carbamoyl)-1-(4-fluorophenyl)-1H-imidazol-2-yl)thio)methyl)-3,5-difluorobenzoate (542)

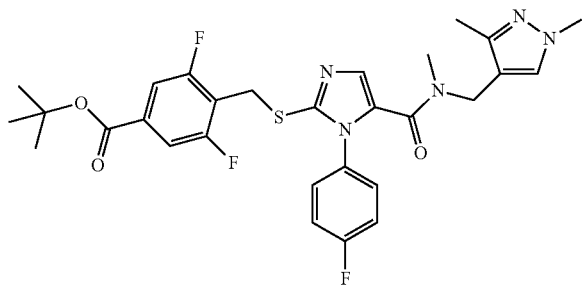 [SMILES: Cc1nn(C)cc1CN(C)C(=O)c1cnc(SCc2c(F)cc(C(=O)OC(C)(C)C)cc2F)n1-c1ccc(F)cc1]

¹H NMR (400 MHz, CDCl₃) δ: 7.43 (d, J=7.7, 2H), 7.33 (s, 1H), 7.18-7.14 (m, 2H), 7.10-7.06 (m, 3H), 4.38 (s, 2H), 4.33 (s, 2H), 3.78 (s, 3H), 2.98 (s, 3H), 2.14 (s, 3H), 1.57 (s, 9H). LC-MS ESI m/z; found 586.2 [M+H]⁺.

Example 44

4-(((5-(((1,3-Dimethyl-1H-pyrazol-4-yl)methyl)(methyl)carbamoyl)-1-(4-fluorophenyl)-1H-imidazol-2-yl)thio)methyl)-3,5-difluorobenzoic acid (543)

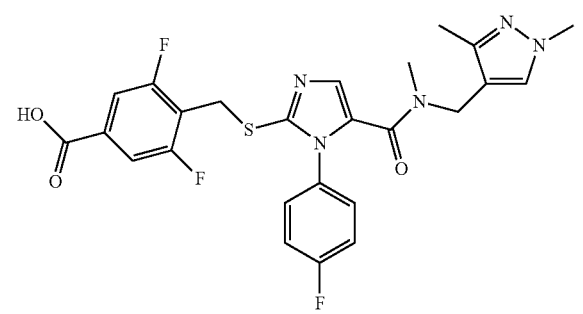 [SMILES: Cc1nn(C)cc1CN(C)C(=O)c1cnc(SCc2c(F)cc(C(=O)O)cc2F)n1-c1ccc(F)cc1]

¹H NMR (400 MHz, DMSO-d₆) δ: 7.56 (d, J=7.5, 2H), 7.49 (s, 1H), 7.44-7.37 (m, 1H), 7.34-7.28 (m, 4H), 4.39-4.27 (m, 4H), 3.76 (s, 3H), 2.97 (s, 3H), 2.01 (s, 3H). LC-MS ESI m/z; found 530.2 [M+H]⁺.

Example 45

N-((1,3-Dimethyl-1H-pyrazol-4-yl)methyl)-1-(4-fluorophenyl)-N-methyl-2-((3,3,3-trifluoro-2-oxopropyl)thio)-1H-imidazole-5-carboxamide (544)

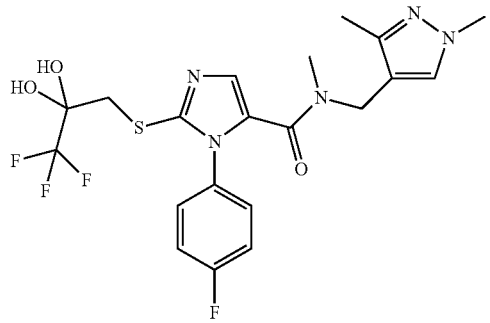 [SMILES: Cc1nn(C)cc1CN(C)C(=O)c1cnc(SCC(O)(O)C(F)(F)F)n1-c1ccc(F)cc1]

¹H NMR (400 MHz, CDCl₃) δ: 7.30-7.26 (m, 2H), 7.23-7.12 (m, 3H), 7.08 (s, 1H), 4.38 (s, 2H), 3.79 (s, 3H), 3.39 (s, 2H), 2.97 (s, 3H), 2.14 (s, 3H). LC-MS ESI m/z; found 488.1 [M+H]⁺.

Example 46

2-((Cyclopropylmethyl)thio)-N-((1,3-dimethyl-1H-pyrazol-4-yl)methyl)-1-(4-fluorophenyl)-N-methyl-1H-imidazole-5-carboxamide (545)

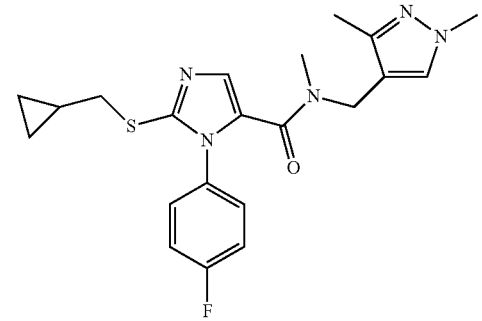 [SMILES: Cc1nn(C)cc1CN(C)C(=O)c1cnc(SCC2CC2)n1-c1ccc(F)cc1]

¹H NMR (400 MHz, CDCl₃) δ: 7.27-7.17 (m, 3H), 7.14-7.05 (m, 2H), 7.02 (s, 1H), 4.34 (s, 2H), 3.73 (s, 3H), 3.07 (d, J=7.2, 2H), 2.92 (s, 3H), 2.09 (s, 3H), 1.07-1.03 (m, 1H), 0.55-0.49 (m, 2H), 0.23-0.18 (m, 2H). LC-MS ESI m/z; found 414.2 [M+H]⁺.

Example 47

N-((1,3-Dimethyl-1H-pyrazol-4-yl)methyl)-1-(4-fluorophenyl)-N-methyl-2-(neopentylthio)-1H-imidazole-5-carboxamide (546)

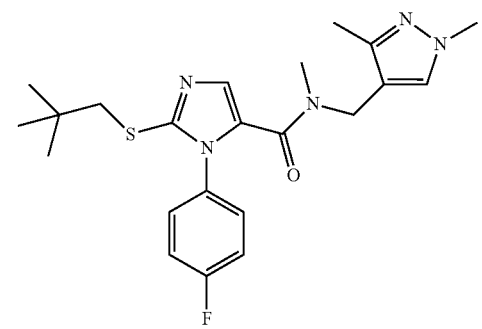 [SMILES: Cc1nn(C)cc1CN(C)C(=O)c1cnc(SCC(C)(C)C)n1-c1ccc(F)cc1]

¹H NMR (400 MHz, CDCl₃) δ 7.31-7.22 (m, 3H), 7.16-7.12 (m, 2H), 7.06 (s, 1H), 4.39 (s, 2H), 3.77 (s, 3H), 3.22 (s, 2H), 2.96 (s, 3H), 2.13 (s, 3H), 0.97 (s, 9H). LC-MS ESI m/z; found 430.2 [M+H]⁺.

Example 48

N-((1,3-Dimethyl-1H-pyrazol-4-yl)methyl)-1-(4-fluorophenyl)-2-(isobutylthio)-N-methyl-1H-imidazole-5-carboxamide (547)

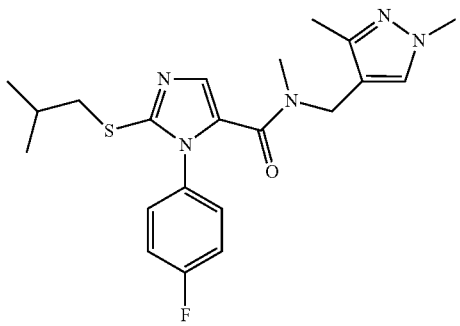 [SMILES: Cc1nn(C)cc1CN(C)C(=O)c1cnc(SCC(C)C)n1-c1ccc(F)cc1]

¹H NMR (400 MHz, CDCl₃) δ: 7.32-7.21 (m, 3H), 7.16-7.12 (m, 2H), 7.06 (s, 1H), 4.39 (s, 2H), 3.77 (s, 3H), 3.08 (d, J=6.8, 2H), 2.96 (s, 3H), 2.13 (s, 3H), 1.97-1.86 (m, 1H), 0.97 (d, J=6.6, 6H). LC-MS ESI m/z; found 416.2 [M+H]⁺.

Example 49

N-((1,3-Dimethyl-1H-pyrazol-4-yl)methyl)-2-((3,3-dimethyl-2-oxobutyl)thio)-1-(4-fluorophenyl)-N-methyl-1H-imidazole-5-carboxamide (548)

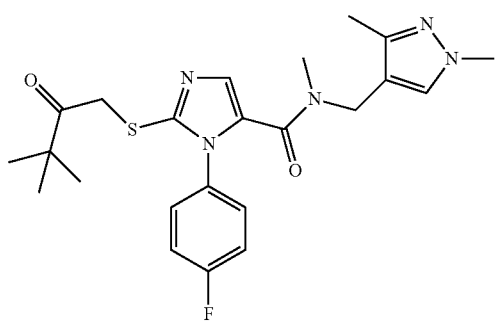 [SMILES: Cc1nn(C)cc1CN(C)C(=O)c1cnc(SCC(=O)C(C)(C)C)n1-c1ccc(F)cc1]

¹H NMR (400 MHz, CDCl₃) δ: 7.33-7.22 (m, 3H), 7.16-7.10 (m, 2H), 7.05 (s, 1H), 4.39-4.35 (m, 4H), 3.77 (s, 3H), 2.95 (s, 3H), 2.13 (s, 3H), 1.20 (s, 9H). LC-MS ESI m/z; found 458.2 [M+H]⁺.

Example 50

2-((2-Chlorobenzyl)thio)-N-((1,3-dimethyl-1H-pyrazol-4-yl)methyl)-1-(4-fluorophenyl)-N-methyl-1H-imidazole-5-carboxamide (549)

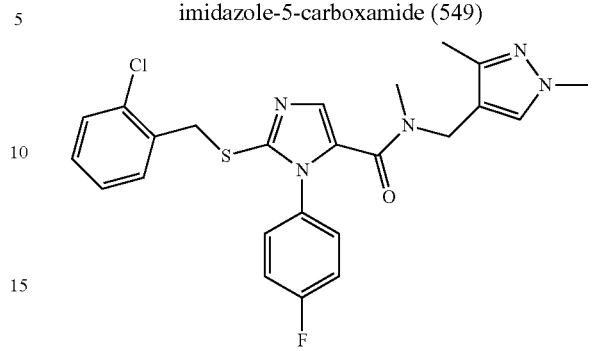

¹H NMR (400 MHz, CDCl₃) δ 7.38-7.29 (m, 3H), 7.22-7.10 (m, 2H), 7.08-7.00 (m, 5H), 4.45 (s, 2H), 4.37 (s, 2H), 3.77 (s, 3H), 2.93 (s, 3H), 2.13 (s, 3H). LC-MS ESI m/z; found 484.2 [M+H]⁺.

Example 51

2-((2-Chlorobenzyl)thio)-1-(4-fluorophenyl)-N-methyl-N-((2-methylpyridin-4-yl)methyl)-1H-imidazole-5-carboxamide (550)

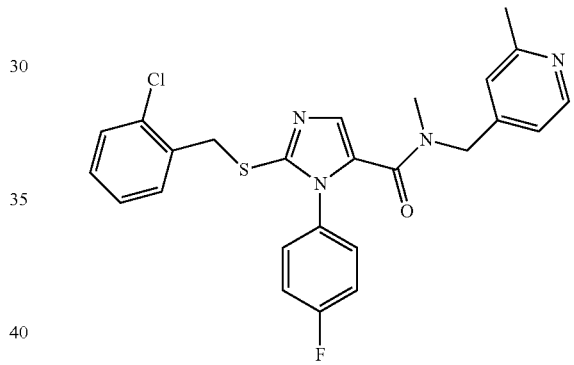

¹H NMR (400 MHz, CDCl₃) δ 8.42 (s, 1H), 7.41-7.27 (m, 2H), 7.26-7.10 (m, 3H), 7.10-7.01 (m, 4H), 6.86 (s, 1H), 6.80 (s, 1H), 4.58 (s, 2H), 4.46 (s, 2H), 2.99 (s, 3H), 2.52 (s, 3H). LC-MS ESI m/z; found 481.1 [M+H]⁺.

Example 52

2-((3-Chloropyridin-2-yl)methyl)thio)-N-((1,3-dimethyl-1H-pyrazol-4-yl)methyl)-1-(4-fluorophenyl)-N-methyl-1H-imidazole-5-carboxamide (551)

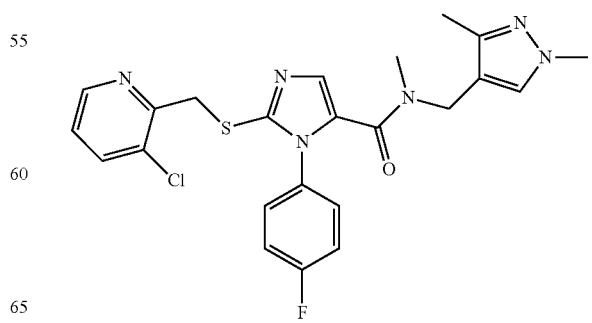

¹H NMR (400 MHz, CDCl₃) δ: 7.56 (m, 1H), 7.34-7.26 (m, 2H) 7.21-7.17 (m, 3H), 7.13-7.06 (m, 3H), 4.42 (s, 2H), 4.38 (s, 2H), 3.78 (s, 3H), 2.96 (s, 3H), 2.14 (s, 3H). LC-MS ESI m/z; found 485.1 [M+H]⁺.

Example 53

N-((1,3-Dimethyl-1H-pyrazol-4-yl)methyl)-1-(4-fluorophenyl)-N-methyl-2-(((5-methyl-1,2,4-oxadiazol-3-yl)methyl)thio)-1H-imidazole-5-carboxamide (552)

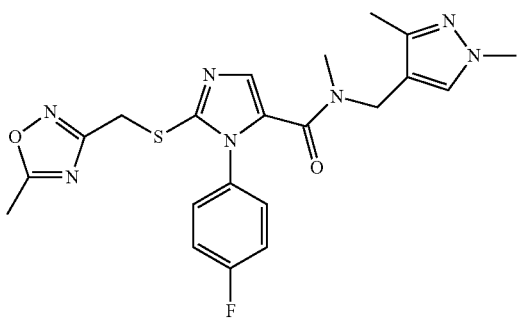

¹H NMR (400 MHz, CDCl₃) δ: 7.34 (s, 1H), 7.27-7.22 (m, 2H) 7.14-7.07 (m, 3H), 4.43-4.39 (m, 4H), 3.77 (s, 3H), 2.98 (s, 3H), 2.55 (s, 3H), 2.14 (s, 3H). LC-MS ESI m/z; found 456.1 [M+H]⁺.

Example 54

2-((2-Chloro-6-fluorobenzyl)thio)-1-(4-chlorophenyl)-N-((1,3-dimethyl-1H-pyrazol-4-yl)methyl)-N-methyl-1H-imidazole-5-carboxamide (553)

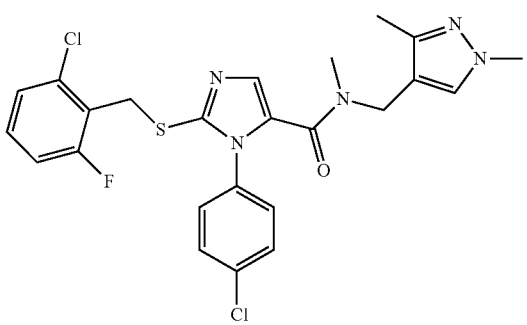 [SMILES: Cc1nn(C)cc1CN(C)C(=O)c1cnc(SCc2c(F)cccc2Cl)n1-c1ccc(Cl)cc1]

¹H NMR (400 MHz, CDCl₃) δ 7.39-7.30 (m, 3H), 7.21-7.01 (m, 5H), 6.96-6.89 (m, 1H), 4.46 (s, 2H), 4.38 (s, 2H), 3.78 (s, 3H), 2.97 (s, 3H), 2.14 (s, 3H). LC-MS ESI m/z; found 518.1 [M+H]⁺.

Example 55

2-((2-Chloro-6-fluorobenzyl)thio)-N-((1,3-dimethyl-1H-pyrazol-4-yl)methyl)-N-methyl-1-phenyl-1H-imidazole-5-carboxamide (554)

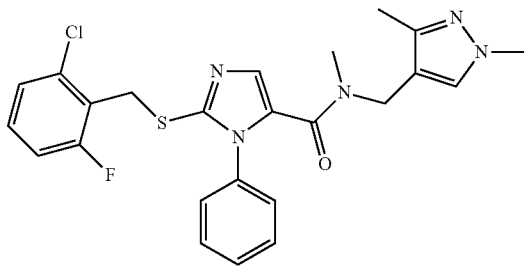 [SMILES: Cc1nn(C)cc1CN(C)C(=O)c1cnc(SCc2c(F)cccc2Cl)n1-c1ccccc1]

¹H NMR (400 MHz, CDCl₃) δ 7.43-7.31 (m, 4H), 7.21-7.08 (m, 4H), 7.02 (s, 1H), 6.96-6.86 (m, 1H), 4.46 (s, 2H), 4.36 (s, 2H), 3.76 (s, 3H), 2.93 (s, 3H), 2.12 (s, 3H). LC-MS ESI m/z; found 484.2 [M+H]⁺.

Example 56

2-((2-Chloro-6-fluorobenzyl)thio)-N-methyl-1-phenyl-N-(pyridin-4-ylmethyl)-1H-imidazole-5-carboxamide (555)

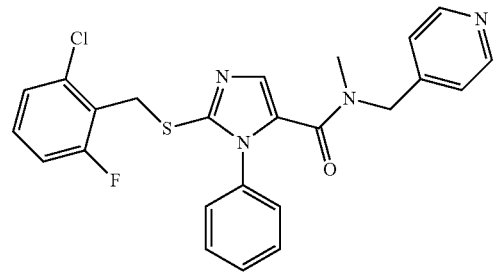 [SMILES: CN(Cc1ccncc1)C(=O)c1cnc(SCc2c(F)cccc2Cl)n1-c1ccccc1]

¹H NMR (400 MHz, CDCl₃) δ 8.51 (s, 2H), 7.48-7.36 (m, 4H), 7.22-7.10 (m, 4H), 7.01-6.86 (m, 3H), 4.61 (s, 2H), 4.48 (s, 2H), 2.99 (s, 3H). LC-MS ESI m/z; found 467.1 [M+H]⁺.

Example 57

2-((2-Chloro-6-fluorobenzyl)thio)-1-(4-chlorophenyl)-N-methyl-N-(pyridin-4-ylmethyl)-1H-imidazole-5-carboxamide (556)

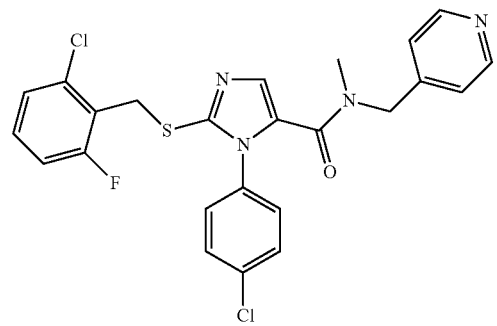 [SMILES: CN(Cc1ccncc1)C(=O)c1cnc(SCc2c(F)cccc2Cl)n1-c1ccc(Cl)cc1]

¹H NMR (400 MHz, CDCl₃) δ 8.56 (s, 2H), 7.39-7.35 (m, 2H), 7.22-7.06 (m, 5H), 7.04-6.87 (m, 3H), 4.64 (s, 2H), 4.48 (s, 2H), 3.04 (s, 3H). LC-MS ESI m/z; found 501.1 [M+H]⁺.

Example 58

2-((2-Chloro-6-fluorobenzyl)thio)-N-methyl-N-(pyridin-4-ylmethyl)-1-(4-(trifluoromethyl)phenyl)-1H-imidazole-5-carboxamide (557)

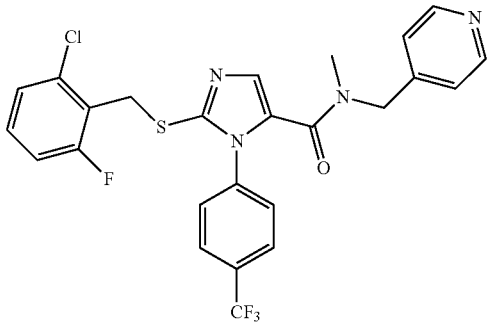 [SMILES: CN(Cc1ccncc1)C(=O)c1cnc(SCc2c(F)cccc2Cl)n1-c1ccc(C(F)(F)F)cc1]

$^1$H NMR (400 MHz, CDCl$_3$) δ 8.56 (s, 2H), 7.67 (d, J=8.3, 2H), 7.41 (s, 1H), 7.31 (d, J=8.3, 2H), 7.23-7.09 (m, 2H), 7.03 (s, 2H), 6.97-6.88 (m, 1H), 4.64 (s, 2H), 4.49 (s, 2H), 3.07 (s, 3H). LC-MS ESI m/z; found 535.1 [M+H]$^+$.

Example 59

2-((2-Chloro-6-fluorobenzyl)thio)-1-(4-ethylphenyl)-N-methyl-N-(pyridin-4-ylmethyl)-1H-imidazole-5-carboxamide (558)

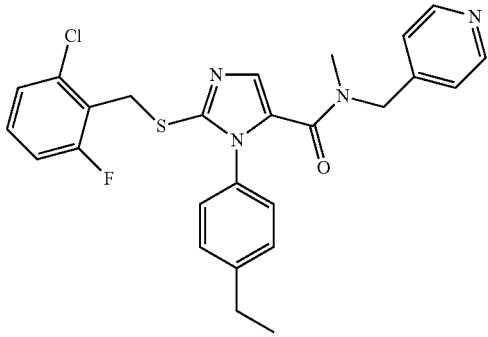 [SMILES: CCc1ccc(-n2c(C(=O)N(C)Cc3ccncc3)cnc2SCc2c(F)cccc2Cl)cc1]

$^1$H NMR (400 MHz, CDCl$_3$) δ 8.50 (s, 2H), 7.43-7.06 (m, 7H), 7.03-6.85 (m, 3H), 4.62 (s, 2H), 4.48 (s, 2H), 2.97 (s, 3H), 2.71 (q, J=7.6, 2H), 1.27 (t, J=7.6, 3H). LC-MS ESI m/z; found 495.1 [M+H]$^+$.

Example 60

2-((2-Chloro-6-fluorobenzyl)thio)-1-(4-methoxyphenyl)-N-methyl-N-(pyridin-4-ylmethyl)-1H-imidazole-5-carboxamide (559)

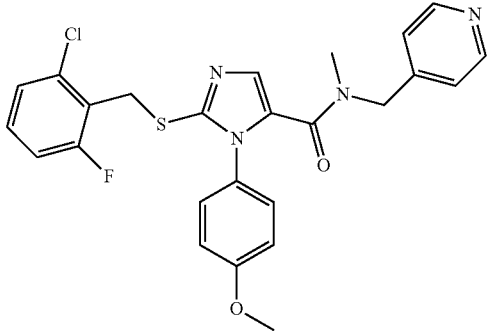 [SMILES: COc1ccc(-n2c(C(=O)N(C)Cc3ccncc3)cnc2SCc2c(F)cccc2Cl)cc1]

$^1$H NMR (400 MHz, CDCl$_3$) δ 8.51 (s, 2H), 7.35 (s, 1H), 7.22-7.06 (m, 4H), 7.00-6.86 (m, 5H), 4.62 (s, 2H), 4.48 (s, 2H), 3.83 (s, 3H), 2.98 (s, 3H). LC-MS ESI m/z; found 497.1 [M+H]$^+$.

Example 61

2-((2,6-Dimethylbenzyl)thio)-1-(4-fluorophenyl)-N-methyl-N-(pyridin-4-ylmethyl)-1H-imidazole-5-carboxamide (560)

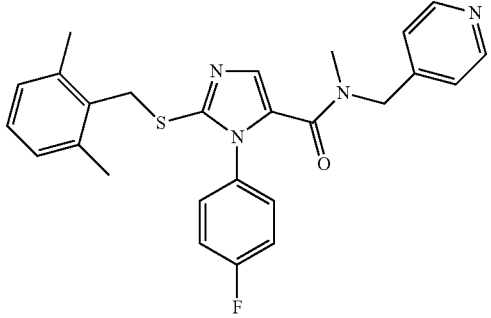 [SMILES: Cc1cccc(C)c1CSc1ncc(C(=O)N(C)Cc2ccncc2)n1-c1ccc(F)cc1]

$^1$H NMR (400 MHz, CDCl$_3$) δ 8.55 (s, 2H), 7.22-6.95 (m, 10H), 4.61 (s, 2H), 4.43 (s, 2H), 3.05 (s, 3H), 2.32 (s, 6H). LC-MS ESI m/z; found 461.3 [M+H]$^+$.

Example 62

2-((2,6-Dichlorobenzyl)thio)-1-(4-fluorophenyl)-N-methyl-N-(pyridin-4-ylmethyl)-1H-imidazole-5-carboxamide (561)

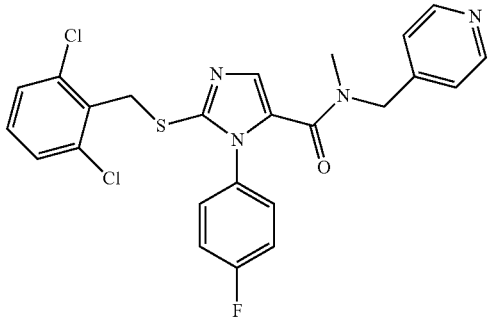 [SMILES: CN(Cc1ccncc1)C(=O)c1cnc(SCc2c(Cl)cccc2Cl)n1-c1ccc(F)cc1]

$^1$H NMR (400 MHz, CDCl$_3$) δ 8.55 (s, 2H), 7.46-7.29 (m, 1H), 7.24 (s, 1H), 7.21-6.96 (m, 8H), 4.61 (s, 4H), 3.05 (s, 3H). LC-MS ESI m/z; found 501.2 [M+H]$^+$.

Example 63

1-(4-Fluorophenyl)-N-methyl-2-((2-methylbenzyl)thio)-N-(pyridin-4-ylmethyl)-1H-imidazole-5-carboxamide (562)

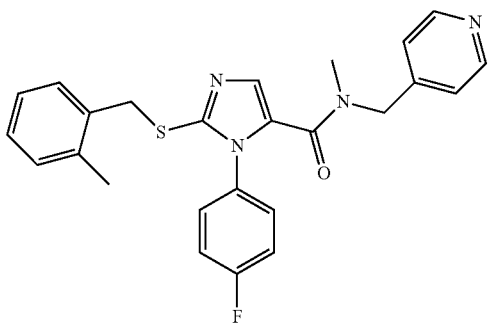 [SMILES: Cc1ccccc1CSc1ncc(C(=O)N(C)Cc2ccncc2)n1-c1ccc(F)cc1]

¹H NMR (400 MHz, CDCl₃) δ 8.54 (s, 2H), 7.20-6.93 (m, 11H), 4.61 (s, 2H), 4.33 (s, 2H), 3.01 (s, 3H), 2.27 (s, 3H). LC-MS ESI m/z; found 447.2 [M+H]⁺.

Example 64

2-((2-Chloro-6-fluorobenzyl)thio)-N-methyl-N-(pyridin-4-ylmethyl)-1-(p-tolyl)-1H-imidazole-5-carboxamide (563)

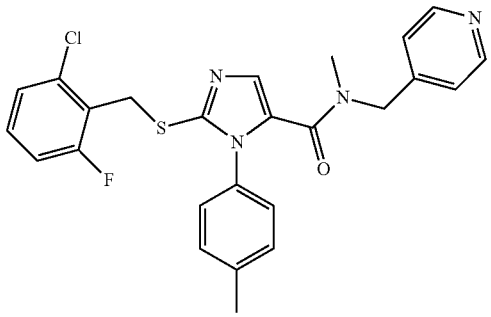 [SMILES: Cc1ccc(-n2c(C(=O)N(C)Cc3ccncc3)cnc2SCc2c(F)cccc2Cl)cc1]

¹H NMR (400 MHz, CDCl₃) δ 8.51 (s, 2H), 7.37 (s, 1H), 7.24-7.04 (m, 6H), 7.02-6.82 (m, 3H), 4.61 (s, 2H), 4.49 (s, 2H), 2.98 (s, 3H), 2.40 (s, 3H). LC-MS ESI m/z; found 481.2 [M+H]⁺.

Example 65

2-((2-Chloro-6-fluorobenzyl)thio)-1-(3-fluorophenyl)-N-methyl-N-(pyridin-4-ylmethyl)-1H-imidazole-5-carboxamide (564)

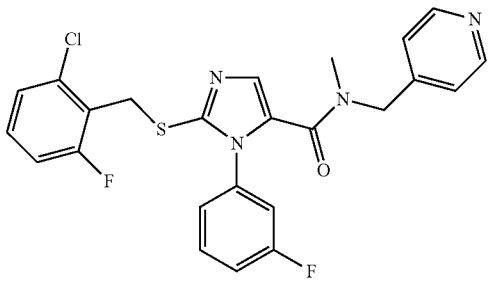 [SMILES: CN(Cc1ccncc1)C(=O)c1cnc(SCc2c(F)cccc2Cl)n1-c1cccc(F)c1]

¹H NMR (400 MHz, CDCl₃) δ 8.55 (s, 2H), 7.45-7.29 (m, 2H), 7.22-7.10 (m, 3H), 7.07-6.97 (m, 3H), 6.96-6.82 (m, 2H), 4.63 (s, 2H), 4.48 (s, 2H), 3.06 (s, 3H). LC-MS ESI m/z; found 485.1 [M+H]⁺.

Example 66

2-((2-Chloro-6-fluorobenzyl)thio)-1-cyclohexyl-N-methyl-N-(pyridin-4-ylmethyl)-1H-imidazole-5-carboxamide (565)

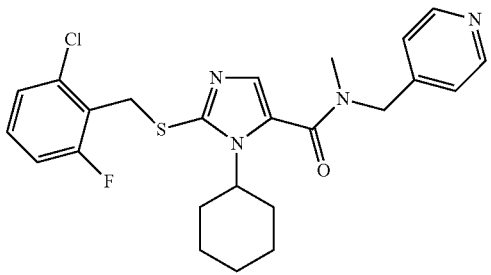 [SMILES: CN(Cc1ccncc1)C(=O)c1cnc(SCc2c(F)cccc2Cl)n1C1CCCCC1]

¹H NMR (400 MHz, cdcl₃) δ 8.68-8.52 (m, 2H), 7.25-7.10 (m, 5H), 7.00-6.88 (m, 1H), 4.72 (s, 2H), 4.48 (s, 2H), 4.31- 4.11 (m, 1H), 3.08 (s, 3H), 2.18-1.94 (m, 2H), 1.84-1.71 (m, 2H), 1.70-1.64 (m, 2H), 1.32-1.07 (m, 4H). LC-MS ESI m/z; found 473.2 [M+H]⁺.

Example 67

2-((2-Chloro-6-fluorobenzyl)thio)-N-methyl-1-neopentyl-N-(pyridin-4-ylmethyl)-1H-imidazole-5-carboxamide (566)

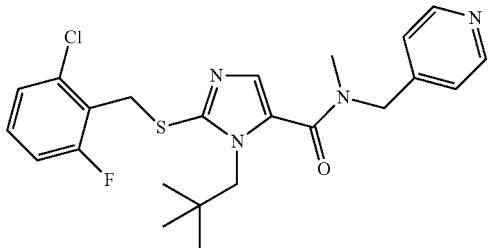 [SMILES: CN(Cc1ccncc1)C(=O)c1cnc(SCc2c(F)cccc2Cl)n1CC(C)(C)C]

¹H NMR (400 MHz, CDCl₃) δ 8.61 (s, 2H), 7.27 (s, 1H), 7.24-7.13 (m, 4H), 7.03-6.91 (m, 1H), 5.05-3.55 (m, 6H), 3.17 (s, 3H), 0.83 (s, 9H). LC-MS ESI m/z; found 461.1 [M+H]⁺.

Example 68

2-(((2,6-Dichlorophenyl)thio)methyl)-N-((1,3-dimethyl-1H-pyrazol-4-yl)methyl)-1-(4-fluorophenyl)-N-methyl-1H-imidazole-5-carboxamide (567)

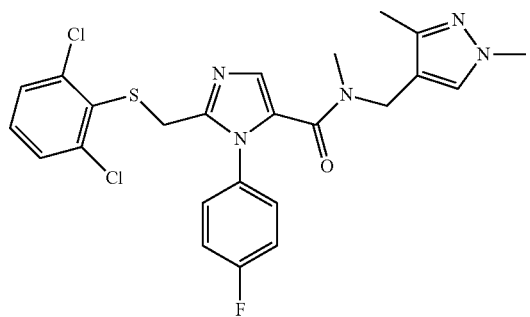 [SMILES: Cc1nn(C)cc1CN(C)C(=O)c1cnc(CSc2c(Cl)cccc2Cl)n1-c1ccc(F)cc1]

¹H NMR (400 MHz, CDCl₃) δ: 7.45-7.29 (m, 4H), 7.24-7.16 (m, 1H), 7.15-7.1 (m, 3H), 7.04 (s, 1H), 4.56-4.12 (m, 2H), 3.94 (s, 2H), 3.78 (s, 3H), 3.16-2.76 (m, 3H), 2.13 (s, 3H). LC-MS ESI m/z; found 518.1 [M+H]⁺.

Example 69

N-((1,3-Dimethyl-1H-pyrazol-4-yl)methyl)-1-(4-fluorophenyl)-N-methyl-2-((2,3,6-trifluorophenoxy)methyl)-1H-imidazole-5-carboxamide (568)

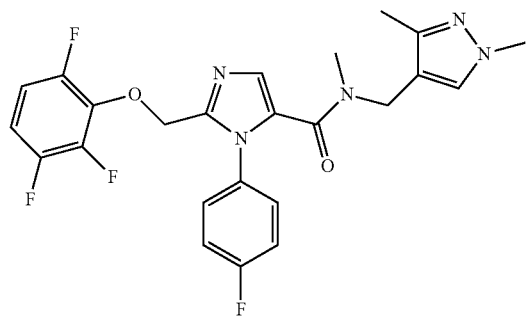 [SMILES: Cc1nn(C)cc1CN(C)C(=O)c1cnc(COc2c(F)ccc(F)c2F)n1-c1ccc(F)cc1]

¹H NMR (400 MHz, CDCl₃) δ: 7.48-7.42 (m, 2H), 7.28-7.24 (m, 1H), 7.16 (t, J=8.5, 2H), 7.02 (s, 1H), 6.90-6.69 (m, 2H), 5.00 (s, 2H), 4.37 (s, 2H), 3.78 (s, 3H), 2.92 (s, 3H), 2.13 (s, 3H). LC-MS ESI m/z; found 488.0 [M+H]⁺.

Example 70

N-((1,3-Dimethyl-1H-pyrazol-4-yl)methyl)-1-(4-fluorophenyl)-N-methyl-2-(((2,3,5,6-tetrafluorophenyl)thio)methyl)-1H-imidazole-5-carboxamide (569)

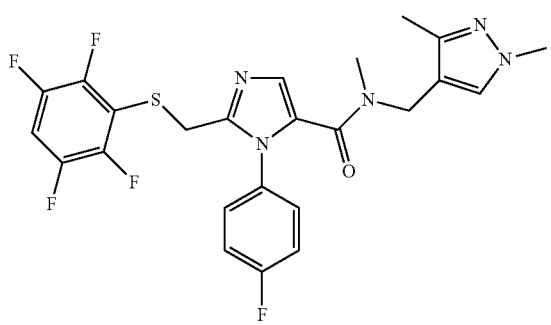 [SMILES: Cc1nn(C)cc1CN(C)C(=O)c1cnc(CSc2c(F)c(F)cc(F)c2F)n1-c1ccc(F)cc1]

¹H NMR (400 MHz, CDCl₃) δ: 7.42-7.32 (m, 2H), 7.2-7.12 (m, 2H), 7.12-7.00 (m, 3H), 4.37 (s, 2H), 3.93 (s, 2H), 3.78 (s, 3H), 2.97 (s, 3H), 2.13 (s, 3H). LC-MS ESI m/z; found 522.1 [M+H]⁺.

Example 71

N-((1,3-Dimethyl-1H-pyrazol-4-yl)methyl)-1-(4-fluorophenyl)-N-methyl-2-((2-(2,3,6-trifluorophenyl)propan-2-yl)thio)-1H-imidazole-5-carboxamide (570)

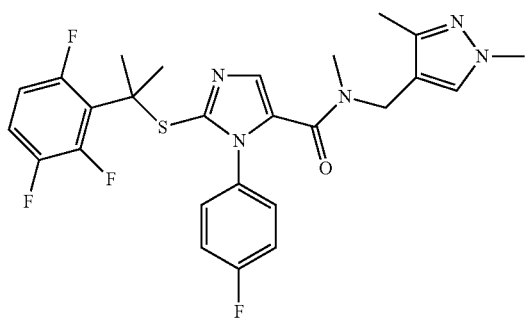 [SMILES: Cc1nn(C)cc1CN(C)C(=O)c1cnc(SC(C)(C)c2c(F)ccc(F)c2F)n1-c1ccc(F)cc1]

¹H NMR (400 MHz, CDCl₃) δ: 7.33-7.28 (m, 1H), 7.33-7.28 (m, 1H), 7.03-6.93 (m, 5H), 6.71-6.51 (m, 1H), 4.30 (s, 2H), 3.76 (s, 3H), 2.84 (s, 3H), 2.11 (s, 3H), 1.83 (s, 6H). LC-MS ESI m/z; found 532.1 [M+H]⁺.

Example 72

1-(4-Fluorophenyl)-N-methyl-N-(pyridin-4-ylmethyl)-2-((2,3,6-trifluorobenzyl)sulfinyl)-1H-imidazole-5-carboxamide (571)

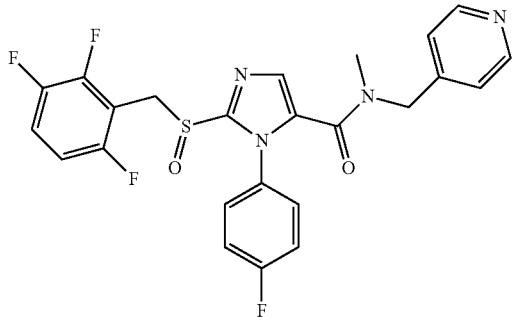 [SMILES: CN(Cc1ccncc1)C(=O)c1cnc(S(=O)Cc2c(F)ccc(F)c2F)n1-c1ccc(F)cc1]

¹H NMR (400 MHz, CDCl₃) δ: 8.55-8.4 (m, 2H), 7.48-7.40 (m, 1H), 7.3-7.2 (m, 2H), 7.13-7.00 (m, 3H), 6.85-6.80 (m, 3H), 4.77 (d, J=13.0, 1H), 4.62-4.4 (m, 3H), 2.94 (s, 3H). LC-MS ESI m/z; found 503.1 [M+H]⁺.

Example 73

N-((1,3-Dimethyl-1H-pyrazol-4-yl)methyl)-1-(4-fluorophenyl)-N-methyl-2-(((2,3,6-trifluorobenzyl)thio)methyl)-1H-imidazole-5-carboxamide (572)

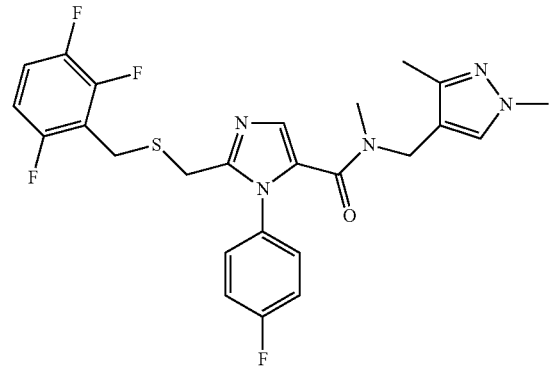 [SMILES: Cc1nn(C)cc1CN(C)C(=O)c1cnc(CSCc2c(F)ccc(F)c2F)n1-c1ccc(F)cc1]

¹H NMR (400 MHz, CDCl₃) δ: 7.3-7.22 (m, 3H), 7.15-6.92 (m, 4H), 6.86-6.68 (m, 1H), 4.38 (s, 2H), 3.83 (s, 2H), 3.77 (s, 3H), 3.65 (s, 2H), 2.99 (s, 3H), 2.12 (s, 3H). LC-MS ESI m/z; found 518.1 [M+H]⁺.

Example 74

N-((1,3-Dimethyl-1H-pyrazol-4-yl)methyl)-1-(4-fluorophenyl)-N-methyl-2-(((2,3,6-trifluorobenzyl)sulfonyl)methyl)-1H-imidazole-5-carboxamide (573)

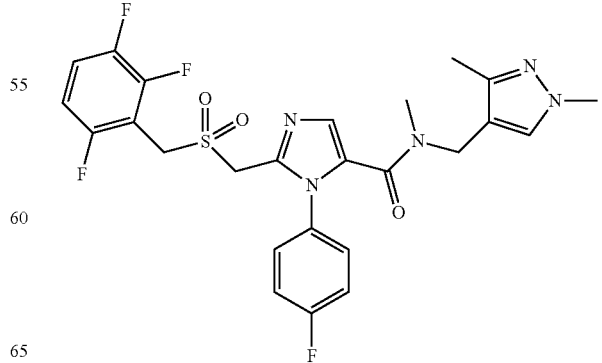

¹H NMR (400 MHz, CDCl₃) δ: 7.4-7.28 (m, 3H), 7.24-7.1 (m, 3H), 7.02 (s, 1H), 6.95-6.88 (m, 1H), 4.86 (s, 2H), 4.37 (s, 2H), 4.31 (s, 2H), 3.77 (s, 3H), 2.96 (s, 3H), 2.13 (s, 3H). LC-MS ESI m/z; found 550.2 [M+H]⁺.

Example 75

(E)-3-(1,3-Dimethyl-1H-pyrazol-4-yl)-1-(1-(4-fluorophenyl)-2-((2,3,6-trifluorobenzyl)thio)-1H-imidazol-5-yl)prop-2-en-1-one (574)

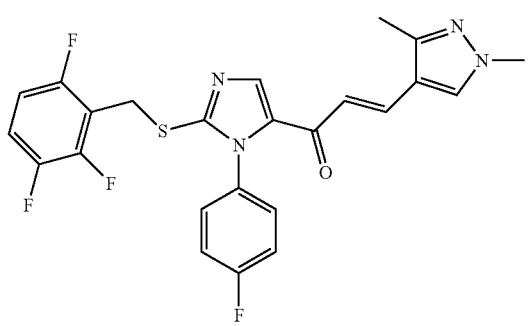 [SMILES: Cc1nn(C)cc1/C=C/C(=O)c1cnc(SCc2c(F)ccc(F)c2F)n1-c1ccc(F)cc1]

¹H NMR (400 MHz, CDCl₃) δ: 7.89 (s, 1H), 7.57 (s, 1H), 7.52 (d, J=15.4, 1H), 7.17-6.93 (m, 5H), 6.82 (d, J=15.6, 1H), 6.78-6.72 (m, 1H), 4.47 (s, 2H), 3.79 (s, 3H), 2.27 (s, 3H). LC-MS ESI m/z; found 487.1 [M+H]⁺.

Example 76

N-((1,3-Dimethyl-1H-pyrazol-4-yl)methyl)-1-(4-fluorophenyl)-N-methyl-2-((2,3,6-trifluorobenzyl)amino)-1H-imidazole-5-carboxamide (575)

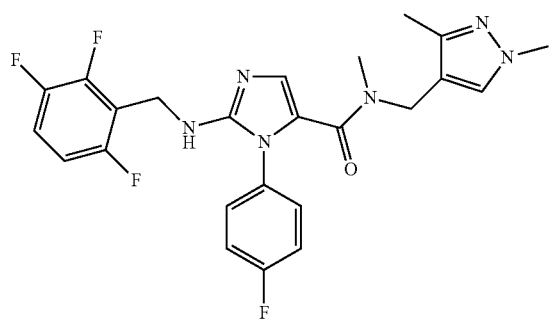 [SMILES: Cc1nn(C)cc1CN(C)C(=O)c1cnc(NCc2c(F)ccc(F)c2F)n1-c1ccc(F)cc1]

¹H NMR (400 MHz, CDCl₃) δ: 7.36-7.33 (m, 2H), 7.25-7.20 (m, 3H), 7.16-7.08 (m, 2H), 6.87-6.82 (m, 1H), 6.31 (br, 1H), 4.60 (s, 2H), 4.37 (s, 2H), 3.81 (s, 3H), 3.02 (s, 3H), 2.12 (s, 3H). LC-MS ESI m/z; found 487.9 [M+H]⁺.

Example 77

N-((1,3-Dimethyl-1H-pyrazol-4-yl)methyl)-1-(4-fluorophenyl)-N-methyl-2-((2,3,6-trifluorobenzyl)oxy)methyl)-1H-imidazole-5-carboxamide (576)

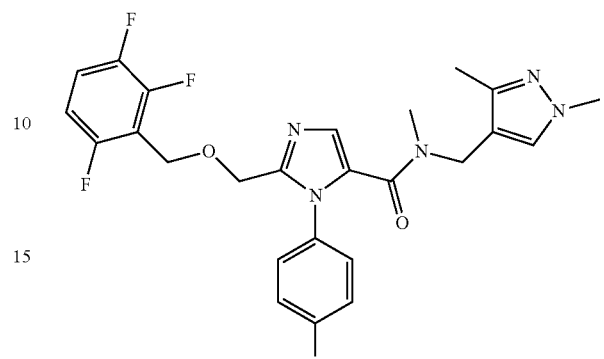

¹H NMR (400 MHz, CDCl₃) δ: 7.48 (s, 1H), 7.29-7.25 (m, 2H), 7.16-7.07 (m, 4H), 6.85-6.80 (m, 1H), 4.59 (s, 2H), 4.56 (s, 2H), 4.34 (s, 2H), 3.82 (s, 3H), 2.96 (s, 3H), 2.14 (s, 3H). LC-MS ESI m/z; found 501.8 [M+H]⁺.

Example 78

1-(4-Fluorophenyl)-N-methyl-N-((2-methylpyridin-4-yl)methyl)-2-((2,3,6-trifluorobenzyl)thio)-1H-imidazole-5-carboxamide (577)

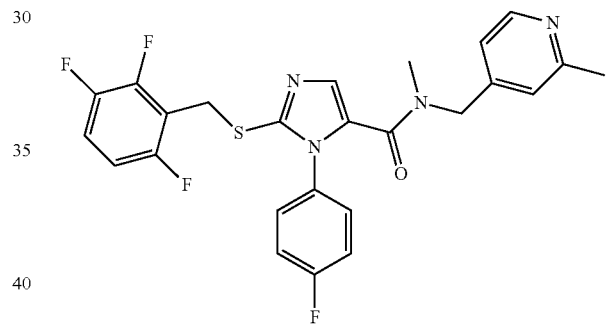

¹H NMR (400 MHz, CDCl₃) δ: 8.40 (s, 1H), 7.33 (s, 1H) 7.19-7.15 (m, 2H), 7.11-6.98 (m, 3H), 6.86-6.73 (m, 3H), 4.58 (s, 2H), 4.34 (s, 2H), 3.01 (s, 3H), 2.50 (s, 3H). LC-MS ESI m/z; found 501.1 [M+H]⁺.

Example 79

N-((2-Chloropyridin-4-yl)methyl)-1-(4-fluorophenyl)-N-methyl-2-((2,3,6-trifluorobenzyl)thio)-1H-imidazole-5-carboxamide (578)

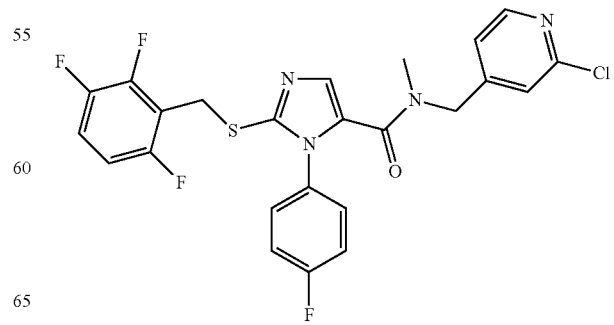

¹H NMR (400 MHz, CDCl₃) δ: 8.29 (d, J=3.6, 1H), 7.37 (s, 1H) 7.17-7.14 (m, 4H), 7.04-7.01 (m, 3H), 6.95 (d, J=4.4, 1H), 6.79-6.75 (m, 1H), 4.59 (s, 2H), 4.36 (s, 2H), 3.07 (s, 3H). LC-MS ESI m/z; found 521.1 [M+H]⁺.

Example 80

N-((1,3-Dimethyl-1H-pyrazol-4-yl)methyl)-1-(4-fluorophenyl)-N-methyl-2-((pyridine-4-ylmethyl)thio)-1H-imidazole-5-carboxamide (579)

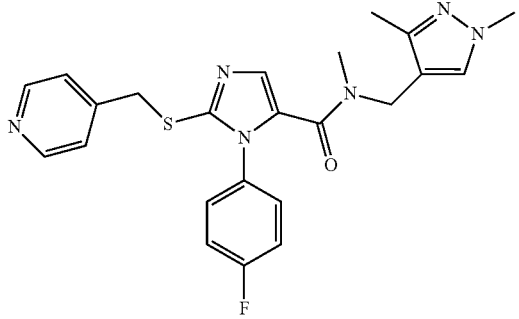 [SMILES: Cc1nn(C)cc1CN(C)C(=O)c1cnc(SCc2ccncc2)n1-c1ccc(F)cc1]

¹H NMR (400 MHz, CDCl₃) δ: 8.45 (d, J=5.6, 2H), 7.28 (s, 1H) 7.16 (d, J=5.6, 2H), 7.06-7.02 (m, 5H), 4.34 (s, 2H), 4.25 (s, 2H), 3.73 (s, 3H), 2.91 (s, 3H), 2.09 (s, 3H). LC-MS ESI m/z; found 451.1 [M+H]⁺.

Example 81

N-((1,3-Dimethyl-1H-pyrazol-4-yl)methyl)-1-(4-fluorophenyl)-N-methyl-2-(methyl(2,3,6-trifluorobenzyl)amino)-1H-imidazole-5-carboxamide (580)

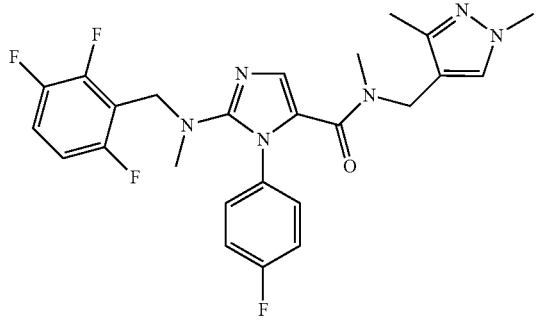 [SMILES: Cc1nn(C)cc1CN(C)C(=O)c1cnc(N(C)Cc2c(F)ccc(F)c2F)n1-c1ccc(F)cc1]

¹H NMR (400 MHz, CDCl₃) δ: 7.36-7.33 (m, 2H), 7.25 (s, 1H), 7.12-7.02 (m, 4H), 6.79-6.75 (m, 1H), 4.41 (s, 2H), 4.16 (s, 2H), 3.77 (s, 3H), 2.98 (s, 3H), 2.57 (s, 3H), 2.14 (s, 3H). LC-MS ESI m/z; found 501.2 [M+H]⁺.

Example 82

N-((4-Ethyl-2-methylthiazol-5-yl)methyl)-1-(4-fluorophenyl)-2-((2,3,6-trifluorobenzyl)sulfinyl)-1H-imidazole-5-carboxamide (581)

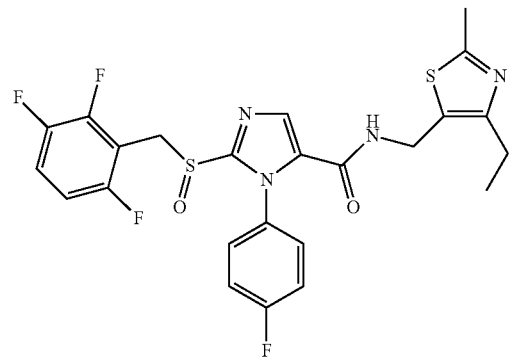 [SMILES: CCc1nc(C)sc1CNC(=O)c1cnc(S(=O)Cc2c(F)ccc(F)c2F)n1-c1ccc(F)cc1]

¹H NMR (400 MHz, CDCl₃) δ: 7.63 (s, 1H), 7.34-7.17 (m, 3H), 7.16-7.07 (m, 3H), 6.89-6.77 (m, 1H), 4.73 (d, J=12.9, 1H), 4.56 (d, J=12.9, 1H), 4.52-4.42 (m, 2H), 2.68-2.52 (m, 5H), 1.16 (t, J=7.5, 3H). LC-MS ESI m/z; found 537.1 [M+H]⁺.

Example 83

1-(4-Fluorophenyl)-N-methyl-N-((1-methyl-5-phenoxy-3-(trifluoromethyl)-1H-pyrazol-4-yl)methyl)-2-((2,3,6-trifluorobenzyl)sulfinyl)-1H-imidazole-5-carboxamide (582)

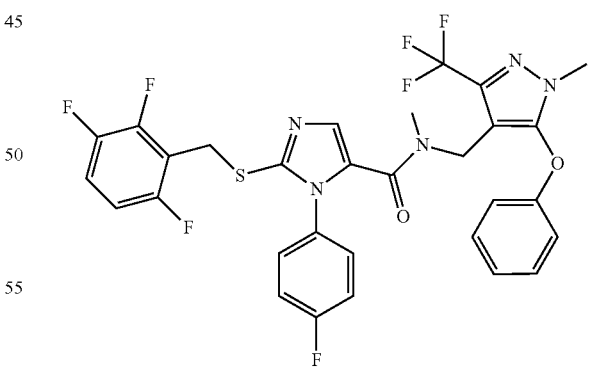

¹H NMR (400 MHz, CDCl₃) δ: 7.36-7.32 (m, 2H), 7.17-7.13 (m, 2H), 7.09-7.04 (m, 5H), 6.81-6.77 (m, 3H), 4.47 (s, 2H), 4.26 (s, 2H), 3.69 (s, 3H), 2.88 (s, 3H). LC-MS ESI m/z; found 650.2 [M+H]⁺.

Example 84

2-((3-Chloro-4-fluorophenethyl)thio)-1-(4-fluorophenyl)-N-((2-methylpyridin-4-yl)methyl)-1H-imidazole-5-carboxamide (583)

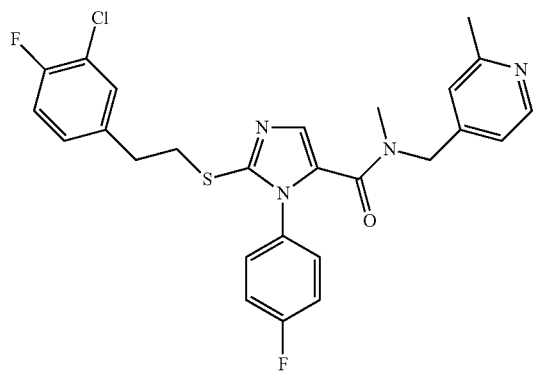 [SMILES: Cc1cc(CN(C)C(=O)c2cnc(SCCc3ccc(F)c(Cl)c3)n2-c2ccc(F)cc2)ccn1]

¹H NMR (400 MHz, CDCl₃) δ: 8.64 (d, J=6.0, 1H), 7.65 (s, 1H), 7.41 (d, J=5.6, 1H), 7.35 (s, 1H), 7.28-7.26 (m, 2H), 7.25-7.17 (m, 3H) 7.16-6.99 (m, 2H), 4.73 (s, 2H), 3.44-3.41 (d, J=7.2, 2H), 3.23 (s, 3H), 2.95-2.89 (d, J=7.2, 2H), 2.74 (s, 3H). LC-MS ESI m/z; found 513.2 [M+H]⁺.

Example 85

N-(4-(Dimethylamino)benzyl))-1-(4-fluorophenyl)-N-methyl-2-((2,3,6-trifluorobenzyl)thio)-1H-imidazole-5-carboxamide (584)

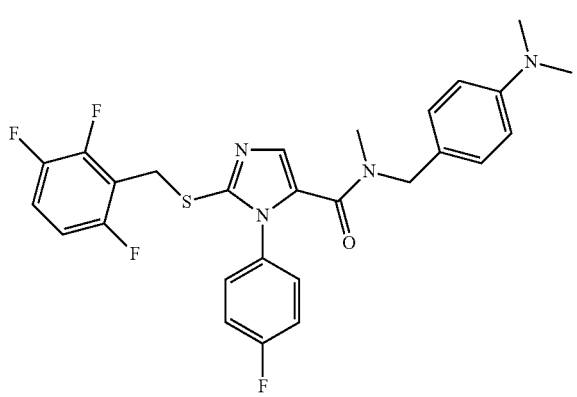 [SMILES: CN(Cc1ccc(N(C)C)cc1)C(=O)c1cnc(SCc2c(F)ccc(F)c2F)n1-c1ccc(F)cc1]

¹H NMR (400 MHz, CDCl₃) δ: 7.33 (s, 1H), 7.19-7.15 (m, 2H) 7.12-7.03 (m, 3H), 7.02-6.96 (m, 2H), 6.79-6.73 (m, 1H), 6.68-6.6 (m, 2H), 4.51 (s, 2H), 4.32 (s, 2H), 2.94-2.84 (m, 9H). LC-MS ESI m/z; found 529.2 [M+H]⁺.

Example 86

1-(4-Fluorophenyl)-N-4-dimethyl-N-((2-methylpyridin-4-yl)methyl)-2-((2,3,6-trifluorobenzyl)thio)-1H-imidazole-5-carboxamide (585)

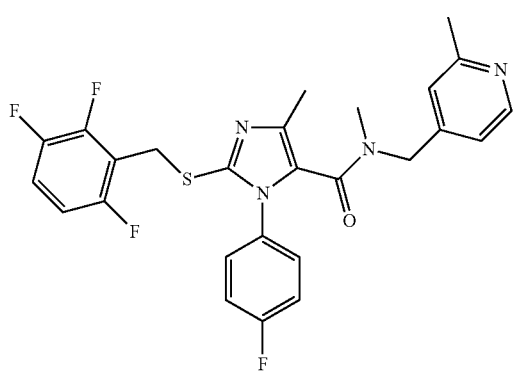 [SMILES: Cc1cc(CN(C)C(=O)c2c(C)nc(SCc3c(F)ccc(F)c3F)n2-c2ccc(F)cc2)ccn1]

¹H NMR (400 MHz, CDCl₃) δ 8.36 (s, 1H), 7.21-6.94 (m, 5H), 6.81-6.65 (m, 3H), 4.48 (s, 2H), 4.25 (s, 2H), 2.86 (s, 3H), 2.48 (s, 3H), 2.30 (s, 3H). LC-MS ESI m/z; found 515.15 [M+H]⁺.

Example 87

2-((3-Chloro-4-fluorophenethyl)sulfonyl)-1-(4-fluorophenyl)-N-methyl-N-((2-methylpyridin-4-yl)methyl)-1H-imidazole-5-carboxamide (586)

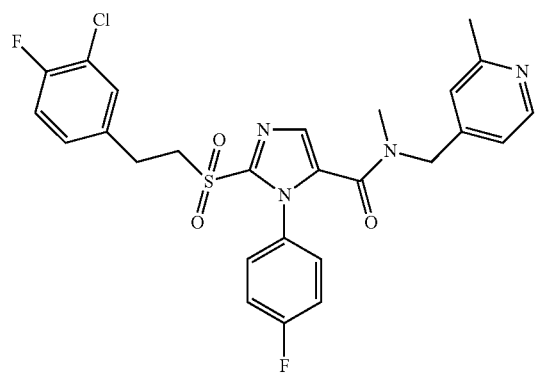 [SMILES: Cc1cc(CN(C)C(=O)c2cnc(S(=O)(=O)CCc3ccc(F)c(Cl)c3)n2-c2ccc(F)cc2)ccn1]

¹H NMR (400 MHz, CDCl₃) δ: 8.36 (s, 1H), 7.42 (s, 2H), 7.34 (s, 1H), 7.24 (d, J=8.8, 1H), 7.19-7.15 (m, 2H), 7.06 (d, J=6.4, 2H), 6.75 (s, 1H), 6.62 (s, 1H), 4.50 (s, 2H), 3.71 (s, 2H), 3.11 (s, 2H), 2.92 (s, 3H), 2.49 (s, 3H). LC-MS ESI m/z; found 545.2 [M+H]⁺.

Example 88

1-(4-Fluorophenyl)-N-methyl-2-((2,3,6-trifluorobenzyl)thio)-N-((2-trifluoromethyl)pyridin-4-yl)methyl)-1H-imidazole-5-carboxamide (587)

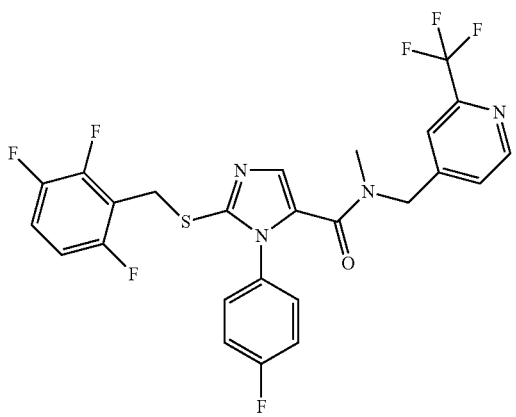 [SMILES: CN(Cc1ccnc(C(F)(F)F)c1)C(=O)c1cnc(SCc2c(F)ccc(F)c2F)n1-c1ccc(F)cc1]

$^1$H NMR (400 MHz, CDCl$_3$) δ: 8.66 (s, 1H), 7.55 (s, 1H), 7.39 (s, 1H), 7.26-7.13 (m, 5H), 7.10-7.03 (m, 1H), 6.81-6.77 (m, 1H), 4.68 (s, 2H), 4.39 (s, 2H), 3.14 (s, 3H). LC-MS ESI m/z; found 555.4 [M+H]$^+$.

Example 89

2-((2-Chloro-6-fluorophenethyl)sulfonyl)-1-(4-fluorophenyl)-N-methyl-N-((2-methylpyridin-4-yl)methyl)-1H-imidazole-5-carboxamide (588)

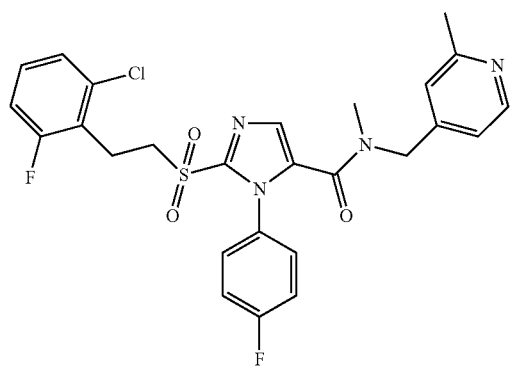 [SMILES: Cc1cc(CN(C)C(=O)c2cnc(S(=O)(=O)CCc3c(F)cccc3Cl)n2-c2ccc(F)cc2)ccn1]

$^1$H NMR (400 MHz, CDCl$_3$) δ: 8.36 (s, 1H), 7.47-7.44 (m, 3H), 7.19-7.14 (m, 4H), 6.98-6.95 (m, 1H), 6.75 (s, 1H), 6.62 (s, 1H), 4.50 (s, 2H), 3.66-3.62 (m, 2H), 3.32-3.26 (s, 2H), 2.93 (s, 3H), 2.49 (s, 3H). LC-MS ESI m/z; found 545.2 [M+H]$^+$

Example 90

1-(4-Fluorophenyl)-2-iodo-N-methyl-N-((2-methylpyridin-4-yl)methyl)-1H-imidazole-5-carboxamide (589)

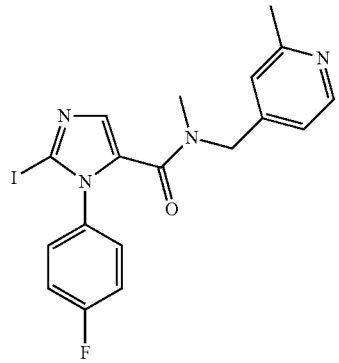 [SMILES: Cc1cc(CN(C)C(=O)c2cnc(I)n2-c2ccc(F)cc2)ccn1]

$^1$H NMR (400 MHz, CDCl$_3$) δ: 8.34 (s, 1H), 7.25-7.17 (m, 5H), 6.92-6.85 (m, 2H), 4.57 (s, 2H), 3.09 (s, 3H), 3.81 (s, 3H). LC-MS ESI m/z; found 451.0 [M+H]$^+$.

Example 91

2-Bromo-N-((1,3-dimethyl-1H-pyrazol-4-yl)methyl)-1-(4-fluorophenyl)-N-methyl-1H-imidazole-5-carboxamine (590)

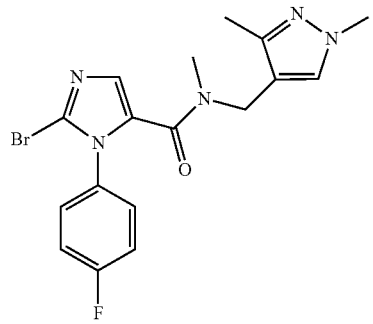 [SMILES: Cc1nn(C)cc1CN(C)C(=O)c1cnc(Br)n1-c1ccc(F)cc1]

$^1$H NMR (400 MHz, CDCl$_3$) δ: 7.25-7.20 (m, 3H), 7.14-7.10 (m, 2H), 7.03 (s, 1H), 4.32 (s, 2H), 3.73 (s, 3H), 2.95 (s, 3H), 1.99 (s, 3H). LC-MS ESI m/z; found 407.1 [M+H]$^+$.

Example 92

(2-((6-Chloro-2-fluoro-3-methoxybenzyl)thio)-1-(4-fluorophenyl)-1H-imidazol-5-yl)(2-(pyridin-4-yl)pyrrolidin-1-yl)methanone (591)

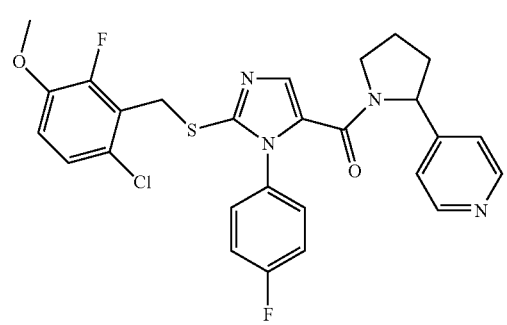 [SMILES: COc1ccc(Cl)c(CSc2ncc(C(=O)N3CCCC3c3ccncc3)n2-c2ccc(F)cc2)c1F]

¹H NMR (400 MHz, CDCl₃) δ: 8.62-8.43 (m, 2H), 7.62 (s, 1H), 7.20-6.92 (m, 6H), 6.86-6.75 (m, 1H), 5.34-5.08 (m, 1H), 4.55-4.36 (m, 2H), 4.03-3.95 (m, 1H), 3.84-3.67 (m, 4H), 2.43-2.35 (m, 1H), 2.00-1.90 (m, 2H), 1.88-1.75 (m, 1H). LC-MS ESI m/z; found 541.1 [M+H]⁺.

Example 93

(2-(2-Fluorophenethyl)-1-(4-fluorophenyl)-1H-imidazol-5-yl)(2-(pyridin-4-yl)pyrrolidin-1-yl)methanone (592)

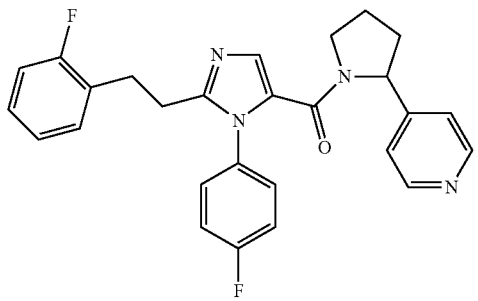 [SMILES: O=C(c1cnc(CCc2ccccc2F)n1-c1ccc(F)cc1)N1CCCC1c1ccncc1]

¹H NMR (400 MHz, CDCl₃) δ: 8.63-8.38 (m, 2H), 7.54 (s, 1H), 7.21-7.10 (m, 1H), 7.09-6.85 (m, 9H), 5.31-5.12 (m, 1H), 3.97-3.69 (m, 2H), 3.01-2.92 (m, 2H), 2.76-2.56 (m, 2H), 2.40-2.36 (m, 1H), 2.04-1.81 (m, 3H). LC-MS ESI m/z; found 459.2 [M+H]⁺.

Example 94

2-(Benzylthio)-N-((1,3-dimethyl-1H-pyrazol-4-yl)methyl)-1-(4-fluorophenyl)-N-methyl-1H-imidazole-5-carboxamide (593)

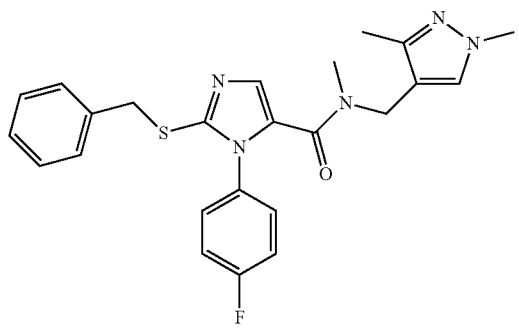 [SMILES: Cc1nn(C)cc1CN(C)C(=O)c1cnc(SCc2ccccc2)n1-c1ccc(F)cc1]

¹H NMR (400 MHz, CDCl₃) δ: 7.34 (s, 1H), 7.25-7.23 (m, 5H), 7.06-7.02 (m, 5H), 4.37 (s, 2H), 4.33 (s, 2H), 3.77 (s, 3H), 2.95 (s, 3H), 2.13 (s, 3H). LC-MS ESI m/z; found 450.2 [M+H]⁺.

Example 95

5-((6-Chloro-2-fluoro-3-methoxybenzyl)thio)-4-(4-fluorophenyl)-N-methyl-N-(pyridin-4-ylmethyl)-4H-1,2,4-triazole-3-carboxamide (594)

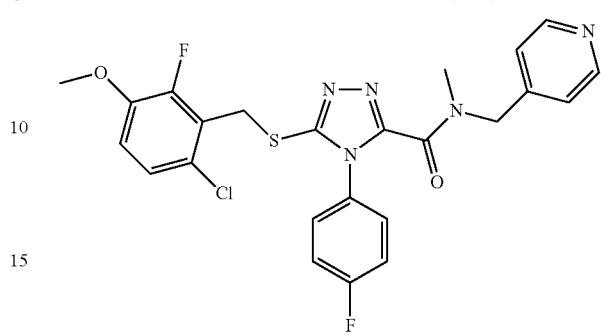

¹H NMR (400 MHz, CDCl₃) δ: 8.67-8.60 (m, 2H), 7.45-7.41 (m, 1H), 7.27-7.08 (m, 6H), 6.87-6.82 (m, 1H), 5.30-5.20 (m, 1H), 4.70-4.62 (m, 3H), 3.86-3.84 (m, 3H), 3.01 (s, 3H). LC-MS ESI m/z; found 516.1 [M+H]⁺.

Example 96

5-((6-Chloro-2-fluoro-3-methylbenzyl)thio)-4-(4-fluorophenyl)-N-methyl-N-(pyridin-4-ylmethyl)-4H-1,2,4-triazole-3-carboxamide (595)

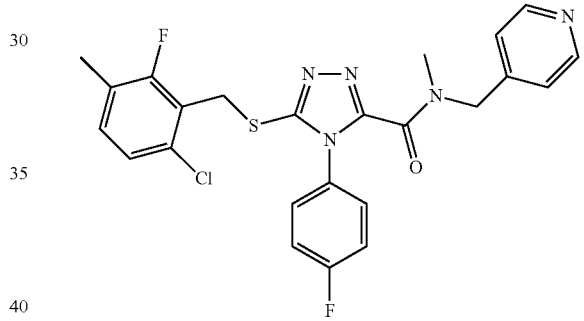

¹H NMR (400 MHz, CDCl₃) δ: 8.81-8.20 (m, 2H), 7.28-7.05 (m, 8H), 5.15 (s, 1H), 4.68-4.57 (m, 3H), 3.36-2.98 (m, 3H), 2.22-2.20 (m, 3H). LC-MS ESI m/z; found 500.1 [M+H]⁺.

Example 97

2-((6-Chloro-2-fluoro-3-methoxybenzyl)thio)-N-((1,3-dimethyl-1H-pyrazol-4-yl)methyl)-1-(4-fluorophenyl)-N-methyl-1H-imidazole-5-carboxamide (596)

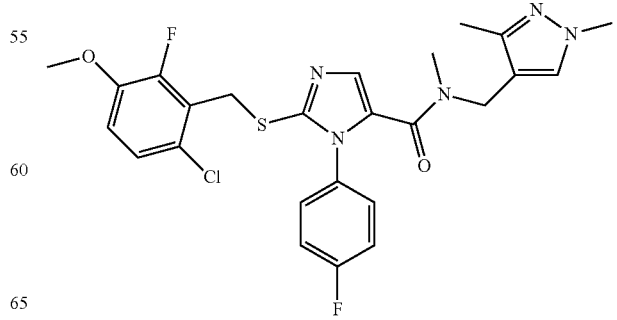

$^1$H NMR (400 MHz, CDCl$_3$) δ: 7.70 (s, 1H), 7.21 (s, 1H), 7.13-7.07 (m, 5H), 6.87-6.83 (m, 1H), 4.37-4.33 (m, 4H), 3.89 (s, 3H), 3.84 (s, 3H), 3.08 (s, 3H), 2.22 (s, 3H). LC-MS ESI m/z; found 532.1 [M+H]$^+$.

Example 98

2-((6-Chloro-2-fluoro-3-methylbenzyl)thio)-N-((1,3-dimethyl-1H-pyrazol-4-yl)methyl)-1-(4-fluorophenyl)-N-methyl-1H-imidazole-5-carboxamide (597)

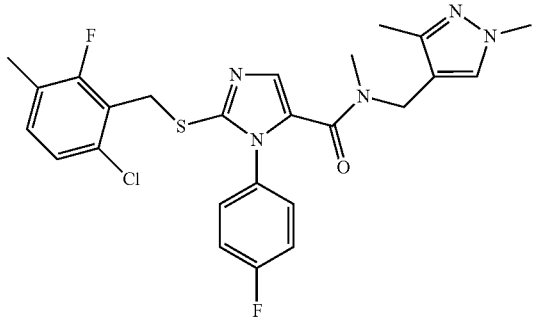

$^1$H NMR (400 MHz, CDCl$_3$) δ: 7.76 (s, 1H), 7.20 (s, 1H), 7.14-7.02 (m, 6H), 4.40-4.32 (m, 4H), 3.89 (s, 3H), 3.07 (s, 3H), 2.21 (s, 3H), 2.17 (s, 3H). LC-MS ESI m/z; found 516.1 [M+H]$^+$.

Example 99

3-((2-Chloro-6-fluorobenzyl)oxy)-5-((2-chloro-6-fluorobenzyl)thio)-4-(2-(trifluoromethyl)phenyl)-4H-1,2,4-triazole (598)

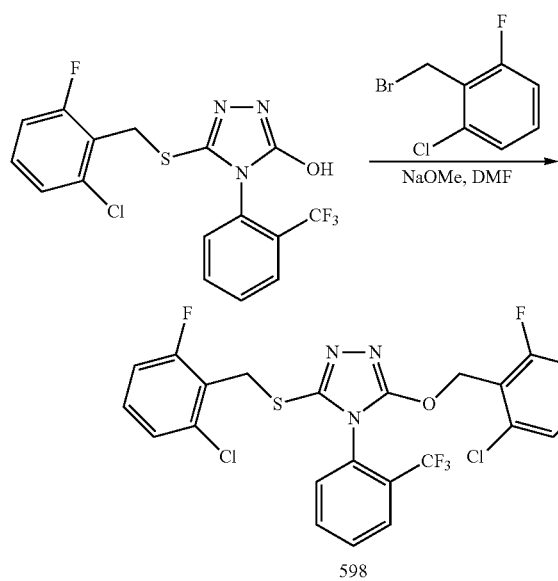

A mixture of 5-((2-chloro-6-fluorobenzyl)thio)-4-(2-(trifluoromethyl)phenyl)-4H-1,2,4-triazol-3-ol (50 mg, 0.124 mmol), 2-chloro-6-fluorobenzyl bromide (39 mg, 0.175 mg), and sodium methoxide (18 mg, 0.33 mmol) in anhydrous DMF was stirred at 80° C. for 8 h. The reaction mixture was cooled to room temperature and neutralized to pH 5 with 5N HCl. The solvent was removed in vacuo and the residue was purified by reverse phase HPLC to afford 3-((2-Chloro-6-fluorobenzyl)oxy)-5-((2-chloro-6-fluorobenzyl)thio)-4-(2-(trifluoromethyl)phenyl)-4H-1,2,4-triazole (598). $^1$H NMR (400 MHz, CDCl$_3$) δ: 7.81-7.79 (m, 1H), 7.63-7.60 (m, 2H), 7.33-7.24 (m, 2H), 7.19-7.14 (m, 2H), 7.10-7.04 (m, 2H), 6.90-6.85 (m, 2H), 5.20 (s, 2H), 4.23 (dd, J=13.0, 1.6, 1H), 4.15 (dd, J=13.0, 1.6, 1H). LC-MS ESI m/z; found 546.0 [M+H]$^+$.

Example 100

4-(3-Chlorophenyl)-3-((2,4-dichlorobenzyl)thio)-5-((2,3-difluorobenzyl)oxy)-4H-1,2,4-triazole (599)

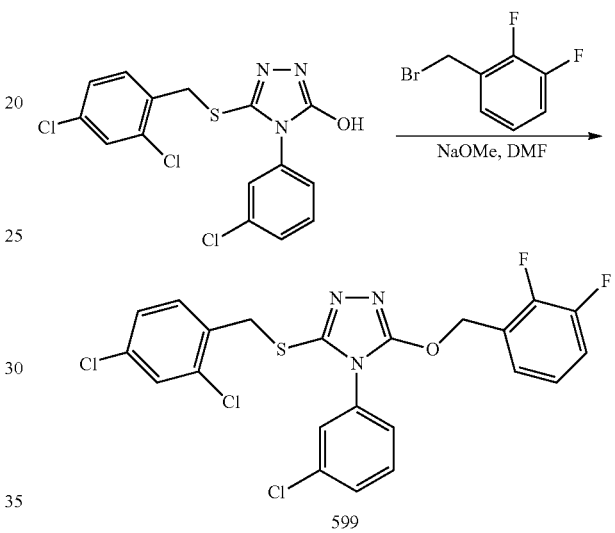

4-(3-chlorophenyl)-3-((2,4-dichlorobenzyl)thio)-5-((2,3-difluorobenzyl)oxy)-4H-1,2,4-triazole (599) was prepared in a similar manner as that described for the synthesis of compound 598 using 4-(3-chlorophenyl)-5-((2,4-dichlorobenzyl)thio)-4H-1,2,4-triazol-3-ol (50 mg, 0.129 mmol), 1-(bromomethyl)-2,3-difluorobenzene (40 mg, 0.194 mmol), sodium methoxide (17.4 mg, 0.322 mmol), and DMF (1.0 mL). $^1$H NMR (400 MHz, CDCl$_3$) δ: 7.40-7.39 (m, 2H), 7.34-7.31 (m, 2H), 7.25-7.05 (m, 6H), 5.11 (s, 2H), 4.24 (s, 2H). LC-MS ESI m/z; found 512.0 [M+H]$^+$.

Example 101

1-(4-Fluorophenyl)-N-methyl-N-((2-methylthiazol-5-yl)methyl)-2-((2,3,6-trifluorobenzyl)-sulfinyl)-1H-imidazole-5-carboxamide (600)

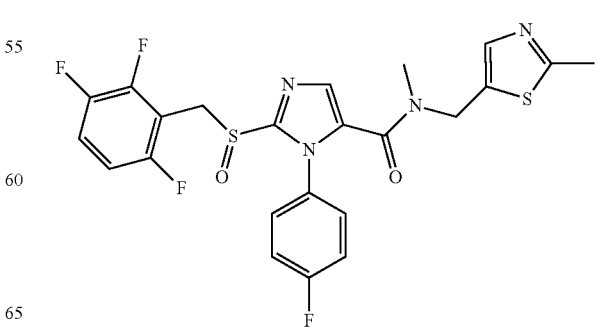

¹H NMR (400 MHz, CDCl₃) δ: 7.70-7.53 (m, 1H), 7.39-7.27 (m, 2H), 7.14 (s, 3H), 6.97-6.94 (m, 1H), 6.89-6.84 (m, 1H), 4.83-4.56 (m, 5H), 3.17 (s, 2H), 2.76 (s, 3H). LC-MS ESI m/z; found 522.9 [M+H]⁺.

Example 102

1-(4-Fluorophenyl)-N-methyl-N-((4-methylthiophen-2-yl)methyl)-2-((2,3,6-trifluorobenzyl)-sulfinyl)-1H-imidazole-5-carboxamide (601)

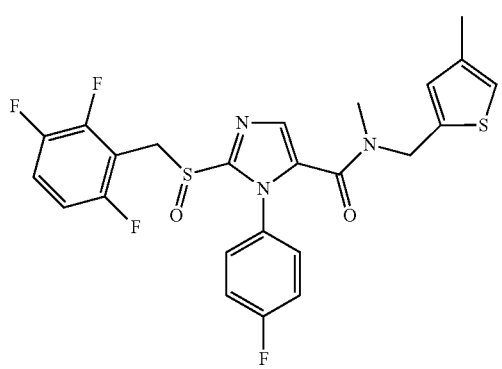 [SMILES: Cc1csc(CN(C)C(=O)c2cnc(S(=O)Cc3c(F)ccc(F)c3F)n2-c2ccc(F)cc2)c1]

¹H NMR (400 MHz, CDCl₃) δ: 7.56-7.51 (m, 1H), 7.30-7.21 (m, 2H), 7.20-7.11 (m, 3H), 6.88-6.80 (m, 2H), 6.66 (s, 1H), 4.83-4.57 (m, 4H), 3.03 (s, 3H), 2.21 (s, 3H). LC-MS ESI m/z; found 521.9 [M+H]⁺.

Example 103

1-(4-Fluorophenyl)-N-methyl-N-((2-methylthiazol-5-yl)methyl)-2-((2,3,6-trifluorobenzyl)thio)-1H-imidazole-5-carboxamide (602)

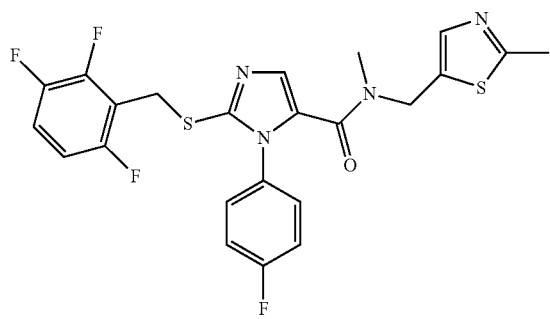 [SMILES: Cc1ncc(CN(C)C(=O)c2cnc(SCc3c(F)ccc(F)c3F)n2-c2ccc(F)cc2)s1]

¹H NMR (400 MHz, CDCl₃) δ: 8.00-7.75 (m, 1H), 7.14-7.06 (m, 6H), 6.83-6.79 (m, 1H), 4.70 (s, 2H), 4.28 (m, 2H), 3.21 (s, 3H), 2.80 (m, 3H). LC-MS ESI m/z; found 506.7 [M+H]⁺.

Example 104

1-(4-Fluorophenyl)-N-methyl-N-(pyridin-3-ylmethyl)-2-((2,3,6-trifluorobenzyl)thio)-1H-imidazole-5-carboxamide (603)

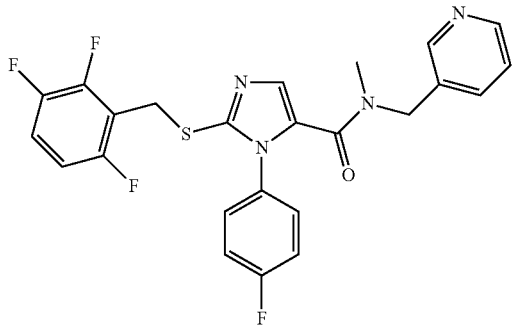 [SMILES: CN(Cc1cccnc1)C(=O)c1cnc(SCc2c(F)ccc(F)c2F)n1-c1ccc(F)cc1]

¹H NMR (400 MHz, CDCl₃) δ: 8.76 (s, 1H), 8.74 (d, J=5.2, 1H), 8.15 (d, J=7.6, 1H), 7.82-7.79 (m, 1H), 7.65 (s, 1H), 7.21-7.06 (m, 5H), 6.83-6.79 (m, 1H), 4.75 (s, 2H), 4.30 (s, 2H), 3.25 (s, 3H). LC-MS ESI m/z; found 486.8 [M+H]⁺.

Example 105

1-(4-Fluorophenyl)-N-methyl-N-(pyrazin-2-ylmethyl)-2-((2,3,6-trifluorobenzyl)thio)-1H-imidazole-5-carboxamide (604)

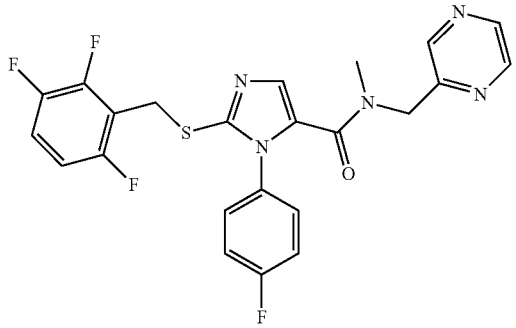 [SMILES: CN(Cc1cnccn1)C(=O)c1cnc(SCc2c(F)ccc(F)c2F)n1-c1ccc(F)cc1]

¹H NMR (400 MHz, CDCl₃) δ: 9.25 (s, 1H), 8.52-8.47 (m, 2H), 7.63 (s, 1H), 7.17-7.04 (m, 5H), 6.82-6.77 (m, 1H), 4.74 (s, 2H), 4.29 (s, 2H), 3.27 (s, 3H). LC-MS ESI m/z; found 487.8 [M+H]⁺.

Example 106

1-(4-Fluorophenyl)-N-methyl-N-(pyrazin-2-ylmethyl)-2-((2,3,6-trifluorobenzyl)sulfinyl)-1H-imidazole-5-carboxamide (605)

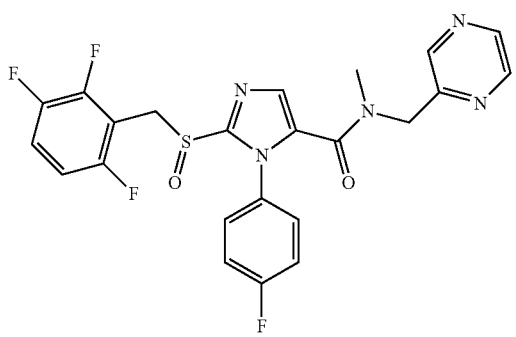 [SMILES: CN(Cc1cnccn1)C(=O)c1cnc(S(=O)Cc2c(F)ccc(F)c2F)n1-c1ccc(F)cc1]

¹H NMR (400 MHz, CDCl₃) δ: 8.67-8.48 (m, 3H), 7.66-7.61 (m, 1H), 7.29-7.27 (m, 2H), 7.19-7.11 (m, 3H), 6.87 (s, 1H), 4.80-4.75 (m, 2H), 4.61 (s, 2H), 3.24 (s, 3H). LC-MS ESI m/z; found 504.0 [M+H]⁺.

Example 107

4-(((1-(4-Fluorophenyl)-2-((2,3,6-trifluorobenzyl)thio)-1H-imidazol-5-yl)methoxy)methyl)-pyridine (606)

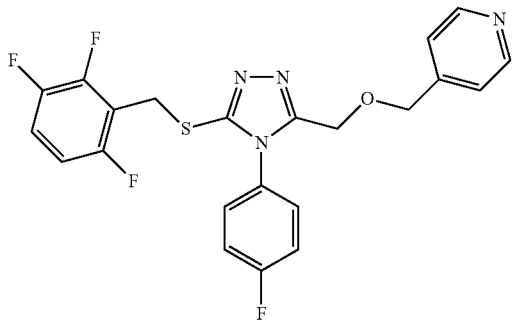 [SMILES: Fc1ccc(-n2c(COCc3ccncc3)nnc2SCc2c(F)ccc(F)c2F)cc1]

¹H NMR (400 MHz, DMSO-d₆) δ: 8.46 (d, J=5.6, 2H), 7.46-7.35 (m, 5H), 7.11-7.07 (m, 3H), 4.53 (s, 2H), 4.41 (s, 2H), 4.23 (s, 2H). LC-MS ESI m/z; found 461.1 [M+H]⁺.

Example 108

2-((2-Fluoro-6-(trifluoromethyl)benzyl)thio)-1-(4-fluorophenyl)-N-methyl-N-(pyridin-4-ylmethyl)-1H-imidazole-5-carboxamide (607)

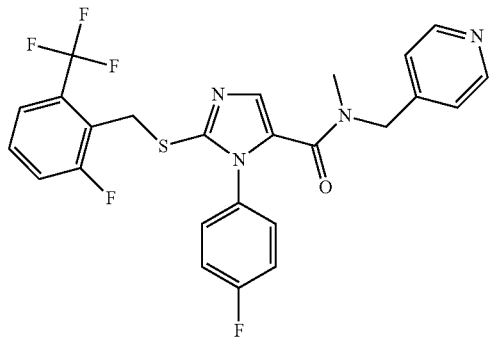 [SMILES: CN(Cc1ccncc1)C(=O)c1cnc(SCc2c(F)cccc2C(F)(F)F)n1-c1ccc(F)cc1]

¹H NMR (400 MHz, CDCl₃) δ: 8.83-8.65 (m, 2H), 8.58 (s, 1H), 7.92-7.80 (m, 2H), 7.48-7.38 (m, 2H), 7.36-7.30 (m, 1H), 7.23-7.15 (m, 4H), 4.84 (s, 2H), 4.71 (s, 2H), 3.40 (s, 3H). LC-MS ESI m/z; found 519.1 [M+H]⁺.

Example 109

2-((4-Fluoro-2-(trifluoromethyl)benzyl)thio)-1-(4-fluorophenyl)-N-methyl-N-(pyridin-4-ylmethyl)-1H-imidazole-5-carboxamide (608)

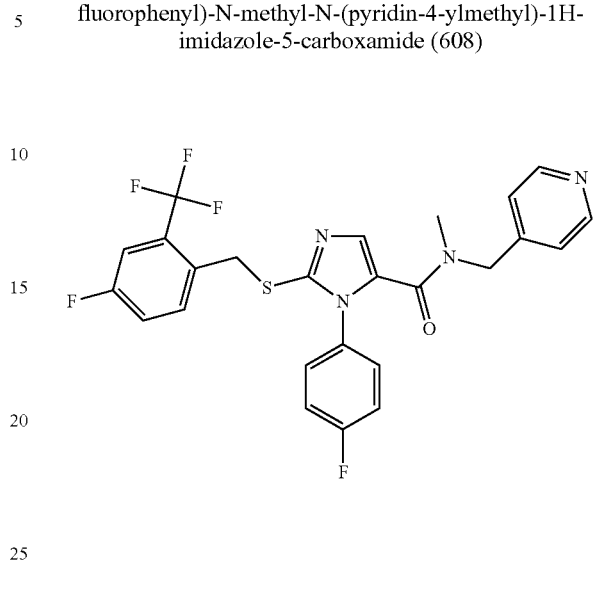

¹H NMR (400 MHz, CDCl₃) δ: 8.88-8.74 (m, 2H), 8.62-8.54 (m, 1H), 7.98-7.82 (m, 2H), 7.62-7.54 (m, 1H), 7.35-7.32 (m, 2H), 7.23-7.16 (m, 4H), 4.80-4.78 (m, 4H), 3.41 (s, 3H). LC-MS ESI m/z; found 519.1 [M+H]⁺.

Example 110

2-((4-Chloro-2-(trifluoromethyl)benzyl)thio)-1-(4-fluorophenyl)-N-methyl-N-(pyridin-4-ylmethyl)-1H-imidazole-5-carboxamide (609)

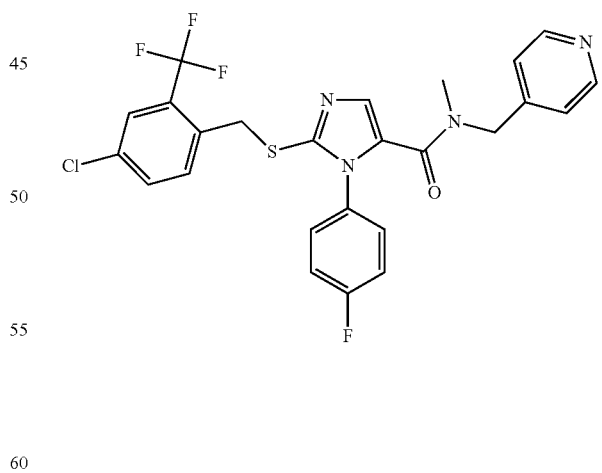

¹H NMR (400 MHz, CDCl₃) δ: 8.97-8.79 (m, 3H), 8.64-8.58 (m, 1H), 8.02-7.80 (m, 2H), 7.61-7.59 (m, 1H), 7.53-7.46 (m, 1H), 7.42-7.39 (m, 2H), 7.22-7.16 (m, 2H), 4.83-4.79 (m, 4H), 3.41 (s, 3H). LC-MS ESI m/z; found 535.1 [M+H]⁺.

Example 111

2-((2-Fluoro-3-(trifluoromethyl)benzyl)thio)-1-(4-fluorophenyl)-N-methyl-N-(pyridin-4-ylmethyl)-1H-imidazole-5-carboxamide (610)

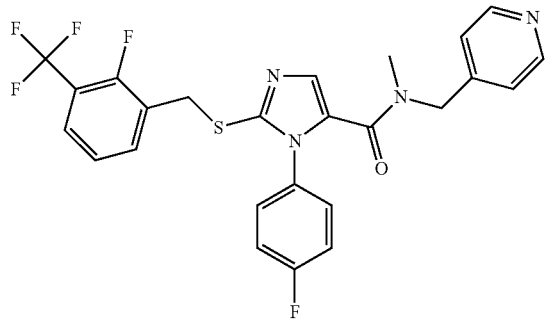 [SMILES: CN(Cc1ccncc1)C(=O)c1cnc(SCc2cccc(C(F)(F)F)c2F)n1-c1ccc(F)cc1]

$^1$H NMR (400 MHz, CDCl$_3$) δ: 8.82 (m, 2H), 8.25-8.14 (m, 1H), 7.80-7.40 (m, 2H), 7.58-7.54 (m, 2H), 7.27-7.17 (m, 5H), 4.81 (s, 2H), 4.57 (s, 2H), 3.32 (s, 3H). LC-MS ESI m/z; found 519.1 [M+H]$^+$.

Example 112

2-((2,5-Difluorobenzyl)thio)-1-(4-fluorophenyl)-N-methyl-N-(pyridin-4-ylmethyl)-1H-imidazole-5-carboxamide (611)

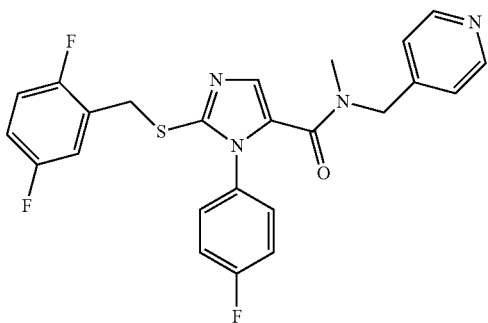 [SMILES: CN(Cc1ccncc1)C(=O)c1cnc(SCc2cc(F)ccc2F)n1-c1ccc(F)cc1]

$^1$H NMR (400 MHz, CDCl$_3$) δ: 8.84-8.78 (m, 2H), 8.17-8.04 (m, 1H), 8.78-7.65 (m, 2H), 7.20-7.18 (m, 4H), 7.03-6.96 (m, 3H), 4.81 (s, 2H), 4.48 (s, 2H), 3.31 (s, 3H). LC-MS ESI m/z; found 469.1 [M+H]$^+$.

Example 113

2-((6-Chloro-2-fluoro-3-methoxybenzyl)thio)-1-(4-fluorophenyl)-N-methyl-N-(pyridin-4-ylmethyl)-1H-imidazole-5-carboxamide (612)

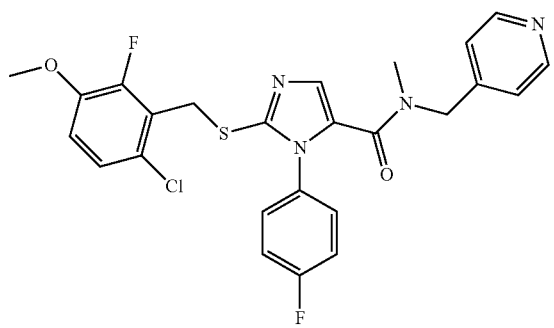 [SMILES: COc1ccc(Cl)c(CSc2ncc(C(=O)N(C)Cc3ccncc3)n2-c2ccc(F)cc2)c1F]

$^1$H NMR (400 MHz, CDCl$_3$) δ: 8.84-8.74 (m, 2H), 8.30-8.20 (m, 1H), 7.80-7.66 (m, 2H), 7.24-7.09 (m, 5H), 6.90-6.85 (m, 1H), 4.83 (s, 2H), 4.53 (s, 2H), 3.85 (s, 3H), 3.35 (s, 3H). LC-MS ESI m/z; found 515.1 [M+H]$^+$.

Example 114

2-((2-Fluorobenzyl)thio)-1-(4-fluorophenyl)-N-methyl-N-(pyridin-4-ylmethyl)-1H-imidazole-5-carboxamide (613)

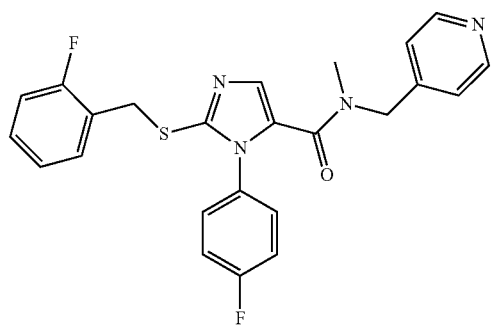 [SMILES: CN(Cc1ccncc1)C(=O)c1cnc(SCc2ccccc2F)n1-c1ccc(F)cc1]

$^1$H NMR (400 MHz, CDCl$_3$) δ: 8.83-8.80 (m, 2H), 8.04 (m, 1H), 7.68-7.66 (m, 2H), 7.32-7.26 (m, 1H), 7.18-7.00 (m, 7H), 4.80 (s, 2H), 4.50 (s, 2H), 3.29 (s, 3H). LC-MS ESI m/z; found 451.1 [M+H]$^+$.

Example 115

1-(4-Fluorophenyl)-N-methyl-N-(pyridin-4-ylmethyl)-2-((2-(trifluoromethyl)benzyl)thio)-1H-imidazole-5-carboxamide (614)

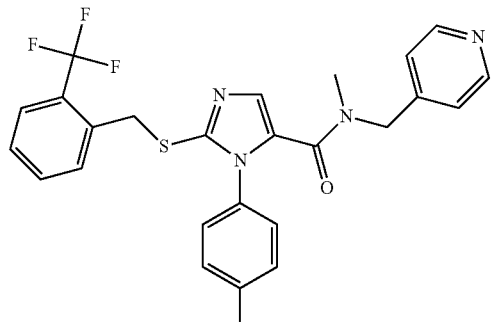

$^1$H NMR (400 MHz, CDCl$_3$) δ: 8.78 (d, J=4.4, 2H), 7.69-7.58 (m, 4H), 7.50-7.45 (m, 2H), 7.42-7.38 (m, 1H), 7.14-7.12 (m, 4H), 4.80 (s, 2H), 4.57 (s, 2H), 3.27 (s, 3H). LC-MS ESI m/z; found 501.1 [M+H]$^+$.

Example 116

2-((2-Chloro-5-fluorobenzyl)thio)-1-(4-fluorophenyl)-N-methyl-N-(pyridin-4-ylmethyl)-1H-imidazole-5-carboxamide (615)

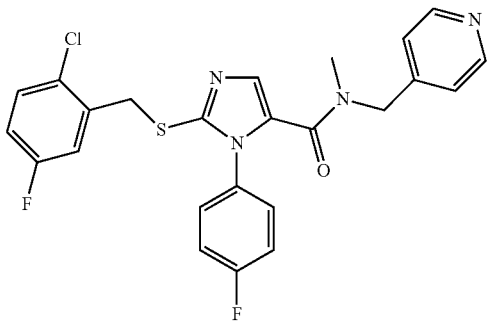 [SMILES: CN(Cc1ccncc1)C(=O)c1cnc(SCc2cc(F)ccc2Cl)n1-c1ccc(F)cc1]

$^1$H NMR (400 MHz, CDCl$_3$) δ: 8.80 (d, J=4.4, 2H), 7.75 (s, 1H), 7.62 (d, J=4.8, 2H), 7.33-7.29 (m, 1H), 7.18-7.10 (m, 5H), 6.98-6.93 (m, 1H), 4.81 (s, 2H), 4.48 (s, 2H), 3.27 (s, 3H). LC-MS ESI m/z; found 485.1 [M+H]$^+$.

Example 117

2-((5-Chloro-2-fluorobenzyl)thio)-1-(4-fluorophenyl)-N-methyl-N-(pyridin-4-ylmethyl)-1H-imidazole-5-carboxamide (616)

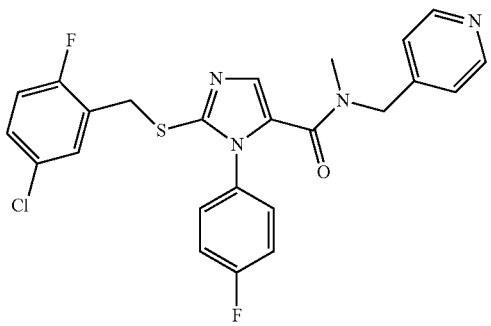 [SMILES: CN(Cc1ccncc1)C(=O)c1cnc(SCc2cc(Cl)ccc2F)n1-c1ccc(F)cc1]

$^1$H NMR (400 MHz, CDCl$_3$) δ: 8.81 (d, J=4.8, 2H), 8.02 (s, 1H), 7.69 (d, J=4.4, 2H), 7.26-7.17 (m, 6H), 7.00-6.95 (m, 1H), 4.81 (s, 2H), 4.44 (s, 2H), 3.31 (s, 3H). LC-MS ESI m/z; found 485.1 [M+H]$^+$.

Example 118

2-((2-Chloro-3,6-difluorobenzyl)thio)-1-(4-fluorophenyl)-N-methyl-N-(pyridin-4-ylmethyl)-1H-imidazole-5-carboxamide (617)

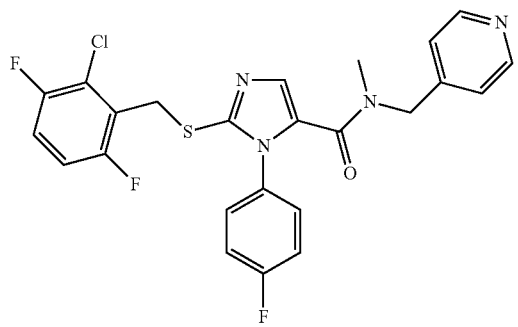 [SMILES: CN(Cc1ccncc1)C(=O)c1cnc(SCc2c(F)ccc(F)c2Cl)n1-c1ccc(F)cc1]

$^1$H NMR (400 MHz, CDCl$_3$) δ: 8.88-8.78 (m, 2H), 8.06 (s, 1H), 7.73-7.68 (m, 2H), 7.21-7.10 (m, 5H), 6.99-6.93 (m, 1H), 4.82 (s, 2H), 4.47 (s, 2H), 3.31 (s, 3H). LC-MS ESI m/z; found 503.1 [M+H]$^+$.

Example 119

2-((2-Chloro-4,5-difluorobenzyl)thio)-1-(4-fluorophenyl)-N-methyl-N-(pyridin-4-ylmethyl)-1H-imidazole-5-carboxamide (618)

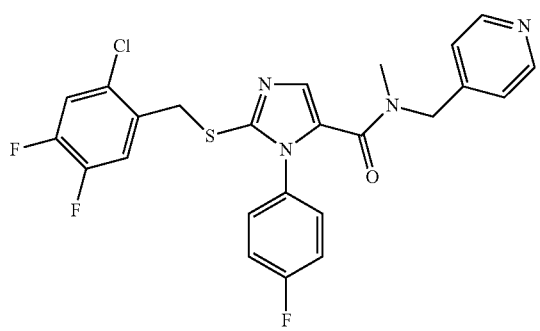 [SMILES: CN(Cc1ccncc1)C(=O)c1cnc(SCc2cc(F)c(F)cc2Cl)n1-c1ccc(F)cc1]

$^1$H NMR (400 MHz, CDCl$_3$) δ: 8.79 (d, J=5.2, 2H), 7.78-7.69 (m, 3H), 7.39-7.34 (m, 1H), 7.23-7.17 (m, 5H), 4.81 (s, 2H), 4.44 (s, 2H), 3.27 (s, 3H). LC-MS ESI m/z; found 503.1 [M+H]$^+$.

Example 120

1-(4-Fluorophenyl)-N-methyl-N-(pyridin-4-ylmethyl)-2-((2,3,5-trifluorobenzyl)thio)-1H-imidazole-5-carboxamide (619)

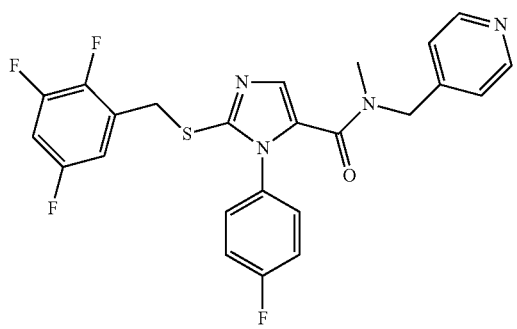 [SMILES: CN(Cc1ccncc1)C(=O)c1cnc(SCc2cc(F)cc(F)c2F)n1-c1ccc(F)cc1]

$^1$H NMR (400 MHz, CDCl$_3$) δ: 8.85-8.80 (m, 2H), 8.01 (s, 1H), 7.77-7.74 (m, 2H), 7.26-7.20 (m, 4H), 6.92-6.89 (m, 2H), 4.82 (s, 2H), 4.56 (s, 2H), 3.34 (s, 3H). LC-MS ESI m/z; found 487.1 [M+H]$^+$.

Example 121

2-((2-Chloro-6-fluoro-3-methylbenzyl)thio)-1-(4-fluorophenyl)-N-methyl-N-(pyridin-4-ylmethyl)-1H-imidazole-5-carboxamide (620)

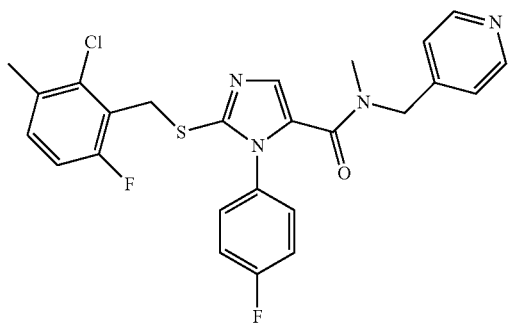 [SMILES: Cc1ccc(F)c(CSc2ncc(C(=O)N(C)Cc3ccncc3)n2-c2ccc(F)cc2)c1Cl]

¹H NMR (400 MHz, CDCl₃) δ: 8.80 (d, J=4.4, 2H), 7.95 (s, 1H), 7.66 (d, J=4.4, 2H), 7.18-7.15 (m, 5H), 6.89-6.84 (m, 1H), 4.81 (s, 2H), 4.52 (s, 2H), 3.30 (s, 3H), 2.31 (s, 3H). LC-MS ESI m/z; found 499.1 [M+H]⁺.

Example 122

1-(4-Fluorophenyl)-N-methyl-N-(pyridin-4-ylmethyl)-2-((3-(trifluoromethyl)benzyl)thio)-1H-imidazole-5-carboxamide (621)

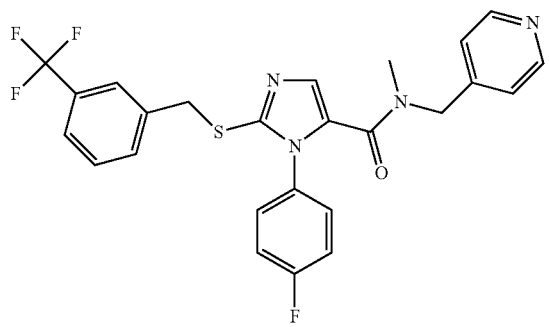 [SMILES: CN(Cc1ccncc1)C(=O)c1cnc(SCc2cccc(C(F)(F)F)c2)n1-c1ccc(F)cc1]

¹H NMR (400 MHz, CDCl₃) δ: 8.78 (d, J=4.8, 2H), 7.89 (s, 1H), 7.63 (d, J=4.8, 2H), 7.54 (d, J=6.8, 1H), 7.48-7.40 (m, 3H), 7.18-7.14 (m, 2H), 7.07-7.04 (m, 2H), 4.79 (s, 2H), 4.47 (s, 2H), 3.25 (s, 3H). LC-MS ESI m/z; found 501.1 [M+H]⁺.

Example 123

2-((6-Chloro-2-fluoro-3-methylbenzyl)thio)-1-(4-fluorophenyl)-N-methyl-N-(pyridin-4-ylmethyl)-1H-imidazole-5-carboxamide (622)

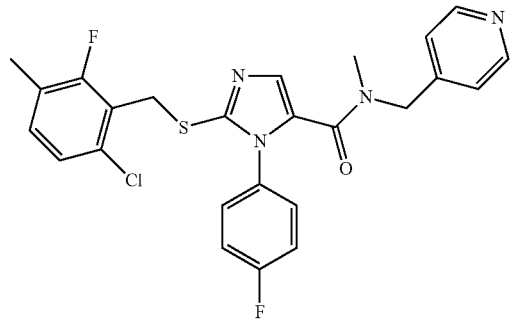 [SMILES: Cc1ccc(Cl)c(CSc2ncc(C(=O)N(C)Cc3ccncc3)n2-c2ccc(F)cc2)c1F]

¹H NMR (400 MHz, CDCl₃) δ: 8.79 (d, J=4.8, 2H), 7.94 (s, 1H), 7.64 (d, J=4.8, 2H), 7.17-7.13 (m, 4H), 7.10-7.03 (m, 2H), 4.82 (s, 2H), 4.43 (s, 2H), 3.29 (s, 3H), 2.18 (s, 3H). LC-MS ESI m/z; found 499.1 [M+H]⁺.

Example 124

2-((5-Chloro-2-(trifluoromethyl)benzyl)thio)-1-(4-fluorophenyl)-N-methyl-N-(pyridin-4-ylmethyl)-1H-imidazole-5-carboxamide (623)

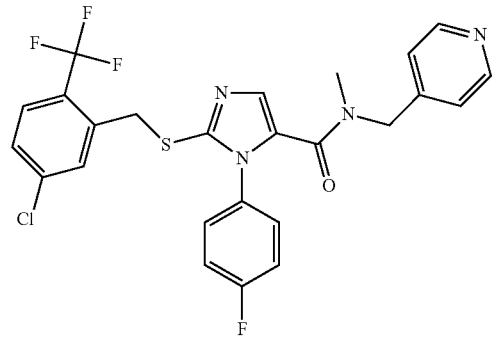 [SMILES: CN(Cc1ccncc1)C(=O)c1cnc(SCc2cc(Cl)ccc2C(F)(F)F)n1-c1ccc(F)cc1]

¹H NMR (400 MHz, CDCl₃) δ: 8.80 (d, J=5.6, 2H), 7.75 (s, 1H), 7.64 (d, J=5.6, 2H), 7.56 (d, J=8.8, 1H), 7.49 (br s, 1H), 7.37 (d, J=8.8, 1H), 7.17-7.15 (m, 4H), 4.82 (s, 2H), 4.54 (s, 2H), 3.29 (s, 3H). LC-MS ESI m/z; found 535.1 [M+H]⁺.

Example 125

2-((2-Cyanobenzyl)thio)-1-(4-fluorophenyl)-N-methyl-N-(pyridin-4-ylmethyl)-1H-imidazole-5-carboxamide (624)

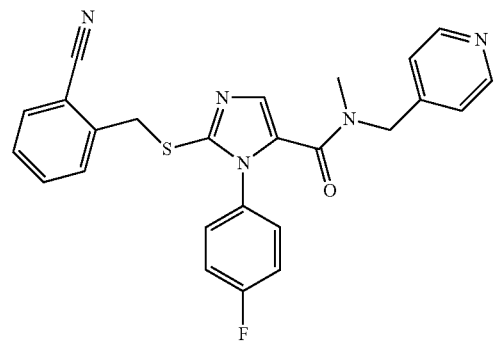 [SMILES: CN(Cc1ccncc1)C(=O)c1cnc(SCc2ccccc2C#N)n1-c1ccc(F)cc1]

¹H NMR (400 MHz, CDCl₃) δ: 8.85-8.79 (m, 2H), 7.86-7.81 (m, 1H), 7.76-7.46 (m, 6H), 7.26-7.22 (m, 4H), 4.84 (s, 2H), 4.70 (s, 2H), 3.37 (s, 3H). LC-MS ESI m/z; found 458.1 [M+H]⁺.

Example 126

1-(4-Fluorophenyl)-N-methyl-2-((5-methyl-2-(trifluoromethyl)benzyl)thio)-N-(pyridin-4-ylmethyl)-1H-imidazole-5-carboxamide (625)

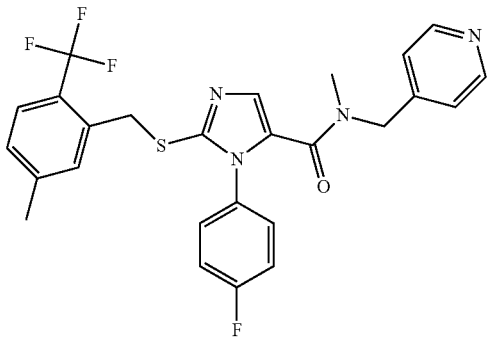 [SMILES: Cc1ccc(C(F)(F)F)c(CSc2ncc(C(=O)N(C)Cc3ccncc3)n2-c2ccc(F)cc2)c1]

¹H NMR (400 MHz, CDCl₃) δ: 8.86-8.80 (m, 2H), 7.80-7.76 (m, 2H), 7.68-7.64 (m, 1H), 7.50-7.48 (m, 1H), 7.21-7.14 (m, 6H), 4.82 (s, 2H), 4.73 (s, 2H), 3.39 (s, 3H), 2.33 (s, 3H). LC-MS ESI m/z; found 515.1 [M+H]⁺.

Example 127

2-((6-Chloro-2-fluoro-3-methoxybenzyl)thio)-N-ethyl-1-(4-fluorophenyl)-N-(pyridin-4-ylmethyl)-1H-imidazole-5-carboxamide (626)

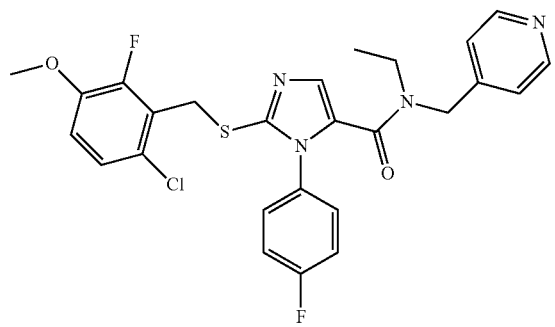 [SMILES: CCN(Cc1ccncc1)C(=O)c1cnc(SCc2c(Cl)ccc(OC)c2F)n1-c1ccc(F)cc1]

¹H NMR (400 MHz, DMSO-d₆) δ: 8.82-8.80 (m, 2H), 7.74-7.62 (m, 3H), 7.31-7.20 (m, 5H), 7.14-7.10 (m, 1H), 4.78 (s, 2H), 4.29 (s, 2H), 3.80 (s, 3H), 3.62-3.50 (m, 2H), 1.20-1.11 (m, 3H). LC-MS ESI m/z; found 529.1 [M+H]⁺.

Example 128

2-((6-Chloro-2-fluoro-3-methylbenzyl)thio)-N-ethyl-1-(4-fluorophenyl)-N-(pyridin-4-ylmethyl)-1H-imidazole-5-carboxamide (627)

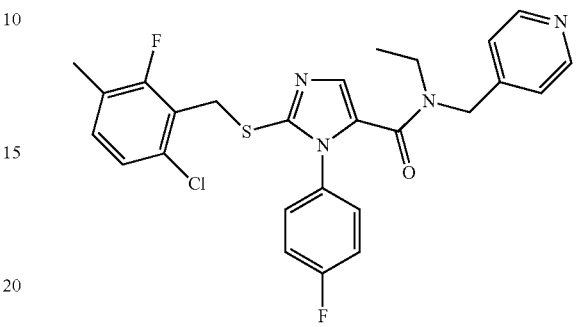

¹H NMR (400 MHz, DMSO-d₆) δ: 8.82-8.80 (m, 2H), 7.78-7.66 (m, 3H), 7.32-7.16 (m, 6H), 4.79 (s, 2H), 4.32 (s, 2H), 3.60-3.52 (m, 2H), 2.14 (s, 3H), 1.20-1.11 (m, 3H). LC-MS ESI m/z; found 513.1 [M+H]⁺.

Example 129

4-((1-(1-(4-Fluorophenyl)-4-methyl-2-((2,3,6-trifluorobenzyl)thio)-1H-imidazol-5-yl)ethoxy)methyl) pyridine (628)

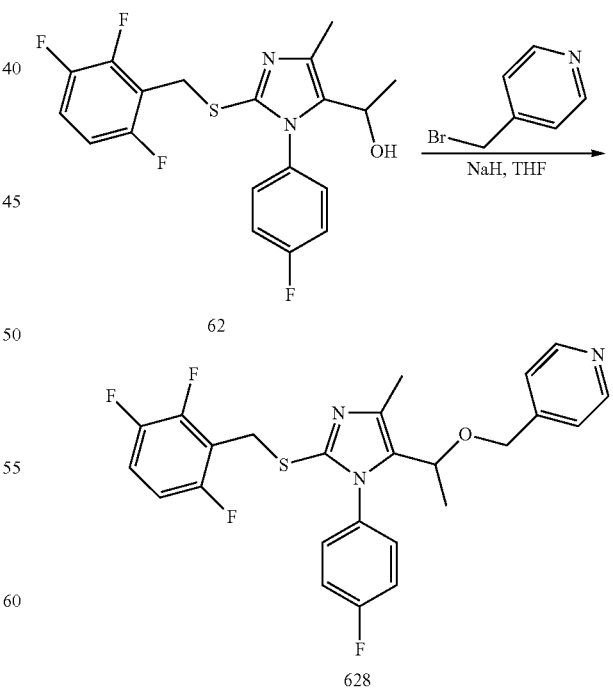

Sodium hydride (60% in mineral oil, 60 mg, 1.44 mmol) was added to a solution of 1-(1-(4-fluorophenyl)-4-methyl- 2-((2,3,6-trifluorobenzyl)thio)-1H-imidazol-5-yl)ethanol (62) (190 mg, 0.48 mmol) in THF (5 mL) and the reaction was allowed to stir at room temperature for 20 min. 4-(bromomethyl)pyridine hydrobromide (146 mg, 0.576 mmol) was added to the reaction mixture and heated to 70° C. overnight. The reaction was cooled to room temperature, quenched with water and extracted with ethyl acetate. The organic layer was washed with brine, dried over sodium sulfate, filtered, and concentrated in vacuo. The residue was purified by flash column chromatography on silica gel (0-100% EtOAc in hexanes) to afford 4-((1-(1-(4-fluorophenyl)-4-methyl-2-((2,3,6-trifluorobenzyl)thio)-1H-imidazol-5-yl)ethoxy)methyl)pyridine (628). $^1$H NMR (400 MHz, CDCl$_3$) δ: 8.56 (d, J=6.0, 2H), 7.20-7.17 (m, 4H), 7.04-6.96 (m, 3H), 6.74-6.68 (m, 1H), 5.31-5.15 (m, 2H), 4.63 (q, J=6.4, 1H), 4.48 (d, J=13.5, 1H), 4.32 (d, J=13.5, 1H), 2.19 (s, 3H), 1.45 (d, J=6.4, 3H). LC-MS ESI m/z; found 488.2 [M+H]$^+$.

Example 130

2-((Benzo[d]oxazol-2-ylmethyl)thio)-N-((1,3-dimethyl-1H-pyrazol-4-yl)methyl)-1-(4-fluorophenyl)-N-methyl-1H-imidazole-5-carboxamide (629)

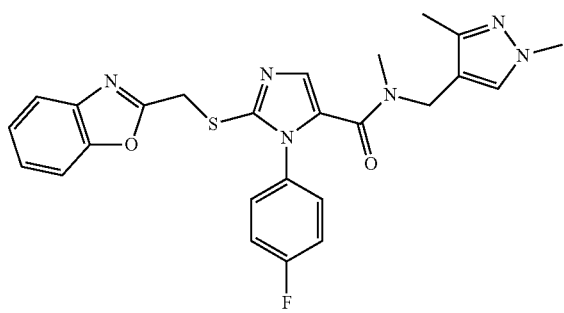 [SMILES: Cc1nn(C)cc1CN(C)C(=O)c1cnc(SCc2nc3ccccc3o2)n1-c1ccc(F)cc1]

$^1$H NMR (400 MHz, CDCl$_3$) δ 7.69-7.64 (m, 1H), 7.50-7.46 (m, 1H), 7.37-7.27 (m, 3H), 7.21-7.15 (m, 2H), 7.09-7.00 (m, 3H), 4.61 (s, 2H), 4.39 (s, 2H), 3.78 (s, 3H), 2.97 (s, 3H), 2.14 (s, 3H). LC-MS ESI m/z; found 491.2 [M+H]$^+$.

Example 131

N-((1,3-Dimethyl-1H-pyrazol-4-yl)methyl)-2-(((3-ethyl-1,2,4-oxadiazol-5-yl)methyl)thio)-1-(4-fluorophenyl)-N-methyl-1H-imidazole-5-carboxamide (630)

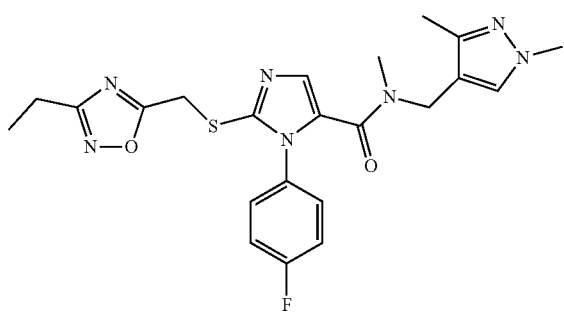 [SMILES: CCc1noc(CSc2ncc(C(=O)N(C)Cc3cn(C)nc3C)n2-c2ccc(F)cc2)n1]

$^1$H NMR (400 MHz, CDCl$_3$) δ 7.32 (s, 1H), 7.28-7.19 (m, 2H), 7.15-7.11 (m, 2H), 7.07 (s, 1H), 4.53 (s, 2H), 4.39 (s, 2H), 3.78 (s, 3H), 2.98 (s, 3H), 2.73 (q, J=7.6, 2H), 2.14 (s, 3H), 1.29 (t, J=7.6, 3H). LC-MS ESI m/z; found 470.2 [M+H]$^+$.

Example 132

N-((1,3-Dimethyl-1H-pyrazol-4-yl)methyl)-1-(4-fluorophenyl)-2-(((3-isopropylisoxazol-5-yl)methyl)thio)-N-methyl-1H-imidazole-5-carboxamide (631)

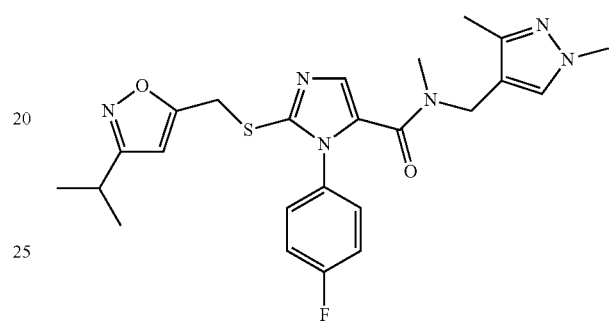

$^1$H NMR (400 MHz, CDCl$_3$) δ 7.34 (s, 1H), 7.23-7.04 (m, 5H), 6.04 (s, 1H), 4.43-4.34 (m, 4H), 3.79 (s, 3H), 3.04-2.90 (m, 4H), 2.15 (s, 3H), 1.24 (d, J=6.9, 6H). LC-MS ESI m/z; found 483.20 [M+H]$^+$.

Example 133

N-((1,3-Dimethyl-1H-pyrazol-4-yl)methyl)-1-(4-fluorophenyl)-N-methyl-2-((pyrazolo[1,5-a]pyridin-2-ylmethyl)thio)-1H-imidazole-5-carboxamide (632)

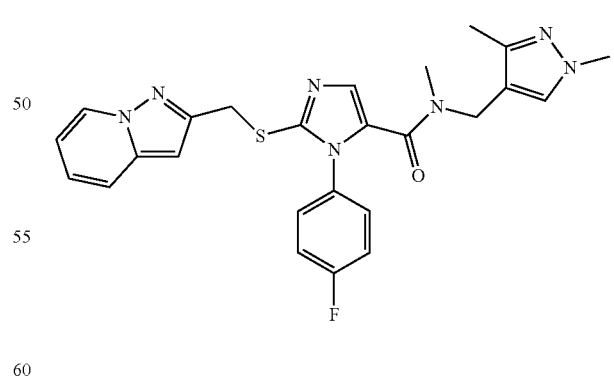

$^1$H NMR (400 MHz, CDCl$_3$) δ 8.35 (d, J=7.2, 1H), 7.42 (d, J=9.0, 1H), 7.37 (s, 1H), 7.21-7.14 (m, 2H), 7.09-7.04 (m, 4H), 6.73-6.70 (m, 1H), 6.43 (s, 1H), 4.59 (s, 2H), 4.39 (s, 2H), 3.78 (s, 3H), 2.97 (s, 3H), 2.15 (s, 3H). LC-MS ESI m/z; found 490.20 [M+H]$^+$.

Example 134

N-((1,3-Dimethyl-1H-pyrazol-4-yl)methyl)-1-(4-fluorophenyl)-N-methyl-2-(((1-methyl-1H-pyrazol-3-yl)methyl)thio)-1H-imidazole-5-carboxamide (633)

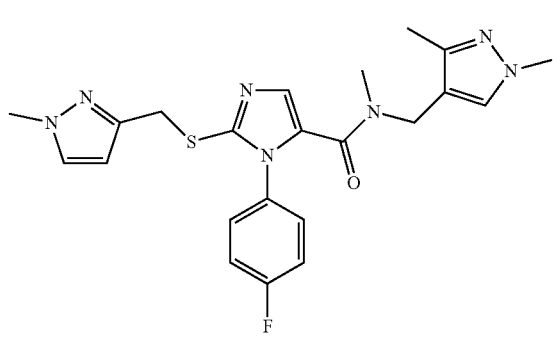

¹H NMR (400 MHz, CDCl₃) δ 7.35 (s, 1H), 7.23-7.19 (m, 3H), 7.14-7.04 (m, 3H), 6.16 (s, 1H), 4.42-4.36 (m, 4H), 3.83 (s, 3H), 3.78 (s, 3H), 2.97 (s, 3H), 2.15 (s, 3H). LC-MS ESI m/z; found 454.2 [M+H]⁺.

Example 135

N-((1,3-Dimethyl-1H-pyrazol-4-yl)methyl)-1-(4-fluorophenyl)-N-methyl-2-(((1-methyl-1H-1,2,4-triazol-3-yl)methyl)thio)-1H-imidazole-5-carboxamide (634)

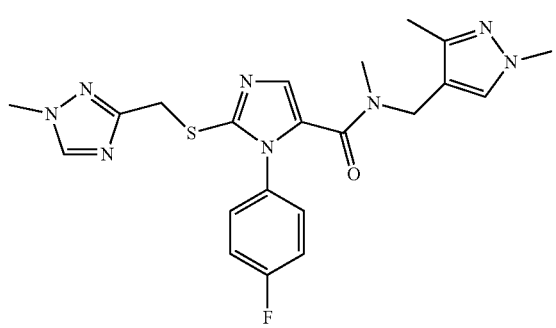

¹H NMR (400 MHz, CDCl₃) δ 7.92 (s, 1H), 7.34 (s, 1H), 7.28-7.20 (m, 2H), 7.12-7.07 (m, 3H), 4.49 (s, 2H), 4.39 (s, 2H), 3.86 (s, 3H), 3.78 (s, 3H), 2.97 (s, 3H), 2.14 (s, 3H). LC-MS ESI m/z; found 456.2 [M+H]⁺.

Example 136

N-((1,3-Dimethyl-1H-pyrazol-4-yl)methyl)-1-(4-fluorophenyl)-N-methyl-2-((pyrimidin-2-ylmethyl)thio)-1H-imidazole-5-carboxamide (635)

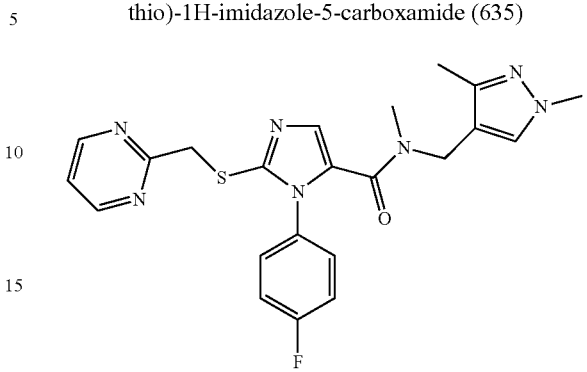

¹H NMR (400 MHz, CDCl₃) δ 8.69 (d, J=4.7, 2H), 7.32 (s, 1H), 7.27-7.25 (m, 2H), 7.19-7.17 (m, 1H), 7.14-7.10 (m, 2H), 7.07 (s, 1H), 4.68 (s, 2H), 4.40 (s, 2H), 3.78 (s, 3H), 2.98 (s, 3H), 2.14 (s, 3H). LC-MS ESI m/z; found 452.2 [M+H]⁺.

Example 137

N-((1,3-Dimethyl-1H-pyrazol-4-yl)methyl)-1-(4-fluorophenyl)-N-methyl-2-(((4-methylthiazol-2-yl)methyl)thio)-1H-imidazole-5-carboxamide (636)

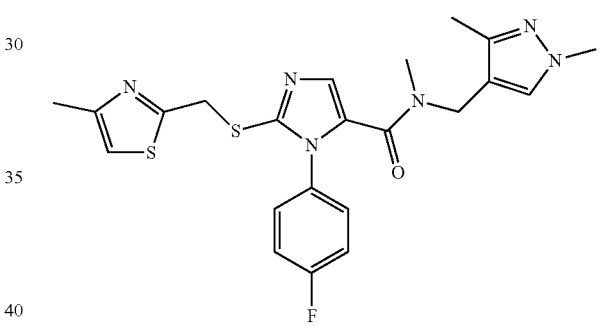

¹H NMR (400 MHz, CDCl₃) δ 7.34 (s, 1H), 7.21-7.15 (m, 2H), 7.13-7.07 (m, 2H), 7.06 (s, 1H), 6.76 (s, 1H), 4.66 (s, 2H), 4.38 (s, 2H), 3.77 (s, 3H), 2.96 (s, 3H), 2.39 (s, 3H), 2.13 (s, 3H). LC-MS ESI m/z; found 471.1 [M+H]⁺.

Example 138

Ethyl 2-((5-(((1,3-dimethyl-1H-pyrazol-4-yl)methyl)(methyl)carbamoyl)-1-(4-fluorophenyl)-1H-imidazol-2-yl)thio)acetate (637)

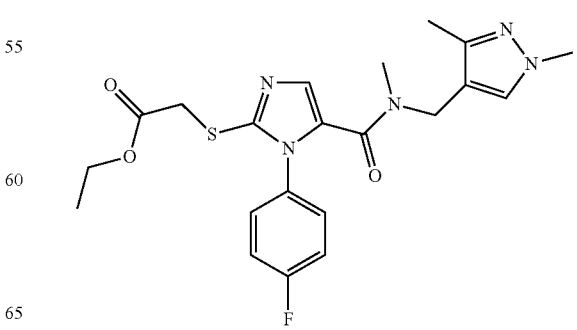

¹H NMR (400 MHz, CDCl₃) δ 7.73 (s, 1H), 7.38-7.31 (m, 2H), 7.28-7.14 (m, 3H), 4.36 (s, 2H), 4.16 (q, J=7.1, 2H), 4.05 (s, 2H), 3.90 (s, 3H), 3.07 (s, 3H), 2.22 (s, 3H), 1.24 (t, J=7.1, 4H). LC-MS ESI m/z; found 446.1 [M+H]⁺.

Example 139

Stimulation of cAMP

Compounds of Formula (I) were evaluated in an assay demonstrating agonism of GPR131. This assay was developed using a stable cell line expressing human GPR131.

To measure cAMP activity in response to GPR131 agonists, GPR131 cells suspended in DMEM/F12 medium with 1 mM IBMX were seeded in 384 well plates at 5000 cells per well. After incubating with test compounds at 37° C. for 30 minutes cAMP was measured using a fluorescene resonance energy transfer cAMP kit from Cis Bio (Bedford, Mass.) according to the manufacturer's instructions. Briefly, cells were lysed, and cAMP levels determined by competitive immunoassay using D2 labeled cAMP, and europium cryptate tagged anti cAMP antibody. Decreases in the FRET signal (fluorescence ratio (665 nm/620 m) correspond to increases in intracellular cAMP levels.

Activities of test compounds in Table 1 below are expressed as % activity at 1.1 µM compound compared to the maximal stimulatory activity of lithocholic acid (LCA) (determined at 3.3 µM LCA)

TABLE 1

| Compound | Percent Activity @ 1.1 µM (of 3.3 uM LCA) (%) |
|---|---|
| 502 | 100 |
| 505 | 99 |
| 506 | 100 |
| 507 | 93 |
| 508 | 82 |
| 518 | 100 |
| 519 | 100 |
| 520 | 98 |
| 522 | 100 |
| 523 | 96 |
| 525 | 96 |
| 526 | 96 |
| 528 | 95 |
| 530 | 100 |
| 531 | 84 |
| 532 | 100 |
| 533 | 100 |
| 538 | 90 |
| 539 | 95 |
| 542 | 100 |
| 549 | 98 |
| 550 | 98 |
| 551 | 99 |
| 552 | 99 |
| 553 | 100 |
| 554 | 99 |
| 555 | 100 |
| 556 | 99 |
| 561 | 95 |
| 562 | 82 |
| 563 | 98 |
| 564 | 99 |
| 565 | 99 |
| 567 | 96 |
| 568 | 83 |
| 569 | 98 |
| 572 | 88 |
| 577 | 100 |
| 578 | 99 |
| 579 | 85 |

TABLE 1-continued

| Compound | Percent Activity @ 1.1 µM (of 3.3 uM LCA) (%) |
|---|---|
| 583 | 96 |
| 585 | 97 |
| 586 | 86 |
| 587 | 86 |
| 589 | 87 |
| 590 | 86 |
| 591 | 94 |
| 593 | 99 |
| 594 | 98 |
| 595 | 98 |
| 596 | 100 |
| 597 | 100 |
| 603 | 82 |
| 606 | 98 |
| 607 | 93 |
| 609 | 86 |
| 610 | 100 |
| 611 | 99 |
| 612 | 100 |
| 613 | 100 |
| 615 | 98 |
| 616 | 100 |
| 617 | 99 |
| 618 | 94 |
| 619 | 96 |
| 620 | 99 |
| 621 | 98 |
| 622 | 100 |
| 626 | 100 |
| 627 | 100 |
| 629 | 100 |
| 630 | 98 |
| 631 | 97 |
| 632 | 100 |
| 633 | 93 |
| 634 | 91 |
| 635 | 98 |
| 636 | 98 |
| 637 | 94 |

Example 140

Oral Glucose Tolerance and Incretin Measurements

Male mice (8-10 week old C57BL/6N, Harlan Laboratories, Inc.) were maintained on 18% Protein Rodent diet (Teklad Global Diets, Harlan Laboratories, Inc). Overnight fasted mice were randomized into groups (n=8-10) to receive the test compounds at a dose of 100 mg/kg or the vehicle (1% CMC, 2% TWEEN 80). Compounds were delivered orally via gavage. Blood glucose levels were measured by glucometer before administration of compounds and at 30 minutes post compound. The mice were then dosed orally with 3 g/kg glucose. Blood glucose measurements were taken 20, 40, 60, 90 and 120 minutes after glucose administration. Glucose levels were plotted against time and the incremental area under the curve (AUC) of the glucose excursion was determined from T=0 to T=120 min.

The effect of test compounds on the secretion of Glucagon-like peptide-1 (GLP-1) in C57/6N mice was determined at the end of the oral glucose tolerance test. Animals were anesthetized with pentobarbital and blood collected by heart puncture in potassium EDTA-coated microtainer tubes containing 10 µl/ml DPP-IV inhibitor and 500 KIU/ml Aprotinin. Total GLP-1 was measured using Mouse/Rat Total Glucagon-like peptide-1 assay kit (Meso Scale Discovery) and MSD SECTOR2400 Imager according to the manufacturer's instructions.

Table 2 shows the results of oral glucose tolerance and incretin activity measurements using representative test compounds of Formula (I). Oral glucose tolerance is expressed as a percent reduction in glucose excursion of animals receiving test compound vs. control animals. Incretin activity (i.e. incretin secretion) is expressed as an x-fold increase in GLP-1 production in animals receiving test compound vs. control animals.

TABLE 2

| Compound | Glucose Reduction (%) | Increase in GLP-1 (Fold) |
|---|---|---|
| 502 | 27.7 | 2.2 |
| 505 | 27.4 | 1.9 |
| 577 | 24.4 | 4.1 |

Example 141

Active GLP-1 Assessment of Test Compound and Sitagliptin in Normal C57BL/6 Mice

Male mice (8-10 week old C57BL/6N, Harlan Laboratories, Inc.) were maintained on 18% Protein Rodent diet as above. Overnight fasted mice were randomized into groups (n=9-10) to receive the test compounds at a dose of 100 mg/kg or sitagliptin at a dose of 1 mg/kg or combination of test compound and sitagliptin or the vehicle (1% CMC, 2% TWEEN 80). Sitagliptin was dosed 30 minutes prior to test compound.

Animals were anesthetized with pentobarbital (80 mg/ml in 10% ethanol) 30 minutes after test compound administration. Blood was collected by heart puncture in potassium EDTA-coated microtainer tubes) containing 10 µl/ml DPP-IV inhibitor and 500 KIU/ml Aprotinin Bioactive GLP-1 was measured using an ELISA assay kit Statistically significant differences between compound treatment and vehicle was determined by One-way ANOVA with Bonferroni's post test. Differences with a p-value ≤0.05 were considered significant (***=P<0.001)

Results of this study are shown in FIG. 1.

Example 142

Oral Glucose Tolerance Test (OGTT) of Test Compound and Sitagliptin in DIO Mice 13-14 week old C57BL/6J diet induced obese (DIO) male mice were maintained on a 60 kcal % fat diet. Overnight fasted mice were randomized into groups (n=9-10) to receive the test compounds at a dose of 100 mg/kg or sitagliptin at a dose of 1 mg/kg or combination of the test compound and sitagliptin formulated together as one solution (test compound+sitagliptin) or vehicle (1% CMC, 2% TWEEN 80). Compounds were delivered orally via gavage. Blood glucose levels were measured by glucometer before administration of compounds and at 30 minutes post compound. The mice were then dosed orally with 2 g/kg glucose. Blood glucose measurements were taken at 20, 40, 60, 90 and 120 minutes after glucose administration. Glucose levels were plotted against time and the incremental area under the curve (AUC) of the glucose excursion was determined from T0 to T120. Statistically significant differences in AUC between compound treatment and vehicle were determined by One-way ANOVA with Bonferroni's post test. Differences with a p-value ≤0.05 were considered significant (*=P<0.05, ***=P<0.001)

Figure 2:
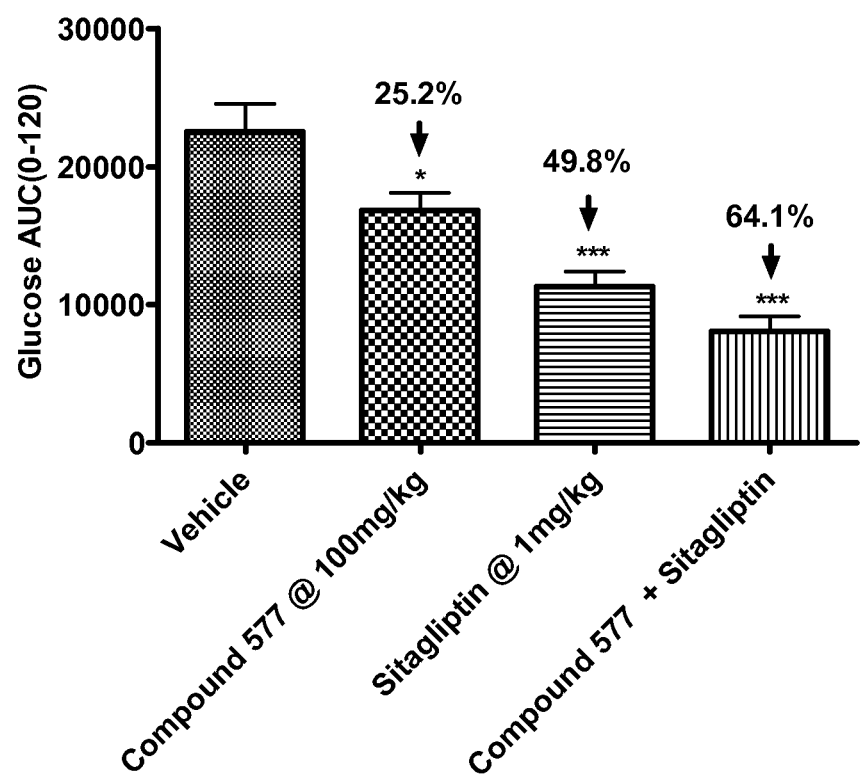
FIG. 2 shows a chart of oral glucose tolerance test of test compound and sitagliptin in diet induced obese mice.

Results of this study are shown in FIG. 2.

Example 143

Oral Glucose Tolerance Test (OGTT) of Test compound and Total Glucagon Like Peptide-2 (GLP-2) and Total Peptide YY (PYY) Measurements 18 week old C57BL/6J diet induced obese (DIO) male mice were maintained on a 60 kcal % fat diet. Mice fasted for 9 hours were randomized into groups (n=9-10) to receive vehicle (1% CMC, 2% TWEEN 80) or test compound at a dose of 100 mg/kg. Compounds were delivered orally via gavage, and 30 minutes later mice were dosed orally with 2 g/kg glucose.

The effect of GPR131 agonists on the secretion of total Glucagon-like peptide-2 (GLP-2) and total Peptide YY (PYY) was determined at the end of the oral glucose tolerance test (2 hours post glucose dosing). Animals were anesthetized with pentobarbital and blood collected by heart puncture in potassium EDTA-coated microtainer tubes containing 10 µl/ml DPP-IV inhibitor and 500 KIU/ml Aprotinin. Total GLP-2 was measured using Total Glucagon-like peptide-2 assay kit and Total PYY was measured using Total Peptide YY assay kit.

Results of this study are shown in Table 3.

TABLE 3

| Compound | Increase in GLP-2 (Fold) | Increase in PYY (Fold) |
|---|---|---|
| 577 | 2.5 | 2.2 |

Example 144

Gastric Emptying

To evaluate the effects of compounds of Formula (I) on gastric emptying, 8-10 week old male C57BL/6J mice (Harlan) are fasted for 16-18 hours, then treated orally or by intraperitoneal injection with either test compounds of Formula (I) (1-100 mg/kg) or vehicle (1% CMC, 2% TWEEN 80) 30 minutes prior to initiation of the gastric emptying study. Phenol red (0.05% PR in deionized water) is administered either in an aqueous or glucose solution (0.05% in 20% glucose). Immediately after PR administration (0 min), control group animals are sacrificed by cervical dislocation and the average amount of phenol red recovered is measured as 100% phenol red retention. The remainder of the animals from each group are sacrificed at various time-points following phenol red administration. The stomachs are isolated after clamping at both the pyloric and the cardiac ends. Clamped stomachs are transferred to a 50 mL conical tube containing 5 mL deionized water. Clamps are removed and each stomach is cut into fine pieces with scissors and stomach content is extracted by centrifugation at 3000 rpm for 10 minutes and supernatant is filtered to remove particulates. 1 mL of 1N NaOH is added to each 2 mL of filtered supernatant for color development. The concentration of phenol read is determine by measuring the absorbance of the extracted material at a wavelength of 558 nm and then converted to concentration by using the extinction coefficient of phenol red in aqueous solution.

The gastric emptying is calculated by the formula: % Gastric emptying=((A−B)/A)×100, where A is the average amount (absorbance) of phenol red recovered immediately after ingestion (the 100% retained group) and B is the amount (absorbance) of phenol red remaining in the stomach at a given time after ingestion.

Example 145

Improvement of Diabetes Parameters in Animal Models of Diabetes

Female ZDF rats (Charles River laboratories) are obtained at 6 weeks of age and acclimatized for 1 week before being placed on a high fat diet (RD 13004, Research Diets). Compounds of Formula (I) are administered to the rats by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer) and insulin is measured using rat insulin ELISA kit (ALPCO). Insulin and glucose levels are compared to those of vehicle treated animals to determine efficacy.

Ob/ob mice (Jackson) are obtained at 6 weeks of age and acclimatized for 1-2 week. Compounds of Formula (I) are administered by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer), insulin is measured using mouse insulin ELISA kit (ALPCO). Insulin and glucose levels are compared to those of vehicle treated animals to determine efficacy.

While the foregoing description describes specific embodiments, those with ordinary skill in the art will appreciate that various modifications and alternatives can be developed. Accordingly, the particular embodiments described above are meant to be illustrative only, and not to limit the scope of the disclosure, which is to be given the full breadth of the appended claims, and any and all equivalents thereof.

We claim:

1. A compound of Formula (I)

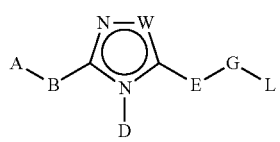

(I)

or a derivative thereof, wherein

A is H, —OH, halo, alkyl, alkoxy, aryl, arylalkyl, aryloxy, cycloalkyl, heteroalkyl, heteroaryl, or heterocycloalkyl, each of which may be optionally substituted;

B is alkyl, alkenyl, or alkynyl, each of which may be optionally substituted, or B is —$(CR^{a1}R^{a2})_iO(CR^{a3}R^{a4})_j$—, —$(CR^{a1}R^{a2})_iC(O)(CR^{a3}R^{a4})_j$—, —$(CR^{a1}R^{a2})_iS(CR^{a3}R^{a4})_j$—, —$(CR^{a1}R^{a2})_iS(O)(CR^{a3}R^{a4})_j$—, —$(CR^{a1}R^{a2})_iS(O)_2(CR^{a3}R^{a4})_j$—, —$(CR^{a1}R^{a2})_iN(R^{a5})(CR^{a3}R^{a4})_j$—, —$C(O)C(R^{a1}R^{a2})_iS$—, or absent;

D is H, alkyl, aryl, arylalkyl, cycloalkyl, heteroalkyl, heteroaryl, or heterocycloalkyl, each of which may be optionally substituted;

E is —$(CR^{b1}R^{b2})_kO$—, —$(CR^{b1}R^{b2})_kC(O)$—, —$(CR^{b1}R^{b2})_kOC(O)$—, —$(CR^{b1}R^{b2})_kS$—, —$(CR^{b1}R^{b2})_kS(O)$—, —$(CR^{b1}R^{b2})_kS(O)_2$—, —$(CR^{b1}R^{b2})_kN(R^{b3})$—, —$(CR^{b1}R^{b2})_kC(O)N(R^{b3})$—, —$(CR^{b1}R^{b2})_kS(O)_2N(R^{b3})$—, or absent;

G is —$(CR^{c1}R^{c2})_m$—, —C(O)—, or optionally substituted alkenyl;

L is H, —OH, halo, alkyl, aryl, arylalkyl, cycloalkyl, heteroalkyl, heteroaryl, or heterocycloalkyl, each of which may be optionally substituted;

W is $CR^1$ or N;

each i, j, and k is independently 0, 1, or 2;

m is 1, 2, or 3;

each $R^{a1}$, $R^{a2}$, $R^{a3}$, $R^{a4}$, $R^{a5}$, $R^{b1}$, $R^{b2}$, $R^{c1}$, and $R^{c2}$ is independently H, F, or optionally substituted alkyl;

$R^{b3}$ is H or optionally substituted alkyl;

or $R^{c1}$ and $R^{b3}$ together with the atoms to which they are attached may form an optionally substituted heterocycloalkyl; and each $R^1$ is independently H, halo, cyano, amino, or optionally substituted alkyl; with the proviso that if G is —$(CR^{c1}R^{c2})_m$— wherein $R^{c1}$ and $R^{c2}$ are both —$CH_3$ and m is 1, then E is not absent.

2. A compound of claim 1, wherein A is aryl or heteroaryl, each of which may be optionally substituted.

3. A compound of claim 1, wherein A is an optionally substituted alkyl.

4. A compound of claim 1, wherein B is —$CH_2CH_2$—, —$CH_2O$—, —$CH_2S$—, —$CH_2S(O)$—, or —$CH_2S(O)_2$—.

5. A compound of claim 1, wherein D is aryl or alkyl, each of which may be optionally substituted.

6. A compound of claim 1, wherein E is —$(CR^{b1}R^{b2})_kC(O)N(R^{b3})$— and wherein $R^{b3}$ is H or $C_{1-3}$ alkyl, and k is 0.

7. A compound of claim 1, wherein G is —$CH_2$—.

8. A compound of claim 1, wherein L is aryl or heteroaryl, each of which may be optionally substituted.

9. A compound of claim 1, wherein W is $CR^1$ wherein $R^1$ is H or $C_{1-3}$alkyl.

10. A compound of claim 1, wherein W is N.

11. A compound of claim 1, wherein i is 1, j is 0, k is 0 or 1, and m is 1.

12. A compound of Formula (II)

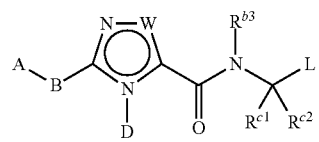

(II)

or a derivate thereof, wherein

A is H, —OH, halo, alkyl, alkoxy, aryl, arylalkyl, aryloxy, cycloalkyl, heteroalkyl, heteroaryl, or heterocycloalkyl, each of which may be optionally substituted;

B is alkyl, alkenyl, or alkynyl, each of which may be optionally substituted, or B is —$(CR^{a1}R^{a2})_iO(CR^{a3}R^{a4})_j$—, —$(CR^{a1}R^{a2})_iC(O)(CR^{a3}R^{a4})_j$—, —$(CR^{a1}R^{a2})_iS(CR^{a3}R^{a4})_j$—, —$(CR^{a1}R^{a2})_iS(O)(CR^{a3}R^{a4})_j$—, —$(CR^{a1}R^{a2})_iS(O)_2(CR^{a3}R^{a4})_j$—, —$(CR^{a1}R^{a2})_iN(R^{a5})(CR^{a3}R^{a4})_j$—, —$C(O)C(R^{a1}R^{a2})_iS$—, or absent;

D is H, alkyl, aryl, arylalkyl, cycloalkyl, heteroalkyl, heteroaryl, or heterocycloalkyl, each of which may be optionally substituted;

L is H, halo, alkyl, aryl, arylalkyl, cycloalkyl, heteroalkyl, heteroaryl, or heterocycloalkyl, each of which may be optionally substituted;

W is $CR^1$ or N;

each i and j is independently 0, 1, or 2;

each $R^{a1}$, $R^{a2}$, $R^{a3}$, $R^{a4}$, $R^{a5}$, $R^{b3}$, $R^{c1}$, and $R^{c2}$ is independently H or optionally substituted alkyl, or $R^{c1}$ and $R^{b3}$ together with the atoms to which they are attached may form an optionally substituted heterocycloalkyl; and each $R^1$ is independently H, halo, or optionally substituted alkyl.

13. A compound of Formula (III)

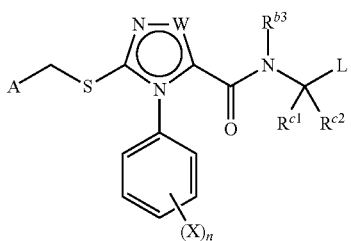

or a derivate thereof, wherein

A is H, halo, alkyl, alkoxy, aryl, arylalkyl, aryloxy, cycloalkyl, heteroalkyl, heteroaryl, or heterocycloalkyl, each of which may be optionally substituted;

L is H, halo, alkyl, aryl, arylalkyl, cycloalkyl, heteroalkyl, heteroaryl, or heterocycloalkyl, each of which may be optionally substituted;

W is $CR^1$ or N;

each X is independently halo, cyano, sulfonamide, optionally substituted alkyl, —$OR^a$, —$NR^aR^b$, —$C(O)R^a$, —$C(O)OR^a$, —$C(O)NR^aR^b$, —$NR^aC(O)R^b$, —$SR^a$, —$S(O)R^a$, —$S(O)_2R^a$, or —$NR^aS(O)_2R^b$, wherein $R^a$ and $R^b$ are independently H or optionally substituted alkyl;

n is 0, 1, 2, 3, 4 or 5;

each $R^{b3}$, $R^{c1}$, and $R^{c2}$ is independently H or optionally substituted alkyl, or $R^{c1}$ and $R^{b3}$ together with the atoms to which they are attached may form an optionally substituted heterocycloalkyl; and each $R^1$ is independently H, halo, or optionally substituted alkyl.

14. A compound selected from the group consisting of

N-Benzyl-2-((2-chloro-6-fluorobenzyl)thio)-1-(4-fluorophenyl)-N-methyl-1H-imidazole-5-carboxamide;

1-(1,3-Dimethyl-1H-pyrazol-4-yl)-N-((1-(4-fluorophenyl)-2-((2,3,6-trifluorobenzyl)sulfinyl)-1H-imidazol-5-yl)methyl)-N-methylmethanamine;

1-(4-Fluorophenyl)-N-methyl-N-((3-methylpyridin-4-yl)methyl)-2-((2,3,6-trifluorobenzyl)thio)-1H-imidazole-5-carboxamide;

4-((1-(4-Fluorophenyl)-N-methyl-2-((2,3,6-trifluorobenzyl)sulfonyl)-1H-imidazole-5-carboxamido)methyl)-3-methylpyridine 1-oxide;

Ethyl 1-(4-fluorophenyl)-2-((2,3,6-trifluorobenzyl)thio)-1H-imidazole-5-carboxylate;

N-((1,3-Dimethyl-1H-pyrazol-4-yl)methyl)-1-(4-fluorophenyl)-N-methyl-2-((2,3,6-trifluorobenzyl)thio)-1H-imidazole-5-carboxamide;

1-(1,3-Dimethyl-1H-pyrazol-4-yl)-N-((1-(4-fluorophenyl)-2-((2,3,6-trifluorobenzyl)thio)-1H-imidazol-5-yl)methyl)-N-methylmethanamine;

N-(3,4-Dimethoxybenzyl)-1-(4-fluorophenyl)-N-methyl-2-((2,3,6-trifluorobenzyl)thio)-1H-imidazole-5-carboxamide;

N-((1,3-Dimethyl-1H-pyrazol-4-yl)methyl)-1-(4-fluorophenyl)-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-1H-imidazole-5-carboxamide;

(E)-N-((1,3-Dimethyl-1H-pyrazol-4-yl)methyl)-1-(4-fluorophenyl)-N-methyl-2-(2,3,6-trifluorostyryl)-1H-imidazole-5-carboxamide;

N-((1,3-Dimethyl-1H-pyrazol-4-yl)methyl)-1-(4-fluorophenyl)-N-methyl-2-((2,3,6-trifluorobenzyl)sulfinyl)-1H-imidazole-5-carboxamide;

N-((1,3-Dimethyl-1H-pyrazol-4-yl)methyl)-1-(4-fluorophenyl)-N-methyl-2-((2,3,6-trifluorobenzyl)sulfonyl)-1H-imidazole-5-carboxamide;

N-((1,3-Dimethyl-1H-pyrazol-4-yl)methyl)-1-(4-fluorophenyl)-N-methyl-2-(((2,3,6-trifluorophenyl)amino)methyl)-1H-imidazole-5-carboxamide;

N-((1,3-Dimethyl-1H-pyrazol-4-yl)methyl)-1-(4-fluorophenyl)-N-methyl-2-(2,3,6-trifluorophenyl)-1H-imidazole-5-carboxamide;

N-((1-Ethyl-3-methyl-1H-pyrazol-4-yl)methyl)-1-(4-fluorophenyl)-N-methyl-2-((2,3,6-trifluorobenzyl)thio)-1H-imidazole-5-carboxamide;

1-(4-Fluorophenyl)-N-methyl-2-((2,3,6-trifluorobenzyl)thio)-N-((1,3,5-trimethyl-1H-pyrazol-4-yl)methyl)-1H-imidazole-5-carboxamide;

1-(4-Fluorophenyl)-N-methyl-N-((1-methylpiperidiN-4-yl)methyl)-2-((2,3,6-trifluorobenzyl)thio)-1H-imidazole-5-carboxamide;

1-(4-Fluorophenyl)-N-methyl-N-(pyridin-4-ylmethyl)-2-((2,3,6-trifluorobenzyl)thio)-1H-imidazole-5-carboxamide;

N-((1,3-Dimethyl-1H-pyrazol-4-yl)methyl)-N-ethyl-1-(4-fluorophenyl)-2-((2,3,6-trifluorobenzyl)thio)-1H-imidazole-5-carboxamide;

1-(4-Fluorophenyl)-N-methyl-N-((1-methyl-1H-pyrazol-4-yl)methyl)-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-2-((methyl(2,3,6-trifluorophenyl)amino)methyl)-1H-imidazole-5-carboxamide;

N-((2,4-Dimethylthiazol-5-yl)methyl)-1-(4-fluorophenyl)-N-methyl-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-2-(2,3,6-trifluorophenethyl)-1H-imidazole-5-carboxamide;

1-(4-Fluorophenyl)-N-methyl-N-((1-methylpyrrolidiN-3-yl)methyl)-2-((2,3,6-trifluorobenzyl)thio)-1H-imidazole-5-carboxamide;

N-((1,3-Dimethyl-1H-pyrazol-4-yl)methyl)-1-(4-fluorophenyl)-N-methyl-2-((2-oxo-2-phenylethyl)thio)-1H-imidazole-5-carboxamide;

N-(1-(1,3-Dimethyl-1H-pyrazol-4-yl)ethyl)-1-(4-fluorophenyl)-N-methyl-2-((2,3,6-trifluorobenzyl)thio)-1H-imidazole-5-carboxamide;

N-((1-(4-Fluorophenyl)-2-((2,3,6-trifluorobenzyl)thio)-1H-imidazol-5-yl)methyl)-N-1,3-trimethyl-1H-pyrazole-4-carboxamide;

1-(4-Fluorophenyl)-N-methyl-N-(pyridin-4-ylmethyl)-2-(2,3,6-trifluorophenethyl)-1H-imidazole-5-carboxamide;

N-((1,3-Dimethyl-1H-pyrazol-4-yl)methyl)-1-(4-fluorophenyl)-N-methyl-2-((2-methyl-1-oxo-1-phenylpropan-2-yl)thio)-1H-imidazole-5-carboxamide;

4-(((1-(4-Fluorophenyl)-2-((2,3,6-trifluorobenzyl)thio)-1H-imidazol-5-yl)methoxy)methyl)pyridine;

1-(1,3-Dimethyl-1H-pyrazol-4-yl)-N-((1-(4-fluorophenyl)-2-((2,3,6-trifluorobenzyl)thio)-1H-imidazol-5-yl)methyl)methanamine;

2-((2-Chloro-6-fluorobenzyl)thio)-N-((1,3-dimethyl-1H-pyrazol-4-yl)methyl)-1-(4-fluorophenyl)-N-methyl-1H-imidazole-5-carboxamide;

2-((2-Chloro-6-fluorobenzyl)thio)-1-(4-fluorophenyl)-N-methyl-N-(pyridin-4-ylmethyl)-1H-imidazole-5-carboxamide;

1-(4-Fluorophenyl)-N-methyl-2-(2-methyl-1-(2,3,6-trifluorophenyl)propan-2-yl)-N-(pyridin-4-ylmethyl)-1H-imidazole-5-carboxamide;

2-((2-Chloro-6-fluorobenzyl)thio)-1-(4-fluorophenyl)-N,N-dimethyl-1H-imidazole-5-carboxamide;

2-((2-Chloro-6-fluorobenzyl)oxy)-1-(4-fluorophenyl)-N-methyl-N-(pyridin-4-ylmethyl)-1H-imidazole-5-carboxamide;

2-((2-Chloro-6-fluorophenyl)ethynyl)-1-(4-fluorophenyl)-N-methyl-N-(pyridin-4-ylmethyl)-1H-imidazole-5-carboxamide;

2-(2-Fluorophenethyl)-1-(4-fluorophenyl)-N-methyl-N-(pyridin-4-ylmethyl)-1H-imidazole-5-carboxamide;

(2-((2-Chloro-6-fluorobenzyl)thio)-1-(4-fluorophenyl)-1H-imidazol-5-yl)(2-(pyridin-4-yl)pyrrolidin-1-yl)methanone;

1-(4-Fluorophenyl)-N-methyl-N-(pyridin-4-ylmethyl)-2-(2-(trifluoromethyl)phenethyl)-1H-imidazole-5-carboxamide;

(2-((2-Chloro-6-fluorobenzyl)thio)-1-(4-fluorophenyl)-1H-imidazol-5-yl)(2-(pyridin-4-yl)piperidin-1-yl)methanone;

tert-butyl 4-(((5-(((1,3-Dimethyl-1H-pyrazol-4-yl)methyl)(methyl)carbamoyl)-1-(4-fluorophenyl)-1H-imidazol-2-yl)thio)methyl)-3,5-difluorobenzoate;

4-(((5-(((1,3-Dimethyl-1H-pyrazol-4-yl)methyl)(methyl)carbamoyl)-1-(4-fluorophenyl)-1H-imidazol-2-yl)thio)methyl)-3,5-difluorobenzoic acid;

N-((1,3-Dimethyl-1H-pyrazol-4-yl)methyl)-1-(4-fluorophenyl)-N-methyl-2-((3,3,3-trifluoro-2-oxopropyl)thio)-1H-imidazole-5-carboxamide;

2-((Cyclopropylmethyl)thio)-N-((1,3-dimethyl-1H-pyrazol-4-yl)methyl)-1-(4-fluorophenyl)-N-methyl-1H-imidazole-5-carboxamide;

N-((1,3-Dimethyl-1H-pyrazol-4-yl)methyl)-1-(4-fluorophenyl)-N-methyl-2-(neopentylthio)-1H-imidazole-5-carboxamide;

N-((1,3-Dimethyl-1H-pyrazol-4-yl)methyl)-1-(4-fluorophenyl)-2-(isobutylthio)-N-methyl-1H-imidazole-5-carboxamide;

N-((1,3-Dimethyl-1H-pyrazol-4-yl)methyl)-2-((3,3-dimethyl-2-oxobutyl)thio)-1-(4-fluorophenyl)-N-methyl-1H-imidazole-5-carboxamide;

2-((2-Chlorobenzyl)thio)-N-((1,3-dimethyl-1H-pyrazol-4-yl)methyl)-1-(4-fluorophenyl)-N-methyl-1H-imidazole-5-carboxamide;

2-((2-Chlorobenzyl)thio)-1-(4-fluorophenyl)-N-methyl-N-((2-methylpyridin-4-yl)methyl)-1H-imidazole-5-carboxamide;

2-(((3-Chloropyridin-2-yl)methyl)thio)-N-((1,3-dimethyl-1H-pyrazol-4-yl)methyl)-1-(4-fluorophenyl)-N-methyl-1H-imidazole-5-carboxamide;

N-((1,3-Dimethyl-1H-pyrazol-4-yl)methyl)-1-(4-fluorophenyl)-N-methyl-2-(((5-methyl-1,2,4-oxadiazol-3-yl)methyl)thio)-1H-imidazole-5-carboxamide;

2-((2-Chloro-6-fluorobenzyl)thio)-1-(4-chlorophenyl)-N-((1,3-dimethyl-1H-pyrazol-4-yl)methyl)-N-methyl-1H-imidazole-5-carboxamide;

2-((2-Chloro-6-fluorobenzyl)thio)-N-((1,3-dimethyl-1H-pyrazol-4-yl)methyl)-N-methyl-1-phenyl-1H-imidazole-5-carboxamide;

2-((2-Chloro-6-fluorobenzyl)thio)-N-methyl-1-phenyl-N-(pyridin-4-ylmethyl)-1H-imidazole-5-carboxamide;

2-((2-Chloro-6-fluorobenzyl)thio)-1-(4-chlorophenyl)-N-methyl-N-(pyridin-4-ylmethyl)-1H-imidazole-5-carboxamide;

2-((2-Chloro-6-fluorobenzyl)thio)-N-methyl-N-(pyridin-4-ylmethyl)-1-(4-(trifluoromethyl)phenyl)-1H-imidazole-5-carboxamide;

2-((2-Chloro-6-fluorobenzyl)thio)-1-(4-ethylphenyl)-N-methyl-N-(pyridin-4-ylmethyl)-1H-imidazole-5-carboxamide;

2-((2-Chloro-6-fluorobenzyl)thio)-1-(4-methoxyphenyl)-N-methyl-N-(pyridin-4-ylmethyl)-1H-imidazole-5-carboxamide;

2-((2,6-Dimethylbenzyl)thio)-1-(4-fluorophenyl)-N-methyl-N-(pyridin-4-ylmethyl)-1H-imidazole-5-carboxamide;

2-((2,6-Dichlorobenzyl)thio)-1-(4-fluorophenyl)-N-methyl-N-(pyridin-4-ylmethyl)-1H-imidazole-5-carboxamide;

1-(4-Fluorophenyl)-N-methyl-2-((2-methylbenzyl)thio)-N-(pyridin-4-ylmethyl)-1H-imidazole-5-carboxamide;

2-((2-Chloro-6-fluorobenzyl)thio)-N-methyl-N-(pyridin-4-ylmethyl)-1-(p-tolyl)-1H-imidazole-5-carboxamide;

2-((2-Chloro-6-fluorobenzyl)thio)-1-(3-fluorophenyl)-N-methyl-N-(pyridin-4-ylmethyl)-1H-imidazole-5-carboxamide;

2-((2-Chloro-6-fluorobenzyl)thio)-1-cyclohexyl-N-methyl-N-(pyridin-4-ylmethyl)-1H-imidazole-5-carboxamide;

2-((2-Chloro-6-fluorobenzyl)thio)-N-methyl-1-neopentyl-N-(pyridin-4-ylmethyl)-1H-imidazole-5-carboxamide;

2-(((2,6-Dichlorophenyl)thio)methyl)-N-((1,3-dimethyl-1H-pyrazol-4-yl)methyl)-1-(4-fluorophenyl)-N-methyl-1H-imidazole-5-carboxamide;

N-((1,3-Dimethyl-1H-pyrazol-4-yl)methyl)-1-(4-fluorophenyl)-N-methyl-2-((2,3,6-trifluorophenoxy)methyl)-1H-imidazole-5-carboxamide;

N-((1,3-Dimethyl-1H-pyrazol-4-yl)methyl)-1-(4-fluorophenyl)-N-methyl-2-(((2,3,5,6-tetrafluorophenyl)thio)methyl)-1H-imidazole-5-carboxamide;

N-((1,3-Dimethyl-1H-pyrazol-4-yl)methyl)-1-(4-fluorophenyl)-N-methyl-2-((2-(2,3,6-trifluorophenyl)propan-2-yl)thio)-1H-imidazole-5-carboxamide;

1-(4-Fluorophenyl)-N-methyl-N-(pyridin-4-ylmethyl)-2-((2,3,6-trifluorobenzyl)sulfinyl)-1H-imidazole-5-carboxamide;

N-((1,3-Dimethyl-1H-pyrazol-4-yl)methyl)-1-(4-fluorophenyl)-N-methyl-2-(((2,3,6-trifluorobenzyl)thio)methyl)-1H-imidazole-5-carboxamide;

N-((1,3-Dimethyl-1H-pyrazol-4-yl)methyl)-1-(4-fluorophenyl)-N-methyl-2-(((2,3,6-trifluorobenzyl)sulfonyl)methyl)-1H-imidazole-5-carboxamide;

(E)-3-(1,3-Dimethyl-1H-pyrazol-4-yl)-1-(1-(4-fluorophenyl)-2-((2,3,6-trifluorobenzyl)thio)-1H-imidazol-5-yl)prop-2-en-1-one;

N-((1,3-Dimethyl-1H-pyrazol-4-yl)methyl)-1-(4-fluorophenyl)-N-methyl-2-((2,3,6-trifluorobenzyl)amino)-1H-imidazole-5-carboxamide;

N-((1,3-Dimethyl-1H-pyrazol-4-yl)methyl)-1-(4-fluorophenyl)-N-methyl-2-((2,3,6-trifluorobenzyl)oxy)methyl)-1H-imidazole-5-carboxamide;

1-(4-Fluorophenyl)-N-methyl-N-((2-methylpyridin-4-yl)methyl)-2-((2,3,6-trifluorobenzyl)thio)-1H-imidazole-5-carboxamide;

N-((2-Chloropyridin-4-yl)methyl)-1-(4-fluorophenyl)-N-methyl-2-((2,3,6-trifluorobenzyl)thio)-1H-imidazole-5-carboxamide;
N-((1,3-Dimethyl-1H-pyrazol-4-yl)methyl)-1-(4-fluorophenyl)-N-methyl-2-((pyridine-4-ylmethyl)thio)-1H-imidazole-5-carboxamide;
N-((1,3-Dimethyl-1H-pyrazol-4-yl)methyl)-1-(4-fluorophenyl)-N-methyl-2-(methyl(2,3,6-trifluorobenzyl)amino)-1H-imidazole-5-carboxamide;
N-((4-Ethyl-2-methylthiazol-5-yl)methyl)-1-(4-fluorophenyl)-2-((2,3,6-trifluorobenzyl)sulfinyl)-1H-imidazole-5-carboxamide;
1-(4-Fluorophenyl)-N-methyl-N-((1-methyl-5-phenoxy-3-(trifluoromethyl)-1H-pyrazol-4-yl)methyl)-2-((2,3,6-trifluorobenzyl)sulfinyl)-1H-imidazole-5-carboxamide;
2-((3-Chloro-4-fluorophenethyl)thio)-1-(4-fluorophenyl)-N-((2-methylpyridin-4-yl)methyl)-1H-imidazole-5-carboxamide;
N-(4-(Dimethylamino)benzyl))-1-(4-fluorophenyl)-N-methyl-2-((2,3,6-trifluorobenzyl)thio)-1H-imidazole-5-carboxamide;
1-(4-Fluorophenyl)-N-4-dimethyl-N-((2-methylpyridin-4-yl)methyl)-2-((2,3,6-trifluorobenzyl)thio)-1H-imidazole-5-carboxamide;
2-((3-Chloro-4-fluorophenethyl)sulfonyl)-1-(4-fluorophenyl)-N-methyl-N-((2-methylpyridin-4-yl)methyl)-1H-imidazole-5-carboxamide;
1-(4-Fluorophenyl)-N-methyl-2-((2,3,6-trifluorobenzyl)thio)-N-((2-trifluoromethyl)pyridin-4-yl)methyl)-1H-imidazole-5-carboxamide;
2-((2-Chloro-6-fluorophenethyl)sulfonyl)-1-(4-fluorophenyl)-N-methyl-N-((2-methylpyridin-4-yl)methyl)-1H-imidazole-5-carboxamide;
1-(4-Fluorophenyl)-2-iodo-N-methyl-N-((2-methylpyridin-4-yl)methyl)-1H-imidazole-5-carboxamide;
2-Bromo-N-((1,3-dimethyl-1H-pyrazol-4-yl)methyl)-1-(4-fluorophenyl)-N-methyl-1H-imidazole-5-carboxamine;
(2-((6-Chloro-2-fluoro-3-methoxybenzyl)thio)-1-(4-fluorophenyl)-1H-imidazol-5-yl)(2-(pyridin-4-yl)pyrrolidin-1-yl)methanone;
(2-(2-Fluorophenethyl)-1-(4-fluorophenyl)-1H-imidazol-5-yl)(2-(pyridin-4-yl)pyrrolidin-1-yl)methanone;
2-(Benzylthio)-N-((1,3-dimethyl-1H-pyrazol-4-yl)methyl)-1-(4-fluorophenyl)-N-methyl-1H-imidazole-5-carboxamide;
5-((6-Chloro-2-fluoro-3-methoxybenzyl)thio)-4-(4-fluorophenyl)-N-methyl-N-(pyridin-4-ylmethyl)-4H-1,2,4-triazole-3-carboxamide;
5-((6-Chloro-2-fluoro-3-methylbenzyl)thio)-4-(4-fluorophenyl)-N-methyl-N-(pyridin-4-ylmethyl)-4H-1,2,4-triazole-3-carboxamide;
2-((6-Chloro-2-fluoro-3-methoxybenzyl)thio)-N-((1,3-dimethyl-1H-pyrazol-4-yl)methyl)-1-(4-fluorophenyl)-N-methyl-1H-imidazole-5-carboxamide;
2-((6-Chloro-2-fluoro-3-methylbenzyl)thio)-N-((1,3-dimethyl-1H-pyrazol-4-yl)methyl)-1-(4-fluorophenyl)-N-methyl-1H-imidazole-5-carboxamide;
3-((2-Chloro-6-fluorobenzyl)oxy)-5-((2-chloro-6-fluorobenzyl)thio)-4-(2-(trifluoromethyl)phenyl)-4H-1,2,4-triazole;
4-(3-Chlorophenyl)-3-((2,4-dichlorobenzyl)thio)-5-((2,3-difluorobenzyl)oxy)-4H-1,2,4-triazole;
1-(4-Fluorophenyl)-N-methyl-N-((2-methylthiazol-5-yl)methyl)-2-((2,3,6-trifluorobenzyl-sulfinyl)-1H-imidazole-5-carboxamide;
1-(4-Fluorophenyl)-N-methyl-N-((4-methylthiophen-2-yl)methyl)-2-((2,3,6-trifluorobenzyl)-sulfinyl)-1H-imidazole-5-carboxamide;
1-(4-Fluorophenyl)-N-methyl-N-((2-methylthiazol-5-yl)methyl)-2-((2,3,6-trifluorobenzyl)thio)-1H-imidazole-5-carboxamide;
1-(4-Fluorophenyl)-N-methyl-N-(pyridin-3-ylmethyl)-2-((2,3,6-trifluorobenzyl)thio)-1H-imidazole-5-carboxamide;
1-(4-Fluorophenyl)-N-methyl-N-(pyrazin-2-ylmethyl)-2-((2,3,6-trifluorobenzyl)thio)-1H-imidazole-5-carboxamide;
1-(4-Fluorophenyl)-N-methyl-N-(pyrazin-2-ylmethyl)-2-((2,3,6-trifluorobenzyl)sulfinyl)-1H-imidazole-5-carboxamide;
4-(((1-(4-Fluorophenyl)-2-((2,3,6-trifluorobenzyl)thio)-1H-imidazol-5-yl)methoxy)methyl)-pyridine;
2-((2-Fluoro-6-(trifluoromethyl)benzyl)thio)-1-(4-fluorophenyl)-N-methyl-N-(pyridin-4-ylmethyl)-1H-imidazole-5-carboxamide;
2-((4-Fluoro-2-(trifluoromethyl)benzyl)thio)-1-(4-fluorophenyl)-N-methyl-N-(pyridin-4-ylmethyl)-1H-imidazole-5-carboxamide;
2-((4-Chloro-2-(trifluoromethyl)benzyl)thio)-1-(4-fluorophenyl)-N-methyl-N-(pyridin-4-ylmethyl)-1H-imidazole-5-carboxamide;
2-((2-Fluoro-3-(trifluoromethyl)benzyl)thio)-1-(4-fluorophenyl)-N-methyl-N-(pyridin-4-ylmethyl)-1H-imidazole-5-carboxamide;
2-((2,5-Difluorobenzyl)thio)-1-(4-fluorophenyl)-N-methyl-N-(pyridin-4-ylmethyl)-1H-imidazole-5-carboxamide;
2-((6-Chloro-2-fluoro-3-methoxybenzyl)thio)-1-(4-fluorophenyl)-N-methyl-N-(pyridin-4-ylmethyl)-1H-imidazole-5-carboxamide;
2-((2-Fluorobenzyl)thio)-1-(4-fluorophenyl)-N-methyl-N-(pyridin-4-ylmethyl)-1H-imidazole-5-carboxamide;
1-(4-Fluorophenyl)-N-methyl-N-(pyridin-4-ylmethyl)-2-((2-(trifluoromethyl)benzyl)thio)-1H-imidazole-5-carboxamide;
2-((2-Chloro-5-fluorobenzyl)thio)-1-(4-fluorophenyl)-N-methyl-N-(pyridin-4-ylmethyl)-1H-imidazole-5-carboxamide;
2-((5-Chloro-2-fluorobenzyl)thio)-1-(4-fluorophenyl)-N-methyl-N-(pyridin-4-ylmethyl)-1H-imidazole-5-carboxamide;
2-((2-Chloro-3,6-difluorobenzyl)thio)-1-(4-fluorophenyl)-N-methyl-N-(pyridin-4-ylmethyl)-1H-imidazole-5-carboxamide;
2-((2-Chloro-4,5-difluorobenzyl)thio)-1-(4-fluorophenyl)-N-methyl-N-(pyridin-4-ylmethyl)-1H-imidazole-5-carboxamide;
1-(4-Fluorophenyl)-N-methyl-N-(pyridin-4-ylmethyl)-2-((2,3,5-trifluorobenzyl)thio)-1H-imidazole-5-carboxamide;
2-((2-Chloro-6-fluoro-3-methylbenzyl)thio)-1-(4-fluorophenyl)-N-methyl-N-(pyridin-4-ylmethyl)-1H-imidazole-5-carboxamide;
1-(4-Fluorophenyl)-N-methyl-N-(pyridin-4-ylmethyl)-2-((3-(trifluoromethyl)benzyl)thio)-1H-imidazole-5-carboxamide;
2-((6-Chloro-2-fluoro-3-methylbenzyl)thio)-1-(4-fluorophenyl)-N-methyl-N-(pyridin-4-ylmethyl)-1H-imidazole-5-carboxamide;
2-((5-Chloro-2-(trifluoromethyl)benzyl)thio)-1-(4-fluorophenyl)-N-methyl-N-(pyridin-4-ylmethyl)-1H-imidazole-5-carboxamide;

2-((2-Cyanobenzyl)thio)-1-(4-fluorophenyl)-N-methyl-N-(pyridin-4-ylmethyl)-1H-imidazole-5-carboxamide;
1-(4-Fluorophenyl)-N-methyl-2-((5-methyl-2-(trifluoromethyl)benzyl)thio)-N-(pyridin-4-ylmethyl)-1H-imidazole-5-carboxamide;
2-((6-Chloro-2-fluoro-3-methoxybenzyl)thio)-N-ethyl-1-(4-fluorophenyl)-N-(pyridin-4-ylmethyl)-1H-imidazole-5-carboxamide;
2-((6-Chloro-2-fluoro-3-methylbenzyl)thio)-N-ethyl-1-(4-fluorophenyl)-N-(pyridin-4-ylmethyl)-1H-imidazole-5-carboxamide;
4-((1-(1-(4-Fluorophenyl)-4-methyl-2-((2,3,6-trifluorobenzyl)thio)-1H-imidazol-5-yl)ethoxy)methyl)pyridine;
2-((Benzo[d]oxazol-2-ylmethyl)thio)-N-((1,3-dimethyl-1H-pyrazol-4-yl)methyl)-1-(4-fluorophenyl)-N-methyl-1H-imidazole-5-carboxamide;
N-((1,3-Dimethyl-1H-pyrazol-4-yl)methyl)-2-(((3-ethyl-1,2,4-oxadiazol-5-yl)methyl)thio)-1-(4-fluorophenyl)-N-methyl-1H-imidazole-5-carboxamide;
N-((1,3-Dimethyl-1H-pyrazol-4-yl)methyl)-1-(4-fluorophenyl)-2-(((3-isopropylisoxazol-5-yl)methyl)thio)-N-methyl-1H-imidazole-5-carboxamide;
N-((1,3-Dimethyl-1H-pyrazol-4-yl)methyl)-1-(4-fluorophenyl)-N-methyl-2-((pyrazolo[1,5-a]pyridin-2-ylmethyl)thio)-1H-imidazole-5-carboxamide;
N-((1,3-Dimethyl-1H-pyrazol-4-yl)methyl)-1-(4-fluorophenyl)-N-methyl-2-(((1-methyl-1H-pyrazol-3-yl)methyl)thio)-1H-imidazole-5-carboxamide;
N-((1,3-Dimethyl-1H-pyrazol-4-yl)methyl)-1-(4-fluorophenyl)-N-methyl-2-(((1-methyl-1H-1,2,4-triazol-3-yl)methyl)thio)-1H-imidazole-5-carboxamide;
N-((1,3-Dimethyl-1H-pyrazol-4-yl)methyl)-1-(4-fluorophenyl)-N-methyl-2-((pyrimidin-2-ylmethyl)thio)-M-imidazole-5-carboxamide;
N-((1,3-Dimethyl-1H-pyrazol-4-yl)methyl)-1-(4-fluorophenyl)-N-methyl-2-(((4-methylthiazol-2-yl)methyl)thio)-1H-imidazole-5-carboxamide; and
Ethyl 2-((5-(((1,3-dimethyl-1H-pyrazol-4-yl)methyl)(methyl)carbamoyl)-1-(4-fluorophenyl)-1H-imidazol-2-yl)thio)acetate;

or a pharmaceutically acceptable salt thereof.

15. A pharmaceutical composition comprising a compound of claim 1 and a pharmaceutically acceptable carrier.

16. A pharmaceutical composition comprising an amount of a compound of claim 1 effective to modulate GPR131, and a pharmaceutically acceptable carrier.

17. A method of treating a subject suffering from or at risk of a disease or condition for which GPR131 modulation provides a therapeutic benefit, comprising administering to the subject an effective amount of a compound of claim 1.

18. The method of claim 17 wherein the disease is type 2 diabetes.

19. A method of treating a subject suffering from or at risk of a disease or condition for which GPR131 modulation provides a therapeutic benefit, comprising the concomitant administration of a compound of claim 1 and a DPP IV inhibitor.

20. The method of claim 19 wherein the DPP IV inhibitor is sitagliptin or vildagliptin.

* * * * *